(12) United States Patent
Bills et al.

(10) Patent No.: US 8,497,984 B2
(45) Date of Patent: Jul. 30, 2013

(54) SYSTEM AND METHOD FOR INSPECTION OF A WORKPIECE SURFACE USING MULTIPLE SCATTERED LIGHT COLLECTORS

(75) Inventors: Richard Earl Bills, Tucson, AZ (US); Neil Judell, Newtonville, MA (US); Timothy R. Tiemeyer, Providence, RI (US); James Peter McNiven, Vail, AZ (US)

(73) Assignee: KLA-Tencor Corporation, Milpitas, CA (US)

( * ) Notice: Subject to any disclaimer, the term of this patent is extended or adjusted under 35 U.S.C. 154(b) by 1522 days.

(21) Appl. No.: 11/311,943

(22) Filed: Dec. 17, 2005

(65) Prior Publication Data

US 2006/0256326 A1 Nov. 16, 2006

Related U.S. Application Data

(60) Provisional application No. 60/638,529, filed on Dec. 19, 2004.

(51) Int. Cl.
*G01N 21/88* (2006.01)
(52) U.S. Cl.
USPC ........................................ 356/237.2; 356/600

(58) Field of Classification Search
USPC .................... 356/237.1–237.5, 445–448, 369
See application file for complete search history.

(56) References Cited

U.S. PATENT DOCUMENTS

| 4,889,998 | A | * | 12/1989 | Hayano et al. | 250/559.41 |
| 5,680,207 | A | * | 10/1997 | Hagiwara | 356/237.3 |
| 6,215,551 | B1 | * | 4/2001 | Nikoonahad et al. | 356/237.2 |
| 6,292,259 | B1 | * | 9/2001 | Fossey et al. | 356/237.2 |
| 2004/0246476 | A1 | * | 12/2004 | Bevis et al. | 356/237.5 |

* cited by examiner

*Primary Examiner* — Hoa Pham
(74) *Attorney, Agent, or Firm* — Luedeka Neely Group, P.C.; Rick Barnes

(57) ABSTRACT

A surface inspection system, as well as related components and methods, are provided. The surface inspection system includes a beam source subsystem, a beam scanning subsystem, a workpiece movement subsystem, an optical collection and detection subsystem, and a processing subsystem. Certain of these components, most notably the beam source subsystem, the beam scanning subsystem and the optical collection and detection subsystem are modular for ready field replacement and/or maintenance. The optical collection and detection system features wing collectors in the front quartersphere and back collectors in the back quartersphere for collected light scattered from the surface of the workpiece. This can greatly improve the measurement capabilities of the system. Also included is a method for detecting asymmetric defects using the wing collectors and back collectors.

1 Claim, 75 Drawing Sheets

706

| | MaxPPM | Back | Center | Front |
|---|---|---|---|---|
| | Slot 01 | 0.0125 | 0.0054 | 0.0259 |
| | Slot 02 | 0.0125 | 0.0054 | 0.0259 |
| | Slot 03 | 0.0132 | 0.0058 | 0.0257 |
| | Slot 04 | 0.0128 | 0.0055 | 0.0259 |
| Process A | Slot 05 | 0.0131 | 0.0055 | 0.0257 |
| | Slot 06 | 0.0133 | 0.0058 | 0.0257 |
| | Slot 07 | 0.0137 | 0.0060 | 0.0257 |
| | Slot 08 | 0.0128 | 0.0054 | 0.0255 |
| | Slot 09 | 0.0131 | 0.0058 | 0.0264 |
| | Slot 10 | 0.0131 | 0.0041 | 0.0332 |
| | Slot 11 | 0.0119 | 0.0037 | 0.0337 |
| | Slot 12 | 0.0121 | 0.0036 | 0.0352 |
| Process B | Slot 13 | 0.0114 | 0.0036 | 0.0330 |
| | Slot 14 | 0.0121 | 0.0037 | 0.0339 |
| | Slot 15 | 0.0106 | 0.0033 | 0.0330 |
| | Slot 16 | 0.0109 | 0.0038 | 0.0337 |
| | Slot 17 | 0.0106 | 0.0035 | 0.0343 |
| | Slot 18 | 0.0110 | 0.0041 | 0.0285 |
| | Slot 19 | 0.0109 | 0.0042 | 0.0281 |
| | Slot 20 | 0.0113 | 0.0040 | 0.0290 |
| Process C | Slot 21 | 0.0112 | 0.0042 | 0.0281 |
| | Slot 22 | 0.0106 | 0.0038 | 0.0285 |
| | Slot 23 | 0.0112 | 0.0043 | 0.0281 |
| | Slot 24 | 0.0110 | 0.0043 | 0.0292 |
| | Slot 25 | 0.0112 | 0.0040 | 0.0283 |
| | MAX | 0.0137 | 0.0060 | 0.0352 |
| | MIN | 0.0106 | 0.0033 | 0.0255 |

| LOWEST | LOW | HIGH | HIGHEST |

FIG.75

METHOD 970: DETERMINE EXTENT OF SURFACE ROUGHNESS

Step 971: determine the in-scan spatial frequency response 702
- Form spatial frequency response region 700.

Step 972: Determine a response range.

Step 973: Determine scatter value for the response range.

Step 974: Determine a scatter value for each collector in set and compare scatter values.
- Step 976: Display values comparison
    - Step 977: Map ideal response ranges 760 into a histogram 780.

Step 975: Determine a scatter value for a plurality of surfaces, and compare scatter values.

FIG.96 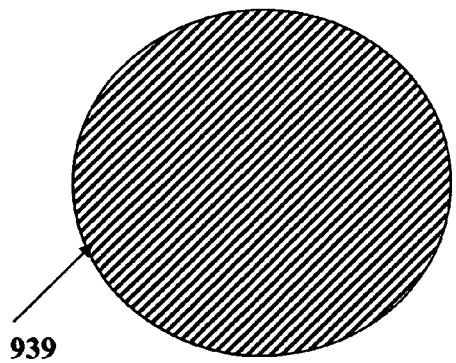

FIG.97 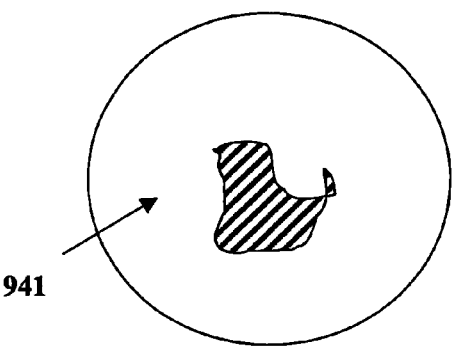

METHOD FOR ANALYZING SURFACE SCATTER

Step 264: Separate surface scatter by surface structure spatial frequency range.

Step 265: Select expected spatial frequency ranges
- high
- medium
- low

Step 266: Identify collectors to provide output for expected spatial frequency ranges.

Step 267: Obtain surface scatter output for each collector.

Step 268: Analyze surface structure spatial frequency range.

FIG.99

Step 268: Analyze surface structure spatial frequency range.

Step 269: Analyze output for surface scatter portion alone or in combination with other portions.

Step 274: Establish visual representation for output for each surface structure spatial frequency range.

Step 275: Assign a characteristic of the visual representation to the presence of surface scatter in output.

Step 276: Represent an extent of surface scatter by an extent of variation in the visual representation.

Step 277: Map values for extent of haze into values for extent of variation in the visual representation.

Step 280: Construct the visual representations:

Step 284a: Construct individual haze map for each selected surface spatial frequency range.

Step 284b: Construct composite haze map.

SYSTEM AND METHOD FOR INSPECTION OF A WORKPIECE SURFACE USING MULTIPLE SCATTERED LIGHT COLLECTORS

CROSS-REFERENCE TO RELATED APPLICATION

The present application claims the benefit of the filing date of U.S. Provisional Patent Application No. 60/638,529, filed Dec. 19, 2004, currently pending, the entire disclosure of which is incorporated herein by reference. The present application is also related to U.S. patent application Ser. No. 11/311,907 (Ref. No. PAT 2004-010.02), U.S. patent application Ser. No. 11/311,919 (Ref. No. PAT 2004-010.03), U.S. patent application Ser. No. 11/311,908 (Ref. No. PAT 2004-010.04), U.S. patent application Ser. No. 11/311,904 (Ref. No. PAT 2004-010.05), U.S. patent application Ser. No. 11/311,905 (Ref. No. PAT 2004-010.06), U.S. patent application Ser. No. 11/311,925 (Ref. No. PAT 2004-010.07), U.S. patent application Ser. No. 11/311,926 (Ref. No. PAT 2004-010.08), and U.S. patent application Ser. No. 11/311,924 (Ref. No. PAT 2004-010.09), all of which were filed on 17 Dec. 2005.

STATEMENT REGARDING FEDERALLY SPONSORED RESEARCH OR DEVELOPMENT

N/A

BACKGROUND OF THE INVENTION

1. Field of the Invention

The present invention relates to technology for the inspection of a surface or surfaces of a workpiece, such as a semiconductor wafer, chip, or the like. More particularly, it relates to apparatus and methods for inspection of such workpiece surfaces using electromagnetic energy, e.g., light, to scan the surface to obtain characteristics of the surface or other information concerning the surface.

2. Description of the Related Art

There are a number of applications in which it is desirable or advantageous to inspect a surface or surfaces of a workpiece to obtain information about the characteristics and/or condition of that surface or surfaces. Examples of workpieces amenable to such application would include, for example, bare or unpatterned semiconductor wafers, semiconductor wafers with an applied film or films, patterned wafers, and the like. Characteristics and conditions of the surface that are commonly of interest include surface geometry such as flatness, surface roughness, etc., and/or the presence of defects, such as particles, crystal originated pits ("COPs") and crystalline growths. Given the increasing drive over the years to reduce device size and density, there has been a need for increasing control over surface characteristics or properties at reduced dimensions, and an increasing demand for a reduction in the size of defects, the types of defects that are permissible, etc. Correspondingly, there is an enhanced need for resolution, detection and characterization of small surface characteristics, properties, defects, etc., and an enhanced need for increased measurement sensitivity and classification capability.

In the face of this demand, a number of systems and methods have emerged to provide this capability. One such system, for example, is disclosed in U.S. Pat. No. 5,712,701 (the "'701 patent"), which is assigned to ADE Optical Systems Corporation of Westwood, Mass. The '701 patent discloses a surface inspection system and related methods for inspecting the surface of a workpiece, wherein a beam of laser light is directed to the surface of the workpiece, the light is reflected off the surface, and both scattered and specular light are collected to obtain information about the surface. An acousto-optical deflector is used to scan the beam as the wafer is moved, for example, by combined rotation and translation, so that the entire surface of the workpiece is inspected.

As our understanding of the physics and phenomenology of optical scattering from surfaces has improved, a capability has been developed and refined in which detailed and high resolution information about defects on the surface can be ascertained. These phenomena largely are obtained from the optical energy that is scattered by the surface, as opposed to the energy in the main reflected beam or the "specular beam." Examples of systems and methods that provide such defect detection capability include that of the '701 patent, as well as U.S. Pat. No. 6,118,525 and U.S. Pat. No. 6,292,259, all of which are assigned to ADE Optical Systems Corporation and all of which are herein incorporated by reference. Systems designed according to these patents have performed admirably and provided major advances over their predecessors. As the drive to smaller device dimensions and higher device densities has continued, however, the need also has continued for the ability to resolve and classify even smaller and smaller surface properties, defects, etc. A need also has developed to detect and characterize a greater range of surface characteristics and defects in terms of the types of defects, their extent or range, etc. Surface scratches are an example. Scratches on the surface of a workpiece often do not lie along a straight line. Surface scratches on semiconductor wafer surfaces, for example, can be the result of polishing, which can leave circular, curved or irregular scratch geometry. As the workpiece surface is moved relative to the beam, the orientation of the scratch relative to the oblique incident beam and collectors changes. This often causes changes in the amplitude and direction of scattered light from the scratch as the wafer rotates. As device dimensions decrease, the ability to detect and characterize the scratches and similar defects with improved sensitivity and reliability has become increasingly important.

Systems that are amenable to inspection and measurement of extremely small dimensions typically must operate in extremely clean environments. This commonly requires that they be contained and operated within a clean room. This highly controlled environment limits normal access to such machines and systems, which increases the difficulty and expense of their maintenance and repair. Accordingly, systems and methods are needed that are amenable to more efficient and effective replacement of precision-aligned optical sub-components within the machines.

OBJECTS OF THE INVENTION

Accordingly, an object of the present invention according to one aspect is to provide apparatus and methods for inspecting a surface of a workpiece with high sensitivity and reliability, e.g., for surface defects.

Another object of the invention according to another aspect is to provide apparatus and methods for inspecting a surface of a workpiece that enable an improved range of detection for surface characteristics, such as defects, defect type, etc., relative to known systems and methods.

Another object of the invention according to another aspect is to provide apparatus and methods for inspecting a surface of a workpiece that are accessible and/or amenable to efficient maintenance, repair, upgrade, and the like.

Additional objects and advantages of the invention will be set forth in the description which follows, and in part will be apparent from the description, or may be learned by practice of the invention. The objects and advantages of the invention may be realized and obtained by means of the instrumentalities and combinations pointed out in the appended claims.

SUMMARY OF THE INVENTION

To achieve the foregoing objects, and in accordance with the purposes of the invention as embodied and broadly described in this document, a surface inspection system is provided for inspecting the surface of a workpiece. The surface inspection system comprises a base, a beam source subsystem, a beam scanning subsystem, a workpiece movement subsystem, an optical collection and detection subsystem, and a processing subsystem. The beam source subsystem comprises a beam source that projects an incident beam toward the surface of the workpiece. The beam scanning subsystem comprises means for receiving the incident beam and scanning the incident beam on the surface of the workpiece. The workpiece movement subsystem moves the surface of the workpiece relative to the incident beam. The optical collection and detection subsystem collects portions of the incident beam that are reflected or scattered from the surface of the workpiece and generates signals in response to the reflected portions of the incident beam. The processing subsystem is operatively coupled to the collection and detection subsystem for processing the signals.

Optionally but preferably, the beam source module comprises a beam source housing for fixedly supporting the beam source, and a beam source mounting means for fixedly mounting the beam source housing relative to the base so that the incident beam is projected at a pointing angle to a pointing position that is within about 50 micro radians of a target spot corresponding to a desired spot on the surface of the workpiece. In addition, again optionally but preferably, the beam source module further comprises means for pre-aligning the incident beam to the pointing angle and the pointing position. In a presently preferred embodiment, the beam source housing mounting means comprises a plurality of pinholes and the beam scanning mounting means comprises a corresponding plurality of pins that mate with the plurality of pinholes. In another, the beam source housing mounting means comprises a plurality of pins and the beam scanning mounting means comprises a corresponding plurality of pinholes that mate with the plurality of pins. The beam source housing also may comprise a plurality of pinholes, and the beam scanning mounting means may comprise a corresponding plurality of pins that mate with the plurality of pinholes.

The beam scanning module preferably comprises a beam scanning module housing for supporting the beam scanning means, and beam scanning mounting means for fixedly mounting the beam scanning module housing relative to the base so that the beam is projected to a pointing position that is within about 50 micro radians of a target spot corresponding to a desired spot on the surface of the workpiece. The beam scanning module also preferably comprises means for pre-aligning the incident beam to the pointing position. In a presently preferred embodiment, the base comprises a plurality of pinholes and the beam scanning mounting means comprises a corresponding plurality of pins that mate with the plurality of pinholes. In another embodiment, the base comprises a plurality of pins and the beam scanning mounting means comprises a corresponding plurality of pinholes that mate with the plurality of pins.

The optical collection and detection module preferably comprises a collection and detection module housing for supporting the optical collection and detection module, and collection and detection module mounting means for fixedly mounting the collection and detection module to the base. In a presently preferred embodiment, the base comprises a plurality of pinholes and the collection and detection module mounting means comprises a corresponding plurality of pins that mate with the plurality of pinholes. In another, the base comprises a plurality of pins and the collection and detection module mounting means comprises a corresponding plurality of pinholes that mate with the plurality of pins.

The collection and detection module, also known as collector detector module, preferably comprises at least one, and preferably two, wing collectors positioned to collect the portions of the incident beam that are scattered from the surface of the workpiece. The wing collector or wing collectors are disposed in a front quartersphere, outside an incident plane defined by the incident beam and a light channel axis, and at or near a maximum of the signal to noise ratio. According to another aspect, the wing collector or wing collectors are positioned in null, or a local minimum, in surface roughness scatter relative to defect scatter, for example, from a defect perspective, at a maximum in the signal to noise ratio of defect scatter to surface roughness scatter when the incident beam is P polarized, or, from a surface roughness scatter perspective, when the surface roughness is at a relative minimum in a bi-directional reflectance distribution function when the incident beam is P polarized.

In accordance with another aspect of the invention, a method is provided for assembling a surface inspection system having a base. The method comprises providing the base to include a first mating device, providing a beam source subsystem having a beam source that projects an incident beam and a beam source housing having a second mating device, wherein the beam source is mounted to the beam source housing, pre-aligning the beam source relative to the beam source housing prior to placement of the beam source housing on the base so that the incident beam is projected at a pointing angle to a pointing position that is within about 50 micro radians of a target spot corresponding to a desired spot on the surface of the workpiece, and positioning the beam source housing on the base using the first and second mating devices, whereby the first and second mating devices automatically cause the incident beam to be in the pointing position.

In presently preferred implementations of this method, the first mating device may comprise a plurality of pinholes, and the second mating device comprises a plurality of pins that mate with the plurality of pinholes. The method also may be implemented so that the first mating device comprises a plurality of pins, and the second mating device comprises a plurality of pinholes that mate with the plurality of pins.

In accordance with another aspect of the invention, a method is provided for assembling a surface inspection system having a base. The method comprises providing a base having a first mating device, and providing a beam source subsystem having a beam source that projects an incident beam and a beam source housing having a second mating device, wherein the beam source is mounted to the beam source housing. The method also comprises providing a beam scanning subsystem having a beam scanning device that scans an incident beam on the surface of the workpiece, wherein the beam scanning subsystem comprises a beam scanning subsystem housing having third and fourth mating devices, and wherein the beam scanning device is mounted to the beam scanning housing. The method further comprises pre-aligning the beam source relative to the beam source housing prior to placement of the beam source housing on the beam scanning subsystem housing so that the incident beam is projected at a pointing angle to a pointing position that is within about 50 micro radians of a target spot corresponding to a desired spot on the surface of the workpiece. The method still further comprises pre-aligning the beam scanning device relative to the beam scanning subsystem housing prior to placement of the beam scanning subsystem housing on the base so that the incident beam is projected to the pointing position. This method also comprises positioning the beam source housing on the beam scanning subsystem housing using the second and third mating devices, whereby the second and third mating devices automatically cause the incident beam to be in the pointing position and at the pointing angle. It also comprises positioning the beam scanning housing on the base using the first and fourth mating devices, whereby the first and fourth mating devices automatically cause the incident beam to be in the pointing position.

In accordance with another method according to the invention, a base having a first mating device is provided, as is a beam scanning subsystem having a beam scanning device that scans an incident beam on the surface of the workpiece. The beam scanning subsystem comprises a beam scanning subsystem housing to which the beam scanning device is mounted. The beam scanning housing comprises a second mating device. The method also comprises pre-aligning the beam scanning device relative to the beam scanning subsystem housing prior to placement of the beam scanning subsystem housing on the base so that the incident beam is project to a pointing position that is within about 50 micro radians of a target spot corresponding to a desired spot on the surface of the workpiece. The method further comprises positioning the beam scanning subsystem housing on the base using the first and second mating devices, whereby the first and second mating devices automatically cause the incident beam to be in the pointing position.

In implementing this method, one may provide the first mating device to comprise a plurality of pinholes, and the second mating device may be provided to comprise a plurality of pins that mate with the plurality of pinholes. In another implementation, the first mating device comprises a plurality of pins, and the second mating device comprises a plurality of pinholes that mate with the plurality of pins.

In accordance with another aspect of the invention, a method is provided for assembling a surface inspection system having a base. The method comprises a base having a first mating device, and providing a collection and detection subsystem that comprises a collector module and a detector module mounted to a collection and detection subsystem housing for supporting the optical and detection subsystem. Prior to placement of the collection and detection subsystem housing on the base, the method includes pre-aligning the collector module and the detector module to receive reflected portions of an incident beam reflected from the surface of the workpiece. The method also includes positioning the collection and detection subsystem housing on the base using the first and second mating devices, whereby the first and second mating devices automatically cause the collector module and the detector module to be positioned to receive the reflected portions of the incident beam. In a presently preferred implementation, the first mating device comprises a plurality of pinholes, and the second mating device comprises a plurality of pins that mate with the plurality of pinholes. In another implementation, the first mating device comprises a plurality of pins, and the second mating device comprises a plurality of pinholes that mate with the plurality of pins.

In accordance with another aspect of the invention, a method is provided for affixing a beam scanning subsystem to a surface inspection system for inspecting a surface of a workpiece. The method comprises providing a beam scanning module, which beam scanning module scans a beam. After providing the beam scanning module, the method includes pre-aligning the beam as it is projected from the beam scanning module so that the beam is projected to a pointing position that is within about 50 micro radians of a target spot corresponding to a desired spot on the workpiece. After this pre-alignment, the method includes fixedly mounting the beam scanning module with the pre-aligned beam to relative the base so that the beam automatically remains pre-aligned to the pointing position. The beam scanning module preferably is mounted to the base and is detachable. The mounting may be accomplished using mating pins and pinholes to mount the beam scanning module.

In accordance with still another aspect of the invention, a method is provided for affixing a collection and detection module to a surface inspection system for inspecting a surface of a workpiece. The method comprises providing the collection and detection module that comprises a collector and a detector module which respectively collect and detect light of a beam reflected from the surface. After providing the collection and detection module, the method includes pre-aligning the collection and detection module so that the collector module and detector module are at desired positions along a collection axis desired spot on the workpiece. After this pre-alignment, the method includes mounting the pre-aligned collection and detection module relative to the base so that the collector and the detector module remain pre-aligned to the desired positions. In preferred implementations of this method, the mounting is detachable. The mounting may comprise the use of mating pins and pinholes to mount the collection and detection module.

In accordance with another aspect of the invention, a method is provided for maintaining a surface inspection system used for inspecting a surface of a workpiece. The surface inspection system has a first beam source module coupled to a base. The method comprises de-coupling and removing the first beam source module from the base, and providing a second beam source module, which second beam source module projects a beam. After these, the method comprises pre-aligning the beam as it is projected from the second beam source module so that the beam is projected to a pointing position that is within about 50 micro radians of a target spot corresponding to a desired spot on the workpiece, and after performing these, mounting the housing with the pre-aligned beam to the base so that the beam automatically remains pre-aligned to the pointing position. The mounting may comprise using mating pins and pinholes to mount the housing to the base so that that beam is in the pointing position.

In accordance with another aspect of the invention, a method is provided for maintaining a surface inspection system used for inspecting a surface of a workpiece, wherein the surface inspection system has a first beam source module coupled to a beam scanning housing. The method comprises de-coupling and removing the first beam source module from the beam scanning housing, and providing a second beam source module, which second beam source module projects a beam. After performing these, the method includes pre-aligning the beam as it is projected from the second beam source module so that the beam is projected to a pointing position that is within about 50 micro radians of a target spot corresponding to a desired spot on the workpiece. This is performed by adjusting the position of the beam scanning module with respect to the target spot. After performing these, the method includes mounting the second beam source module with the pre-aligned beam to the beam scanning housing so that the beam automatically remains pre-aligned to the pointing position. The mounting may comprise using mating pins and pinholes to mount the housing to the beam scanning housing so that that beam is in the pointing position.

In accordance with yet another aspect of the invention, a method is provided for maintaining a surface inspection system used for inspecting a surface of a workpiece. The surface inspection system has a first beam scanning module coupled to a base. The method comprises de-coupling and removing the first beam scanning module from the base, and providing a second beam scanning module, which second scanning beam source scans a beam. After performing these, the method includes pre-aligning the beam as it is projected from the beam scanning module so that the beam is projected to a pointing position that is within about 50 micro radians of a target spot corresponding to a desired spot on the workpiece. After performing this, the method includes mounting the beam scanning module with the pre-aligned beam to the base so that the beam automatically remains pre-aligned to the pointing position. The mounting may comprise using mating pins and pinholes to mount the housing to the base so that that beam is in the pointing position.

In accordance with another aspect of the invention, a variable scanning speed acousto-optical deflector assembly is provided. It comprises an acousto-optical deflector, means operatively coupled to the acousto-optical deflector for varying the scan speed at which the acousto-optical deflector scans a beam passing through the acousto-optical deflector, and beam compensating means for compensating for astigmatism of the beam associated with the variation of scan speed.

In preferred embodiments of the variable scanning speed acousto-optical deflector assembly, a scanning speed selection device operatively coupled to the acousto-optical deflector selects one of a plurality of scan speeds, and compensating optics compensate for astigmatism of the beam associated with the variation of scan speed. The compensating optics comprise a plurality of lenses and a lens positioning device operatively coupled to the plurality of lenses, for example, as described above, wherein the lens positioning device positions a selected one of the lenses in the beam at the output of the acousto-optical deflector, and each of the lenses provides a unique amount of compensation relative to others of the lenses. As noted, cylindrical lenses are optional but preferred.

The beam compensating means preferably comprises a plurality of lenses and a lens positioning device operatively coupled to the plurality of lenses, and the lens positioning device positions a selected one of the lenses in the beam at an output of the acousto-optical deflector. In this event, each of the lenses preferably causes the acousto-optical deflector to provide a unique amount of compensation relative to others of the lenses. The lenses in the plurality of lenses preferably comprise cylindrical lenses. Preferably there are two lenses, although this is not necessarily limiting and more such lenses may be provided. It also is preferred that the focal lengths of the lenses differ. The lens positioning device may comprise a housing for the plurality of lenses, wherein the housing moves the respective lenses into and out of the beam. The variable speed scanning device may include a pneumatic pressure source for moving the respective lenses into and out of the beam. The lenses may be rotated in and out using a carousel arrangement, or may be exchanged using a slide mechanism.

In a presently preferred embodiment, each of the lenses comprises a cylindrical lens having a longitudinal lens axis, the lens positioning device housing holds the lenses so that the longitudinal lens axes are substantially aligned, and the lens positioning device moves the cylindrical lenses in a direction parallel to the longitudinal lens axes. In another presently preferred embodiment, each of the lenses comprises a cylindrical lens having a longitudinal lens axis, and the lens positioning device housing moves the cylindrical lenses by rotating the respective lenses into the beam. In each of these preferred embodiments, it also is preferred that the lenses are positioned immediately adjacent to the acousto-optical deflector.

In accordance with another aspect of the invention, a method is provided for scanning a surface of a workpiece. The method comprises using an acousto-optic deflector to scan a beam on the surface of the workpiece at a first scanning speed, selecting a second scanning speed different than the first scanning speed, using the acousto-optic deflector to scan the beam on the surface of the workpiece at the second scanning speed, and compensating for changes to the beam caused by scanning at the second scanning speed relative to the first scanning speed. This typically will involve compensating for astigmatism of the beam associated with the change from the first scanning speed to the second scanning speed. The compensating preferably comprises selectively positioning a selected one of a plurality of lenses in the beam at the output of the acousto-optical deflector, wherein each of the lenses provides a unique amount of compensation relative to others of the lenses. This also preferably comprises using cylindrical lenses, and preferably at least two such lenses, each having a focal length that is unique relative to others lenses of the plurality of lenses. The compensating preferably comprises moving the respective lenses and the beam relative to one another so that one of the respective lenses is positioned within the beam. This preferably comprises moving the respective lenses, e.g., longitudinally or rotating the lenses into and out of the beam.

In accordance with another aspect of the invention, an optical collection system is provided for use in a surface inspection system for inspecting a surface of a workpiece. The surface inspection system has an incident beam projected through a back quartersphere and toward a desired spot on the surface of the workpiece so that a specular portion of the incident beam is reflected along a light channel axis in a front quartersphere. Inspection systems that comprise the optical collection system according to this aspect of the invention comprise an additional aspect of the invention. The incident beam and the light channel axis form an incident plane. The optical collection system according to this aspect of the invention comprises at least one wing collector positioned to collect a scattered portion of the incident beam. The wing collector or wing collectors are disposed in the front quartersphere, outside the incident plane, and at a maximum of the signal to noise ratio when the incident beam is P polarized and the collector incorporates a P-polarizing polarizer. The wing collectors also may be positioned in the front quartersphere, outside the incident plane, and at a null or a local minimum, in surface roughness scatter relative to defect scatter, for example, from a defect perspective, at a maximum in the signal to noise ratio of defect scatter to surface roughness scatter when the incident beam is P polarized, or, from a surface roughness scatter perspective, when the surface roughness is at a relative minimum in a bi-directional reflectance distribution function.

In presently preferred embodiments according to this aspect of the invention, the signal comprises a P-polarization component, and the wing collector is disposed at least one of the maximum of the signal to noise ratio of the P-polarization component, the null of the P-polarization component of the bi-directional distribution function, and/or the minimum, or a local minimum, of the P-polarization component of that function, when the incident beam is P polarized. This may and preferably is accomplished using a polarization analyzer orthogonal to the polarization of the surface roughness scatter.

It is preferred that two such wing collectors be used, although this is not necessarily limiting. Where two or more wing collectors are used, it is preferred but not required that they be substantially identical. It also is optional but preferred that they be located symmetrically with respect to the incident plane, and/or equidistant from the desired spot and/or from the surface. In presently preferred embodiments, a first wing collector has an azimuth angle with respect to the light channel axis of about 5 to 90 degrees, and a second wing collector has an azimuth angle with respect to the light channel axis of about −5 to −90 degrees. In these embodiments, the first wing collector has an elevation angle with respect to the surface of the workpiece of about 30 to 90 degrees, and the second wing collector also has an elevation angle of about 30 to −90 degrees. It is more preferred that the first wing collector has an elevation angle with respect to the surface of the workpiece of about 45 degrees, and the second wing collector also has an elevation angle of about 45 degrees. In the presently preferred embodiments according to this aspect of the invention, each of the first and second wing collectors has a collection angle of up to about 40°, and more preferably the collection angle is about 26°. In the presently preferred embodiments, the optical collection further comprises a polarizing beamsplitter disposed in an optical path of the incident beam between the desired spot and at least one of the wing collectors. In these embodiments, the system further comprises a light channel collector positioned in the incident plane to receive the specular portion of the incident beam, and a central collector. These collectors may be positioned and configured, for example, as is described in the '701 patent. The system also preferably comprises at least one back collector, as will be described more fully herein below.

In accordance with another aspect of the invention, a method is provided for inspecting a surface of a workpiece. The method comprises scanning an incident beam on the surface of the workpiece so that a specular portion of the incident beam is reflected along a light channel axis in a front quartersphere, the incident beam and the light channel axis defining an incident plane. The method also comprises collecting a portion of the scattered light beam at a wing collector disposed in the front quartersphere, outside the incident plane, and at least one of a maximum of the signal to noise ratio, and/or null or a minimum in surface roughness scatter relative to defect scatter, for example, from a defect perspective, at a maximum in the signal to noise ratio of defect scatter to surface roughness scatter when the incident beam is P polarized, or, from a surface roughness scatter perspective, when the surface roughness is at a relative minimum in a bidirectional reflectance distribution function when the incident beam is P polarized. The method further comprises detecting the collected portions of the incident beam that are reflected from surface of the workpiece and generating signals in response, and processing the signals to obtain information about the surface. The beam scanning preferably comprises directing the incident beam through a back quartersphere and toward the desired spot on the surface of the workpiece at an oblique angle with respect to the surface.

In accordance with still another aspect of the invention, an optical collection system is provided for use in a surface inspection system for inspecting a surface of a workpiece. The surface inspection system has an incident beam projected through a back quartersphere and toward a spot on the surface of the workpiece so that a specular portion of the incident beam is reflected along a light channel axis in a front quartersphere. As noted herein above, the incident beam and the light channel axis form an incident plane. The optical collection system according to this aspect of the invention comprises a plurality of back collectors positioned in the back quartersphere for collecting scattered portions of the incident beam. In presently preferred embodiments according to this aspect of the invention, the plurality of back collectors consists of two back collectors. Preferably the collectors in the plurality of back collectors are positioned outside the incident plane. It also is optional but preferred that the plurality of back collectors are substantially identical. It also is optional but preferred that the two back collectors are located symmetrically with respect to the incident plane, and preferably equidistant from the incident plane and/or from the surface of the workpiece. In presently preferred embodiments, the two back collectors are positioned at an azimuth angle of up to about 90° with respect to the incident beam, more preferably at an azimuth angle of about 10 to about 90° with respect to the incident beam, and even more preferably at an azimuth angle of at least about 45° to 55° with respect to the incident beam. In the preferred embodiment described more fully herein below, two back collectors are positioned at an azimuth angle of about 55° with respect to the incident beam. The back collectors preferably have an elevation angle with respect to the desired spot on the surface of the workpiece of about 55°. In presently preferred embodiments, each of the back collectors has a collection angle of about 20 to about 60, and more preferably they have a collection angle of about 30.

In presently preferred embodiments according to this aspect of the invention, the system optionally comprises a polarizing beam splitter disposed in an optical path of the beam between the desired spot and each of the back collectors. Such embodiments also optionally but preferably comprise a light channel collector positioned in the incident plane to receive the specular portion of the incident beam, and a central collector.

Optical collection systems according to this aspect of the invention may be provided individually, or as part of a surface inspection system.

In accordance with yet another aspect of the invention, a method is provided for inspecting a surface of a workpiece. The method comprises scanning an incident beam on the surface of the workpiece so that a specular portion of the incident beam is reflected along a light channel axis in a front quartersphere, wherein the incident beam and the light channel axis define an incident plane. The method further comprises collecting scattered portions of the incident beam at a plurality of back collectors disposed in the back quartersphere, detecting the collected portions of the scatter and generating signals in response, and processing the signals to obtain information about the surface.

In presently preferred implementations of this method, one or more back collectors as described above, and as more fully described herein below, are used to collect scattered light from the surface of the workpiece. It is optional but preferred that the beam scanning comprises directing the incident beam through a back quartersphere and toward the desired spot on the surface of the workpiece at an oblique angle with respect to the vector normal to the surface.

In accordance with still another aspect of the invention, a surface inspection system is provided for inspecting a surface of a workpiece. The surface inspection system according to this aspect of the invention comprises an illumination subsystem that projects a beam to the surface of the workpiece. The beam comprises a collimated portion and a non-collimated portion. The illumination subsystem comprises an absorber for absorbing the non-collimated portion of the beam. The system also comprises a collection subsystem for collecting scattered portions of the beam scattered by the surface of the workpiece, and a processing subsystem operatively coupled to the collection subsystem for processing signals received from the collection subsystem to provide information about the surface of the workpiece.

The illumination subsystem preferably comprises an acousto-optic deflector or the like having an output, and the absorber preferably is positioned at the output of the acousto-optic deflector or its equivalent or substitute. The absorber preferably comprises baffling.

In accordance with another aspect of the invention, a surface inspection system is provided for inspecting a surface of a workpiece. The surface inspection system comprises an illumination subsystem that projects an incident beam to the surface of the workpiece, wherein the incident beam after interacting with the surface comprises a reflected (light channel) portion and a scattered (dark channel) portion. The system comprises a light channel that receives the reflected portion of the incident beam. The light channel comprises a beam receiving input and an attenuator at the beam receiving input. The system further comprises a collection subsystem that collects the scattered portion of the incident beam and generates signals in response, and a processing subsystem operatively coupled to the collection subsystem that processes the signals received from the collection subsystem to provide information about the surface of the workpiece. In related aspects of the invention, noise attenuating features may be provided, for example, by including baffling or the like at or in the optical path about objective lenses in the system, adding glare stops, and the like.

In accordance with another aspect of the invention, a surface inspection system is provided for inspecting a surface of a workpiece. The surface inspection system comprises an illumination subsystem that projects a beam to the surface of the workpiece. The illumination subsystem comprises a plurality of lenses, wherein each of the lenses has a surface roughness of that does not exceed a desired maximum roughness (such as about 5 Angstroms). The system further comprises a collection subsystem for collecting scattered portions of the beam scattered from the surface of the workpiece, and a processing subsystem operatively coupled to the collection subsystem for processing signals received from the collection subsystem to provide information about the surface of the workpiece. In addition or alternatively, the collection subsystem comprises a plurality of collection lenses, each of the collection lenses having a surface roughness of that does not exceed a desired maximum roughness (such as about 5 Angstroms).

Other aspects of the invention also are included herein and are further described herein below. These include, for example, a polarizing beamsplitter/analyzer, a virtual mask, and a switchable edge exclusion mask. In addition, processing subsystems and related methods are provided for processing signals obtained from a surface inspection system, and for obtaining useful information from the collected light.

BRIEF DESCRIPTION OF THE DRAWINGS

The accompanying drawings, which are incorporated into and constitute a part of the specification, present illustrative but not presently preferred embodiments and methods of the invention and, together with the general description given above and the detailed description of the embodiments and methods given below, serve to explain the principles of the invention.

Other advantages will appear as the description proceeds when taken in connection with the accompanying drawings, in which:

FIG. 75 is a block diagram of a method for determining an extent of a contribution of surface roughness frequencies on the scattering surface;

FIGS. 96 and 97 are diagrams shown an example of subdividing selected surface structure spatial frequency ranges in haze maps;

FIG. 98 is a block diagram showing a multiple spatial frequency haze analysis method of the present invention;

FIG. 99 is a block diagram showing one embodiment of a method for analyzing scatter by its associated surface structure spatial frequency range;

DETAILED DESCRIPTION OF THE PREFERRED EMBODIMENTS AND METHODS

Figure 1:
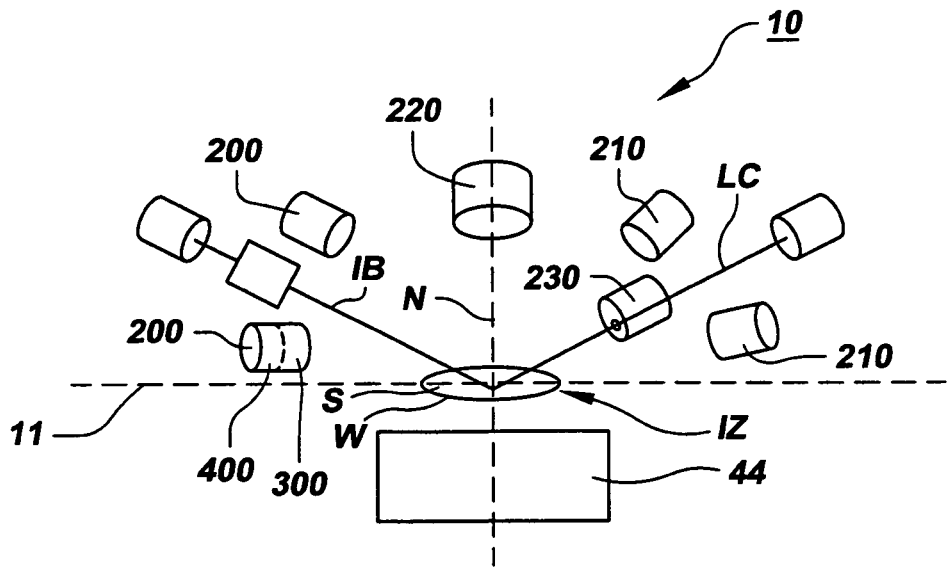
FIG. 1 is a perspective view of components of a surface inspection system according to a presently preferred embodiment of one aspect of the invention.

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

Surface Inspection System

A surface inspection system 10 and related components, modules and subassemblies in accordance with various aspects of the invention will now be described. Surface inspection system 10 is designed to inspect a surface S or surfaces of a workpiece W, such as a silicon wafer. More specifically, these illustrative embodiments are adapted for inspection of unpatterned silicon wafers, with or without surface films. Systems according to the invention also would be suitable for inspecting other types of surfaces as well. They are particularly well suited for inspecting optically smooth surfaces that at least partially absorb and scatter the incident beam energy. Examples would include glass and polished metallic surfaces. Wafer W may comprise known wafer designs, such as known 200 millimeter (mm) wafers, 300 mm wafers, and the like.

Figure 2:
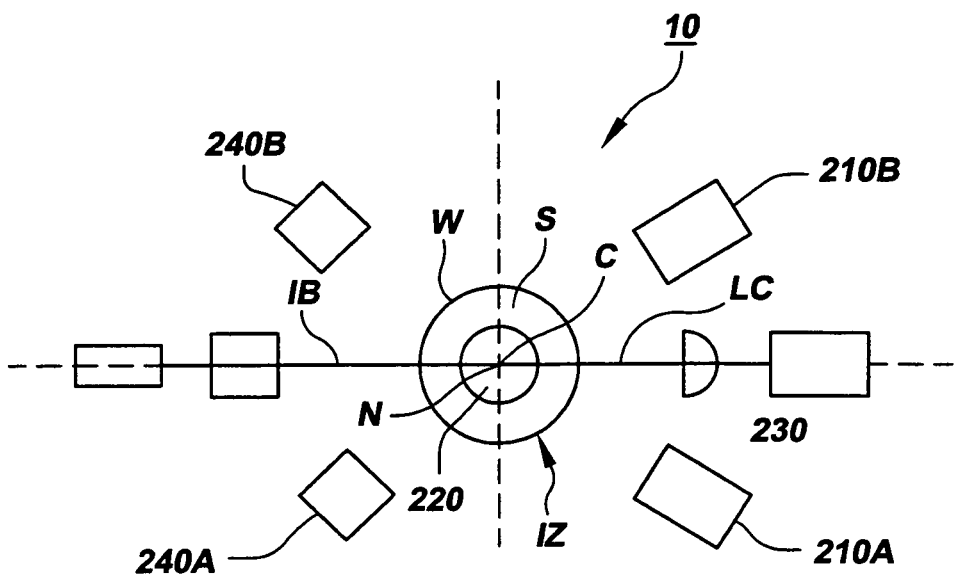
FIG. 2 is a top or plan view of the components shown in FIG. 1.
Figure 3:
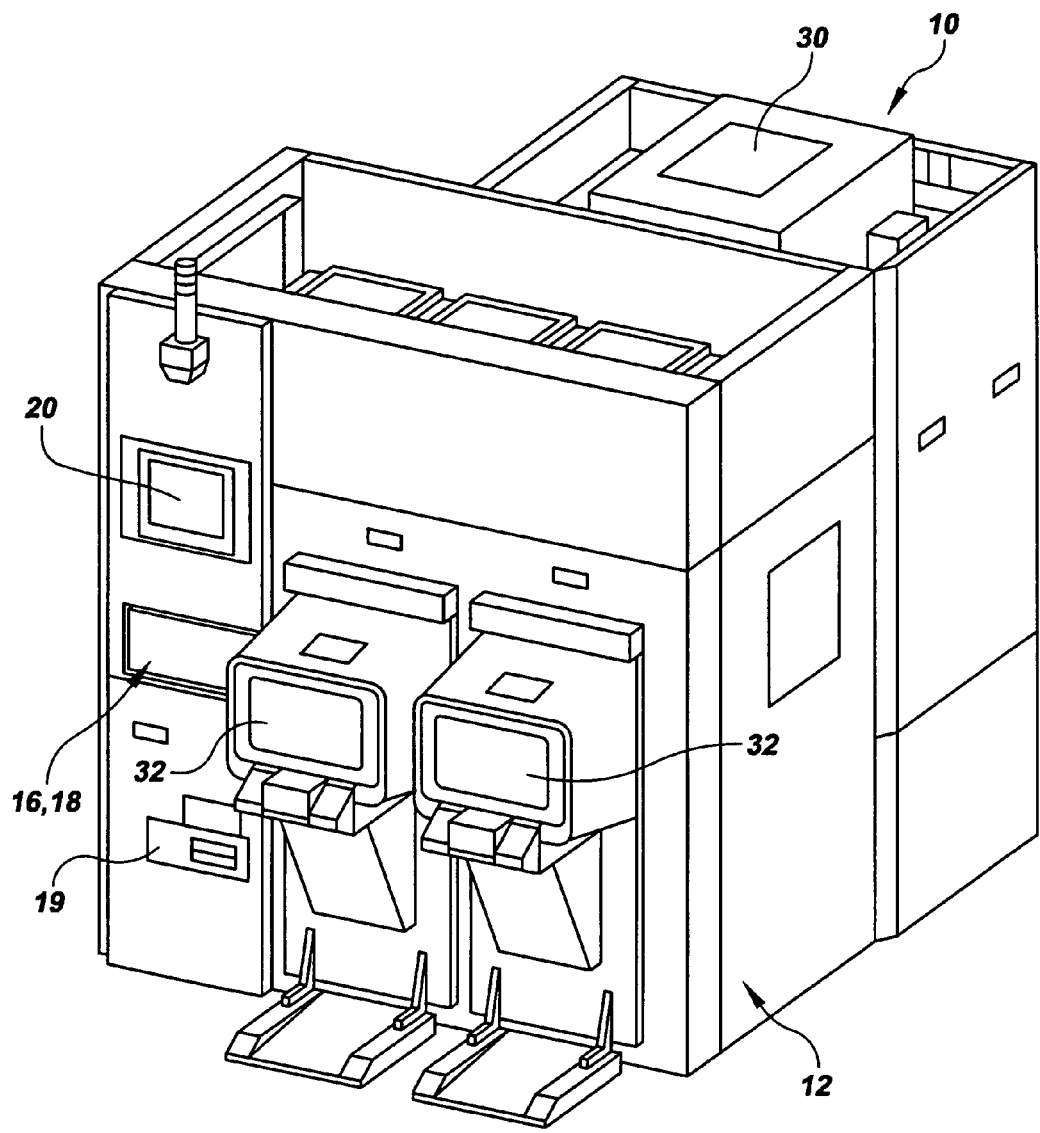
FIG. 3 is a front perspective view of the system, the components of which are shown in FIG. 1, with the system contained in its cabinet.
Figure 4:
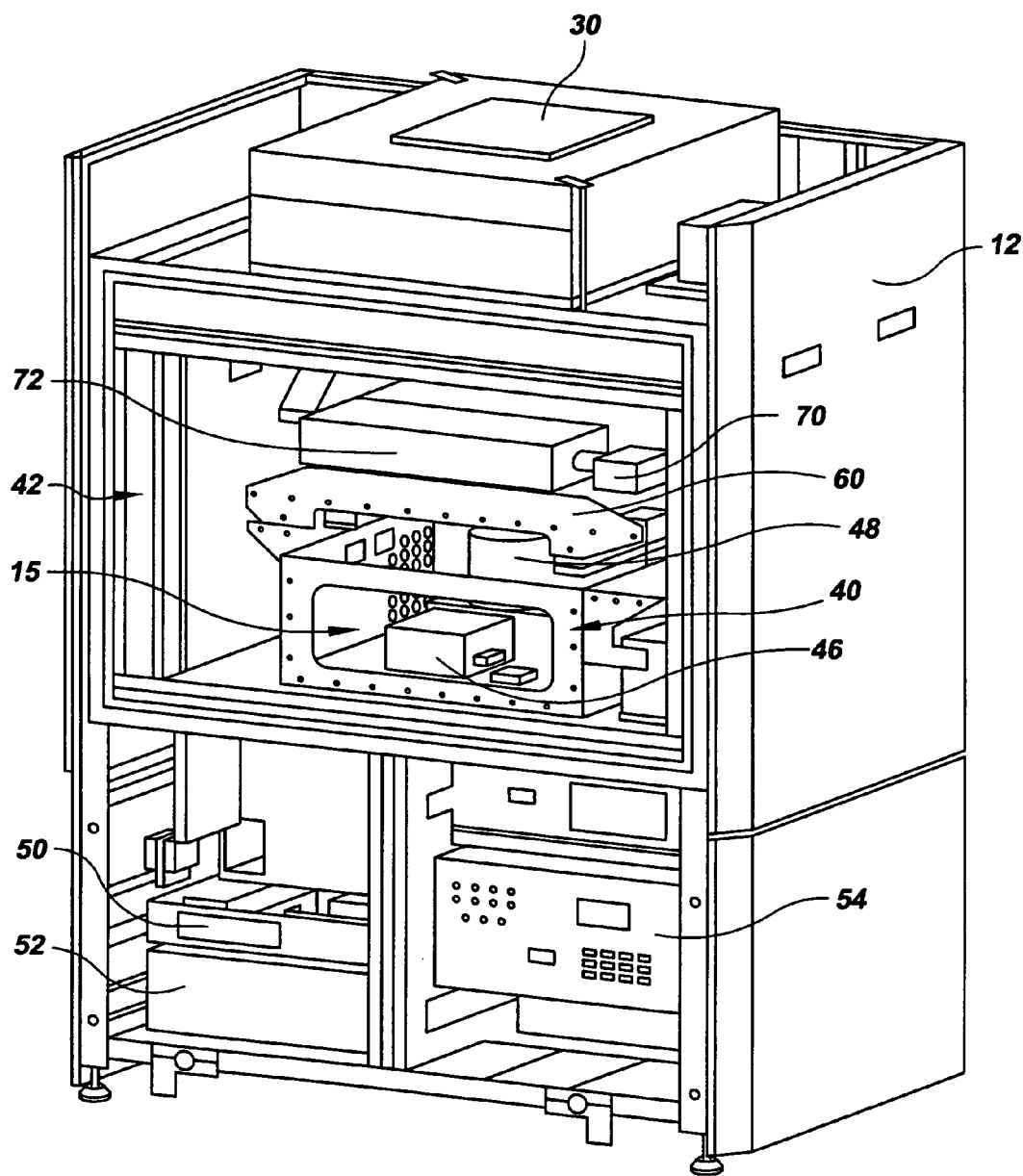
FIG. 4 shows a back view of the system shown in FIG. 3.

System 10 is shown from various perspectives in FIGS. 1-4. FIG. 1 shows a side perspective view block diagram of principal components of the system. FIG. 2 shows the same type of block diagram, but from a top or plan view. FIG. 3 provides a front perspective view of system 10 contained in its cabinet. FIG. 4 shows a back view of system 10 in its cabinet.

System 10 is contained within a cabinet 12. It includes an operator interface 14 comprising a keyboard or similar input device 16, a mouse or similar pointing device 18, and a display device 20 such as a video monitor. Other peripherals may be provided, such as a printer, network connection, and the like. An air filtration device 30, such as a HEPA air filter, is provided for removing dust particles and purifying the air to desired specificity. An external wafer handling system 32, also known as robotic wafer handling subsystem 32 and external workpiece handling system 32, provides workpieces.

With reference to FIG. 4, within cabinet 12 system 10 includes a vibration isolation module 40 within a housing 42. It is within this housing area that the workpieces W, shown in FIGS. 1 and 2, are iteratively inspected, as described more fully herein below.

System 10 includes a workpiece movement subsystem for movement of the wafer relative to the incident scanned beam. The manner of moving the workpiece may vary, depending upon the application, the overall system design, and other factors. A number of scan patterns, for example, may be implemented, as is described more fully below. Indeed, in some applications it may be desirable to move the beam or scanning subsystem instead of the wafer, i.e., while maintaining the wafer in a stationary location. As implemented in system 10, an internal workpiece handling subsystem 44, also known as robotic wafer handling subsystem 44 and a motorized γ-θ stage 44, is provided which comprises a scanner gauge, not shown, and robot, not shown, are housed in cabinet 12. This subsystem is configured to work in cooperation with external workpiece handling system 32 to receive the workpieces to be inspected. Internal workpiece handling subsystem 44 comprises a motorized linear stage 46 and a rotary stage 48. It therefore is capable or both rotating and translating the workpiece (γ-θ), for example, to provide a number of scan patterns. This permits the wafer to be scanning in a variety of generally curved paths that provide full and efficient coverage of the entire wafer surface. It enables such scan patterns as concentric cylinder scans, spiral scans and the like. In the preferred embodiments and methods, a "hybrid scan" pattern is used in which the beam travels in a generally helical or Archimedes spiral scan, but in which the beam is oscillated in a series of short scans as the spiral is traced out. This pattern is disclosed in U.S. Pat. No. 5,712,701, U.S. Pat. No. 6,118, 525, and U.S. Pat. No. 6,292,259, each of which is assigned to ADE Optical Systems Corporation. Subsystem 44 receives the workpiece and is used to perform appropriate calibration, as well as moving the workpiece according to one or more desired scan paths.

System 10 also includes appropriate support subsystems, such as a power supply 50. A processor 52 and data acquisition subsystem 54 also are contained within cabinet 12, as will be described more fully herein below.

With reference to FIGS. 1 and 2, the workpiece W, which in this illustrative example is a semiconductor wafer, resides in an inspection zone IZ within housing 42 during inspection, as will be described more fully herein below. Motorized γ-θ stage 44 is disposed so that the workpiece under inspection is positioned within this inspection zone IZ. The workpiece W is placed on this stage for inspection and remains there during the inspection.

Spatial Reference Frame Information and Nomenclature

Figure 5:
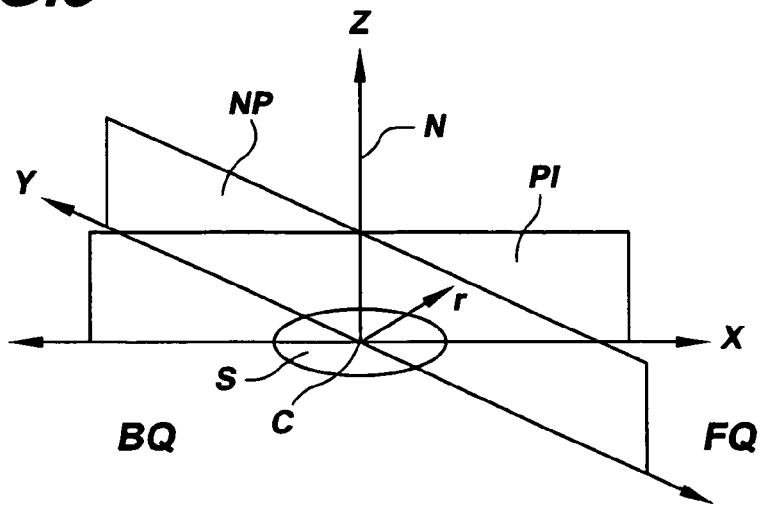
FIGS. 5-7 are diagrams illustrating reference geometry to aid in the description of the system shown in FIG. 1.
Figure 6:
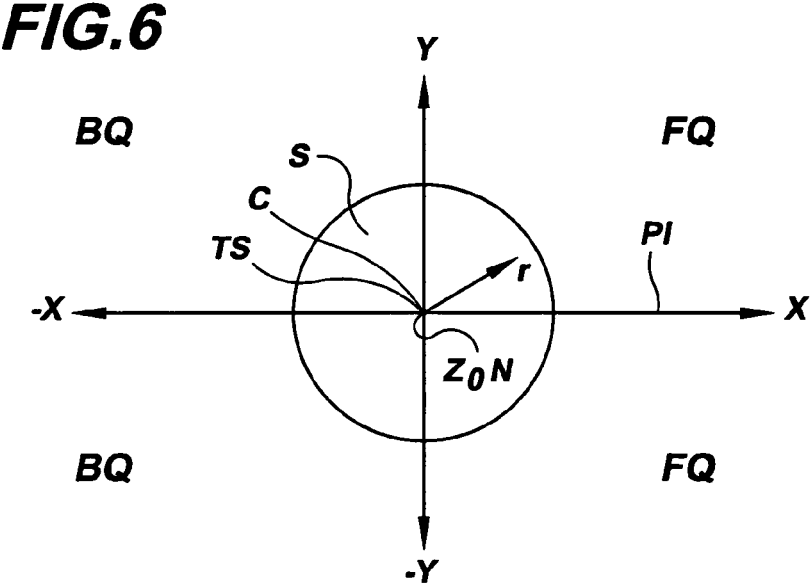
Figure 7:
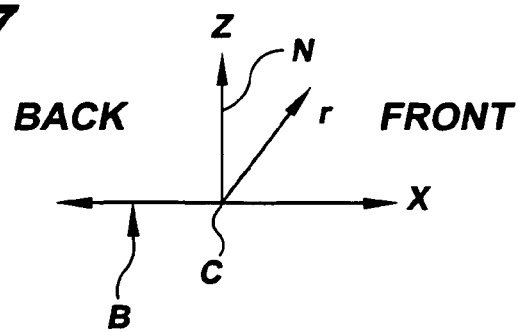

To better illustrate the principles of the invention as manifested in the presently preferred embodiments and methods, some spatial reference frame information and nomenclature is useful. These geometric relationships are illustrated in FIGS. 5-7 with reference to FIG. 1. The plane defined by the inspection stage, and which generally will be substantially coplanar with the surface of the workpiece, is referred to herein as the "inspection stage plane" or the "base plane" B. The "incident beam vector" IB is the vector or ray along which the incident beam propagates between the beam scanning subsystem and the surface of the workpiece. The center C of the inspection stage B is referred to herein as the "stage center of rotation." In the presently preferred embodiments and methods as disclosed herein, a "target spot" TS corresponds to the center of scan position of the output scanner beam. All collectors point to or are configured to receive light emanating from this target spot TS. (The stage center of rotation C is located at the target spot TS when the center of the wafer is being scanned. During the spiral scan of the wafer, the spiral scan being described in more detail below, the target spot TS will move further away from the stage center of rotation C.) After the incident beam is reflected from the workpiece surface, it propagates along a light channel axis LC. The incident beam vector IB and the light channel axis LC define a plane of incidence PI. A normal plane NP is perpendicular to the base plane B and the plane of incidence PI. A vector normal N, corresponding to the z-axis, which is perpendicular to the base plane B and which is in the plane of incidence PI, goes through the target spot TS. In addition, the center collector axis is on the vector normal N, as will be described more fully herein below.

One may construct a hemisphere above the base plane, having a center at the target spot TS and having a radius approximately equal to the distance from the stage center of rotation C to the beam scanning subsystem output, or the collectors as described herein below. This hemisphere may be bisected into a back quartersphere BQ and a front quartersphere FQ. The back quartersphere BQ lies between the base plane B and the normal plane NP and contains the incident beam along the incident beam vector IB. The front quartersphere FQ lies between the base plane B and the normal plane NP, and contains the light channel axis LC.

Wafers are inserted into inspection zone IZ for inspection and retrieved from inspection zone IZ after inspection using the wafer handling subsystems 32 and 44. In semiconductor inspection applications and others as well, the handling of the wafers within the housing preferably is done automatically, without contact by human hands, to avoid damaging or impairing the surface, e.g., with smudges, scratches, etc. Wafer handling subsystems 32 and 44 provide a plurality of wafers to be inspected. This may be done sequentially or, for system configurations designed to inspect multiple wafers simultaneously, it may provide multiple wafers in parallel. Robotic wafer handling subsystem 44 places the wafer or wafers on an inspection stage or table 9 within the inspection zone IZ of housing 42. The robotic wafer handling subsystems 32 and 44 may comprise commercially available versions known in the industry. In the presently preferred embodiments, the robotic wafer handling subsystem 44 comprises a FX3000/2 robotic wafer handling subsystem, from Brooks Automation, Inc. (Chelmsford, Mass.). It uses one or more cassettes, with each cassette holding multiple workpieces (up to ten wafers). After placement on the inspection table 9, the wafer is automatically aligned according to alignment techniques known to those of ordinary skill in the art.

Figure 8:
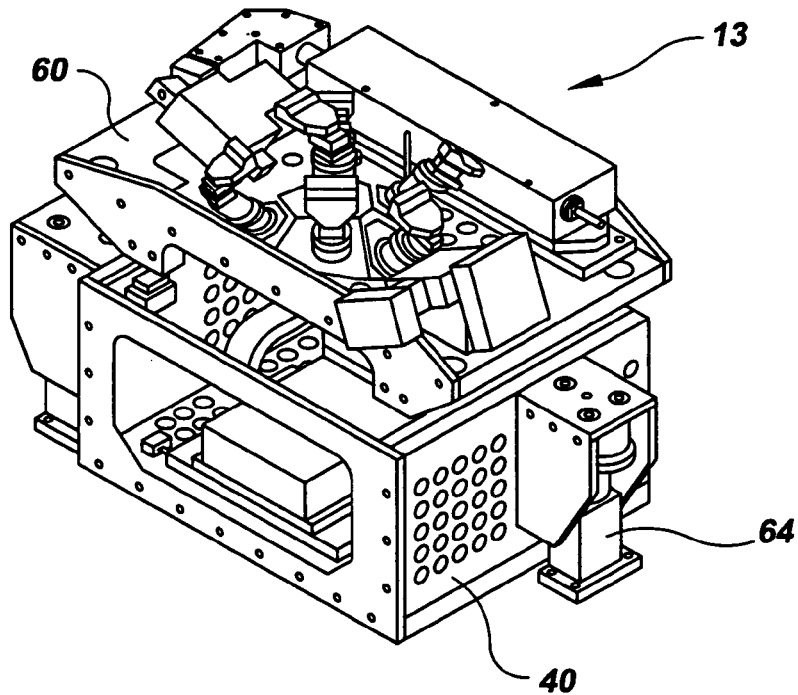
FIG. 8 is a perspective view of the base plate for the system of FIG. 1; with system components.
Figure 9:
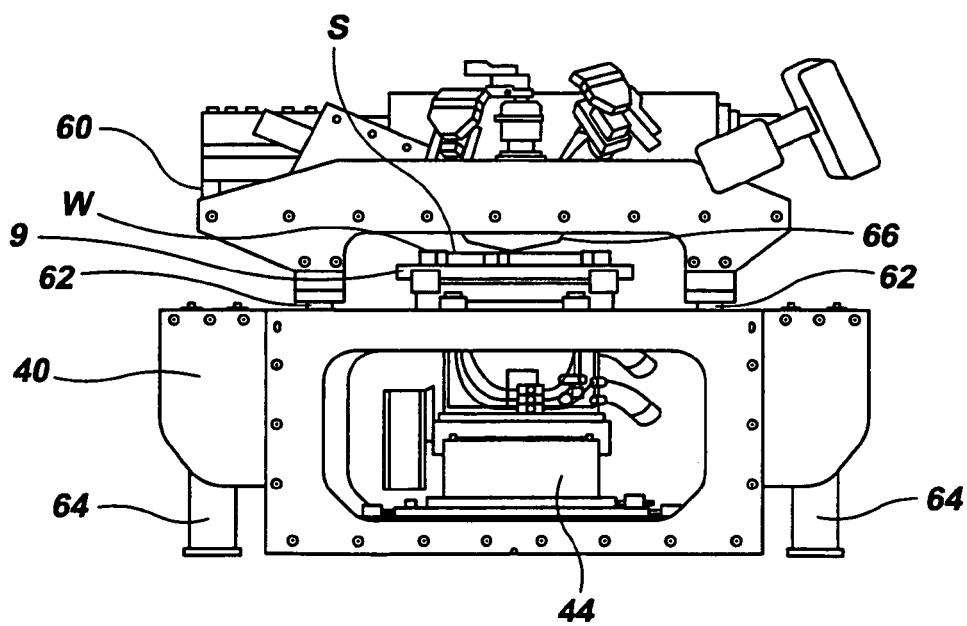
FIG. 9 is a side view of the base plate of FIG. 8.
Figure 10:
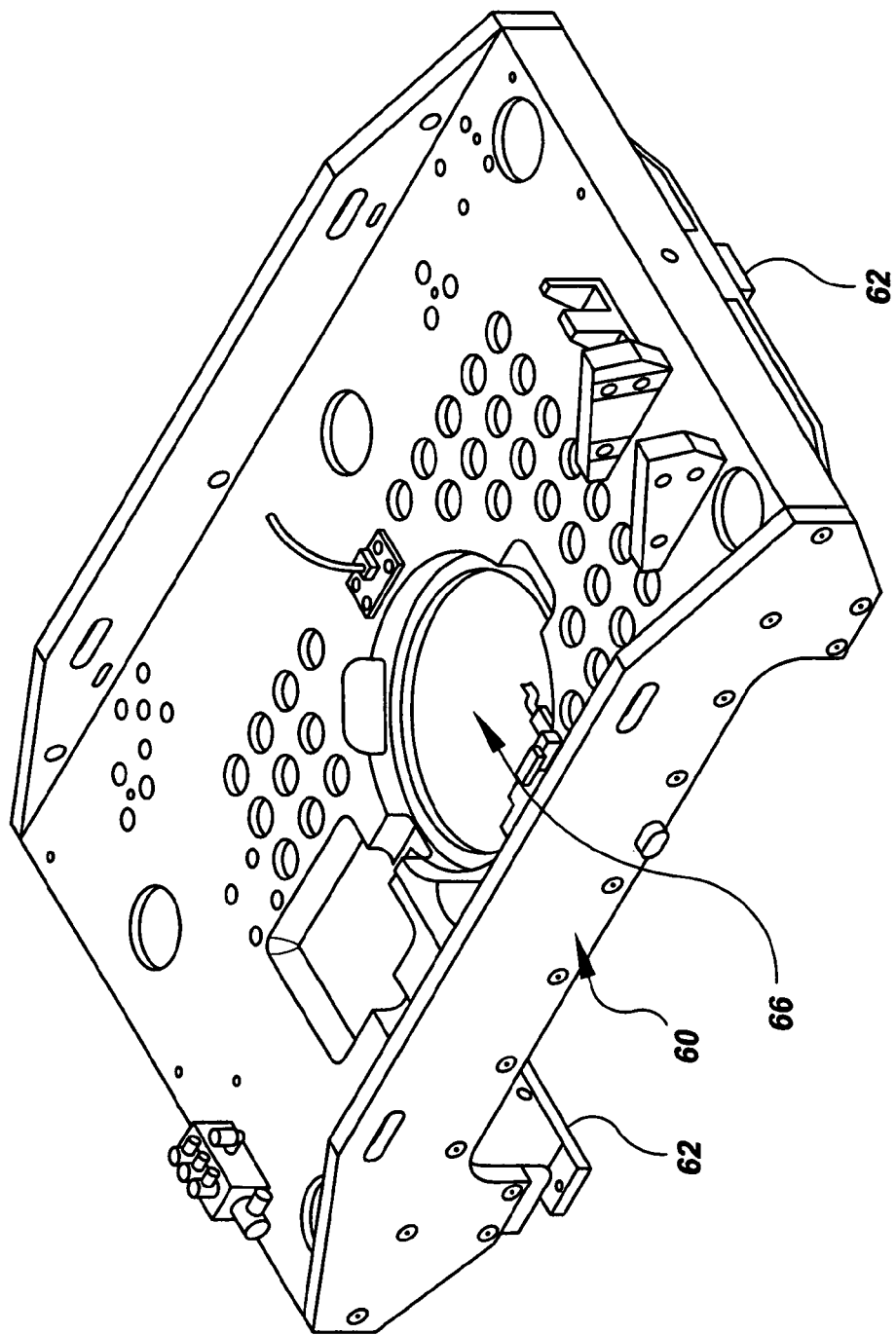
FIG. 10 provides a perspective view of the base plate of FIGS. 8 and 9, without system components.
Figure 21:
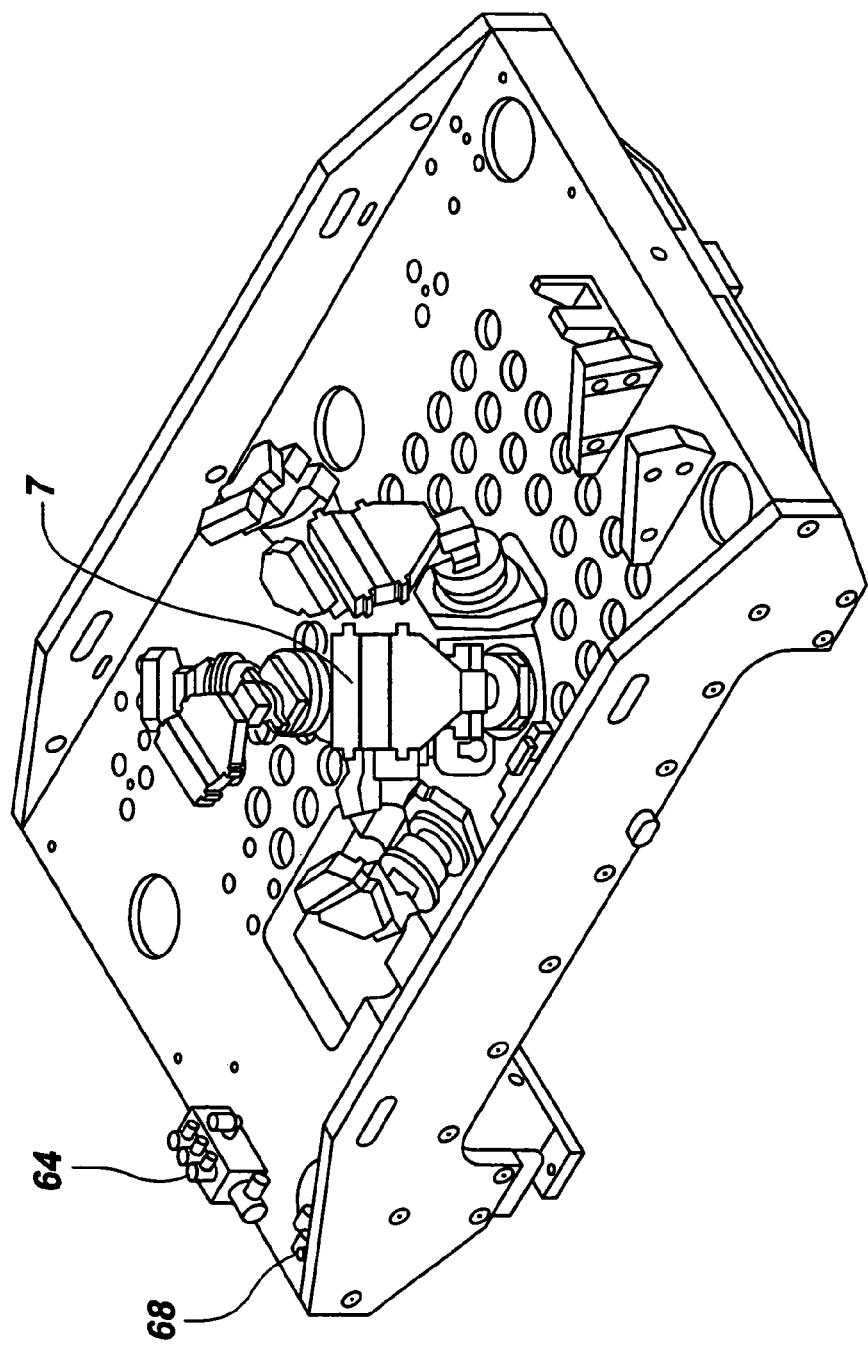
FIG. 21 is a perspective view of the base for the system of FIG. 1, with the collection and detection subsystem module attached.

System 10 comprises a base 11 that serves as a physical or mechanical support for other components of the system. As implemented in system 10, the base 11 comprises an optics base plate 60 fixedly mounted within inspection zone IZ of housing 42. FIG. 10 provides a perspective view of base plate 60. FIGS. 8 and 9 illustrate its positioning and arrangement in system 10. FIG. 21 is a perspective view of the base for the system of FIG. 1, with the collection and detection subsystem module attached. Base plate 60 in this embodiment is fabricated of black anodized aluminum. Its surface is coated with a light absorbing coating or treatment to eliminate or greatly reduce its optical reflectivity. Base plate 60 includes three kinematic interface points 62 for mounting to the vibration isolation module, or VIM 40. The VIM 40, which holds the motorized γ-θ stage 44, rests on isolation mounts 64 to prevent vibration from disturbing the light channel signal. Base plate 60 also has vacuum lines 64 to remove particles that may be produced by the motorized assemblies located throughout the base plate 60, and pressurized air line port to connect the pneumatic ports 162 for supplying air pressure to drive the drive shafts 154 of the the AOD variable speed assembly 104, described below.

The workpiece W provided for inspection is held in position approximately 1 inch below base plate 60. Base plate 60 includes an aperture 66 approximately in its center and arranged to provide a viewpoint through which the workpiece is viewable. Thus, the workpiece W resides below aperture 66 during the inspection operations.

Modular Surface Inspection System

Figure 74:
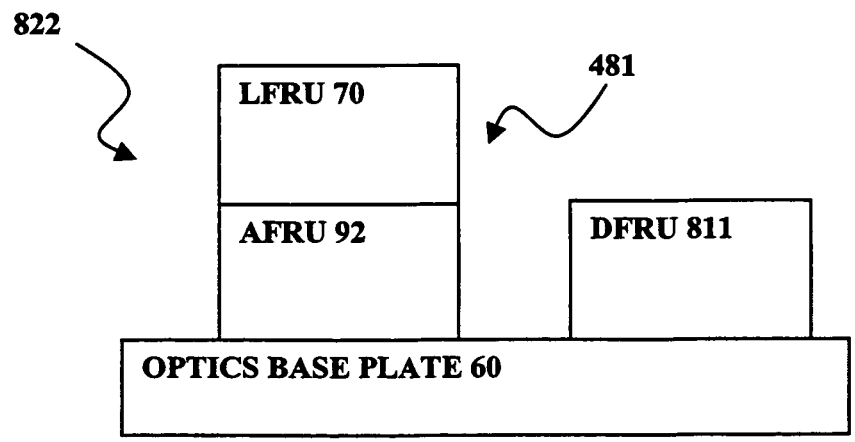

It has been noted herein above that, in accordance with an aspect of the invention, a modular surface inspection system is provided. Preferred systems according to this aspect of the invention comprise an illumination subsystem 13 having a beam source subsystem 6 for projecting a beam and a beam scanning subsystem 8 for receiving the incident beam from the beam source subsystem and scanning the incident beam on the surface of the workpiece, a workpiece movement subsystem 15 that moves the surface of the workpiece relative to the incident beam, an optical collection and detection subsystem 7 that collects the reflected beam and photons scattered from the surface of the workpiece and generates signals in response thereto, and a processing subsystem 19 operatively coupled to the collection and detection subsystem 7 for processing the signals. Any one or combination of these components may be modular, each may comprise a field replaceable unit 811. A block diagram illustrating the use of field replaceable units 811 is shown in FIG. 74. For example, the beam source subsystem 6 preferably comprises a field replaceable beam source module 70 (also known as laser field replaceable unit 70 or LFRU 70). Further, the beam scanning subsystem 8 preferably comprises a field replaceable beam scanning module 92 (also known as AOD field replaceable unit 92 or AFRU 92). In addition, the collection and detection subsystem 7 preferably comprises a field replaceable collection and detection assembly 200 (also known as a collector-detector field replaceable unit or "DFRU" 200). This modular design enables each such component to be assembled during original manufacture, or to be maintained or repaired, efficiently and cost effectively. This is particularly necessary in applications, such as semiconductor-related inspection applications, wherein it is important to minimize system downtime and to maintain critical optical component alignments in a clean or otherwise controlled environment. Semiconductor wafer inspection systems, for example, typically must operate in clean rooms. The use of pre-aligned modular components enables the inspection systems to be serviced or repaired while being maintained in these clean or otherwise controlled environments. In addition to their system configurations, each of the modular components as disclosed herein comprises separate aspects of the invention.

Beam Source Subsystem

The beam source subsystem 6 projects the beam used to illuminate the surface of the workpiece. The light propagating from the surface, both specular and scattered, is then used to characterize or otherwise provide useful information about the workpiece surface. The beam source subsystem 6 in this preferred embodiment is modular, and comprises a field replaceable beam source module 70, also known as laser field replaceable unit 70 or LFRU 70. Beam source module 70 is shown in exploded view in FIG. 11, and in assembled state with respect to the base plate 60 in FIG. 12.

Beam source module 70 comprises a beam source that projects an incident beam toward the surface S of the workpiece. Beam source module 70 has a beam source that preferably comprises a laser 72 that projects a beam having the desired quality and optical properties for the application at hand. The specific characteristics of the laser and the beam it projects may vary from application to application, and are based on a number of factors. In applications involving inspection of semiconductor wafers, suitable lasers comprise Argon lasers having a wavelength of about 488 nm, semiconductor laser diodes, at several wavelengths (e.g. GaN (405 nm), AlGaInP (635 nm-670 nm), and AlGaAs in the 780-860 nm range). Other lasers include diode-pumped laser such as frequency doubled Nd:YVO4, Nd:YAG, and Nd:YLF (532 nm) and quasi-CW diode pumped UV lasers (355 nm). The laser 72 may project a beam that is monochromatic, or which includes a plurality of frequencies, etc., depending upon the specific application, the desired surface features to be measured, etc.

As implemented in this embodiment, the beam source of beam source module 70 comprises a frequency-doubled Nd:YVO4 laser (Spectra Physics MG-532C) operating at 532 nm frequency. The beam comprises a substantially monochromatic beam having approximately a 532 nm frequency. The beam has a beam size at the laser output of 2 mm (full width at $1/e^2$ level). The beam is outputted from laser 72 with a power of about 1-2 watts.

Beam source module 70 also comprises a beam source module housing 74 that provides structural support for other components of the beam source module 70. In the presently preferred embodiment, beam source module housing 74 comprises a beam source module base plate 76 upon which laser 72 is fixedly disposed. Base plate 76 is constructed of black anodized aluminum.

Figure 13:
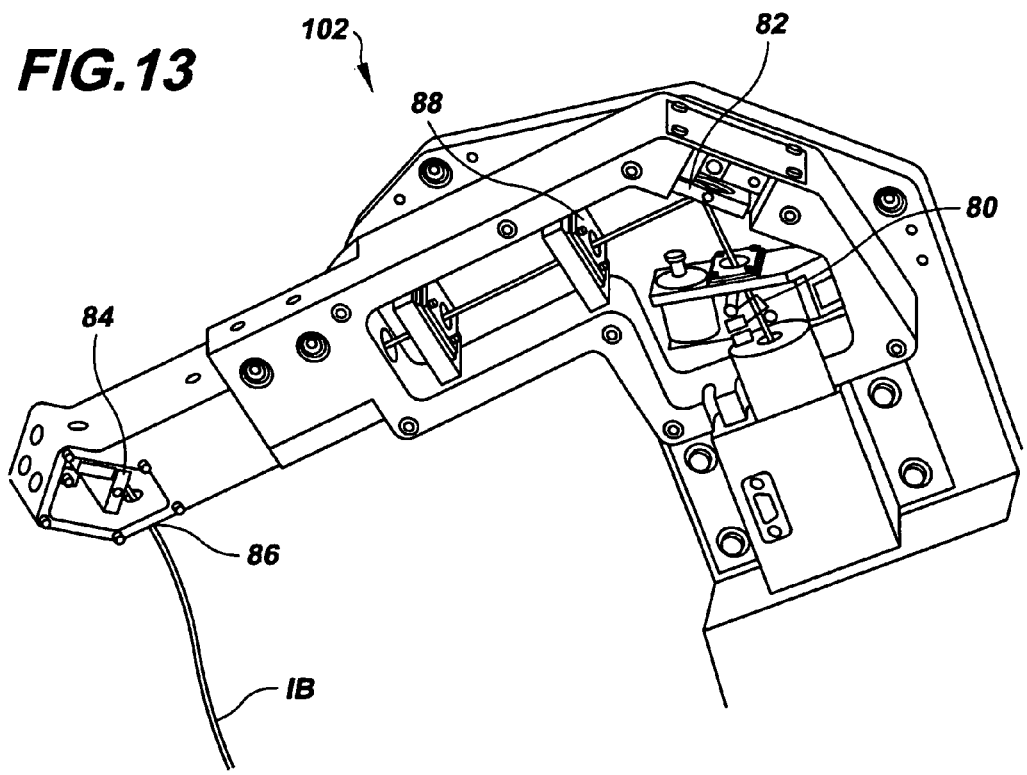
FIG. 13 is a pictoral diagram of the optics of the beam source module.

Beam source module 70 also comprises laser unit optics 78 for receiving the beam outputted by the laser 72 and directing it to an appropriate pointing angle and pointing position. With reference to FIG. 13, the output of laser 72 passes through a laser shutter 80, provided as a safety mechanism, through a pair of turn mirrors 82 and 84, also known as turning mirrors or fold mirrors, and through an output aperture 86. A set of baffles 88 is disposed in the beam path between the turning mirrors 82 and 84 for limiting light that is not contained within the main beam. The alignment of the laser output, the turning mirrors 82 and 84 and the output aperture 86 are such that the beam is projected from the output substantially at a precise pointing angle and pointing position. The pointing angle preferably is within 10 to 50 micro radians of the desired or ideal pointing angle that corresponds to placing the beam at a desired spot position and angle at the acousto-optic device 100, (also known as "acousto-optic deflector", "AO deflector" or "AOD" and described more fully herein below). The diffracted beam from the AOD 100 defines the spot position at the surface of the workpiece W.

Beam source module 70 further includes mounting means for mounting and fixing the beam source module housing 74 relative to the beam scanning module base 90, described in more detail below. This mounting means preferably fixes the position of the beam source, and more particularly the beam projected from the output, relative to the base plate 60 so that, after the beam passes through the AOD 100, the beam is projected by a pointing angle to a pointing position that is within about 10 to about 50 micro radians of the desired pointing angle into the AOD. The diffracted beam from the AOD 100 defines a target spot TS corresponding to a desired spot on the surface of the workpiece. The purpose of the "desired spot" and "desired angle" is to set and fix a point at which the laser beam is directed so that, when the system 10 is assembled and a workpiece W is under inspection, the beam is directed to the desired scanning location on the surface of the workpiece W. The "pointing position" refers to the location of the beam when it is pointed at the desired spot TS. The beam source module 70 in this modular embodiment is designed to be substantially automatically aligned when placed onto the base plate 60, so that little or no additional alignment is required after placing the beam source module housing 74 in position. The beam source module housing 74 may be mounted directly and fixedly on the beam scanning module base 90. Alternatively, the beam source module housing 74 may be fixed relative to the base 90 by other means, for example, by mounting it to another component that in turn is mounted to the base 90. In the presently preferred embodiment according to this aspect of the invention, as shown particularly in FIG. 11, the beam source module base plate 76 is mounted to a beam scanning module 92, which is a component of the beam scanning subsystem 8, which in turn is directly mounted to the base plate 60. This will be explained more fully below.

Figure 11:
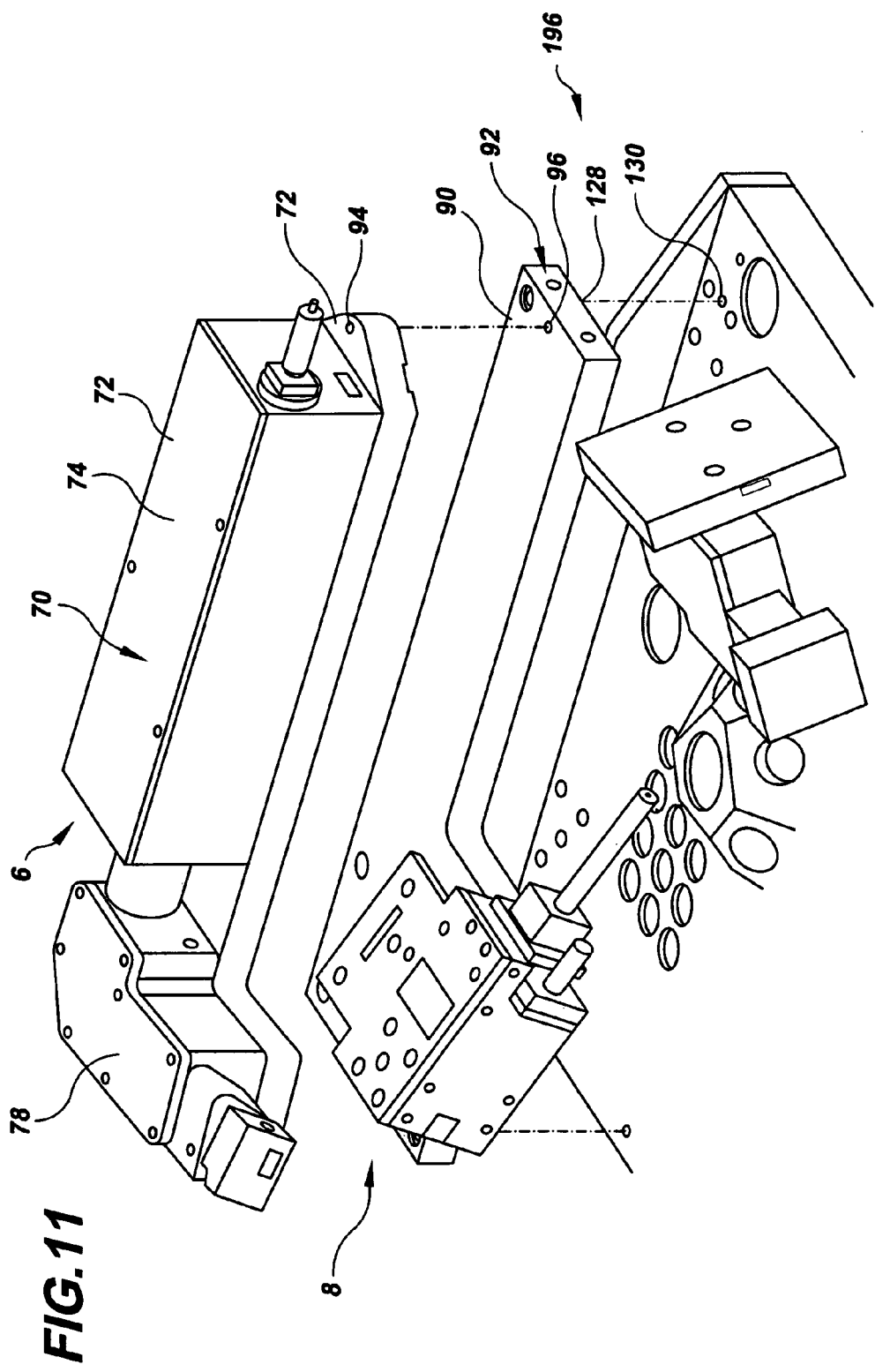
FIG. 11 is an exploded perspective view of the base plate, beam source module, beam scanning module and light channel assembly for the system of FIG. 1.
Figure 14:
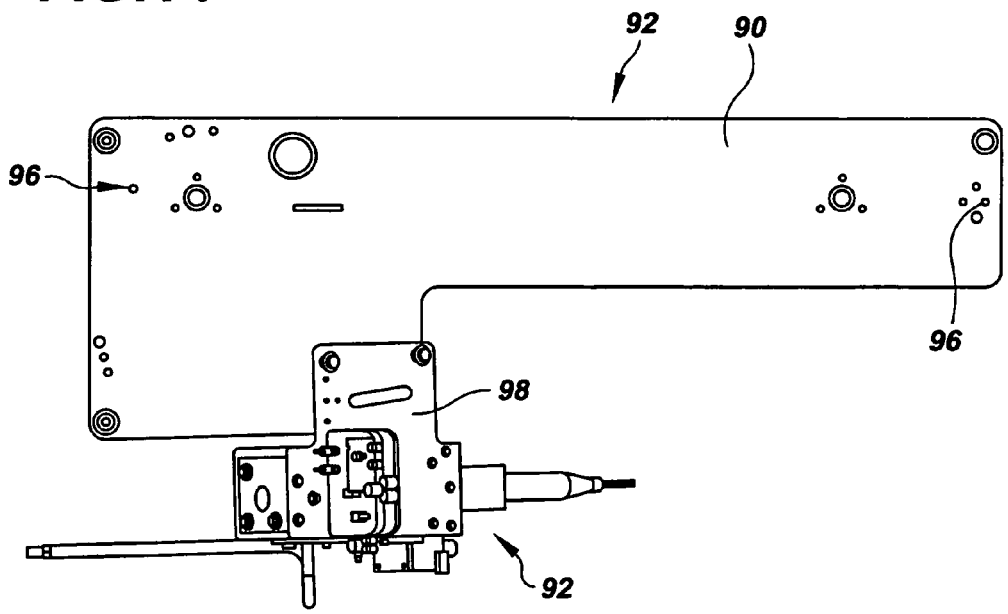
FIG. 14 is a top view of the beam scanning module of FIG. 11.

The mounting means for the beam source module housing 74 in accordance with this embodiment comprises a plurality of holes or pinholes 94 located in the housing 74, preferably in the bottom portion of laser unit base plate 76, designed, sized and configured to receive a corresponding plurality of pins or posts 96 disposed in or on another component to which the beam scanning module 92 is to be mounted, such as the beam scanning module base plate 90, so that the pins or posts fit securely into pinholes 94. Similarly, the mounting means may comprise a plurality of pins fixedly located in the beam source module housing 74, e.g., in beam source module base plate 76, and projecting outwardly from it that would mate to a corresponding plurality of holes located in the base plate 90 or other component to which the beam source module housing 74 is to be affixed. In system 10, the mounting means comprises the plurality of holes 94, as shown in FIG. 11, disposed in the bottom portion of laser unit base plate 76 and configured to mate with the corresponding plurality of pins 96, as shown in FIG. 14, located on the upper surface or portion of the beam scanning module 92, more specifically beam scanning module base plate 90. The beam source module housing 74 is detachably locked into position using socket head cap screws (SHCS) (not shown).

This modular beam source subsystem design provides the beam source subsystem in a self-contained and pre-aligned unit that is modular and field replaceable. By providing the modular mounting capability and beam pre-alignment, this design facilitates the ready installation or replacement of the unit on the system, quickly, efficiently, and without the need for substantial additional adjustments, alignments, etc. commonly required in prior known systems. A separate alignment fixture may be used to ensure that all of the laser source assemblies are co-aligned to ensure that no alignment is necessary in the field.

Beam Scanning Subsystem

System 10 also includes means for receiving the incident beam and scanning the incident beam on the surface of the workpiece. In this presently preferred embodiment, the beam scanning means comprises a beam scanning subsystem 8, which, in this preferred embodiment, is modular and, in this illustrative modular system, comprises a field-replaceable beam scanning module 92 (also known herein as AOD field replaceable unit 92 or AFRU 92).

The beam scanning module 92 receives the beam from the beam source module 70 and scans it on the surface S of the workpiece W in desired fashion. As noted herein above, a variety of different scan patterns are available, and the one used in a particular instance may vary from application to application.

Beam scanning module 92 is shown in perspective and exploded view relative to base plate 60 and beam source module 70 in FIG. 11. It is shown in its assembled stated mounted to base plate 60 in FIG. 12. A top view of beam scanning module 92, shown separately, is provided in FIG. 14.

Figure 15:
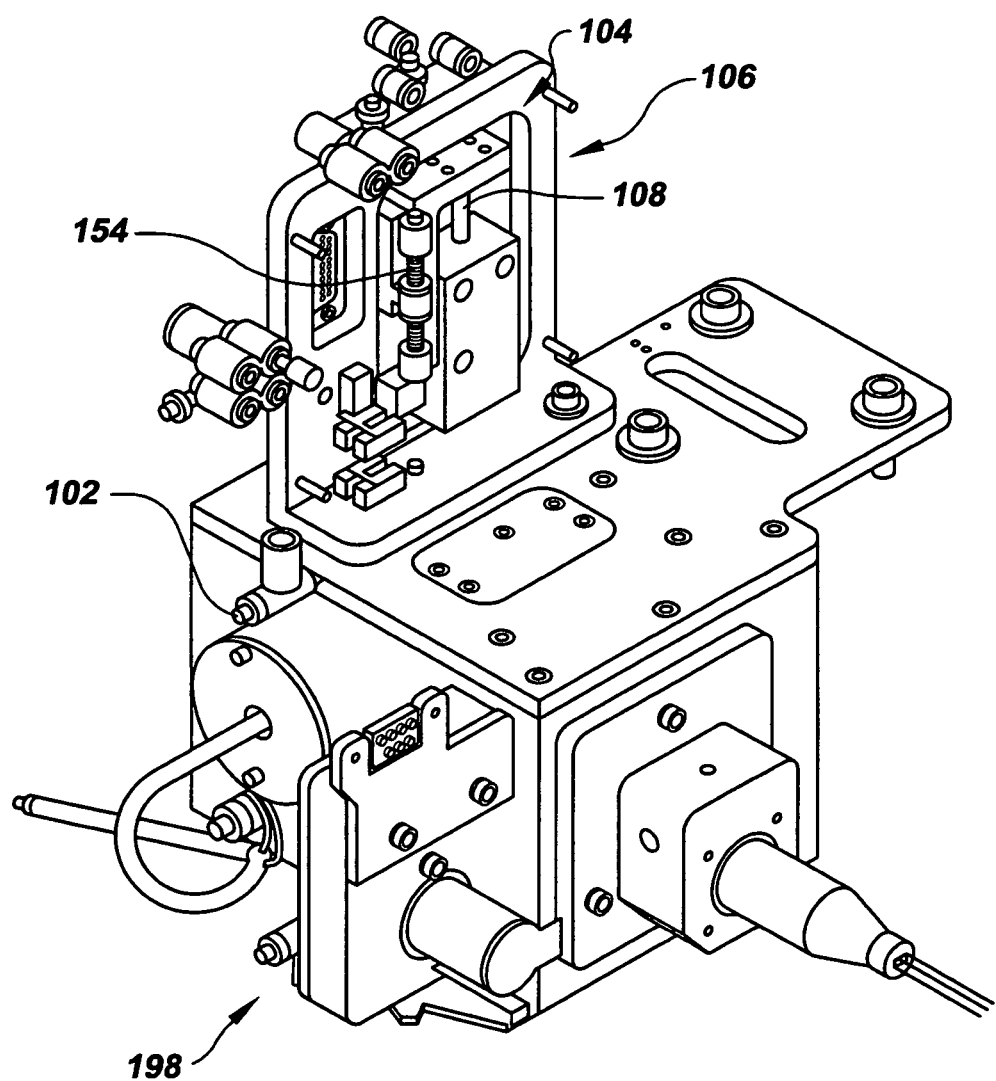
FIG. 15 is a perspective view of the AOD assembly of the beam scanning module of the system of FIG. 1.

The beam scanning subsystem 8 comprises means 198, mounted in a fixed position relative to the housing, for scanning the beam on the surface S of the workpiece W, also known as beam scanning means 198 and shown generally in FIG. 15. A number of alternative scanning means may be used to scan the beam in desired fashion. Examples include acousto-optic deflectors (AODs), rotating mirrors, and the like. In the presently preferred embodiments and method implementations, the beam scanning means 198 comprises an acousto-optic deflector (AOD) 100, shown generally in FIG. 16.

The acousto-optic deflector 100 may be any acousto-optic deflector, including but not limited to those commercially available, that is capable of or suited for the beam and beam source to be used, the desired scanning parameters (e.g., beam and spot size, scan pattern, scan line dimensions, etc.), and other design requirements and constraints. The AOD 100 according to the presently preferred embodiment and method implementations comprises the ISOMET Model OAD-948R (488 nm) or, alternatively, the ISOMET OAD-971 (532 nm), both of which are available from Isomet Corporation of Springfield, Va.

The beam scanning module 92 also comprises a beam scanning module housing 98 fixedly coupled to or integral with base plate 90 for supporting the beam scanning means 198. Housing 98, shown in FIG. 14, comprises an AOD assembly 102 that houses the AOD 100, which comprises an AOD crystal 112 and related components. AOD assembly 102 is mounted to or fixed to beam scanning module base plate 90, or with which it forms an integral part.

Variable Speed AOD

Figure 16:
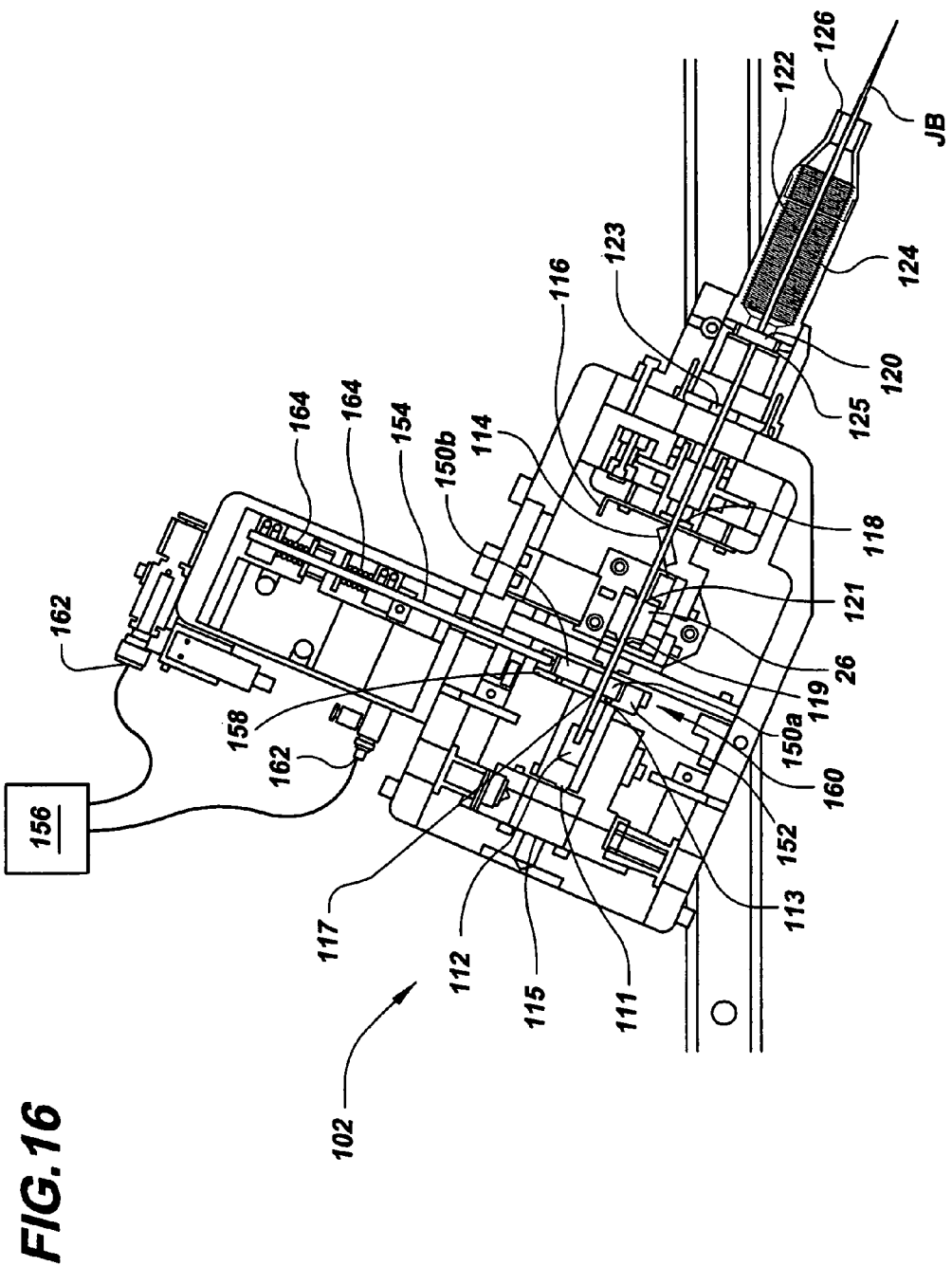
FIG. 16 is a cutaway view of a portion of the AOD assembly for the beam scanning module.
Figure 17:
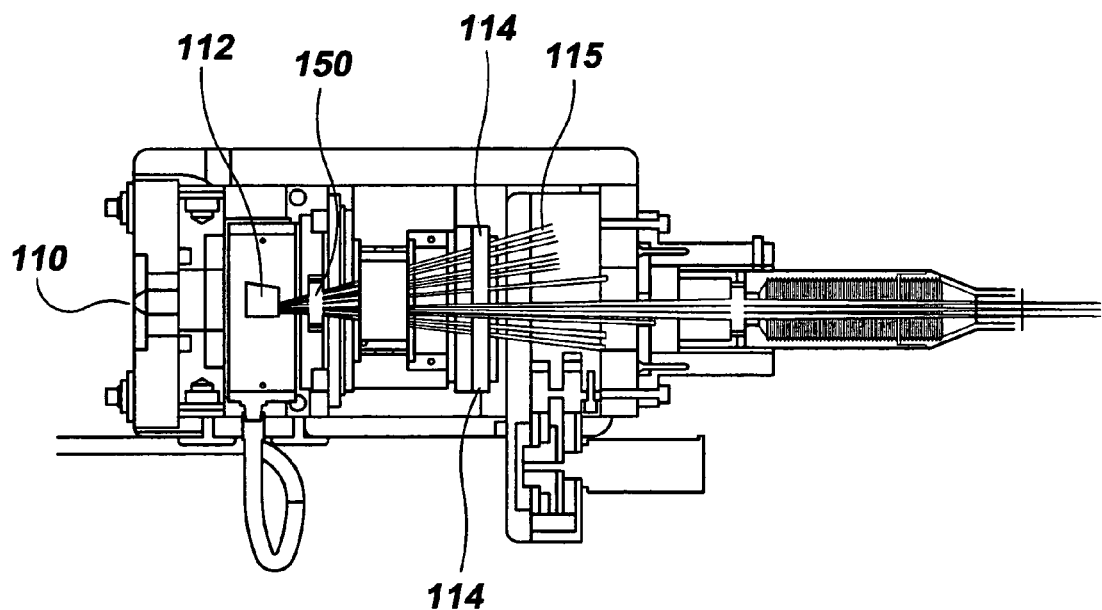
FIG. 17 is a top or plan view of the AOD assembly for the beam scanning module.

With reference to FIG. 15, AOD assembly 102 comprises a variable speed assembly 104 for selecting or varying the scanning speed of the AOD 100 while maintaining good beam quality. Variable speed assembly 104 comprises a motor drive assembly 106 (if using an electric motor) or an air drive cylinder 108 (if driven pneumatically), and at least one drive shaft 154. Referring to FIG. 16, which shows a cutaway view of a portion of the AOD assembly 102, and FIG. 17, which shows a top view, AOD assembly 102 includes a beam input or aperture 110 at which AOD assembly 102 receives the incident beam from beam source module 70. AOD assembly 102 also includes an AOD crystal 112 positioned in the optical path of the beam. An RF drive system (not shown) is provided to scan the output angle of the diffracted beam emitted by the AOD crystal. In operation, the RF drive system provides an acoustic signal across AOD crystal 112, which causes the refractive index of the crystal to vary across its face. As the frequency of the RF drive system is changed, the light passing through the crystal interacts with the acoustic beam and is diffracted with an angle that is directly related to the frequency of the RF drive. This incident light also is split into separate beams, so that the zeroth order beam passes straight through the crystal 112, but other orders, e.g., the 1st order, the −1 st order, etc. are deflected. These orders are shown in FIG. 17 at 115. In the presently preferred embodiment, i.e., system 10, the drive signal is varied in frequency in proportion to a sawtooth voltage signal, so the beam is deflected in the plane of the page for FIG. 17. Stops or baffles 114 in the form of well polished black glass are provided within AOD assembly 102 for blocking orders other than the $+1^{st}$ order, and for limiting and clipping the scan of the beam. These stops 114 are oriented with respect to the beam at the Brewster's angle to maximize the absorption of the unwanted diffracted beams from the AOD crystal 112. An adjustable aperture 116 is located in the optical path of the beam. A wave plate 118 is disposed in the optical path to rotate the output polarization of the light. A telecentric lens 120 is positioned in the optical path after the wave plate 118. This lens 120 focuses the beam down to a spot at the surface under test or inspection. The spot size in this preferred embodiment is nominally 50 microns in the in-scan direction and 120 microns in the cross-scan direction.

AOD SNR Improvement

The AOD assembly 102 also includes a beam scan absorbing system 24 for absorbing light that is not collimated in the beam. In this embodiment this beam scan absorbing system 24 comprises a series of apertures, baffles and threads, including optical baffling or optical threads 122 located in the snout 124 of the AOD assembly 102 near its output 126. The beam is output from AOD assembly 102 at a beam output aperture 126.

Beam Scanning Module 92 Mounting

The beam scanning module 92 further includes beam scanning module mounting means 196 for fixedly mounting the beam scanning module housing 98 relative to the base 11 so that the beam is projected at a pointing angle to the pointing position. As was noted in connection with the beam source module 70, it is desirable for the beam scanning module 92 to be easily mounted, pre-aligned, and to require a minimum of alignment or other adjustment to install it onto the system. Proper operation of a laser-based surface inspection system requires AOD alignment tolerances to be quite tight. It can be difficult to obtain the required diffraction efficiency and power uniformity necessary for proper AOD operation when aligning the AOD 100 during system assembly. Replacing the AOD assembly 102 in system 10, as is occasionally necessary during servicing of surface inspection systems, requires duplicating the AOD alignment in order to obtain the same diffraction efficiency and power uniformity. Re-alignment could therefore result in loss of system sensitivity. Obtaining correct alignment, while critical, is made even more difficult when the AOD 100 must be replaced in the field. It is difficult to enable field replaceability of the AOD while ensuring that the laser beam will be aligned with respect to the AOD within such tight tolerances. The beam scanning module 92 according to the presently preferred embodiments therefore comprises a modular and field replaceable unit.

In this specific yet illustrative embodiment, the beam scanning module mounting means 196 comprises a plurality of pins 96 in the beam scanning module base 90 that mate a corresponding plurality of pinholes 94 in the beam source module base plate 76. Alternatively, or in combination, the plurality of pinholes could be in another system component to which the beam scanning module 92 and the beam source module 70 are to be affixed. Also alternatively or in combination, the mounting means may comprise a plurality of pinholes in the surface of beam scanning module base 90 that would mate to a corresponding plurality of pins in the bottom surface or portion of the beam source module base plate 76.

As noted above, beam scanning base plate 90 also comprises means 196 for mounting the beam scanning module 92 to base plate 60 or other system component through which the beam scanning module 92 is to be affixed to base plate 60. In this presently preferred embodiment, the mounting means 196 comprise a plurality of pins 128 on the bottom surface of beam scanning module base plate 90 that mate with pinholes 130 in base plate 60. Alternatively or in combination, the mounting means 196 may comprise a plurality of pinholes in the bottom surface of base plate 90 that would mate to a corresponding plurality of pins in the top surface or portion of base plate 60.

Variable Speed AOD, Contd.

In accordance with another aspect of the invention, a variable scanning speed acousto-optical deflector assembly 194 is provided. This assembly may be provided separately, or it may comprise a component in a surface inspection system. This assembly comprises an AOD 100, means 190 operatively coupled to the AOD 100 for varying the scan speed at which the AOD 100 deflects a beam passing through the AOD 100 (the means 196 also known as the AOD scan speed varying means 196), and beam astigmatism compensating means 160 for compensating for astigmatism of the laser beam associated with the variation of scan speed.

Beam scanning module 92 as described herein is designed to make better use of the relatively high detection-throughput capability of system 10 over prior known systems. "Detection-throughput" is analogous to the "gain-bandwidth product" known by those skilled in the art of electrical engineering. Detection-throughput determines how many wafers per hour a scanner can scan at a given detection sensitivity performance level. Alternately, it is the ultimate detection sensitivity the system can achieve at a given throughput level. As the detection-throughput capability increases, the wafer can detect smaller defects at higher throughput, thereby lowering the cost of ownership. Methods for increasing the overall detection-throughput include increasing the laser power, improving the collection efficiency of the detection collectors, and increasing the quantum efficiency of the detectors.

The ability of a beam scanning subsystem 8 to flexibly trade between detection sensitivity and throughput can be and often is very important. In some prior systems, the scan speed is fixed, and therefore the sensitivity that can be achieved also is fixed. If a system could scan more slowly, the system could effectively integrate more photons, thereby reducing the shot noise levels (described in more detail below) and improving the sensitivity of the system to smaller defects. If a system could be scanned more quickly, the throughput could be increased beyond its current speed, reducing the cost of ownership of the tool at the expense of defect sensitivity. By enabling such systems to scan multiple speeds, the user can advantageously trade off throughput for sensitivity in a flexible manner. By offering multiple or even many effective speeds, the user can choose the speed that is right for their particular process.

Multiple speed operation in surface inspection systems having short scanning capability can be achieved by two methods: 1) changing the cross-scan speed or the cross-scan pitch (slower stage rotational rate) in cooperation with cross-scan filtering to match the filter coefficients of the cross-scan pulse signal shape (see, e.g., U.S. Pat. No. 6,529,270, which is hereby incorporated by reference), and 2) changing the in-scan speed and adjusting the in-scan filter for proper matched filtering. Preferred systems and methods according to this aspect of the invention use both methods to provide a series of selectable scan speeds.

Method 1 does not require any changes to the optical design while Method 2 often will. Method 2 requires changing the AOD modulation frequency per unit time, requiring the AOD frequency chirp range (or scan length) to be reduced while holding the AOD scan time invariant in order to scan the spot more slowly during the same in-scan time base. The in-scan speed is controlled by the total change in the AOD modulation frequency per unit time. If the AOD scan length is reduced, the effective internal lens focal length in the AOD will also change, requiring the cylinder lens focal length to change in order to compensate for the new AOD in-scan focal length. If the active compensation is incorrect (i.e., the cylinder lens focal length does not match that of the AOD lens), the in-scan spot size will be too large at the wafer plane, and the effective sensitivity of the scanner will be reduced.

Reducing the AOD scan speed provides an improvement in particle diameter sensitivity, which is the result of quantum mechanical shot noise. It may be quantified as $$[(\sqrt{R})^{1/6}] = d_f/d_s, \text{ where:}$$

R is the ratio of a full scan speed to a slower scan speed;
$d_f$ is the diameter of the particle that is discernable at full speed; and
$d_s$ is the diameter of the particle that is discernable at the slower speed.

By using a combination of both Methods 1 and 2, a large selection of scan speeds can be chosen along the detection-throughput curve. For example, in an illustrative but not necessarily preferred embodiment, the AOD scan rate is 20 microseconds per AOD scan, with 16 microseconds for the AOD scan and 4 microseconds for the fly-back to the AOD scan start position, nominally 4, 3, 2, and 1 mm AOD scan lengths are selectable, and 23, 11, 6, and 3 micron AOD cross scan pitches are selectable. If the cross scan filter can support 23, 11, 6, and 3 micron cross scan pitches, and the in-scan beam scanning subsystem 8 can support 4, 3, 2, and 1 mm AOD scan lengths, the system 10 can operate at a total of 4×4=16 scan speeds. The 3 micron cross scan pitch, when utilized with the 1 mm AOD scan length, can provide the best sensitivity at the lowest throughput, while the 23 micron pitch and 4 mm scan length would provide the highest throughput. By providing 16 or more scan speeds along the detection-throughput curve, the user can select the optimal speed/sensitivity setting for their particular processes.

In the presently preferred yet merely illustrative embodiment, once an AOD scan speed is selected, it is maintained throughout the wafer scan. The setting does not vary within a given AOD scan.

Figure 84:
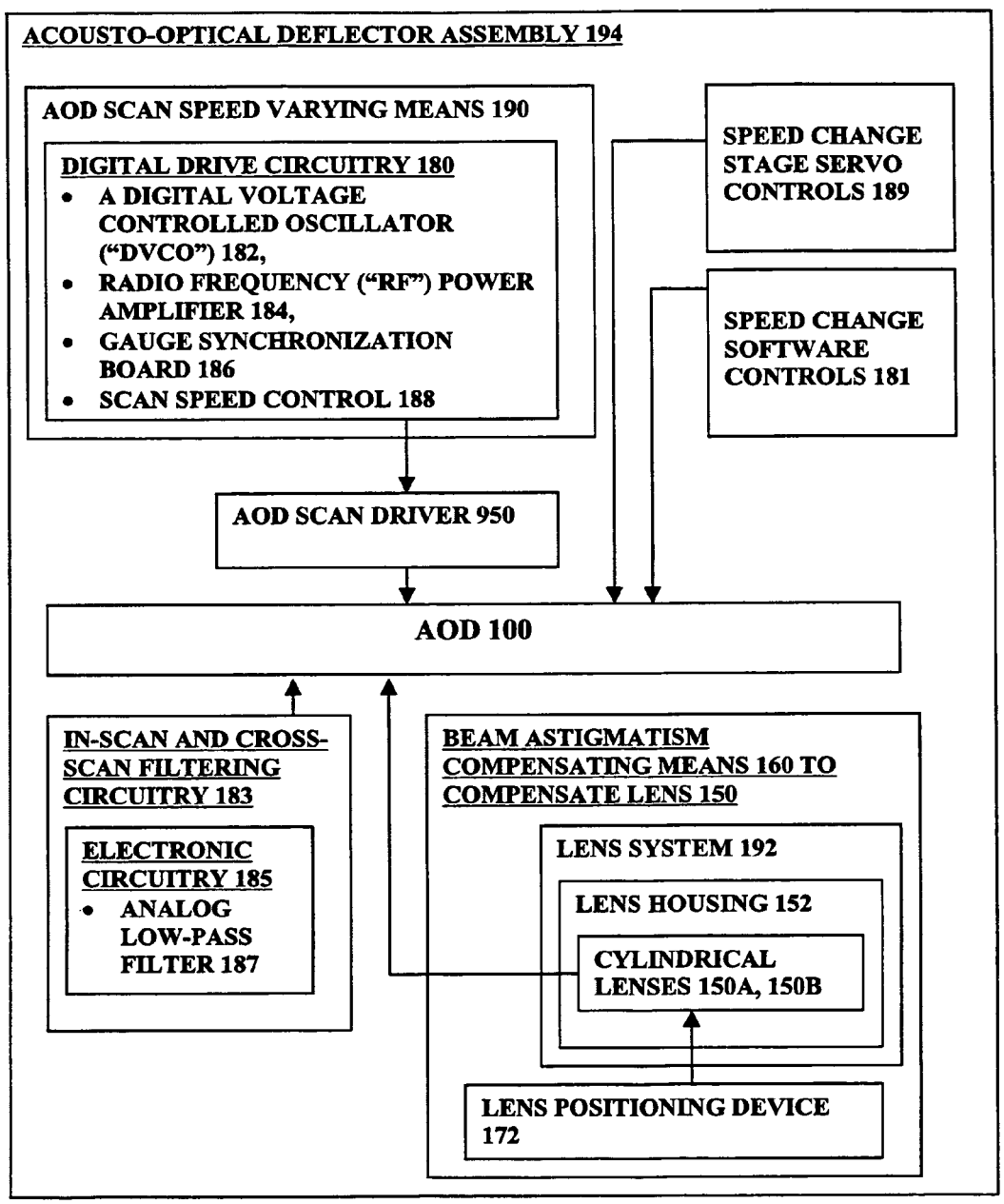
FIG. 84 is a block diagram of the AOD assembly shown in FIGS. 15-17.

A variable speed acousto-optic deflector assembly 194 according to a presently preferred yet merely illustrative embodiment of this aspect of the invention is shown in FIGS. 15-17 and in block diagram form in FIG. 84. The acousto-optical deflector according to this aspect of the invention may comprise any AOD suitable for the application and capable of meeting the technical requirements at hand. The presently preferred AOD is AOD 100 of AOD assembly 102.

The variable speed AOD assembly 194 also comprises means 190 operatively coupled to the AOD 100 for varying the AOD scan speed at which the acousto-optical deflector scans a beam passing through it. The specific means 190 that may be used to perform this task will depend upon the specific AOD used and in some cases other factors as well. It normally will involve drive electronics used to drive the AOD, such as that commercially available from AOD suppliers.

In the presently preferred embodiment, the AOD scan speed varying means 190 comprises digital drive circuitry 180 comprising a digital voltage controlled oscillator ("DVCO") 182, such as IDDS-1-SE Direct Digital VCO, and radio frequency ("RF") power amplifier 184, such as IA-100-3-826 RF Power Amplifier, both commercially available from ISOMET of Springfield, Va. It also comprises a gauge synchronization board 186 (also known herein as gauge synchronization control 186) with synchronization signals that trigger the DVCO 182 to initiate AOD scans. The digital drive circuitry 180 includes a control 188 to selectively vary the scan speed of the AOD, and/or to select discrete scan speeds. The AOD scan speed varying means 190 has software controls 181 and stage servo controls 189 to accomplish the speed changes necessary when changing the cross-scan speed or the cross-scan pitch.

The AOD scan speed varying means 190 also has in-scan and cross-scan filtering circuitry 183 comprising electronic circuitry 185, which may comprise digital circuitry. However, in the presently preferred yet merely illustrative embodiment, the filtering circuitry 185 comprises an analog low-pass filter 187 with an impulse function which matches the pulse width produced by the AOD scan to maximize signal to noise ratio in the in-scan direction.

Beam Compensating Means

The variable scan speed AOD assembly 194 also comprises has a beam compensating lens 150 that operates to produce a focal length difference between in-scan and cross-scan direction and a beam astigmatism compensating means 160 for varying the focal length difference in order to compensate for astigmatism of the beam associated with the variation in scan speed. As the scan speed of the AOD 100 is changed, the astigmatism of the beam also changes. This astigmatic effect usually is disadvantageous, for example, in that it spreads and defocuses the beam. The beam astigmatism compensating means 160 is used to compensate for this astigmatism so that its adverse effects can be offset or eliminated and the desired beam geometry can be obtained.

The focal length (L) for a selected AOD in-scan speed is a function of the laser beam size, the frequency shift across half of the laser beam, and the laser wavelength. It is calculated as follows:

The AOD Sweep rate (R) is calculated as:

$$R = \frac{\Delta F}{P} (\text{Hz/s}),$$

where
  $\Delta F$=Total frequency difference between lowest and highest frequencies during AOD sweep; and
  P=Sweep Period, defined to be the total time required for the AOD to sweep from lowest to highest frequency.

The time across beam (T) is calculated as:

$$T = \frac{B}{S};$$

where
  B=Beam size, and
  S=Speed of sound in crystal.
The frequency shift across half of the beam (H) may be calculated as $$H = R*T/2.$$

The focal length L for a selected AOD in-scan speed may then be calculated as $$L = \frac{B}{2*[\text{Tan}(H*W/S)]},$$

where
  B=beam size;
  H=frequency shift across half of beam;
  W=laser wavelength; and
  S=Speed of sound in crystal.

As noted above, the telecentric lens 120 is positioned in the optical path after the wave plate 118 and before the optical threads 122 near the optical threads 122 to convert the angular scan to a spot position scan at the workpiece surface, while simultaneously focusing the beam at the workpiece. The telecentric lens 120, when it is properly matched to the effective lensing effect in the AOD (lens 150), ensures that the in-scan and cross-scan waists are located at the same position along the optical axis. However, as the AOD scan speed varying means 190 varies scan speed, the focal length (L) changes and. Therefore, the effective lensing effect in the AOD 100 changes in response to the AOD scan speed, introducing an astigmatism. The beam astigmatism compensating means 160 performs an astigmatic correction. The beam astigmatism compensating means 160 operates to modify the effective lensing effect in the AOD 100 in order to allow the telecentric lens 120 to maintain focus of the beam at the workpiece W onto a spot position at the workpiece surface at varying scan speeds.

The beam astigmatism compensating means 160 may comprise any means in which the focal length of a lens system may be varied in response to a change in the index of refraction or lens surface curvature. For example, the beam astigmatism compensating means 160 may comprise a liquid lens, in which the surface curvature is changeable, or preferably a lens system 192 comprising a plurality of lenses in which the focal lengths of the respective lenses differ from one another and are selected to appropriately compensate for the beam deformation at each of the respective desired scan speeds. Cylindrical lenses are particularly preferred. The beam astigmatism compensating means 160 also preferably comprises a lens positioning device 172 operatively coupled to the plurality of lenses. The lens positioning device 172 is used to position a selected one of the lenses in the lens system 192 in the beam at the output of the AOD 100, in the optical path of the beam. Each lens in the lens system 192 is designed to provide the desired beam compensation for a given AOD scan speed and provides a unique amount of compensation relative to that of others of the lenses in the lens system 192. The lens positioning device 172 is used to alternately position the lens that corresponds to the selected scan speed into the beam path at or near the AOD output. When the AOD scan speed is changed, the current lens is moved away from this position, and another one of the lenses, this one being compatible with the newly selected AOD scan speed, is moved into position at or near the AOD output and in the beam path.

In the presently preferred embodiments, and with reference to FIGS. 15-17, the beam astigmatism compensating means 160 comprises a lens system 192, having two cylindrical lenses 150a, 150b housed in a lens housing 152 located between the AOD crystal 112 and near the optical threads within AOD assembly 102, and a lens positioning device 172 for controlling the positioning of the lenses with a sliding plate 158 for moving the variable speed assembly cylindrical lens 150A or 150B into position. The lens positioning device 172 comprises a variable speed assembly 104 that uses a motor drive assembly 106 comprising an electric motor, not shown, or, alternatively, an air drive cylinder 108, connected to drive shafts 154 that rigidly connect the motor drive assembly 106 to the cylinder lens housing 152. Motor drive assembly 106 may comprise any drive assembly to move the lenses, e.g., such as those means noted herein above. In the presently preferred yet merely illustrative embodiment, the motor drive assembly 106 operates pneumatically and thus includes a pneumatic pressure source 156 and pneumatic ports 162 for supplying air pressure to drive the drive shafts 154. A pair of springs 164 is positioned on drive shafts 154 to prevent the lens assembly 192 from being overdriven.

When AOD assembly 102 and its associated drive circuitry are set to scan at a first scan speed, variable speed assembly 104, including motor drive assembly 106, are used to position lens 150a, 150b in the beam path (the up position for variable speed assembly 104 as shown in FIG. 16). Lens 150a provides the amount of compensation appropriate to offset the astigmatism associated with the first scan speed. When AOD and its associated drive circuitry are set to scan at a second scan speed different from the first scan speed, in this case, slower than the first scan speed, the variable speed assembly moves the drive shafts down to position lens in the beam path. Lens 150b is designed to provide the appropriate amount of compensation to offset the astigmatism associated with the second scan speed.

Figure 18:
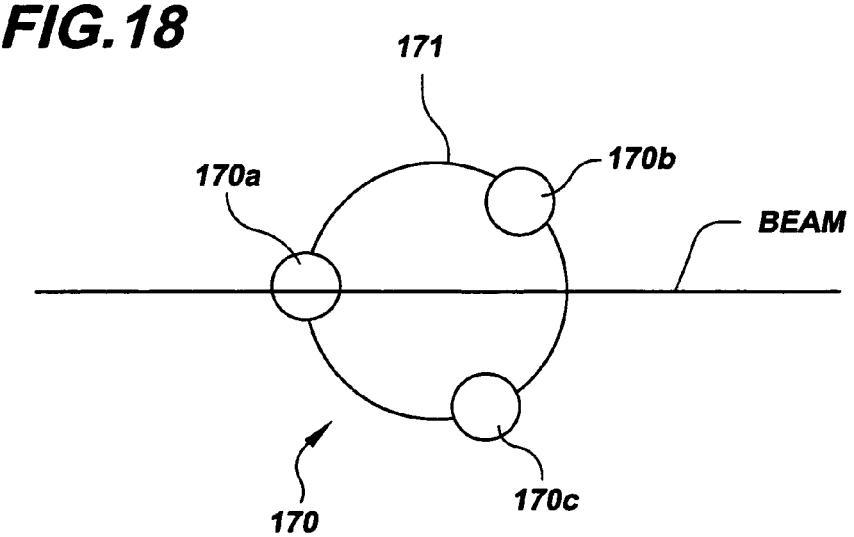
FIG. 18 is a diagram of an alternative embodiment of the beam compensation means for the variable speed beam scanning device according to the present invention.

Another embodiment of a variable speed AOD in accordance with this aspect of the invention is shown in FIG. 18. In it, the beam astigmatism compensating means 160 comprises a lens housing 170 with a rotating carousel 171 that contains multiple lenses, preferably cylindrical lenses, 170a, 170b and 170c. Housing 170 selectively moves one of the plurality of lenses 170a, 170b, 170c into the beam path by rotating the carousel 171.

In each of these embodiments, the lenses preferably but optionally are positioned immediately adjacent to the acousto-optical deflector 100.

Scan Repetition Mode and Station

Figure 82:
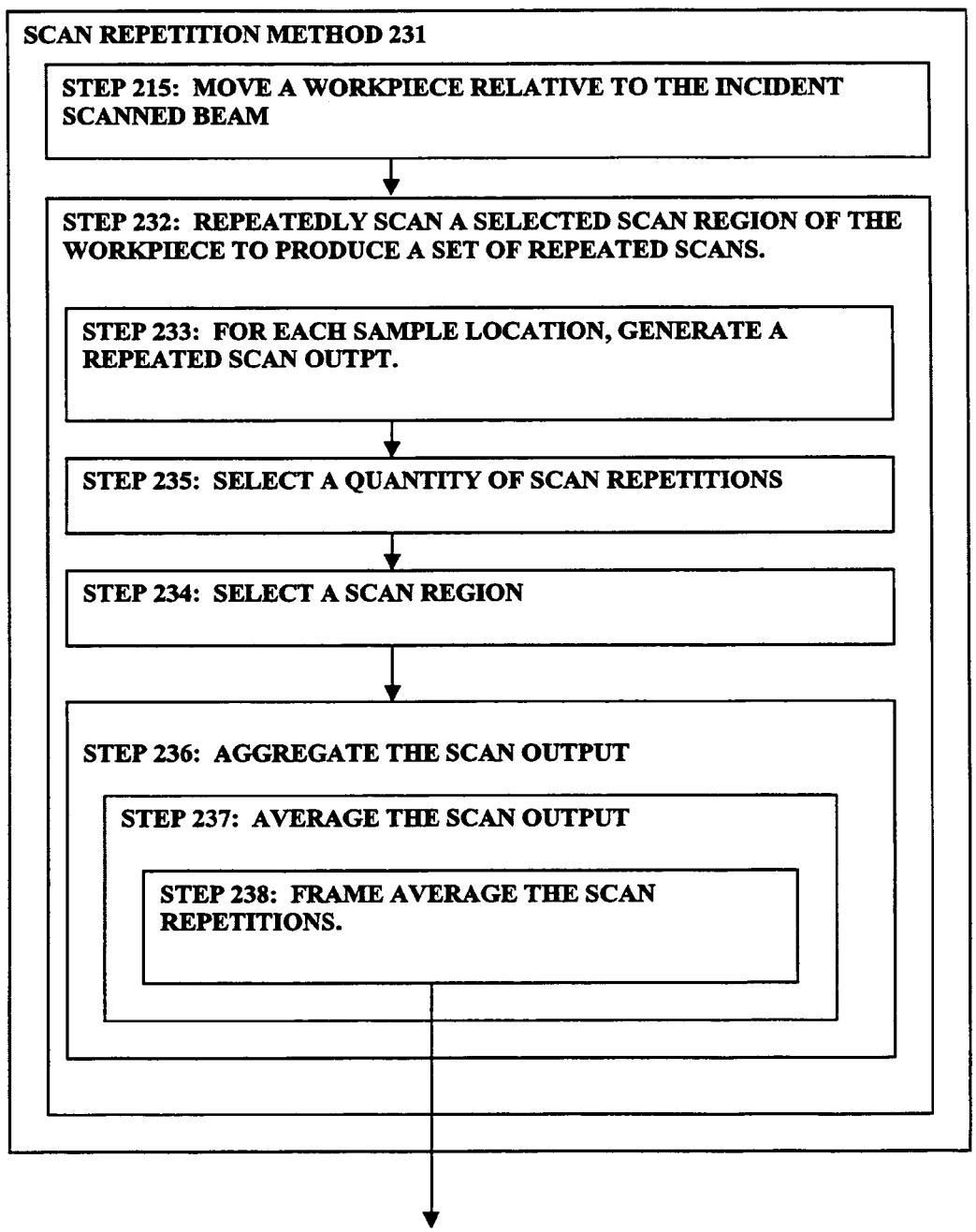
FIG. 82 is a block diagram of the scan repetition method 23 of the present invention.

In accordance with another aspect of the invention, a method for inspecting the surface of a workpiece, in which an incident beam is projected toward the surface of the workpiece, and the surface of the workpiece is scanned to generate a scan output representative of the effects on the surface of the incident beam, comprises a method 231 for repeatedly scanning a selected scan region of a workpiece. As shown in FIG. 82, the scan repetition method 231 comprises the step 215 of moving a workpiece relative to the incident scanned beam and the step 232 of repeatedly scanning a selected scan region of the workpiece to produce a set of repeated scans.

In a further embodiment, the selected scan region has a plurality of sample locations, and the step 231 of repeatedly scanning a selected scan region of the workpiece further comprises a step 233 of generating a repeated scan output comprising, for each of said sample locations, generating a set of signals associated with the sample location over the set of repeated scans.

In a multi-collector surface inspection system such as system 10, a surface scan produces, from each collector, a signal associated with each sample location, and the step 233 of generating a scan output comprises, for each of said sample locations, generating a set of signals associated with the sample location, from each collector and over the set of repeated scans.

In another embodiment, the step 232 of repeatedly scanning a selected scan region of the workpiece further comprises the step 235 of selecting a quantity of scan repetitions, for defining the number of scans to be run on a selected scan region of the surface, and a step 234 of selecting a scan region for defining a region of the workpiece to be scanned.

The resulting scan repetitions may be used to increase the Signal to Noise Ratio (SNR) of the selected scan region and thus reveal greater details of the surface under consideration. SNR may be improved by aggregating the output of a set of scans that are repeated on a selected region. Therefore, in another embodiment, the scan repetition method 231 further comprises the step 236 of aggregating the scan output. In one embodiment, the step of aggregating comprises the step 237 of averaging the scan output, for example finding the arithmetic mean of the scan output. In a more preferred embodiment, the step 237 of averaging the scan output comprises the step 238 of frame averaging the scan repetitions.

Frame averaging is a mathematical process in which several frames of identical scenes are coincided to produce an increase in detail and thereby resolution of the scene. In the context of scan repetition in a surface inspection system such as system 10, frame averaging comprises averaging each of the sample signals associated with a sample location within a selected scan region over the set of repeated scans. In the context of scan repetition in a multi-collector surface inspection system such as system 10, frame averaging comprises, for a sample location, averaging each of the sample signals associated therewith from each collector. A discussion of frame averaging may be found at *The Image Processing Handbook,* 3rd ed., John C. Russ (CRC Press IEEE Press 1998). Frame averaging minimizes shot noise and enhances the signal from persistent scatter sources by lowering the signal value of shot noise in those locations where shot noise is present.

While the random nature of shot noise results in random signals during a scan, real surface scatter sources may produce a signal at the same location for each collector. Further, real surface scatter sources may produce a signal at the same location for each collector every time that a scan is repeated. When signals which are the output from a set of scans that are repeated on a selected scan region are averaged, signals from a real surface scatter source will more likely produce a higher average signal. However, shot noise signals from the region, which by definition generally do not repeat in the same locations, will result in a lower average signal. Thus the SNR will be improved by frame averaging a set of scans that are repeated on a selected scan region.

Figure 83:
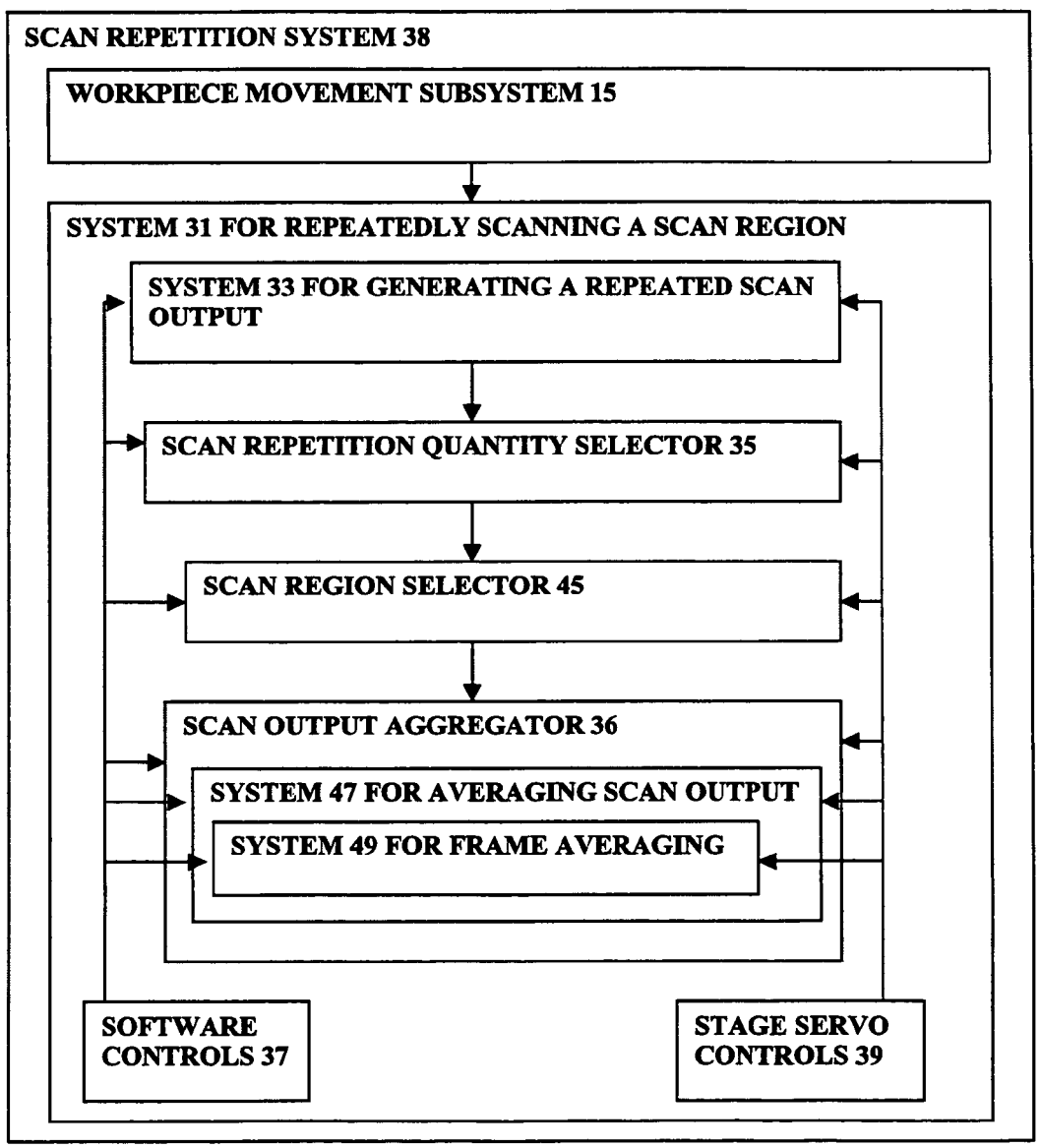
FIG. 83 is a block diagram of the scan repetition system 38 of the present invention.

In accordance with another aspect of the invention, a scan repetition system 38 is provided. The scan repetition system 38, which may be provided separately, or which may comprise a component in a surface inspection system, comprises a workpiece movement subsystem 15 for movement of the wafer relative to an incident scanned beam and a system 31 operatively coupled for repeatedly scanning a scan region of the workpiece. The scan repetition system 38 is shown in FIG. 83.

In a further embodiment, the selected scan region has a plurality of sample locations, and the system 31 operatively coupled for repeatedly scanning a scan region of the workpiece further comprises a system 33 for generating a repeated scan output, which generates, for each of said sample locations, a set of signals associated with the sample location over the set of repeated scans. In a multi-collector surface inspection system, the system 33 for generating a repeated scan output generates, for each of said sample locations, a set of signals associated therewith from each collector and over the set of repeated scans.

In a further embodiment, the scan repetition system 38 further comprises a scan repetition quantity selector 35, for defining the number of scans to be run on a surface, and a scan region selector 45 for defining a region of the workpiece to be scanned.

The scan repetition system 38 may comprise any scan repetition system suitable for the application and capable of meeting the technical requirements at hand. The scan repetition system 38 preferably comprises software controls 37 and stage servo controls 39. In addition, each of the specific implementations of the system 31 for repeatedly scanning a scan region of the workpiece scan, the repetition quantity selector 35, and the scan region selector 45 will depend upon the specific workpiece movement subsystem 15 used and in some cases other factors as well. In the presently preferred embodiment, the repetition scan system 31 and its systems 33, 35, 45, 36, 47, 49 are operable using software controls 37 and stage servo controls 39.

In a further embodiment, the scan repetition system 38 further comprises a scan output aggregator 36 to aggregate the output of a set of scans that are repeated on a selected region. In one embodiment, the scan output aggregator comprises a system 47 for averaging scan output. In a more preferred embodiment, the system 47 for averaging output comprises a system 49 for frame averaging for averaging each of the sample signals of each collector from each of the sample locations within the repetition region.

Using the scan repetition system 38 and scan repetition method 231, the surface inspection system may scan an entire wafer and then make multiple scans of sub-regions of the wafer wherever there are defects of interest. Use of the scan repetition system 38 and method 231 can allow detection of defects with <30 nm PSL equivalent sizes.

Optical Collection and Detection Subsystem

In accordance with another aspect of the invention, an optical collection and detection subsystem 7 is provided. The optical collection and detection subsystem 7 may be provided as an independent assembly, or it may be incorporated into a surface inspection system, for example, such as system 10. It comprises a collection system 380 and a detection system 480. The collection system 380 comprises components used to collect the beam portions reflected from the surface of the workpiece and scattered from the surface due to surface roughness, defects in the surface, and the like. The detection system 480 is operatively coupled to the collection subsystem 380 and works in conjunction with it to detect the collected light and convert it into corresponding signals, e.g., electrical signals, that can be utilized by the processing subsystem to obtain information pertaining to the surface of the workpiece.

Architecture

The optical collection and detection subsystem 7 (FIG. 21) in accordance with the presently preferred embodiment of this aspect of the invention operates to collect portions of the incident beam that are scattered and reflected from the surface of the workpiece and generates signals in response to them. As implemented in system 10 and shown in FIG. 20, the collection and detection subsystem 7 comprises an optical collector subsystem 380 and a detector subsystem 480, and the signals comprise electrical signals, each of which having a voltage that is proportional to the optical power illuminating the detector subsystem 480. The collection and detection subsystem 7 in its various implementations as described herein and claimed herein below, comprise additional aspects of the invention, in the system embodiments as well as separately.

The optical collection and detection subsystem 7 comprises means 250 for developing a light channel, for collecting the beam reflected from the surface of the workpiece into a light channel, and means 260 for developing a dark channel, for collecting the portions of the beam scattered from the surface into a dark channel collector. The means 260 for developing a dark channel further comprises components of the optical collection and detection subsystem 7, described in more detail below.

Figure 19:
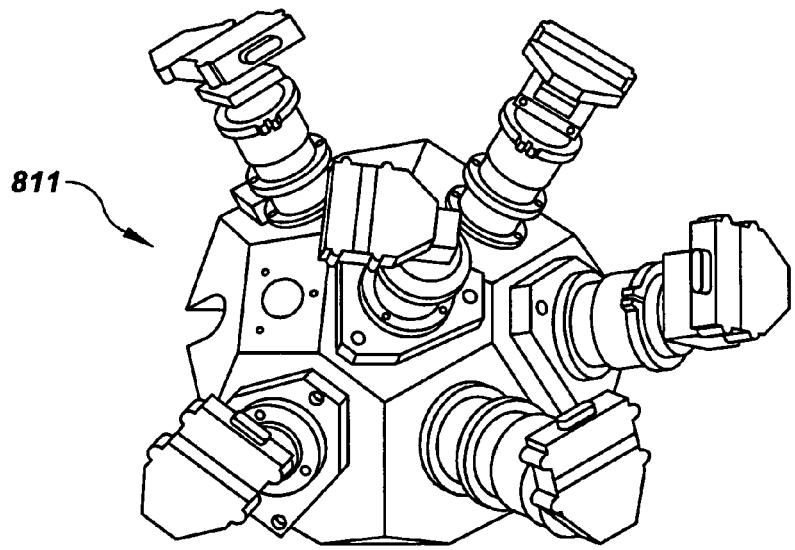
FIG. 19 is a perspective view of the collection and detection subsystem module for the system of FIG. 1.
Figure 20:
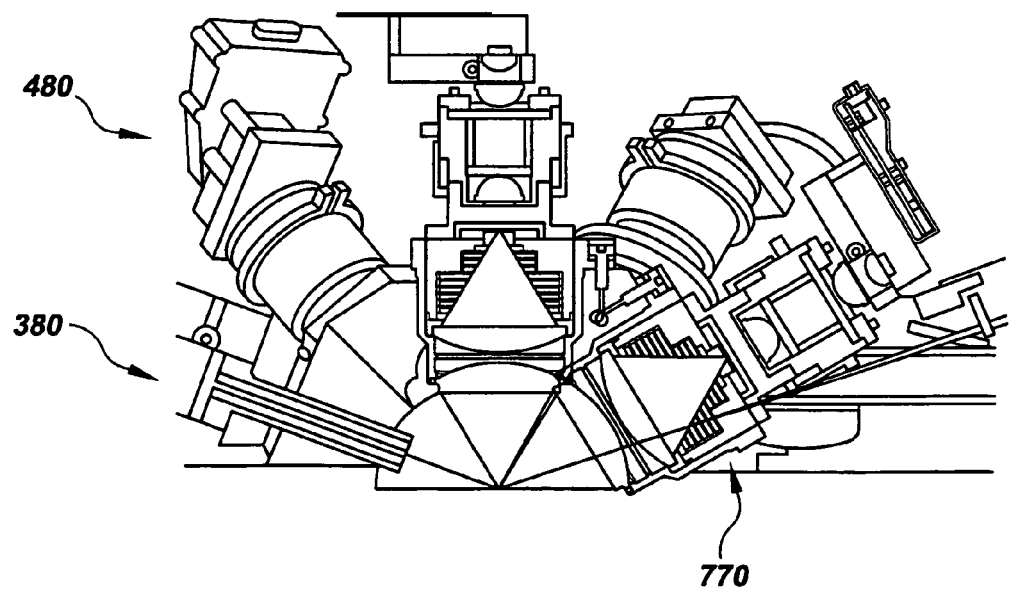
FIG. 20 is a side cutaway view of the module shown in FIG. 19.
Figure 22:
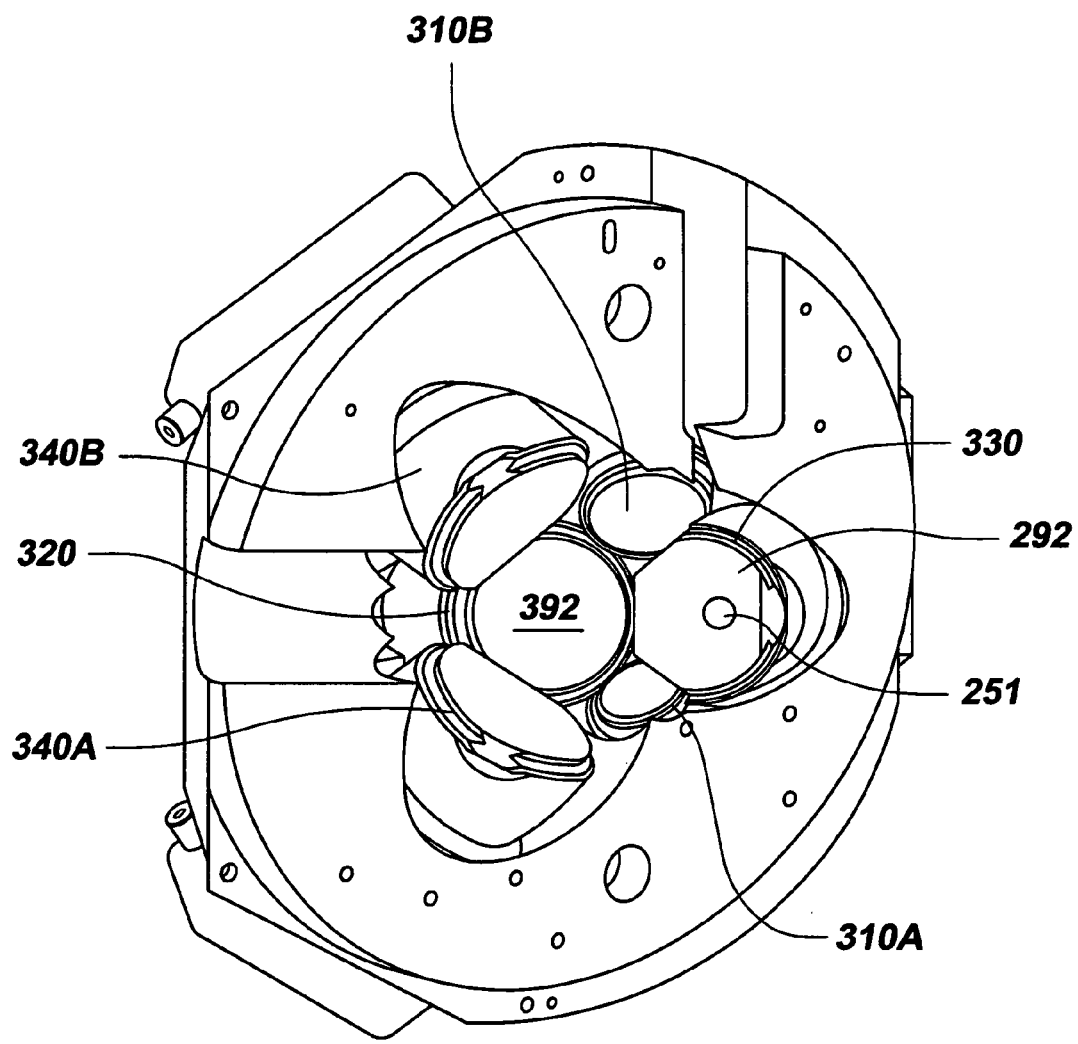
FIG. 22 is a bottom view of the collection optics of the collection and detection subsystem for the system of FIG. 1.

As shown in FIG. 1, the optical collection and detection subsystem 7 comprises a series of collection and detection assemblies 200 (also known as collection and detection modules 200), each assembly 200 comprising components of the optical collection subsystem 380 and the detection subsystem 480 and each assembly 200 organized into a collector module 300 (also referred to herein as "collector") for collecting portions of the beam, and a detector module 400 associated therewith. The means 250 for developing a light channel comprises the components of the collection and detection assemblies 200 for collecting and detecting the specular beam and, the means 260 for developing a dark channel comprises the components of the collection and detection assemblies 200 for collecting and detecting the scattered portions of the beam, In the illustrative but not necessarily preferred embodiment and as shown in FIGS. 1 and 2, the series of collection and detection assemblies 200 comprises a front collection and detection module 230, a center (or central) collection and detection module 220, a pair of wing collection and detection modules 210A, 210B, and a pair of back collection and detection modules 240A, 240B. FIG. 19 provides a perspective view of optical collection and detection subsystem 7. FIG. 20 shows a side cutaway view of it. FIG. 21 shows the subsystem 7 attached to base plate 60. FIG. 22 shows a bottom view of the collection and detection subsystem 7.

Figure 23:
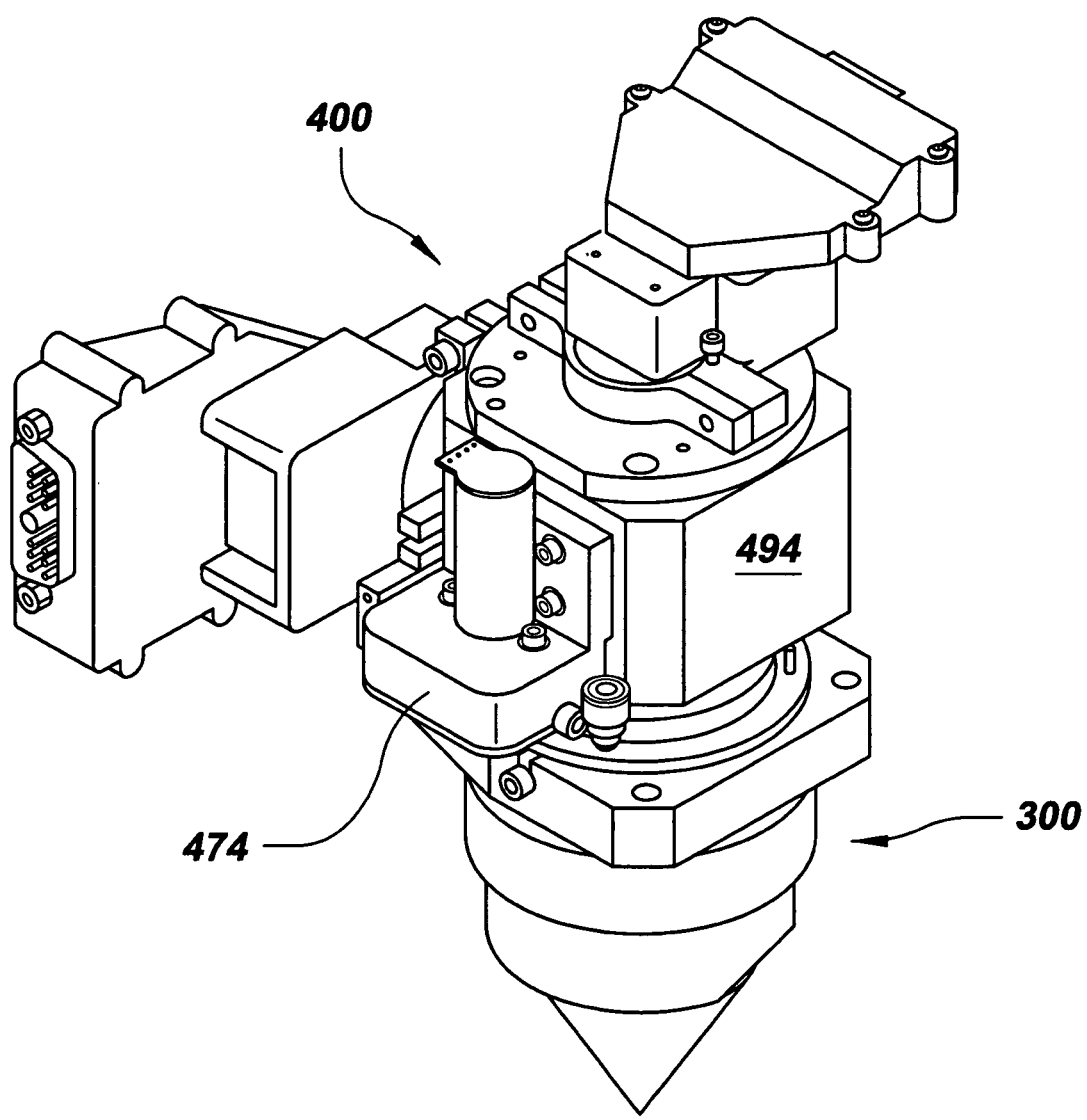
FIG. 23-24 are perspective views of the collector-detector assembly.
Figure 24:
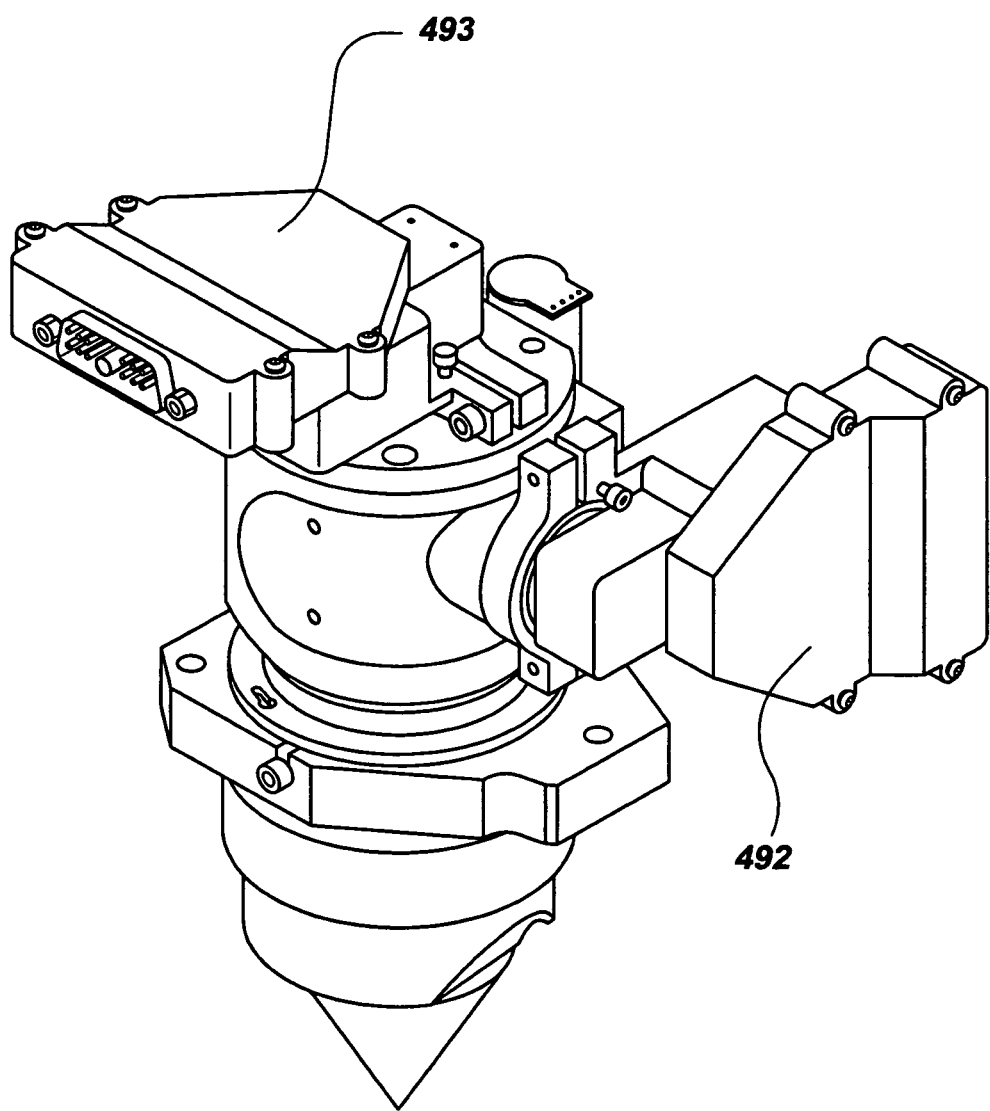
Figure 25:
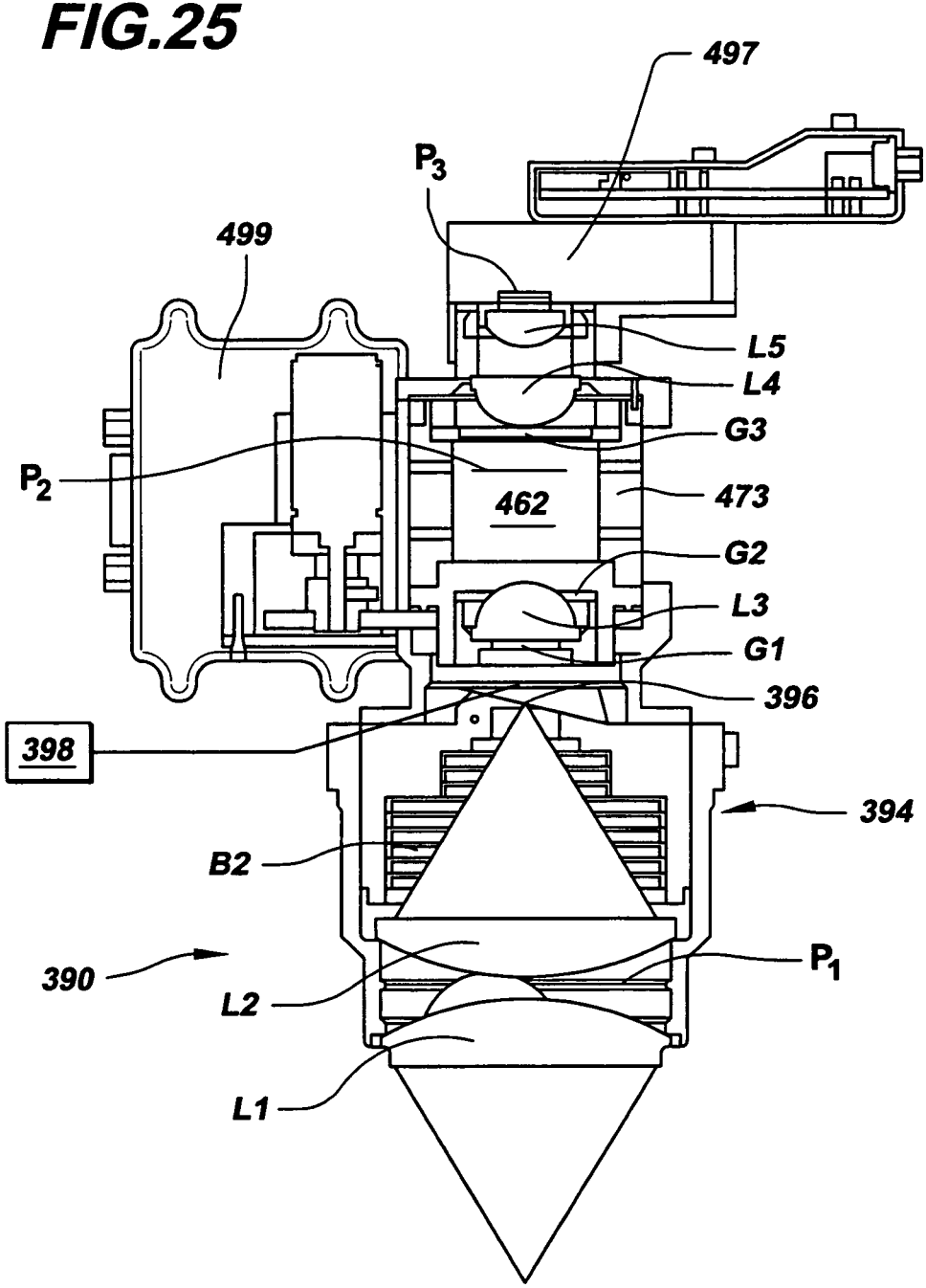
FIG. 25 is a side cutaway view of a collector and detector assembly.

Although all of the collector-detector assemblies 200 need not necessarily all be of the same design and construction, in this preferred embodiment each of them has the same basic design, which is illustrated by back collector-detector assembly 240A in FIGS. 23-26. FIG. 23 provides a perspective view of the assembly 240A from a first or front perspective, FIG. 24 provides a perspective view from a view opposite the first or front perspective, and FIG. 25 is a side cutaway view.

Referring to FIG. 25, the collector-detector assembly 240A comprises a collector module 300 that includes a collection optics subassembly 390 mounted in a barrel housing 394. A variety of lens designs may be used, for example, depending upon the specific application, the budget, etc. In other embodiments, the collector module 300 could comprise arrangements other than lens assemblies. For example, mirrors could be used to direct the scatter to a detector. In the illustrative but not necessarily preferred embodiment, the collection optics subassembly 390 comprises collector objective lens optics 392 having aspheric lenses L1, L2. Objective lens optics 392 focuses the incoming beam to a slit 396. Lens L1 collimates the light scattered from the workpiece, while L2 focuses the light to the slit 396, which operates as a field stop to absorb scatter outside of the region being scanned by the laser spot. When the collector objective lens optics 392 comprise aspheric lenses, a wide collection angle, such as about a 60 degree total angle) may be achieved while a small image spot Point Spread Function ("PSF") is produced at the slit 396. Alternatively, the collector objective lens optics 392 could comprise doublet lenses.

Figure 26:
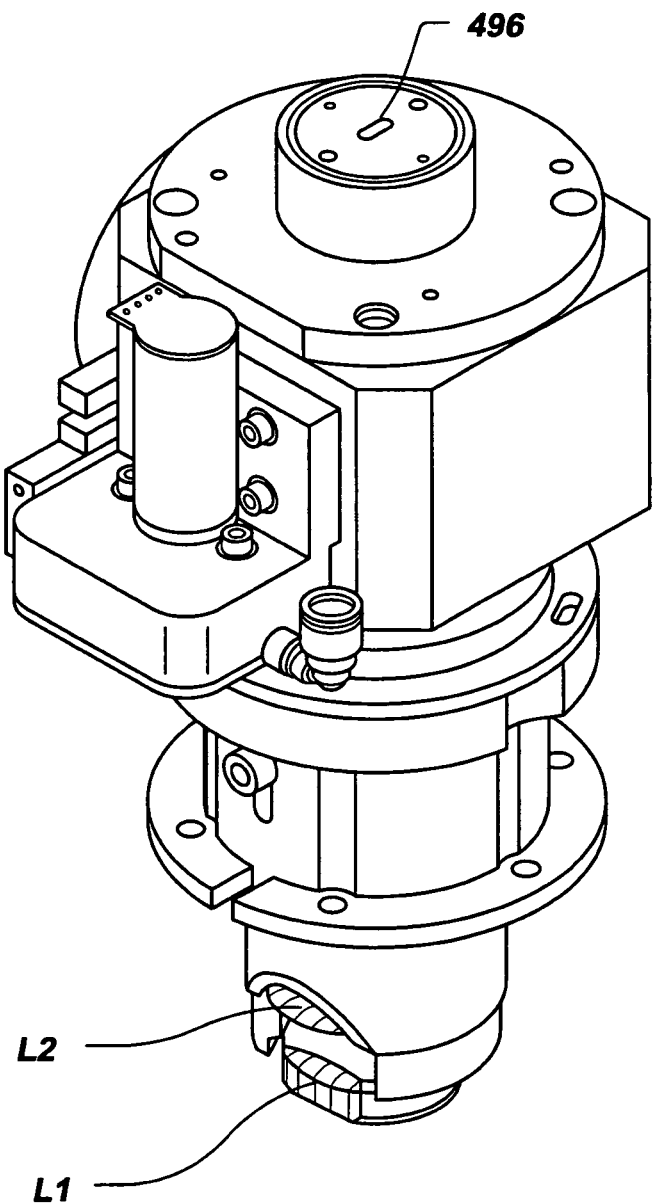
FIG. 26 is a perspective view of a partially assembled collector and detector assembly of FIG. 23-25.

A detector module 400 is mounted to the collector module 300. Detector module 400 includes a detector module barrel housing 494 that mates with collector module barrel housing 394 adjacent to slit 396 and a relay lens assembly 490. Relay lens assembly 490 comprises a relay optic collimating lens L3 that is disposed in housing in the beam path adjacent to slit 396, a relay optic focusing lens L4 that is positioned at the opposite end of housing 494, and a lens L5 (between L4 and the final slit 496) that produces the desired spot size on the photocathode surface. FIG. 26 is a perspective view of collector module 300 and a portion of the detector module 400, excluding the detection units shown in FIG. 25. As shown in FIG. 26, a slit 496 also is provided in the relay lens assembly 490 near the detection unit.

A first detection unit 492 is mounted to detector barrel housing 494 adjacent to the focusing relay optics lens L4. Detection unit 492 comprises a detector 497, such as a photomultiplier tube ("PMT"), such as the Hamamatsu H6779-20, or an Avalanche Photodiode (APD) Detector (e.g. Advanced Photonix 197-70-74-581), or other type of detector that is sensitive to receive and detect portions of the light beam passing through a lens. A second detection unit 493 is provided at the side of detector barrel housing 494. Second detection unit 493 according to this embodiment is substantially identical to first detection unit 492, and includes a detector 499 such as the PMT identified above (although it is permitted in the illustrative embodiment that the PMTs found in detection units 492 or 293 may be different in design, hereinafter a PMT may be referred to generally as PMT 495). Each of the detectors 497, 499 detects a specific polarization orientation. For example, while one PMT 495 collects scattered light that is polarized in the "P" orientation, the other PMT 495 collects light in the "S" orientation. This is because each PMT 495 is positioned to collect the "P" and "S" polarized light that is emitted by the polarizing beam splitter cube 472 that is located in the relay lens assembly 490.

Beam Scanning Subsystem, Contd.
PMT at a Telecentric Plane and Stationary Laser Spot In accordance with another aspect of the invention, one or more of the detectors 497, 499 is designed so that the photomultiplier tube 495 or other detection device is located at a telecentric plane or stop 498 with respect to the collection optics. This can help to ensure that the laser spot is stationary on the PMT photocathode surface during the AOD scan, or is limited in movement on the detector. This correspondence can help to eliminate detector-induced banding effects across the scan. As implemented in the presently preferred embodiment, the plane of each detector 497, 499 in collector and detector assemblies 200 is located at a telecentric plane 498 with respect to the collection optics 392. Referring to FIG. 25, which shows a back collector-detector assembly 240A but is illustrative of the other collector-detector assemblies 200 as well, telecentric planes or stop locations 498 are imaged at P1, P2, P3 so as to ensure minimal spot movement at the detector, thereby reducing background signal non-uniformity. Refer to pages 142-143 of *Modern Optical Engineering*, 2$^{nd}$ ed., Warren J. Smith (McGraw-Hill, 1990), for a description about telecentric stops.

Optical Collection and Detection Subsystem, Contd.
Variable Polarization

In accordance with yet another aspect of the invention, the collection and detection assembly 200 comprises a relay assembly 490 (FIG. 72) further comprising a polarizing relay assembly 450 positioned between the collection optics subassembly 390 and the detectors 497, 499. In a further aspect of the invention, the polarizing relay assembly 450 further comprises a variable polarizing assembly 470. This variable polarizing assembly 470, also known herein as rotational analyzer 470 and rotational polarization filter 470, is capable of selectively passing solely P polarization, or solely S polarization, or combinations thereof. Referring to the back collection and detection assembly 240A illustrated in FIG. 25, a presently preferred variable polarizing assembly 470 according to this aspect of the invention will now be described. Variable polarizing assembly 470 in this embodiment is integrated into the detector module 400. Assembly 470, in this embodiment also known herein as dual channel variable rotational analyzer assembly 470, comprises a motor-driven rotational polarizer analyzer 461 (also known as dual detector polarization analyzer 461) having a beamsplitter cube 472 and dual detectors 497, 499. The polarizing beamsplitter 472 is fixedly positioned in a chamber 473 of detector module 400, in the light scatter path. The beamsplitter 472 is positioned so that a transmitted portion of the scattered light passes through the beamsplitter 472 and impinges upon a first detector 497 in first detector unit 492 as a flux of photons having a first selected polarization, and a reflected portion of the scattered light passes through the beamsplitter 472 and impinges on a second detector 499 in a second detector unit 493 as a flux of photons having a second selected polarization, for dual PMT implementations. A rotational mechanism 474, such as motor, rotates the chamber 473 and thus the polarizing beamsplitter 472 to alter the polarization of the light impinging on the detection units 492, 493. Second detector 499 is fixed with respect to first detector 497, and thus second detector 499 also rotates with the assembly 470. A motor 476 or similar drive mechanism is provided which, upon actuation, causes the chamber 473, including beamsplitter 472, and second detector 499 to rotate.

To illustrate the construction and operation of this assembly 470, assume that the incident photons are unpolarized, and that beamsplitter 472 is oriented in chamber 473, and chamber 473 is oriented, so that polarizing beamsplitter 472 transforms a portion of the unpolarized beam into P polarized light for transmission to the first detector 497. Simultaneously, polarizing beamsplitter 472 transforms a portion of the photons' S-polarized light for transmission to the second detector 499. If a different polarization mix is desired, motor 476 causes the assembly 470, including chamber 473, polarizing beamsplitter 472, and detectors 497, 499 to rotate. This causes the polarizing beamsplitter 472 to transform the portion of the scattered light impinging on the first detector 497 into a first selected mixture of P polarized light and S polarized light. This also causes the polarizing beamsplitter 472 to transform the portion of the scattered light impinging on the second detector 499 into a second selected mixture of P polarized light and S polarized light. Preferably, the polarizing beamsplitter 472 according to this aspect of the invention has multiple selectable polarization settings, and more preferably are infinitely selectable over a desired range.

The motor 476 may causes the assembly to rotate to any desired polarization mix, or it may be arranged to step through selected polarization mixes. Alternatively, the assembly 470 may have a programmed polarization mix mechanism 478, which may be any known combination of hardware and software elements, that is arranged to provide a combination of infinitely selectable mixes and stepped polarization mixes, with the stepped polarization mixes changeable at the option of the user.

Figure 71:
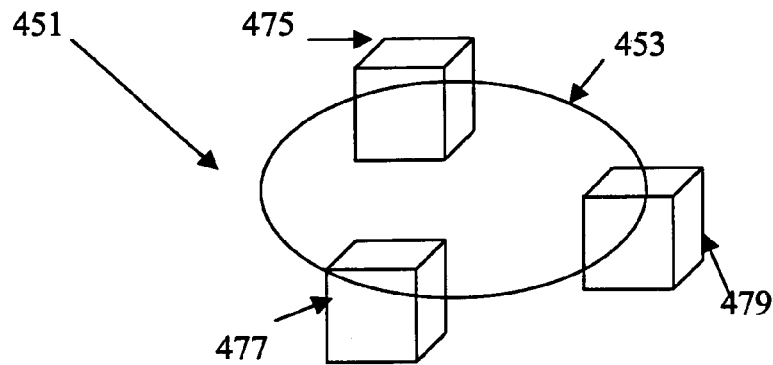
FIG. 71 is a diagram of an alternative embodiment of the variable polarization assembly according to the present invention.

A variable polarization assembly 470 according to a second preferred embodiment, shown in FIG. 71, comprises an optional motor-driven rotating carousel polarization analyzer 451 with a rotating carousel 453 that contains multiple glass cubes. Carousel 453 selectively moves one of the plurality of cubes 475, 477, 479 into the beam path. In an illustrative but not necessarily preferred embodiment of the present invention, the motor-driven rotating carousel polarization analyzer 451 comprises three glass cubes 262: one polarization beamsplitter cube ("PBS") 475 oriented for local P-polarization, one PBS cube 477 oriented for S-polarization, and one non-polarizing cube 479 for unpolarized light. By using a glass cube 479 for the unpolarized light, the effective optical path length through the relay lens assembly is maintained. This is required to maintain the same spot shape at the PMT photocathode. Incorporating three cubes into the rotating carousel polarization analyzer 451 simplifies the assembly design, and enables the analyzer to change polarization states quickly and accurately. This analyzer 451 can be easily interchangeable with the fixed polarizer relays. As noted herein, different virtual masks 131, which are described in more detail below, can be switched in and out using this assembly as well.

Rotational carousel analyzers 451 as described herein can be used to electronically select each of a plurality of cubes 475, 477, 479, each of which can utilize a different virtual mask 131 shape and size. This enables the detection subsystem 480 to have a refined angular resolved scatter defect detection capability in a versatile manner by either selectively blocking or passing angular sub-regions of scatter that are collected by a collection optics subassembly 390.

Figure 72:
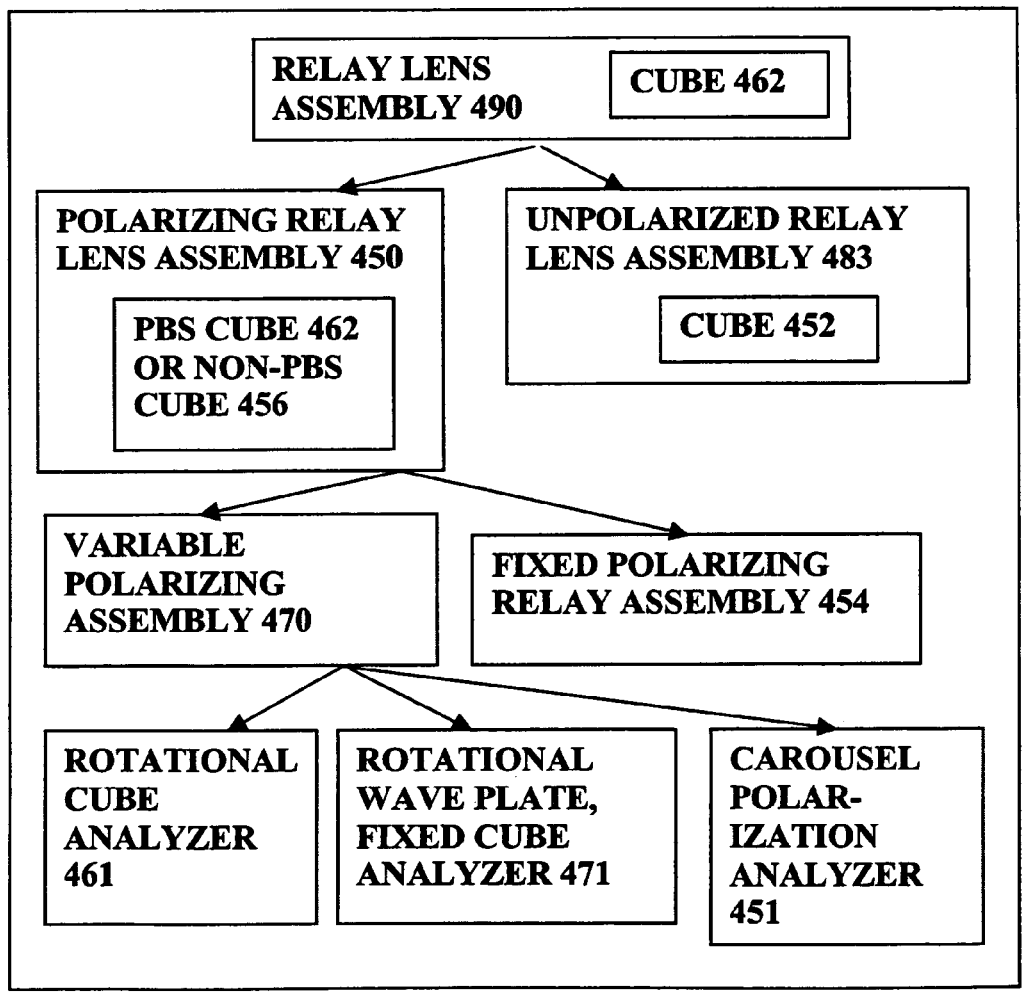
FIG. 72 is a block diagram showing some of the relay lens assemblies 490 contemplated by the present invention.

FIG. 72 is a block diagram showing some of the relay lens assemblies 490 contemplated by the present invention. As seen in FIG. 72, the types of relay assemblies 490, using glass cubes 462 to pass the beam of light into the detection units, may be used at each collector-detector assembly 200 include: 1) unpolarized relay assembly 483, using an unpolarizing cube 452, 2) a fixed polarizing relay assembly 454 that is oriented in a fixed polarization state, and 3) a variable polarization device 470, such as a rotational PBS analyzer 461. The fixed polarizing relay assembly 454 and variable polarization device 470, collectively known as polarizing relay lens assembly 450, may use either a polarizing beamsplitter, such as cube 472 or a polarizing non-beamsplitter cube such as cube 456. The variable polarization device 470 in turn may comprise, for example, a carousel cube assembly, such as rotating carousel polarization analyzer 451, for selecting between "P", "S", and "unpolarized" detector polarization states.

When inspecting surfaces bearing a film, however, such as semiconductor wafers with applied films, the three fixed detector polarization states provided by the rotating carousel polarization analyzer 451 may be insufficient, because some films require ±45° as well as other intermediate polarizer orientation angles in order to achieve the best SNR. One approach to address this is to adjust the polarization of the incident beam in coordination with the detector polarization angle to achieve the optimal detector performance. The optimal SNR is related to both the particle signal peak amplitude and the background level obtained from the film surface. These parameters change for each type of film that is present on the wafer surface. In accordance with another aspect of the invention, new rotational analyzer assemblies are provided to permit the intermediate polarizer orientation angles that are necessary to achieve the optimal SNR when the surface produces circularly polarized scatter. The rotational cube analyzer 461 and rotational waveplate, fixed PBS analyzer 471 both described in detail below, both provide increased variation in polarizer orientation angles.

Figure 27:
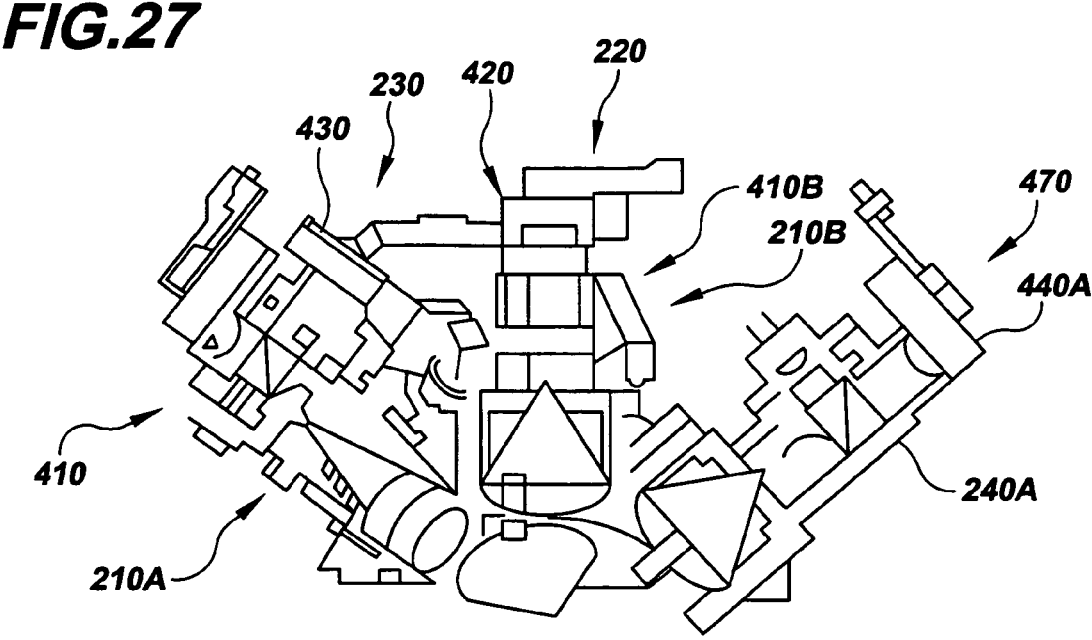
FIG. 27 is a front cutaway view of the collector and detector assembly, showing the operation of polarizing beam-splitters according to present invention.

FIG. 27 shows a cut-away of a collector detector module 200 according to the presently preferred embodiment described herein above, and which comprises a dual detector rotational polarizing cube analyzer 461 that provides P polarization, S-polarization and no polarization, as well as the opportunity to provide combinations therebetween. The analyzer 461, referred to in FIG. 72, has a single polarizing beamsplitter 472 and dual detectors 497, 499. The collector detector assembly 200 on the right hand side is a back collector detector module, such as back collector detector module 240A, and the one on the left is a wing collector detector module, such as wing collector detector module 210A. The assembly in the center is the center collector detector module 220. The front collector detector module 230 also is shown. The PBS cube 472 in each dual PMT assembly 461 can rotate around the detector collector optical axis.

Dual detector rotational polarizer analyzer 461 comprises a single polarization beam-splitter cube 472 and two PMT photodetectors 497, 499. The cube 472 can be rotated to the desired rotational angle around the detector optical axis by manual means, not shown, or motorized means 476. Therefore the PMT signals are directly associated with the orthogonal polarization states. If the polarizer is oriented so that PMT #1 sees "P" light, then PMT #2 will detect "S" light. If PMT #1 detects "+45°" light, then PMT #2 will detect "−45°" light. Furthermore, by electrically adding the signals from both the PMTs 495, the resulting signal is effectively the same as that obtained with no polarizer present (assuming the polarizer is lossless). Consequently, the assembly 470 can simultaneously detect "P", "S", and "Unpolarized" light, or "+45°", "−45°", and "Unpolarized" light, or, more generally, "θ", "θ-90°", and "Unpolarized" light during a single scan of the wafer or surface. The "unpolarized" signal is useful, for example, for scanning bare silicon surfaces and for some film inspection applications.

By adding the signals from the PMTs 495 for the unpolarized signal, one can eliminate the need to mechanically exchange the polarized cube 472 with an unpolarized cube 452. The equivalent optical path should be maintained in the relay lens assembly 470 by including the unpolarized cube 452. If the polarized cube 472 were removed and not replaced with an unpolarized cube 452, the spot would size would not be imaged correctly onto the PMT 495. The sides of the cube 472 or 452 are painted black as well, and it therefore acts as a baffle structure to further reduce stray light. By eliminating the need to exchange the cube 472 or 452, the mechanical design can be simplified and this facilitates modularization.

Detection of COPs Using Polarization Information

The incorporation of an optical collection and detection subsystem 7 comprising a series of collection and detection modules 200 into the surface inspection system 10 enables more optimal use of the beam scanning subsystem 8. For example, some defects (such as scratches) are more readily detectable in signals from a channel 600 formed from output associated with a wing collector 310A, 310B, when it is operated using "S" polarization, than signals from a channel 600 formed from output associated with the wing collector 310A, 310B, when it is operated using "P" polarization, while particles are more readily detected in signals from a channel 600 formed from output associated with the wing collectors 310A, 310B, when they are operated using "P" polarization than signals from a channel 600 formed from output associated with the wing collector 310A, 310B, when it is operated using "S" polarization. By simultaneously providing both signals, the overall defect detection performance of the inspection system 10 can be improved.

When scanning bare polished wafers, the dual detector rotational polarization analyzer 461 preferably is oriented so that one PMT 495 is "P" and the other is "S." In some applications, a variable polarizing assembly 470 is not necessary. In others, however, for example, such as some film inspection applications, polarizer orientation can be and is changed routinely.

In summary, the collection and detection assembly 200 comprises a collector-detector field replaceable unit ("DFRU") 811 configuration of the preferred embodiment of the present invention that is particularly useful in inspecting polished bare wafers using a fixed "P" and "S" relay assemblies 454 in each wing detector module 410A, 410B and unpolarized relay assemblies 483 (comprising unpolarized glass cubes 452) in all of the other detector modules 420, 430, 440A, 440B. The DFRU 811 configuration of the preferred embodiment of the current invention that is particularly useful in inspecting wafers on which films are deposited uses variable polarizing relay assemblies 470 such as motorized dual PMT rotational polarization analyzers 461, in the back detector modules 440A, 440B and wing detector modules 410A, 410B, and unpolarized relay assemblies 483 (comprising unpolarized glass cubes 452) in the center detector module 420 and front detector module 430.

Figure 28:
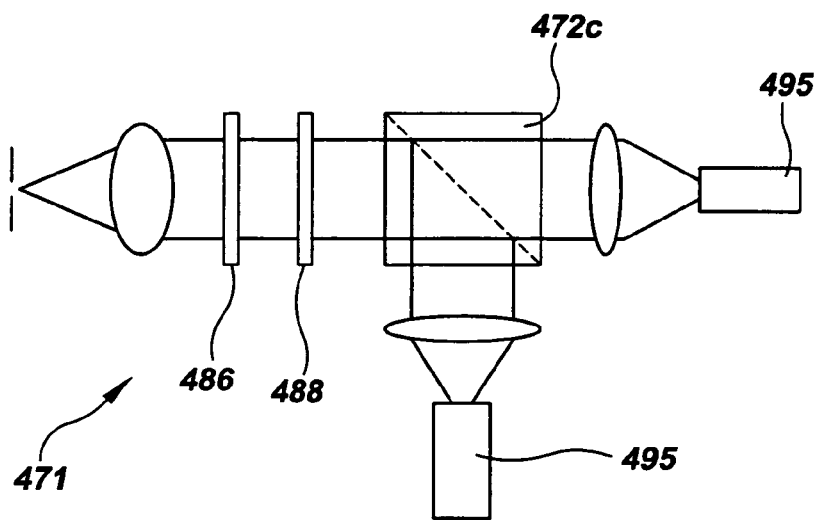
FIG. 28 is an alternative preferred embodiment of the polarizing beamsplitter according to the invention.

A variable polarization analyzer 470 according to a further embodiment is shown in FIG. 28. In this analyzer design, the analyzer 470 comprises a rotational waveplate, fixed beamsplitter polarization analyzer 471 having a polarization beamsplitter ("PBS") cube 472C and dual detectors 495 that are rotationally fixed. A rotatable quarter waveplate ("QWP") 486 and half waveplate ("HWP") 488 are located in front of the PBS cube 472C. This enables the suppression of the background light, as described in U.S. Pat. No. 6,034,776, which is herein incorporated by reference. By using a QWP/HWP combination, linear as well as elliptical polarized light can be substantially attenuated in one of the detectors 497, 499. By making the QWP/HWP combination rotatable, both linear and elliptical polarized light of selectable polarization mixes can be presented to the detectors 497, 499. As before, an unpolarized detector signal can be generated by adding signals from the two PMTs 495.

The polarization filters 450, 470 and non-polarizing assemblies 483 as described here can be used in connection with any of the collectors used in system 10, or any combination of them.

Front Collectors

As noted above, the optical collection and detection subsystem 7 comprises means 250 for developing a light channel, for collecting the specular beam reflected from the surface of the workpiece into a light channel 650, and means 260 for developing a dark channel, for collecting the scatter from the workpiece surface S into a dark channel 655. The means 260 for developing a dark channel further comprises a series of collection and detection modules 200, one of which comprises a front collection and detection module 230. The front collection and detection module 230 and the means 250 for developing a light channel are both generally positioned in the path of the reflected incident beam.

Front collection and detection module 230 comprises a collector and detector assembly having a front collector assembly 330 and a front detector assembly 430. Front collection and detection module 230 is similar to the back collector and detector assembly 240A shown in FIGS. 23-26. Objective lens optics 392 in the front collector 330 focus the incoming scattered (not specular) light to a slit 396, which operates as a field stop to absorb scatter outside of the illuminated localized region of the wafer being scanned. Light then passes to a relay lens assembly 490 in the front detector assembly 430. The front collector 330 is similar to the back collector 430 shown in FIG. 25, with the exception that the slit 396 in the front collector 330 is disposed at the appropriate Schiempflug angle, to match the angle of the image of the wafer surface W. FIG. 25, which shows the back collector and detector module 240A, shows the slit 396 also arranged at the Schiempflug angle that corresponds to the angle of the back collector 340A with respect to the wafer normal. The Schiempflug angle will be different for the back, front, and wing collectors since they are positioned at different angles with respect to the wafer normal. The center collector 330 (or central collector 330) does not have a Schiempflug angle, because it is disposed normal to the wafer surface, and therefore has no Schiempflug condition. For more information about the Schiempflug condition and how the Schiempflug angle is calculated, refer to FIG. 2.21 in *Modern Optical Engineering*, $2^{nd}$ ed., Warren J. Smith (McGraw-Hill, 1990).

Specular Beam Guiding System

In addition, the objective lens optics 392 in the front collector 330 differs from the objective lens optics 392 in the back collector 340A in that front collector objective lens optics 292 also has a light channel assembly 253 comprising an aperture (or hole) 251 (FIG. 22), which is positioned in the front collector objective lens optics 292 at the intersection of the light channel axis LC to permit the specular beam to pass through the optics 292.

Figure 29:
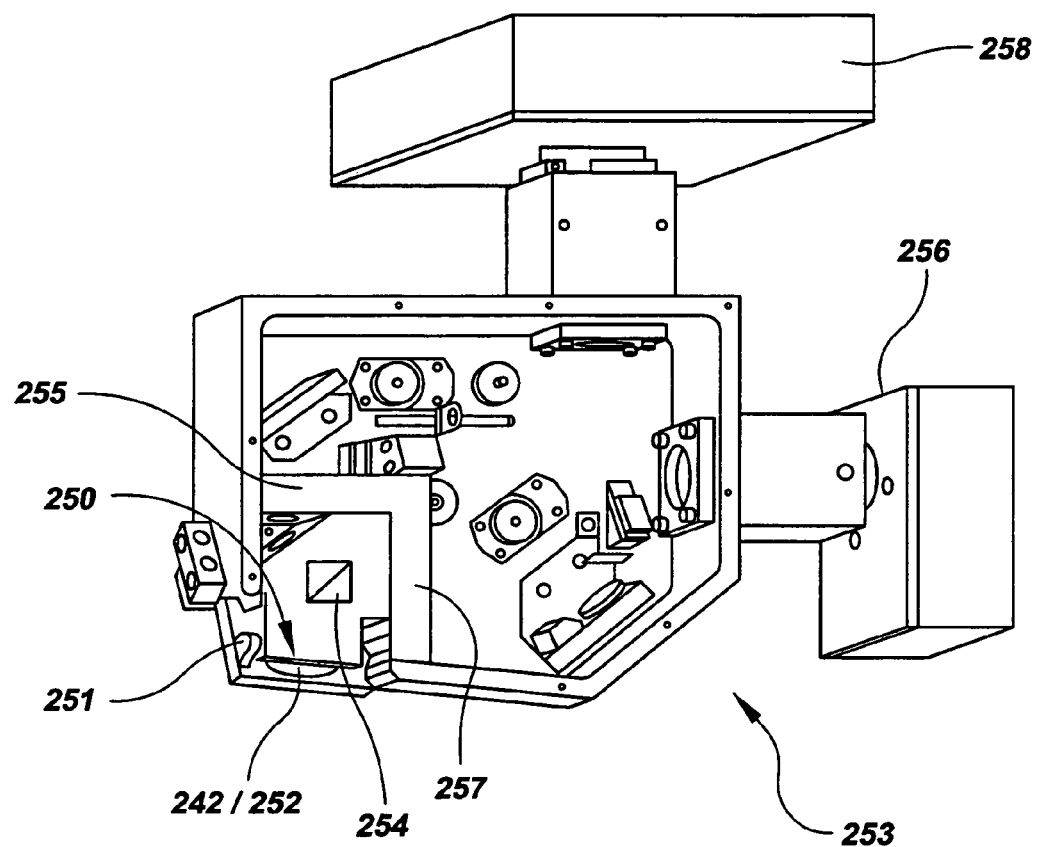
FIG. 29 is a top cutaway view of the light channel optics.

The means 250 for developing a light channel also comprises a light channel assembly 253 that is positioned adjacent to the front collector 330 to receive the specular beam. As shown in FIG. 29, the light channel assembly 253 also comprises an input aperture 251 for receiving the specular beam. The beam passes through an absorptive attenuation filter 252 (composed of glass such as Schott NG4 from Schott Glass). After passing through the attenuator 252, it passes through a 50/50 beamsplitter 254, which splits or evenly divides the beam into transmitted and reflected components. The transmitted component passes through a cylindrical lens 255, such as the SCX-50.8-127.1-C lens from CVI Corporation (Albuquerque, N. Mex.), and is then received at a Linear Position Sensitive Detector (LPSD) 256, such as the SLI5 detector from UDT Sensors, Inc. The LPSD 256 detects the centroid of the target spot TS. The cylindrical lens 255 ensures that the beam does not move during the AOD scan at the LPSD 256, which is located at the telecentric plane.

The reflected portion of the beam from the 50/50 beamsplitter 254 passes through a spherical lens 257, such as the Melles Griot 01LPX282 plano convex lens, and is then is received at a position sensitive detector 258, such as the SPOT-9DMI segmented photodiode detector (or "quad cell") from UDT Sensors, Inc. The quad cell detector 258 is sensitive to movement of the reflected spot caused by both radial and tangential tilt, which is useful for detecting slurry rings, slip lines, and other potentially non-scattering defects that exhibit low spatial frequencies.

Both differences in wafer height and wafer tangential tilt cause the spot to move on the LPSD 256. By linearly combining signals from the quad cell detector 258 and the LPSD 258, the signal component related to tangential tilt can be removed from the LPSD signal, leaving only the signal component related to workpiece height. Determining wafer height relative to the collection optics is important for properly computing the x,y coordinates of wafer defects, since their apparent position with respect to the beam changes with wafer height. Determining wafer height relative to the collection optics is also important to increase knowledge of the wafer and the processes in which the wafer is involved.

Back Collectors

The optical collection and detection subsystem 7 according to another aspect of the invention comprises one or more wing collection and detection modules positioned to collect at least one portion of the scattered light. It is preferable in some applications, such in particle detection, that there be two wing collection and detection modules 240A, 240B, having, respectively, a wing collector assembly 340A, 340B and its associated wing detector assembly 440A, 440B. In some applications, however, it is desirable to collect signal from only one such back collector, or more than two.

As with the center collector 320 and front collector 330, the objective lens optics 392 in back collectors 340A, 340B focus the incoming photons to slits 396, each slit 396, as the slit 396 in the center and front collectors, operating as a field stop to absorb scatter outside the illuminated region of the wafer. Light then passes to the relay lens assembly 490 in the back detector assembly 440A, 440B, associated therewith. The slit 396 in the back collector 340A, 340B is disposed at the Schiempflug angle corresponding to the angle of the back collector 340A, 340B with respect to the wafer normal.

The back collector module or modules are disposed in the back quartersphere BQ, outside the incident plane PI, and at or substantially at a maximum in the signal-to-noise ratio of defect scatter to surface roughness scatter. The wing collectors 310A, 310B may be positioned at or near a null or a minimum in to provide a reduction of noise from Rayleigh scatter. The reduction of Rayleigh scatter is discussed in detail below.

Center Collector

Surface inspection system 10 further also includes a center collection and detection module 220 that, in this embodiment, comprises a center collector 320 located directly above the desired spot on the workpiece surface S (i.e., the center of the inspection table) whose optical axis is aligned to the vector that is normal to the surface S. The center collector 320 in this embodiment is part of a collection and detection subsystem 7 as shown in FIGS. 23-26.

Center collection and detection module 220 comprises a collector and detector assembly 200 having a center collector assembly 320 and a front detector assembly 420. As with the front collector 330, objective lens optics 392 in the center collector 320 focus the incoming photon flux to a slit 396, which, as the slit 396 in the front collector, operates as a field stop to absorb scatter outside the region on the wafer that is illuminated by the scanned laser beam. Light then passes to a relay lens assembly 490 in the center detector assembly 420. The center collector 320 is similar to the back collector 340A shown in FIG. 21, with the exception that the slit in the center collector 320 is disposed normal to the light passing through it because the wafer is disposed normal to the light passing through the center collector 320; therefore there is no Schiempflug condition.

Wing Collectors

The optical collection and detection subsystem 7 according to another aspect of the invention comprises one or more wing collection and detection modules positioned to collect a portion of the scattered light. It is preferable in some applications, such as those involving inspection of bare or unpatterned semiconductor wafers, that there be two wing collection and detection modules 210A, 210B, having, respectively, a wing collector assembly 310A, 310B and its associated wing detector assembly 410A, 410B. In some applications, however, including but not limited to bare or unpatterned wafers, it is desirable to collect signal from only one such wing collector, or more than two.

As with the center collector 320 and front collector 330, the objective lens optics 392 in wing collectors 310A, 310B focus the incoming photons to slits 396 in wing collectors 310A, 310B, each slit 396, as the slit 396 in the center and front collectors, operating as a field stop to absorb scatter outside the illuminated region of the wafer. Light then passes to the relay lens assembly 490 in the wing detector assembly 410A, 410B, associated therewith. A wing collector 310A, 310B is similar to the back collector 340A shown in FIG. 21, with the exception that the slit 396 in the wing collector 310A, 310B is disposed at the Schiempflug angle corresponding to the angle of the wing collector 310A, 310B with respect to the wafer normal rather than at the Schiempflug angle corresponding to the angle of the back collector 340 with respect to the wafer normal.

The wing collector module or modules are disposed in the front quartersphere FQ, outside the incident plane PI, and at or substantially at a maximum in the signal-to-noise ratio of defect scatter to surface roughness scatter. The wing collectors 310A, 310B may be positioned at or near a null or a minimum in surface roughness scatter relative to defect scatter for scattered light from the surface S, or the P component thereof. For example, wing collectors 310A, 310B may be positioned at about a minimum in the bidirectional reflectance distribution function ("BRDF") for the surface when the incident beam is P polarized and the detector assembly 400 is also P-polarized. The calculation of the BRDF is discussed in detail below.

It is desirable to locate the wing collectors 310A, 310B at such locations, for example, because, at these locations, the haze, which may be defined to be the diminished atmospheric visibility that results, in the case of a surface inspection tool, from light scattered from a surface, and which determines background noise (due to BRDF) is minimized, but the defect scatter signals remain, preferably at or near a maximum relative to the noise. The haze or background noise (due to BRDF) is minimized because, when, as in the present invention, the collection optics contains a polarizer that is oriented in local "P" polarization, the light scattered from the surface has "S" orientation. The polarizer that is oriented in local "P" polarization thus counteracts the haze or background noise that has an "S" orientation.

Figure 30:
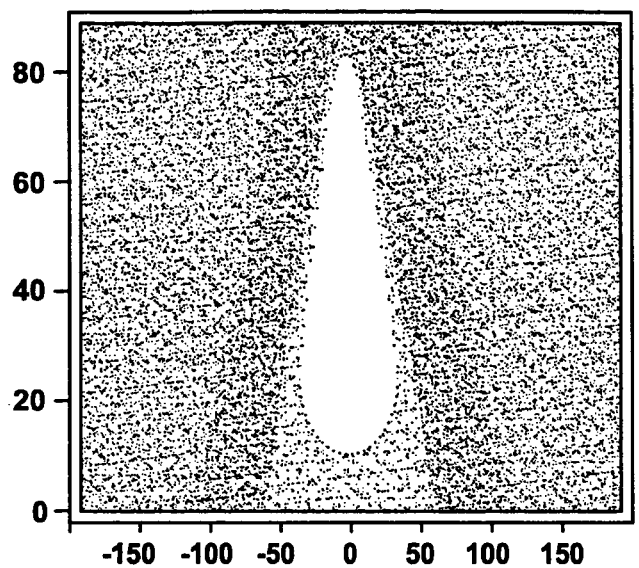
FIG. 30 is a graphical illustration of the bi-directional reflectance distribution function; using linear intensity, for P-polarized light incident on the workpiece surface from an angle of 65 relative to the normal, and for a P-polarized receiver.
Figure 31:
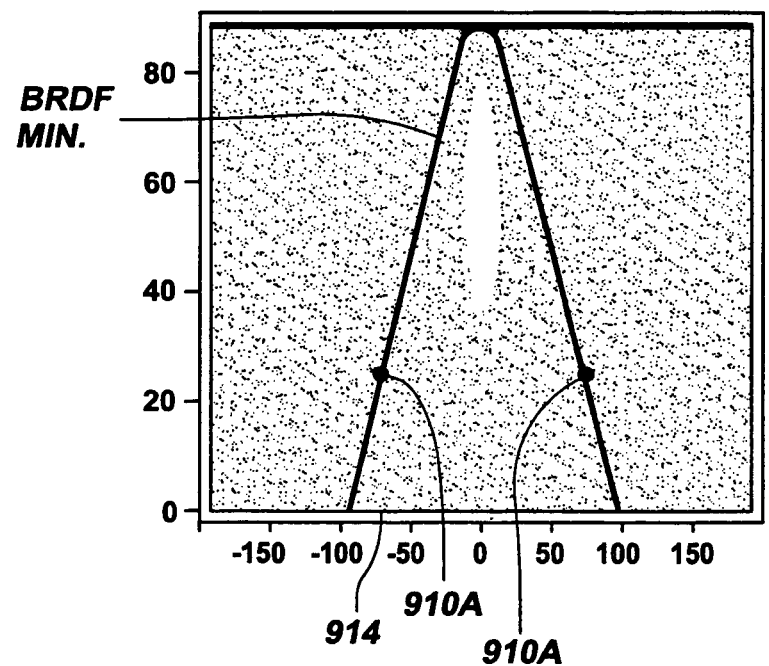
FIG. 31 is a graphical illustration of the bidirectional reflectance distribution function, using linear intensity, for P-polarized light incident on the workpiece surface from an angle of 65 relative to the normal, and for a P-polarized receiver.

Thus, collection at or near a null or a minimum in surface roughness scatter relative to defect scatter, for example, from a defect perspective, at a maximum in the signal to noise ratio of defect scatter to surface roughness scatter when the incident beam is P polarized, or, from a surface roughness scatter perspective, when the surface roughness is at a relative minimum for scattered light from the surface S resulting from the bi-directional reflectance distribution function ("BRDF") of the surface S, or the P component thereof, when the incident beam is P polarized and the detector assembly 400 is also P-polarized, provides an enhanced signal to noise ratio for these signals. This is illustrated by FIGS. 30 and 31. These figures show a BRDF for P-polarized light incident on the workpiece surface S at 650 with respect to the normal vector N, and where beamsplitter 472 is configured to pass P-polarized scattered light to the detector while blocking S-polarized light. FIG. 30 shows the BRDF using linear intensity, and FIG. 31 uses log intensity. In both, the y-axis is representative of the spherical coordinate theta, or an angle of elevation, and the x-axis is representative of spherical coordinate phi, or an azimuthal angle. The location (0,0) is normal to the wafer, and pointing along the optical axis of the center collector 320. From these graphs one may identify the local minima or nulls of the BRDF (hereinafter referred to as $BRDF_{MIN}$), and correspondingly select a location for the wing collectors, in terms of azimuth and elevation. Referring particularly to FIG. 31, one can see BRDF$_{MIN}$ as the darker region extending upward from the x-axis to the point (0,80) and then downward toward the x-axis again. Points 910A, 910B identify one combination of angles of elevation and azimuth for placing, respectively, the collectors 310A, 310B at locations in which haze which determines background noise is minimized. Specifically, the coordinates of points 910A, 910B define the angles of elevation and azimuth for such preferred placement. Once the decision is made to place the wing collectors 310A, 310B at a selected angle of elevation 912, the collectors' azimuthal placement is determined by the x-coordinate of the two locations of the BRDF$_{MIN}$ associated with the elevation angle 912s, namely azimuthal angles 914, 916, and the combination of desired angles are defined by the coordinates of points 910A, 910B.

The optical collection and detection subsystem 7 further comprises a pair of wing collection and detection assemblies 210A, 210B positioned in the front quartersphere FQ but outside the incident plane PI. Wing collectors 310A, 310B are substantially identical to one another. Each comprises a portion of a collection and detection assembly 200 as shown in FIGS. 23-26. Wing collectors 310A, 310B in this embodiment are located symmetrically with respect to the incident plane PI, and when they have identical focal lengths, they are equidistant from a point on the light channel axis LC and equidistant from the surface S of the workpiece W. This also applies where multiple pairs of wing collectors are used. Wing collectors 310A, 310B are positioned to receive a desired and preferably optimal or near optimal amount of light scattered from defects on the workpiece surface S. By positioning the wing collection and detection assemblies 210A, 210B out of the plane of incidence PI, the amount of light coupled into the wing detector assemblies 410A, 410B associated with wing collectors 310A, 310B due to Rayleigh air scatter is reduced, thereby reducing the background light and improving the signal to noise ratio (SNR).

The optical collection and detection subsystem 7 uses P-polarized incident light at 65° of incidence, as noted above. The scattered light from an optically smooth surface exhibits a minimum at a specific angle if the optical detector detects only P-polarized light since the surface roughness scatter from the wafer is S-polarized when the incident beam is P-polarized for the desired wing collector locations. This is only true for surfaces that exhibit Rayleigh-Rice scatter, as described in *Optical Scattering Measurement and Analysis* 2nd ed., John C. Stover, (SPIE Optical Engineering Press 1995) (hereinafter the Stover reference). This effect is shown in the plots in FIGS. 24 and 25. These plots were derived from Equations 4.1 and 5.12-5.17 in *Optical Scatter*. The null is the multi-dimensional equivalent of the Brewster angle. The location of the null, therefore, is dependent upon the index of refraction of the surface.

The wing collectors 310A, 310B of the wing collection and detection modules 210A, 210Bs of the optical collection and detection system 7 are also designed and placed to provide, along with the front collector 330 of the front collection and detection module 230, symmetrical and nearly complete collection of forward scattered light. This can improve the scratch detection performance of the system.

The collection angle of wing collectors 310A, 310B in the present embodiment are about 26° (half angles of about 13°). As stated above, the spherical angle corresponding to the desired surface roughness scatter null will be dependent on the index of refraction of the material. For some types of surfaces, it may be desirable to increase the size of the wing collectors 310A, 310B to 30 degrees or more and adjust the angular position of the optical axis for optimal SNR. Note that the detector assembly 400 design incorporates selective subaperture masking ("virtual mask 131," described below), which can enable selective subaperture collection to collect light only from angular regions where the SNR is highest.

The first wing collector 310A is positioned with an azimuth angle with respect to the light channel axis LC of about 5 to 90°, and the second wing collector 310B is positioned at an azimuth angle with respect to the light channel axis LC of about −5° to −90°. The azimuth angles used in the presently preferred embodiments are about +50 and −50 degrees. It should be noted that, in referencing the positioning of the collectors 300 herein, the angular position of the collector 300 is measured to a central point on the central axis of the collector 300, i.e., an optical axis of the lens corresponding to the axis of the optical path of the beam as it passes through the center of the lenses in the collector's objective lens optics 392.

The wing collectors 310A, 310B preferably have an elevation angle with respect to the surface S of the workpiece W of about 30° to 90°. In the presently preferred embodiments and method implementations, the elevation angle of wing collectors 310A, 310B is about 45°.

In the preferred embodiments and implementations, a polarizing beamsplitter in each of the wing collection and detection modules 210, 210B, such as the beamsplitter 472 illustrated in FIGS. 23-26, is disposed in the relay lens assembly 490 at the input to each wing detector assembly 410A, 410B that is associated with a wing collector 310A, 310B, i.e., in the optical path of the region between the desired spot and the wing detector assembly associated with a wing collector or collectors 310A, 310B. This enables one of the detectors 497, 499 of the collection and detection assemblies 210A, 210B to receive solely P-polarized radiation, and thereby take full advantage of this effect.

In accordance with this aspect of the invention, the method for locating the positions of the wing collectors 310A, 310B can be further explained and elaborated upon. U.S. Pat. No. 6,034,766 describes the use of a plurality of small solid-angle collectors over the surface of a scattering hemisphere to detect defects on a microrough surface. The patent indicates that large number of these collectors should be employed to cover a large solid angle. The patent also suggests that a polarization analyzer should be employed at each collector to be orthogonal to the scatter from microroughness so as to maximize signal-to-noise ratio.

The '776 patent fails to take into account two concerns that often are present in such systems. First, while each collector can be set to be "microroughness-blind," the detectors will still be subject to Rayleigh scatter from the molecules of air near the surface of the workpiece. Rayleigh scatter is the scatter of light off the gas molecules of the atmosphere, principally Nitrogen for normal air. When surface inspection systems are operated in air, the illumination source generates Rayleigh scatter. This effect can be reduced by operating in partial vacuum, or by use of a gas with lower scattering cross-section such as Helium. Because both of methods for reducing Rayleigh scatter are difficult and expensive to implement, typically surface inspection systems are operated in air. Therefore, each collector in such systems has a constant background flux caused by Rayleigh scatter from the atmosphere. Even though Rayleigh scatter is a relatively small scatter component compared to surface roughness scatter, it is more significant, especially in the back collector of a multi-collector surface inspection system such as system 10, when the surface scatter level is relatively low, for example when wafer surfaces with an extremely good polish are inspected.

(See "A Goniometric Optical Scatter Instrument for Bidirectional Reflectance Distribution Function Measurements with Out-of-Plane and Polarimetry Capabilities", Germer and Asmail, from "Scattering and Surface Roughness," Z.-H. Gu and A. A. Maradudin, Editors, Proc. SPIE 3131, 220-231 (1997)). Second, building a system with a large number of collectors usually is expensive, difficult to set up and difficult to maintain. Furthermore, by setting the polarizer in each detector to minimize the background from surface roughness scatter, some detectors will also substantially reject important defect signal as well. The shot noise of the low level signals result in large defect voltage variations that could be confused with voltage signals representative of defects.

Because of the high cost associated with using a large number of collectors, it is desirable to reduce the number of collectors in the system. In accordance with this aspect of the invention, this objective can be achieved by placing the collectors at the locations on the scattering hemisphere where they can achieve the greatest advantage. Thus, the collectors are placed where they will have the highest signal-to-noise ratio for a selected range of workpiece surfaces and materials.

Because of the presence of the Rayleigh scatter from molecules in the atmosphere, each collector will have a constant background flux due to the Rayleigh scatter. Measuring photon flux has an inherent unavoidable noise associated with it called "shot noise." It is expected that shot noise will be present in any surface inspection system. When the collectors are operated in air, the shot noise in the output associated with P-polarized wing collectors tends to be dominated by Rayleigh scatter. The shot noise in the output associated with the back collectors tends to be dominated by surface roughness scatter.

Shot noise consists of random fluctuations of the electric circuit in a photodetector, which are caused by random fluctuations that occur in the detector or by fluctuations in the number of electrons (per second) arriving at the detector. The amplitude of shot noise increases as the average current flowing through the detector increases. The flux measurement is really counting a rate of how many photons per second are collected by the detector. The longer the period of counting, the more accurately one can measure the rate. It can be shown that the power-equivalent noise from the Rayleigh scatter is given by:

$$\sigma_{Rayleigh}^2 = 2E_{photon}P_{Rayleigh}XBW/QE,$$

where
  $\sigma_{Raleigh}^2$ is the variance of the measured Rayleigh scatter at the detector (in Watts$^2$),
  $E_{photon}$ is the energy of each photon in Joules,
  $P_{Rayleigh}$ is the Rayleigh scatter present at the detector (in Watts),
  QE is the quantum efficiency of the detector (dimensionless),
  BW is the bandwidth of the measurement system (in Hz—equivalent to 1/sec), and
  X is the excess noise factor of the detector (dimensionless).
Furthermore, this noise is nearly Gaussian whenever $$\frac{QE\sigma_i^2}{E_{photon}} \gg 1.$$

For practical scattering systems, this ratio is typically several hundred. We see that the RMS noise level (square root of variance) can be given by: $\sigma_{Rayleigh} = K\sqrt{P_{Rayleigh}}$, where K encompasses system contributions to noise, such as bandwidth, quantum efficiency, excess noise factor and photon energy. A defect particle will scatter with power $P_{particle}$. To maximize the signal-to-noise ratio (SNR), we maximize $$\frac{P_{particle}}{K\sqrt{P_{Rayleigh}}}.$$

Note that the optical powers $P_{particle}$ and $P_{Rayleigh}$ are functions of incident wavelength, incident polarization, particle size, particle material, substrate material, incident declination angle, collector solid angle, collector declination angle and collector azimuth angle. These scatter powers are also controlled by the polarizer at the collector, which preferably is set to null the scatter from microroughness. For typical designs, the incident wavelength and incident declination angle are fixed. The collector solid angles are also fixed, and typically small. We now want to find the locations to place collectors 300 on the scattering hemisphere that maximize SNR.

In this illustrative example, silicon is used as the substrate or surface to be inspected. Using a beam having a wavelength fixed at 532 nm, an incident declination of 65 degrees, and p-polarization for the incident beam, the SNR plots for a small variety of particle sizes and materials can be shown. While the actual SNR values depend heavily on particle size and particle material, the scattering hemisphere locations of maximum SNR change very little. This can be used in accordance with this aspect of the invention to set the locations of the wing collectors 310A, 310B, e.g., using "microroughness-blind" collectors that are positioned according to their maximum SNR regions based solely upon incident wavelength, incident declination, incident polarization and substrate material.

Using this method, and in the particular case of a 532 nm beam source, a 65 degree incident declination, and p-incident polarization on a silicon substrate, the wing collectors 310A, 310B are placed in the regions of 40-70 degrees of declination, and either 40-70 degrees azimuth or 290-320 degrees azimuth to maximize SNR.

In order to fit the collectors 300 into the space above the wafer W, it may become necessary to cut sections out of the collectors 300. Cuts may be seen in FIG. 22. As noted above, the output signal associated with the wing collectors 310A, 310B may be combined with output signals associated with selected other collectors 300 in order to provide improved defect detection and/or classification. Specifically, as will be described in further detail below, the back collectors 340A, 340B and P-polarized wing collectors 310A, 310B receive proportionately more signal from particles on the wafer surface than they receive from pits on the wafer when scanning defects <100 nm in size and using P-incident polarized light. Therefore, in order to facilitate the identification of pits on the surface of the wafer, it is preferable to cut as little as possible from the center collectors 320 (preferably no more than about 10%).

Collector System with Back and Wing Collectors

In accordance with another aspect of the invention, an optical collection system is provided for use in a surface inspection system 10 such as those described herein. In this aspect of the invention as in others, the surface inspection system 10 has an incident beam projected through a back quartersphere BQ and toward a spot on the surface S of the workpiece W so that a specular portion of the incident beam is reflected along a light channel axis LC in a front quartersphere FQ. The optical collection system according to this aspect of the invention preferably comprises a subsystem of a surface inspection system 10. Thus, to illustrate and further describe this aspect of the invention, a presently preferred optical collection system embodiment will be described in the form of an optical collection subsystem 380 of system 10. It will be appreciated, however, that the optical collection system is not necessarily limited in this respect.

In accordance with this aspect of the invention, an optical collection subsystem is provided that comprises a plurality of back collectors positioned in the back quartersphere BQ and outside the incident plane PI for collecting scatter from the workpiece surface. The number of back collectors may vary depending upon the application. Preferably there are two such collectors, such as collectors 340A, 340B. The back collectors 340A, 340B preferably are substantially identical to one another. Where more than two back collectors 340A, 340B are employed, it is preferred that they be used in pairs, and positioned symmetrically with respect to one another and with respect to the incident plane for a given pair. The back collectors 340A, 340B also preferably are located symmetrically with respect to the incident plane PI, and, when they have identical focal lengths, they are equidistant from the incident plane PI and the desired spot on the workpiece surface S, in general or at least for given pairs of the collectors 340A, 340B.

As with the center collector 320 and front collector 330, objective lens optics 392 in the back collectors focuses the incoming beam to a slit 396, which operates as a field stop to absorb scatter outside the illuminated scan region of the wafer being scanned. Light then passes to a relay lens assembly 490 in the detector assembly 400. While the slit 396 in the center collector 320 was disposed normal to the light passing through it, in the back collector, the slit 396 is arranged at the Schiempflug angle, to accommodate for the angle of the back collector with respect to the wafer normal. FIG. 25, which shows the back collector 340A, shows the slit 396 arranged at the Schiempflug angle corresponding to the angle of the back collector 340A with respect to the wafer normal.

Back collectors 340A, 340B according to this aspect of the invention preferably are positioned at azimuth angles of up to about 90°, and more preferably about 10° to 90°, with respect to incident plane in the back quartersphere BQ. These angles equate to about 90° to 180° and about 90° to 170°, respectively, with respect to the light channel axis LC. Azimuth angles of at least about 45° to 55° are even more preferred, particularly in semiconductor wafer surface inspection systems, for example, such as system 10.

The presently preferred elevation angles for back collectors 340A, 340B according to this aspect of the invention are about 35-60 degrees with respect to the workpiece surface S. More preferably, the elevation angles of the back collectors 340A, 340B are about 53° with respect to the workpiece surface normal vector.

The collection angle of back collectors 340A, 340B according to this aspect of the invention preferably are about 20° to about 60° (i.e., half angles of about 10° to about 30°), and more preferably about 60° (i.e., half angle of about 30°).

As implemented in the presently preferred embodiments, an optical collection subsystem is provided with two back collectors 340A, 340B. Collector 340A is positioned at an azimuth angle of 55° with respect to the projection of the incident beam on the surface in the back quartersphere. Collector 340B is positioned at an azimuth angle of about −55° with respect to this same incident beam projection. In this embodiment of an optical collection subsystem, collectors 340A, 340B are equidistant from the surface S of the workpiece W, and each has an elevation angle with respect to the desired spot on the surface S of about 53°. When scanning polished wafer surfaces, the relay lens assembly 490 in back detectors 440A, 440B associated with back collectors 340A, 340B uses unpolarized cubes. When scanning films, a rotating analyzer 472 such as described above can be used to minimize background from the film surface in some applications.

Front Collectors, Contd.

Switchable Edge Exclusion Mask

In accordance with another aspect of the invention, a switchable edge exclusion mask 132 is provided in the front collector 330 in order to cover the region of the objective lens optics 292 between the specular beam hole 251 and the outer edge of the lens L1. It is frequently desirable to scan the edge of a workpiece W, e.g., a silicon wafer, to calculate or determine such things as the placement of the wafer with respect to the center of rotation, to look for edge chips, etc. Unfortunately, the wafer or workpiece edge typically is beveled in such a way that the laser beam may be reflected directly into the front collector 330. This can cause the detector or detectors 497, 499 in the detector 430 associated with the collector 330 to saturate, and can actually damage them in some cases, e.g., the anode of the PMTs 495. To limit or prevent this, an edge exclusion mask 132 according to this aspect of the invention may be placed in front of the front collector 330 to absorb the specularly reflected beam as it scans across the edge of the wafer W.

In accordance with this aspect of the invention, switchable edge exclusion mask 132 is provided. In an illustrative but not necessarily preferred embodiment of this aspect of the invention, switching is performed electro-mechanically.

Figure 32:
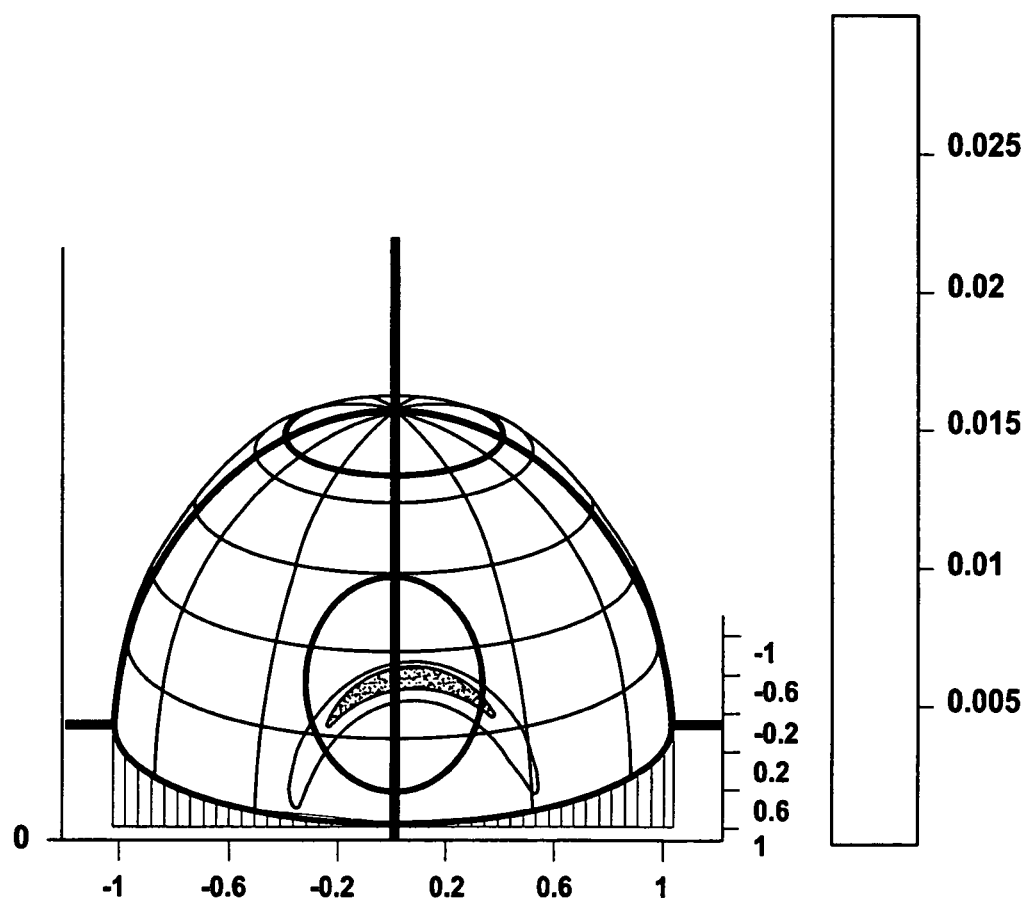
FIG. 32 is a scratch scatter distribution diagram.

Using an edge exclusion mask 132 can substantially reduce the edge exclusion zone on the wafer (the region over which data can be reliably collected near the edge of the wafer). Unfortunately, however, it also can reduce the sensitivity of the front collector 330 to scratches that are perpendicular to the AOD scan direction. An example of this is shown in FIG. 32, which shows a scratch distribution plot. This problem can be minimized using a switchable edge exclusion mask 132 as described herein.

Figure 33:
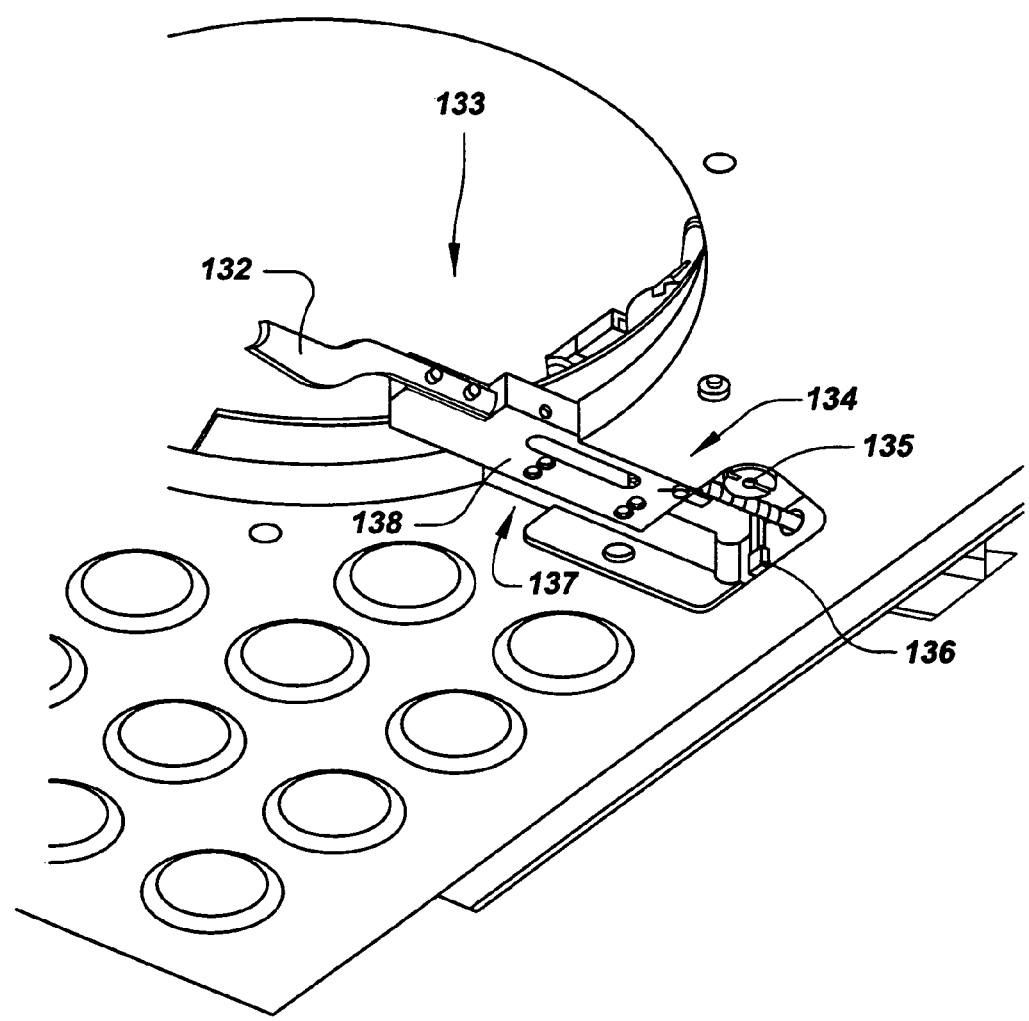
FIG. 33 is a bottom view of the collection and detection module for the system of FIG. 1, and shows the switchable edge exclusion mask according to another aspect of the invention.

A mask 132 according to this aspect of the invention is illustrated in FIG. 33. Mask 132 is normally energized so that it is outside the collection field of the front collector 330 when scanning the interior of the workpiece surface S. This maximizes the front collector collection efficiency, and enables complete collection of scratches that are perpendicular to the AOD scan direction. When the AOD scan approaches within 1-3 mm of the edge of the scan, the mask 132 is electromechanically moved in front of the lens and blocks the scatter and reflection from the wafer bevel.

The mask 132 is designed to cover the region of the front collector lens between the specular beam hole and the outer edge of the lens. The mask 132 is connected to an electromechanical means 133 having an edge exclusion actuator 137 for moving the edge exclusion mask 132. A sensor 136 is employed to sense the position of the mask, enabling the control computer 500 (described more fully herein below) to sense if the edge exclusion actuator 137 is working correctly. The electromechanical means 133 for moving the edge exclusion mask 132 could comprise a rotary motor, a two-position motor, a stepper motor, a DC servo motor, or a pneumatic means. In an illustrative but not necessarily preferred embodiment of this aspect of the invention, as illustrated in FIG. 33, the electromechanical means 133 comprises a drive mechanism 134 with a drive mechanism stage 138 and an air drive 135 for holding and moving the edge exclusion mask 132.

Edge exclusion masks 132 in accordance with this aspect of the invention advantageously can enable one to obtain a small edge exclusion zone near the edge of the wafer or workpiece surface S without sacrificing overall front collector sensitivity.

Moveable, Switchable Virtual Mask

In accordance with still another aspect of the invention, a moveable, switchable virtual mask 131 is provided. Most of the optical scatter from a semiconductor wafer or similar workpiece is produced by the lowest spatial frequencies, and is therefore confined to a small angular range around the specular beam in the forward scatter direction. This background scatter tends to dominate the signal detected by the front collector PMT 495, masking the presence of critical defects, such as microscopic scratches, that comprise higher spatial frequencies. Defects associated with higher surface structure spatial frequency content generally scattered light into larger angles with respect to the specular beam. It is possible to partially or fully absorb or otherwise exclude excessive scattered light associated with low surface structure spatial frequency from the wafer surface using an appropriate masking device.

In past inspection systems, in order to improve the defect detection performance of the front collector, an elliptical mask was installed in front of the lens to block this scatter. The mask was elliptically shaped in order to block the light scattered from surface structures of low spatial frequency relative to the collection geometry for the in-scan and cross-scan directions (based on the 2D grating equation expressions in the Stover reference, page 75). However, the placement of the black anodized aluminum mask in front of the lens in the front collector tended to reflect scatter back to the wafer, therefore introducing additional scatter into other detectors 497, 499.

In addition, when introducing such a mask, however, it is often undesirable to position the mask in front of the collection lens since this would scatter light back to the test surface. The mask in this instance can block desired light that includes important information about the surface. For example, it is desirable to detect "flat particles" shallow bumps or dimples whose aspect ratio is large, With diameters greater than 1 micron and heights of a few nanometers. These defects scatter light associated with a lower surface structure spatial frequency range (near the specular beam) than do typical spherical defects <100 nm in diameter. Therefore, when scanning a wafer for flat particles or dimples, it may be desirable to use a mask that blocks scattered light associated with higher or lower surface structure spatial frequencies than those associated with the defects of interest in the front collector but allows the scattered light associated with these particular defects to pass through to the detector 497 or 499.

In order to enable the system to optimally detect either small particles or flat particle defects, a moveable, switchable virtual mask 131 is provided according to this aspect of the invention. Switching and moving a virtual mask 131 can allow the user to select the angular range of light that must be masked based on the surface structure spatial frequency content of the wafer or other like surface, and can allow optimization of defect sensitivity for defects that have unusual angular scatter distributions.

Figure 34:
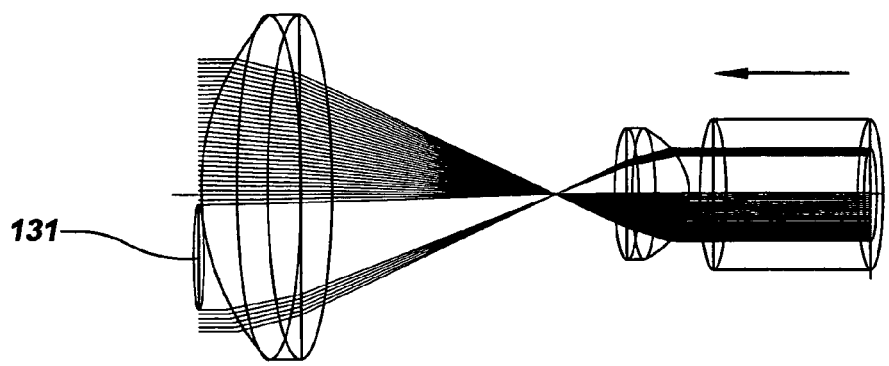
FIG. 34 is a side view ray trace through the collection optics which shows the effects of a virtual mask in accordance with another aspect of the invention.
Figure 35:
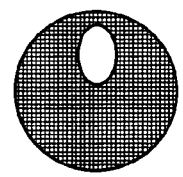
FIG. 35 is an axial view of the ray trace of FIG. 34.
Figure 36:
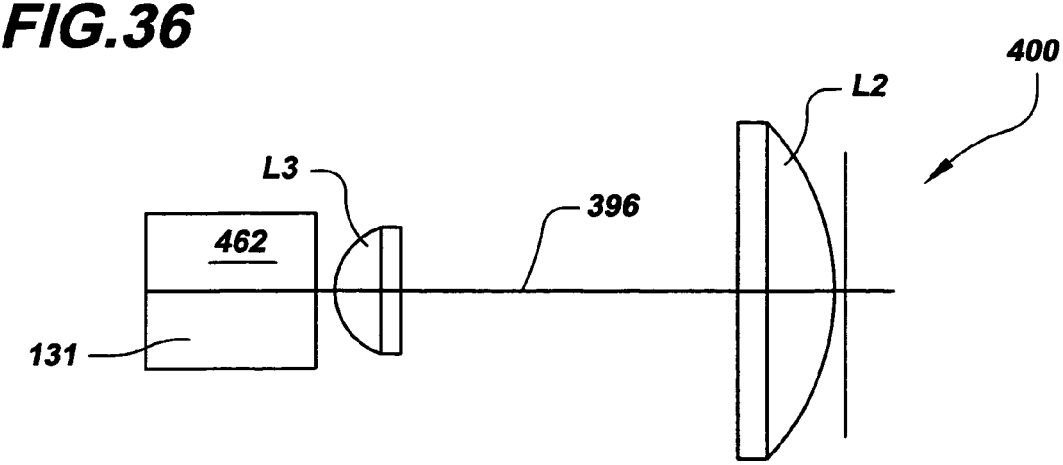
FIG. 36 is a ray trace through the collection optics of a given one of the collectors.

A virtual mask 131 according to a presently preferred yet merely illustrative embodiment of this aspect of the invention is shown in FIGS. 34 and 36. The virtual mask 131 comprises a black or otherwise light absorbing glass mask, preferably elliptical in shape, which is optically bonded to the glass cube 462 that is located in the detector relay lens assembly 490 of the detector module 430. Alternatively, the mask 131 could comprise a black anodized aluminum sheet metal mask that is positioned in a correct optical imaging position in the detector module 430, which is located along the beam path after the collector module 330.

The virtual mask 131 is used to block the scatter near the specular beam. As shown in FIG. 34, scattered light from the wafer or other workpiece surface S is collected by the collector 200 over the solid angle subtended by the objective lens optics 392. After the light travels through the objective lens optics 392, it passes through a slit 396, and then to the cube 462, which may comprise polarizing beamsplitter 472, polarizing cube 456, or unpolarized cube 452. Light that reaches the virtual mask 131 is blocked from reaching the PMT 495.

Scatter that is reflected off of the mask 131 is minimized by the manner in which the virtual mask 131 is attached to the cube 462 and by the placement of the mask 131 after the slit 396. Since the black glass piece that comprises the virtual mask 131 is bonded to the cube glass 396 with index-matching optical cement, the optical interface between the black glass mask 131 and cube 396 exhibits minimal scatter. In addition, any residual scattered light that bounces back from the mask 131 must pass through the slit 396 to pass back through the collector 330 and arrive at the wafer W, and is therefore substantially reduced relative to prior known systems.

In the presently preferred yet merely illustrative embodiment, as shown in FIG. 36, the black glass piece mask 131 is located at an x-y position within the front collector detector module 230 slightly off the optical axis, mapping the specular beam, in order to force the mask to be coincident on the specular beam hole 251. The location of the black glass mask 131 at a z-position such that the real image of the black glass mask 131 is located between the two aspheric objective lenses L1, L2 causes the glass piece to comprise a "virtual mask" rather than a physical mask that is in front of the objective lens optics assembly 392 of the front collector 330.

The virtual mask 131 shown in FIGS. 34 and 36 is fixed (bonded to the back of the cube). It may be rendered switchable by exchanging a mask (such as an aluminum mask) in/out of the desired position, for example, by manually replacing the glass cube 362 in the detector module 430. The only way to move it is to either or Alternatively, the virtual mask 131 is rendered switchable and moveable by moving the glass cube 362 into another location, for example, using a carousel approach. As noted above, in the presently preferred yet merely illustrative embodiment of this aspect of the invention, the virtual mask 131 is a black glass piece, which is optically bonded to the glass cube 362 that is located in the relay lens assembly 490 of the detector module 430. As noted above, in the presently preferred yet merely illustrative embodiment of this aspect of the invention, the polarizing beam splitter glass cube 472 is switchable to provide variable polarization. As the glass cube 472 is moved, so is the glass piece mask 131 attached to it.

Figure 37:
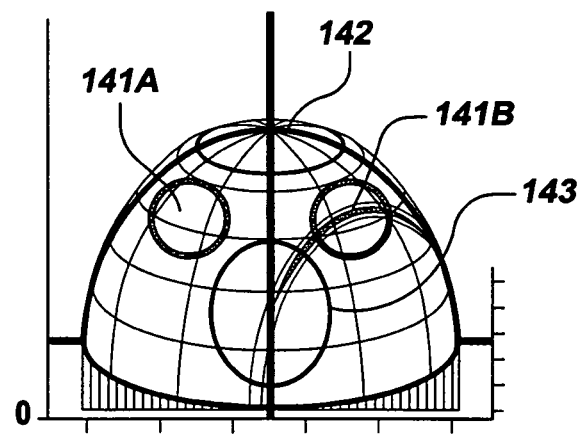
FIGS. 37-38 are scratch scatter distribution diagrams.
Figure 38:
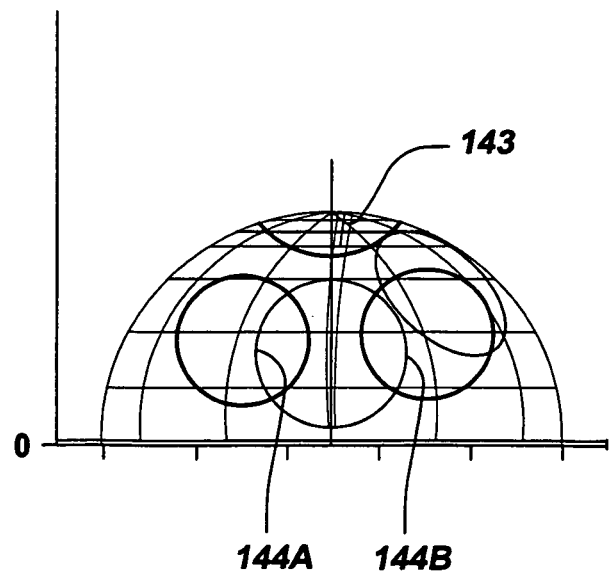

Although the virtual mask 131 according to the presently preferred embodiment is depicted only in the front detector module 430, it can be used in any of the detector assemblies 400 to either limit the solid angle collection range of the detector module 400 or to mask off unwanted solid angles. The solid angle range of collection is specified by the size and shape of the virtual mask 131. Annular virtual masks can be used to reduce the effective solid angle of collection of the detector module 400. Other shapes may be used to collect the desired light from a sub-region of the lens assembly. The virtual mask 131 could also be employed in the wing collection and detection modules 210A, 210B to limit collection of the scattered light associated with surface structure spatial frequency spectrum to only a defined sub-region of a workpiece region wing. The wing collection and detection modules 210A, 210B of preferred system 10 as described herein are optimized to detect light within the BRDF null (BRD-$F_{MIN}$) while achieving reasonable sensitivity to 45 degree scratch signals. As shown in the surface structure spatial frequency plot of FIGS. 37-38, the wing collectors are designed to cover a portion of the surface structure spatial frequency spectrum between the front collector 330 and back collectors 340A, 340B. FIG. 37 shows the front collector surface structure spatial frequency spectrum coverage 143, the wing collectors' surface structure spatial frequency spectrum coverage 141A, 141B, and a portion of the center collector surface structure spatial frequency spectrum coverage 142. FIG. 38 shows the back collectors' surface structure spatial frequency spectrum coverage 144A, 144B and the remainder of the center collector surface structure spatial frequency spectrum coverage 142.

If in a particular application it is desirable or necessary to achieve more complete wing collectors' surface structure spatial frequency spectrum coverage 141A, 141B in the region between the front collector surface structure spatial frequency spectrum coverage 143 and back collectors' surface structure spatial frequency spectrum coverage 144A, 144B, in order to provide fuller coverage of this region, an aspheric lens design can be used in this region if the azimuth angle is increased to about 60 degrees. In certain semiconductor wafer applications there are primarily three reasons for collecting a sub-region of this region: 1) the BRDF null would be located to one side of the lens if the azimuth angle were set to 60 degrees, 2) the location of the BRDF null is dependent upon the index of refraction of the material, therefore it can move to slightly different locations for different materials, and 3) Rayleigh scatter adds an additional background contribution that can increase the overall background light collected by the wing (or other) collector and can partially shift the effective location of the BRDF null. It also may be desirable to use the virtual mask 131 in the relay to collect a sub-region of the wing collector surface structure frequency spectrum 141A, 141B to compensate for these three effects. As with the virtual mask 131 in the front collection and detection module 230, the virtual mask 131 could be moveable or it could be selectable in a carousel fashion in order to collect a sub-region of the wing collector solid angle for optimal SNR.

Signal Processing Subsystem

Signal Processing Architecture

A number of the systems and their illustrative but not necessarily preferred embodiments as disclosed herein comprise a processing subsystem or module 19 operatively coupled to an optical collection and detection subsystem or module 7 for processing the signals generated by light detection. This processing module 19 performs processing on the signals obtained from the optical collection and detection subsystem 7 to provide desired information concerning the surface S of the workpiece W under inspection, such as its geometry, characteristics, defect information, and the like. The processing system 19 as implemented in the illustrative but not necessarily preferred embodiment comprises a controller such as system and processing unit 500.

As best illustrated in the perspective view of FIGS. 3 and 4, the surface inspection system 10 preferably is computer controlled. The system controller and processing unit 500 operates the inspection system 10 under the supervision and direction of a human operator, stores and retrieves data generated by the system 10, and performs data analysis preferably responsive to predetermined commands. The relative position of the article being inspected is communicated to the system controller 500 via motors, not shown, and encoders, not shown, mounted thereto. The position data is transmitted to the gauge synchronization control 186, which responsively drives the AO deflector 100 via an AOD scan driver 950.

As understood by those skilled in the art, data signals from the collectors are conventionally electrically communicated to the processing electronics 750. The processing electronics 750 could comprise digital electronics (not shown) and analog electronics comprising an Analog Combining Board (not shown) for processing the signals, such as that described in the '701 patent. In a presently preferred yet merely illustrative embodiment, the signals are processed digitally using the data processing system shown as system controller and processing unit 500 in block diagram form in FIG. 46.

Figure 46:
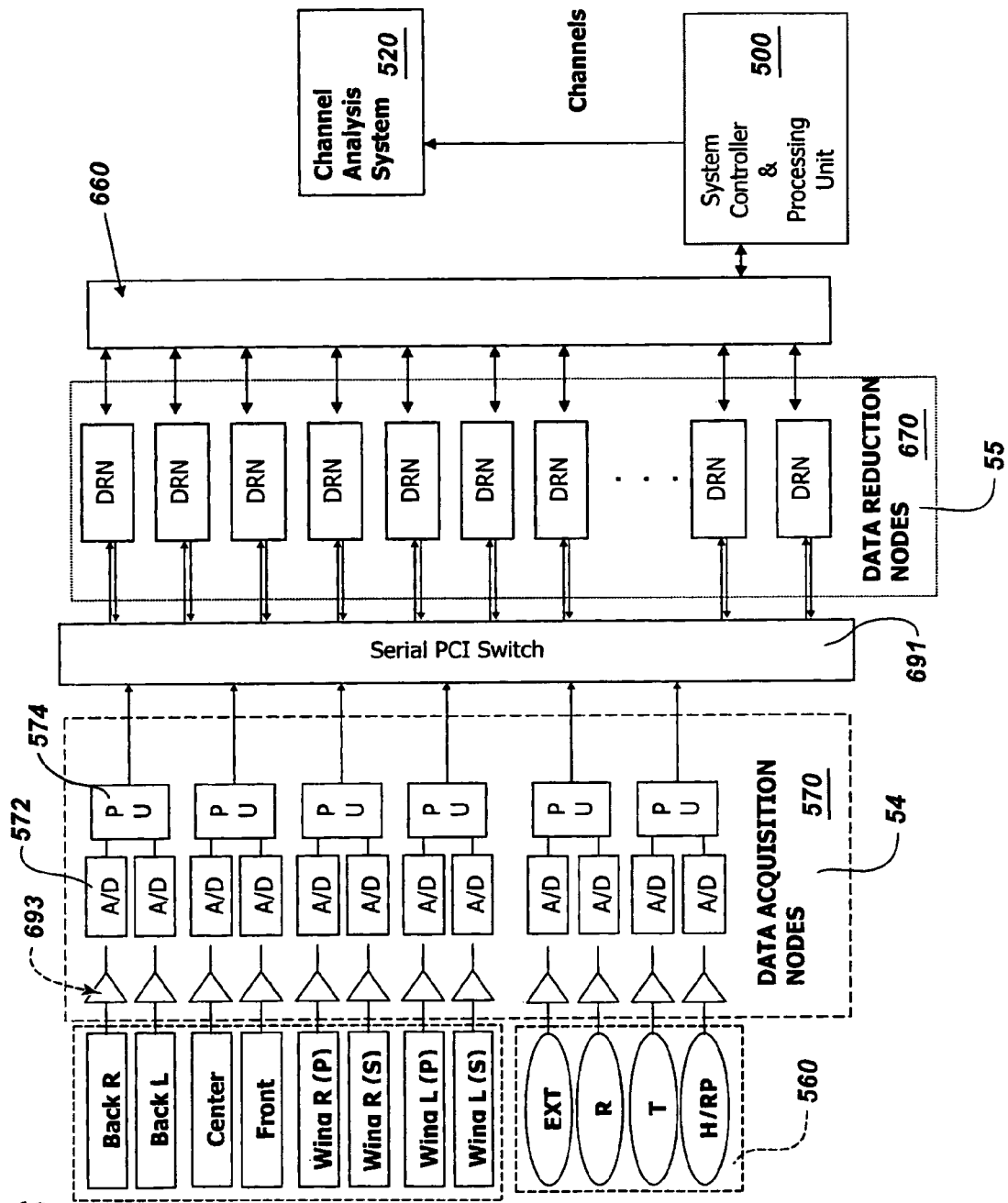
FIG. 46 is a block diagram of a data processing system for the current invention.
Figure 48:
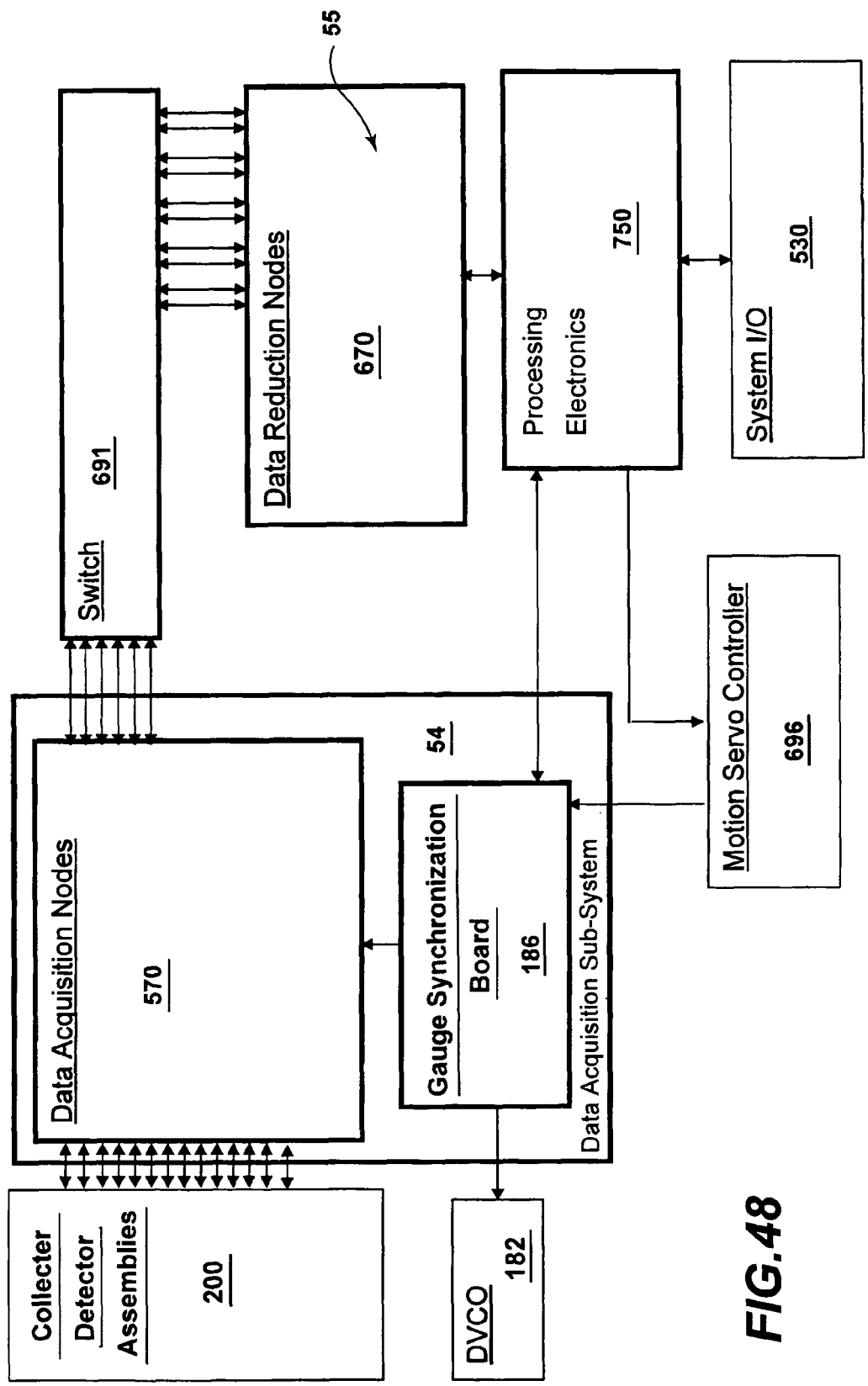
FIG. 48 is a block diagram showing data flow of the present invention.

As shown in FIGS. 46 and 48, a data processing subsystem or module 19 for use in inspecting a surface of a workpiece has a data acquisition system 54 comprising a plurality of data acquisition nodes 570 (DANs 570) connected by a communication network to a data reduction system 55 comprising a plurality of data reduction nodes 670 (DRNs 670). A system controller and processing unit 500 is connected to the data reduction system 55 via an interface or switch 660 arranged for a communication network or other system controller and processing unit 500 communication. The system controller and processing unit 500 is operated using keyboard 16, mouse 18, etc., and it presents output on display 20 or other suitable peripherals, e.g., a printer. The system controller and processing unit 500 outputs the data representative of the selected set of collectors to a channel analysis system 520 through System I/O 530.

Channel Definition and Channel Combining

Figure 47:
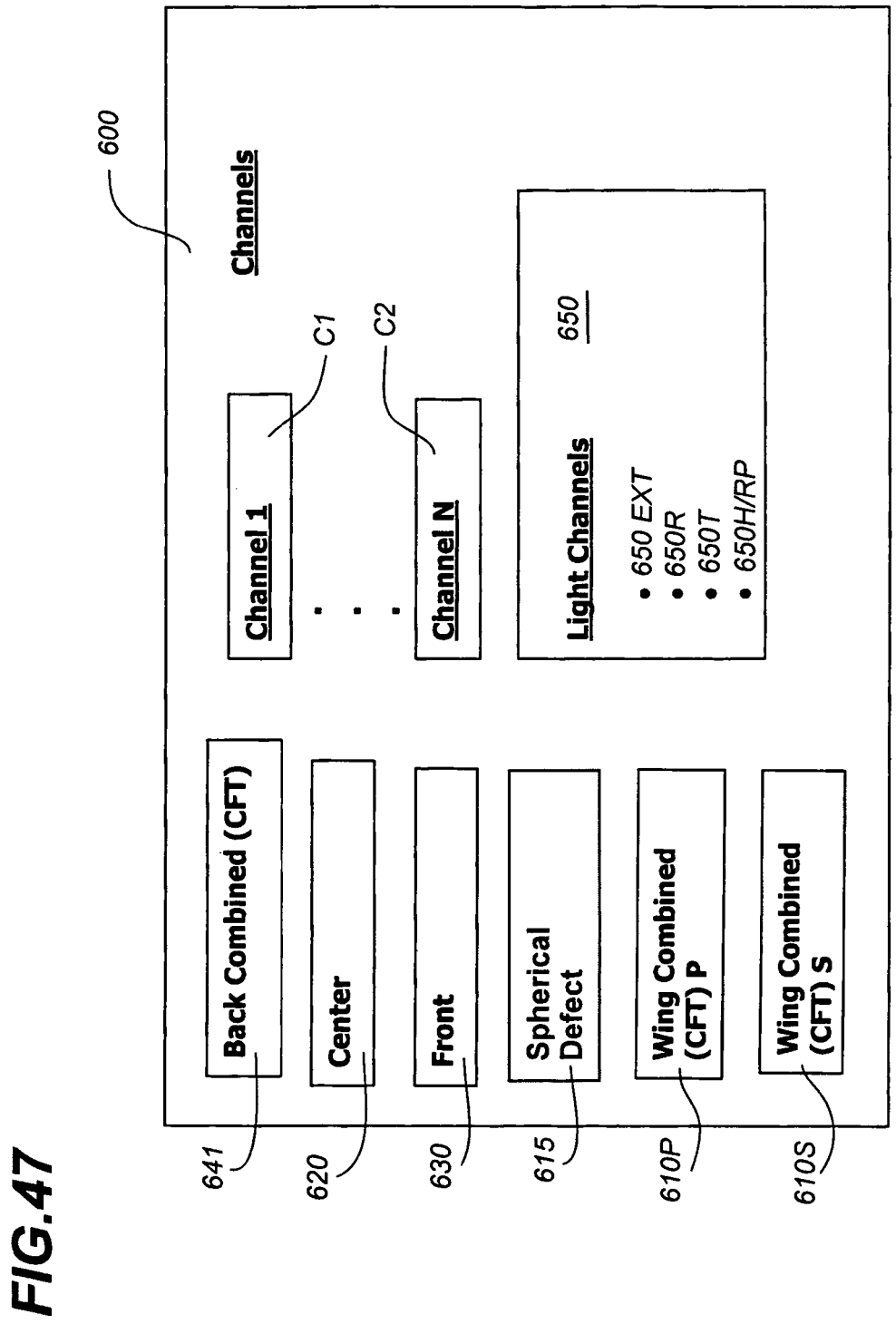
FIG. 47 is a block diagram of channel formation using the data processing system of FIG. 46.

Output from the optical collection and detection subsystem 7 is organized into defined channels 600. FIG. 47 lists a set of channels 600 that could be formed for the presently preferred but merely illustrative embodiment described herein. Certain channels 600 comprise the set of data comprising the output associated with an individual collector module 300, such as the center channel 620 formed from data from the center collection and detection module 220 and the front channel 630 formed from data from the front collection and detection module 230.

Other channels 600 are formed from the set of data comprising the output associated with a combination of collection and detection modules 200, such as the spherical defect channel 615, which would be particularly sensitive to the detection of small spherical objects such as 50 nm polystyrene latex spheres (PSLs) and defects with like geometries, formed from data from the wing collection and detection modules 210A, 210B when operated in P-polarized format and the dual back collection and detection modules 240A, 240B. In addition, channels 600 comprise the set of output data associated with selected combinations of collector modules 300 operated in a selected format or in which the data are processed using a selected method. For example, back combined (CFT) channel 641 is formed from output data associated with back collection and detection modules 240A, 240B when they are combined using a selected signal combining CFT method 812 involving first combining, then filtering/thresholding the data (the method is described in more detail below). Similarly, the wing combined (CFT) P channel 610P and wing combined (CFT) S channel 610S are formed from data from the wing collection and detection modules 210A, 210B when the resulting data are operated in a selected polarization format (P or S, respectively) and the resulting data combined first by combining, then filtering/thresholding. Generally, channels C1 through CN could be formed from the output data associated with any individual collection and detection module 200 or any desired combination of collection and detection modules 200.

Light channels 650 are similarly formed with output data collected from the light channel assembly 253, which has as input the specular beam reflected from the surface S of the workpiece W. Light channels 650 comprise, specifically, the extinction channel 650EXT, the radial channel 650R, the tangential channel 650T, and the height/reflected power channel 650H/RP.

As noted herein, an illustrative channel 600 could comprise the spherical defect channel 615 defined from the combination of wing modules 210A, 210B when operated in P-polarized format and the dual back modules 240A, 240B, which would be particularly sensitive to the detection of small spherical objects such as 50 nm polystyrene latex spheres (PSLs) and defects with like geometries. Channels are defined to comprise sets of collectors, using any of the combinations of collector sets described herein (such as channel 615) or any other desired combination, and output signals associated with the sets of collectors are combined according to any conventional methods or the methods described herein into output to be associated with the defined channel. The resultant output may be analyzed using any methods such as those described herein or any known defect detection method, such as those described in U.S. Ser. No. 10/864,962, entitled *Method and System for Classifying Defects Occurring at a Surface of a Smooth Substrate Using Graphical Representation of Multi-Collector Data*, which is assigned to ADE Corporation of Westwood, Mass. and which is herein incorporated by reference.

It should be noted that the present invention should not be limited to the embodiment of the present invention, in which channels 600 are formed from combinations of collectors 200 disposed at selected locations in the space above a workpiece surface. It should be noted that the present invention should not be limited to the collectors as described above. For example, collectors 300 have collection optics subassemblies 390 that direct the scatter to detectors 400. Alternatively mirrors could be used to direct the scatter to detectors 400. In addition, the present invention should not be limited to defining channels from collector response to light scattered from surface structural conditions.

Fundamentally, the invention involves combining signal representative of light of selected characteristics scattered from surface structural conditions, with characteristics comprising, for example, selected polarization and/or presence in a selected solid angles over a workpiece surface. As an example, the spherical defect channel 615 is preferably formed from signal representative of P-polarized scatter collected at a plurality of solid angles over a workpiece surface in the front quartersphere FQ and from signal representative of scatter collected at plurality of solid angles over a workpiece surface in the back quartersphere BQ of the space above a wafer, outside the incident plane PI.

Preferably, the plurality of solid angles in the front quartersphere FQ represent locations at or substantially at a maximum in the signal-to-noise ratio of defect scatter to surface roughness scatter, or, from a surface roughness scatter perspective, when the surface roughness is at a relative minimum in a bidirectional reflectance distribution function when the incident beam is P polarized. More preferably, the solid angles represent two locations, preferably substantially identical to one another and positioned symmetrically with respect to one another and with respect to the incident plane. In system 10, such solid angles represent the location of the wing collectors 210A, 210B.

Preferably, the solid angles in the back quartersphere BQ represent two locations, preferably substantially identical to one another and positioned symmetrically with respect to one another and with respect to the incident plane. In system 10, such solid angles represent the location of the back collectors 240A, 240B.

Signal Architecture, Contd.

The communication network that is represented in FIG. 46 as switch 691 could be any suitable communication system, such as an Ethernet™ communication system or, preferably, a Serial PCI compatible, switched interconnect communication system such as one based on the StarFabric™ open interconnect standard, "PICMG 2.17 CompactPCI StarFabric Specification" (ratified in May 2002).

Turning to FIG. 46, the data acquisition system 54 comprises a plurality of data acquisition nodes 570 connected by the serial PCI switch 691 to a data reduction system 55 comprising a plurality of data reduction nodes 670. Each data acquisition node 570 is connected to and has associated therewith a collection and detection module 200 in the optical collection and detection subsystem 7. Each light channel collection and detection module 560 and dark channel collection and detection module 200 has an output that is connected through an associated amplifier 693 to the input of a filtering unit comprising an A/D 572 (also known herein as an A/D converter 572) and a Processing unit (PUs) 574. The processing unit 574 comprises a microprocessor or, alternatively, a field programmable gate array (FPGA), and provide digital filtering and have outputs to the serial PCI switch 691.

The light channel collection and detection module 560 has associated therewith elements of the quad cell detector 258, specifically the extinction element, radial element, tangential element, and height/reflected power element. The dark channel collectors 300 comprise back left collection and detection module 340B, back right collection and detection module 340A, center collection and detection module 320, and front collection and detection module 330s, and further comprise right wing collection and detection module 310A and left wing collection and detection module 310B, each of which can be operated in P-polarized and S-polarized configurations.

The data reduction subsystem 55 comprises a selected number of data reduction modules 670, also called data reduction nodes 670. In the illustrative but not necessarily preferred embodiment, the data reduction nodes 670 comprise dual PC-type processors in the workstation class, specifically having a 64-bit architecture. The nodes 670 could also comprise a series of standard rack-mounted computers (blade processors). Each data reduction module 670 has an input that is connected to the serial PCI switch 691. As mentioned above and described in more detail below, a data reduction module 670 may be provided for each of the desired combinations of collection and detection modules 300 to be processed into a channel 600 by the surface inspection system 10.

The networking of a plurality of data reduction nodes 670 with a plurality of a data acquisition nodes 570, each of which is dedicated to a collection and detection module 200, provides a signal processing architecture in which multiple generic data recipients are available on a peer to peer basis to multiple sensors, thus essentially providing multiple computing destinations for the collector output. In addition, networking of DANs and DRN allows for simultaneous delivery of identical data to multiple destinations, thus allowing for simultaneous usage of the data product. For example, the signal processing architecture allows a user of system 10 to perform "Total Integrated Scatter"-based haze analysis in tandem with "Angle-Resolved Scatter"-based haze analysis, both of which are described in further detail below.

The resultant flexibility allows the system 10 to combine any suitable combination of collectors 300 into a channel 600. The ability to define channels 600 using any desired set of collectors 300 allows for unprecedented flexibility in surface inspection system output, resulting in improved investigation of surface aberrations.

Figure 49:
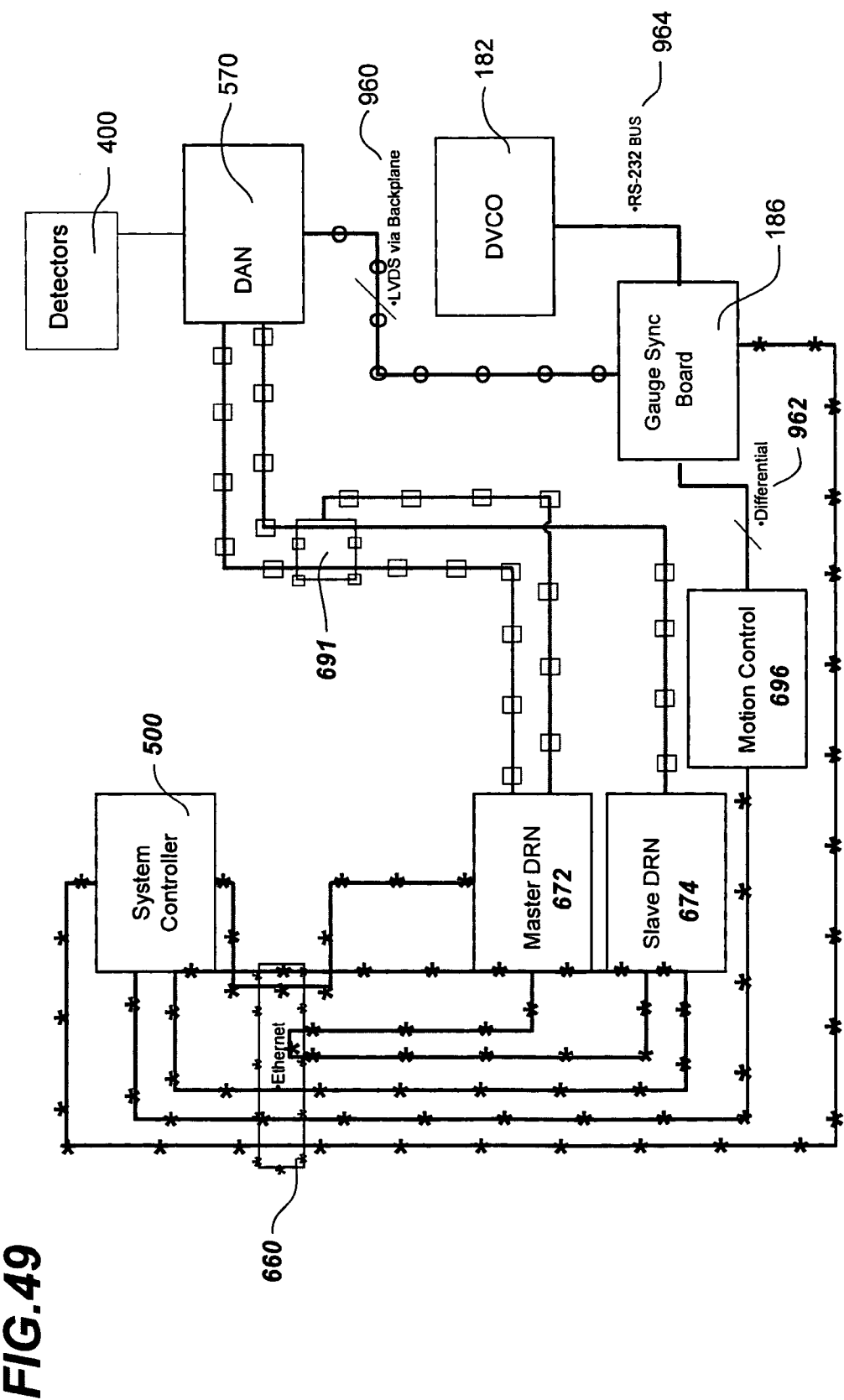
FIG. 49 is a block diagram showing the systems communication for the present invention.

Referring to FIGS. 48 and 49, there is shown a block diagram showing data flow in the surface inspection system 10 of the presently preferred yet merely illustrative embodiment of the present invention. An optics plate 60 has a plurality of collector/detector assemblies 200. In the preferred embodiment, the optics plate 60 has twelve collector/detector assemblies 200, a plurality of PMT units 495 and associated preamplifiers, one quad cell detector 258 with three output signals (radial, tangential, and extinction) and associated preamplifier, and a LPSD 256 with associated preamplifier with output signals representative of wafer height changes.

In the embodiment of the present invention that is arranged for the inspection of bare semiconductor wafers, the optics plate 60 has eight PMTs 495, one for each of the center collector/detector assembly 220, front collector/detector assembly 230, and back collector/detector assemblies 240A, 240B, and two for each wing collector/detector assembly 310A, 210B; each wing collector/detector assembly having one PMT 495 for its S-polarized configuration and one for its P-polarized configuration. In the embodiment of the present invention that is arranged for the inspection of semiconductor wafers with transparent films, the optics plate may have ten PMTs 495 (an additional two on the back collector/detector assemblies 240A, 240B).

The optics plate 60 is connected to a data acquisition subsystem 54 having a gauge synchronization board 186 that is connected to the plurality of data acquisition nodes (DANs) 570. In the presently preferred yet merely illustrative embodiment, the gauge synchronization board 186 has a 25 MHz master clock and sends synchronization scan initiation signals to six DANs 570. The DANs 570 comprise a low noise receiver A/D 572, filters and processing units 574 that as a unit is operable to perform anti-aliasing filtering, a software-configurable in-scan filtering, analog compression, A/D conversion, digital decompression of analog compression function, data decimation, and preparation of the data for transmission. In an illustrative but not necessarily preferred embodiment, the filters are a component of the processing unit, which comprises a digital signal processor and programmable logic such as field programmable gate arrays (FPGA).

The DANs 570 are connected via a switch 691 to the data reduction subsystem 55, which comprises a plurality of data reduction nodes (DRNs) 670. The switch 691 maps output associated with the collector/detector assemblies 200 to processor inputs in the DRNs 670. In the presently preferred yet merely illustrative embodiment, surface inspection system 10 comprises seven DRNs 670 that have a combination of hardware and software that is operable to perform linear combining, digital filtering, threshold/haze calculation, and data collation and formatting.

The DRNs 670, which comprise a master DRN 672 and at least one slave DRN 674, with the master DRN 672 providing set up communications to the slave DRNs 674, are connected via a switch 660 to a system controller and processing unit 500, which comprises a combination of hardware and software that is operable to provide system control and monitoring, graphics user interface, and defect identification and sizing. The system controller and processing unit 500 is connected to a system I/O unit 530 that comprises a combination of hardware and software that is operable to provide subassembly control and monitoring and diagnostics.

The system controller and processing unit 500 is also connected to a motion servo controller 696, which comprises a combination of hardware and software that is operable to perform stage control and AOD sweep initiation. The motion servo controller 696 is connected to the gauge synchronization board 186 in the data acquisition subsystem 54, which is connected to the digital voltage controlled oscillator DVCO 182 to provide sweep line control to the AOD 100.

Figure 50:
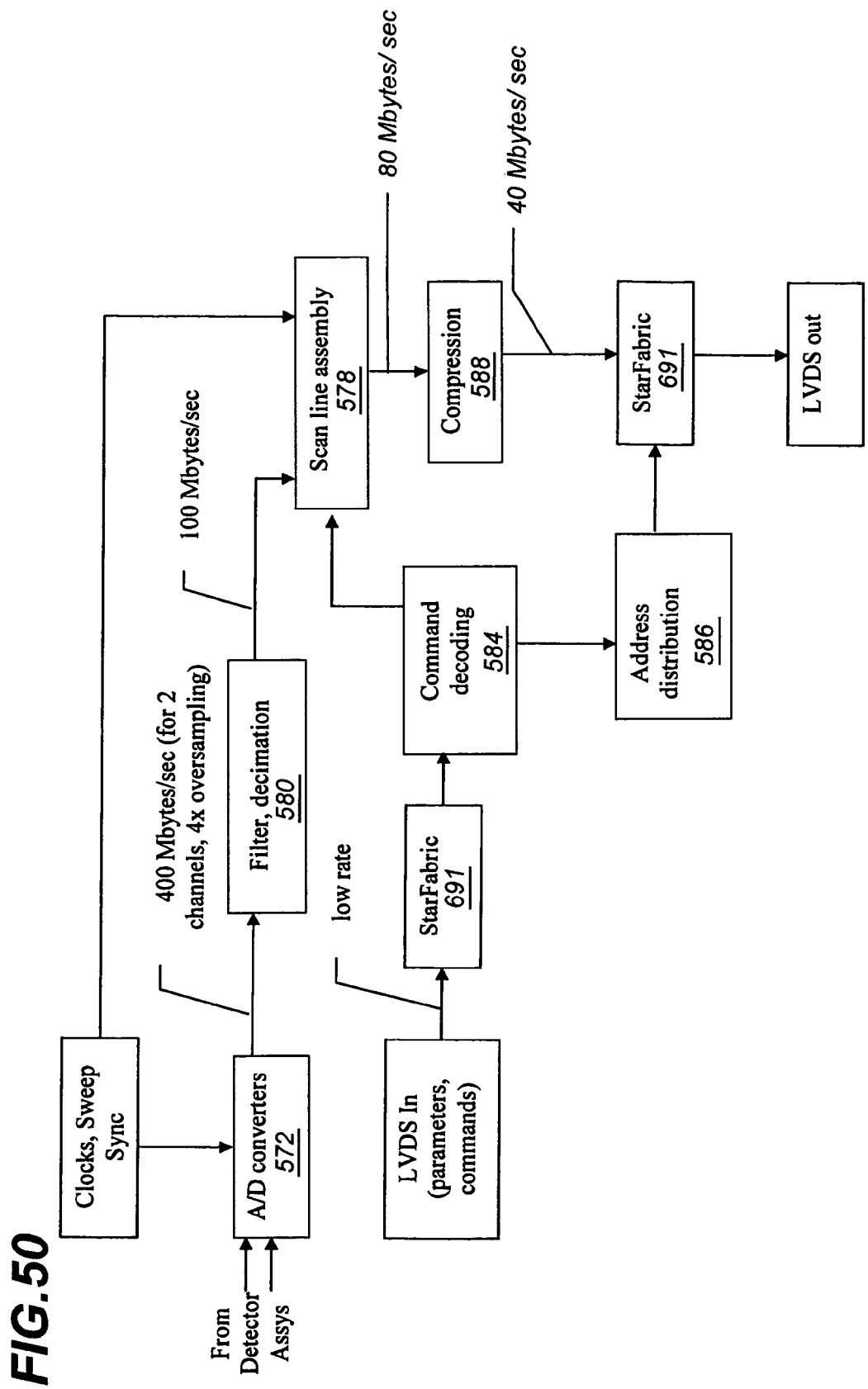
FIG. 50 is a block diagram showing data flow in the Data Acquisition Nodes.

FIG. 50 is a block diagram showing data flow in the DANs 570. As noted above, DANs 570 have a combination of hardware and software that is operable to perform digital filtering, and data collation and formatting. In the DANs 570, clock, sync and sweep signals are transmitted to the A/D converters 572 and the Scan line assembly unit 578. Also as noted above, raw data is transmitted from the collector/detector assemblies 200 to the DANs 570, first arriving in the A/D converters 572. The digital data are then transmitted at a rate of 400 Mbytes/sec (for 2 channels, 4× oversampling) to a filter/decimation unit 580 for filtering and decimation. The digital data are then transmitted a rate of 100 Mbytes/sec to a scan line assembly unit 578.

Also as noted above, parameters and commands arrive at the DANs 570 at a low rate from the DRNs 670 via the StarFabric™ connection 691. The commands are decoded by a command decoding unit 584, which decodes commands from the signals and sends them to an address distribution unit 586 and scan line assembly unit 578.

The decoded commands control the scan line assembly unit 578 in assembling scan lines from the digital data. The assembled digital data are then transmitted at a rate of 80 Mbytes/sec to a compression unit 588 for data compression, and then transmitted out as low voltage data signals via the Serial PCI switch 691 to the DRNs 670. The address distribution unit 586 sends command signals to indicate the DRN destination of the newly compressed digital data.

Figure 51:
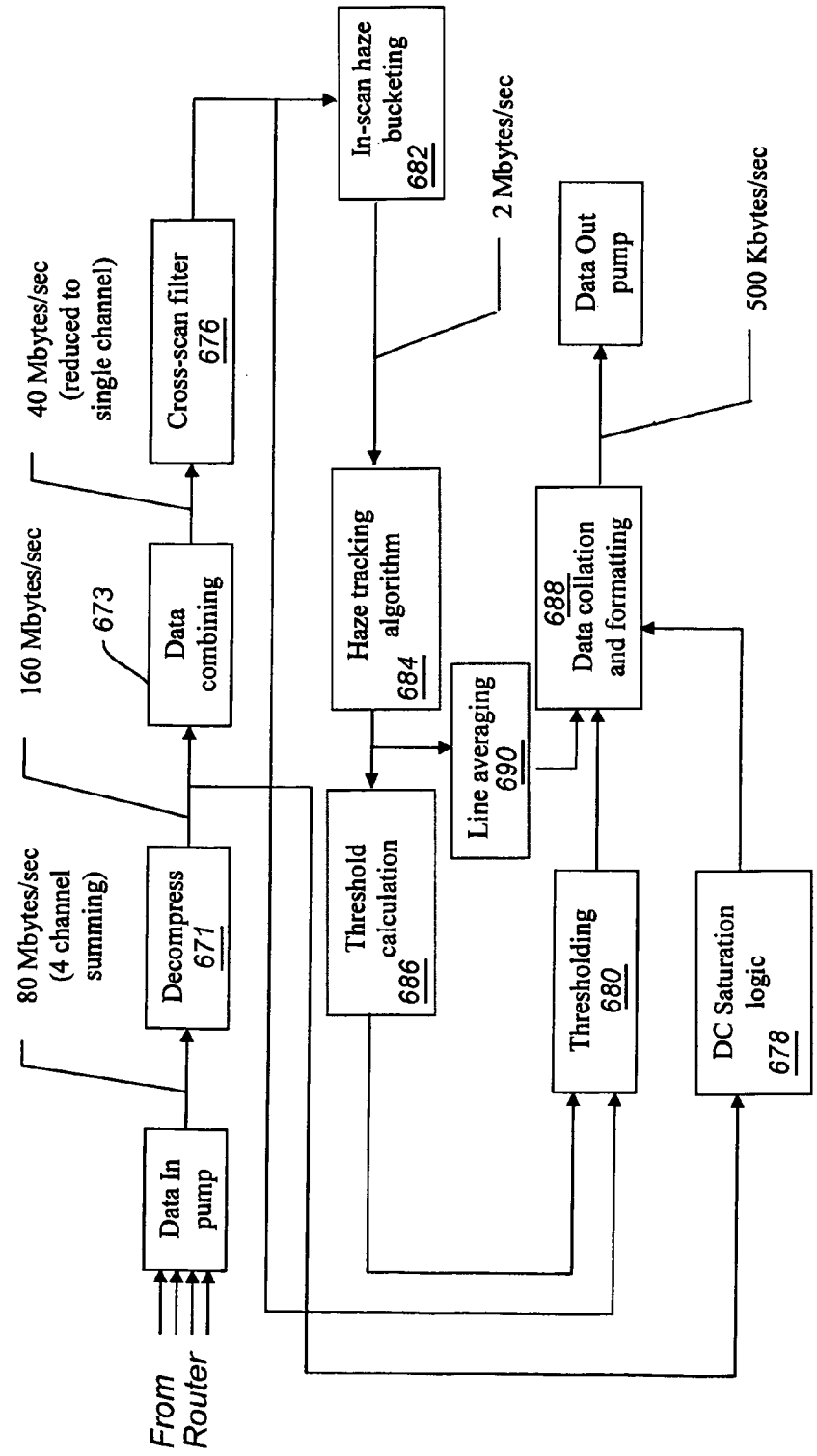
FIG. 51 is a block diagram showing the data flow in the Dark Channel Data Reduction Nodes.

FIG. 51 is a block diagram showing the data flow in the Dark Channel Data Reduction Nodes 670, which as described above, comprise a combination of hardware and software that is operable to perform linear combining, digital filtering, threshold/haze calculation, and data collation and formatting. The compressed digital data, which is assembled into scan lines, are transmitted at a rate of 80 Mbytes/sec (4 channel summing) to a decompression unit 671. The data are decompressed at the data decompression unit 671 and then transmitted at a rate of 160 Mbytes/sec to a data combining unit 673 (in which channels are created as described in accordance with the present invention) and to DC Saturation logic 678, for use in monitoring that will be described in more detail below.

The combined data are then transmitted at a rate of 40 Mbytes/sec (reduced to single channel) to a cross scan filter unit 676 for cross-scan filtering to be performed on the data in accordance with the methods described in the U.S. Pat. No. 6,529,270, which is hereby incorporated by reference, for background.

The cross-scan filtered data are then transmitted to a thresholding unit 680, for use in the thresholding of data as described in detail above, and at a rate of 2 Mbytes/sec to a haze tracking algorithm unit 684 for haze analysis. In the presently preferred yet merely illustrative embodiment, an in-scan haze bucketing unit 682 is provided so that the cross-scanned filtered data may be prepared for haze analysis. In the in-scan haze bucketing unit 682, the number of in-scan elements is reduced from 400 to 20, with each surviving element representative of 20 original elements and a haze[1] value comprising the mean scatter intensity value from surface roughness scatter, associated with the surviving element comprises an average of the haze values of the 20 original elements associated therewith. In the presently preferred yet merely illustrative embodiment, signals representative of the surviving elements are then transmitted to the haze tracking algorithm unit 684 for haze analysis.

The haze tracking algorithm unit 684 performs haze analysis in accordance with the methods described in the '701 patent, as well as U.S. Pat. No. 6,118,525 and U.S. Pat. No. 6,292,259. Haze analysis will be discussed in more detail below.

After the haze tracking algorithm unit 684, the data are transmitted to the threshold calculation unit 686 for use in determining the threshold value. Thresholds can be calculated from the data using conventional methods such as averaging or by actual measuring noise levels and thresholding accordingly. As described in detail above, the threshold value may be calculated using a value γ determined by the accepted false alarm rate and a background level, of which haze is a part and the calculation of which the signals representing haze are used by the threshold calculation unit 686.

The calculated threshold value is then transmitted to the thresholding unit 680, where it is used in thresholding the data received from the cross-scan filtering unit 676. The thresholded data are then transmitted to the data collation and formatting unit 688, which is described in more detail below.

After the haze tracking algorithm unit 684, the data also are transmitted to the line averaging unit 690 in order to perform cross-scan averaging of haze data. The haze output is then transmitted to the data collation and formatting unit 688.

The DC saturation logic 678 operates to monitor the extent of saturation of the PMTs 495. When the PMTs 495 receive too much haze signal, they start to become nonlinear and their size detection accuracy is diminished. Additionally, excess DC current through the PMT 495 causes premature aging of the detector. Therefore, an upper limit is set on the amount of current that may be obtained from the voltage output of the PMT 495.

If a DRN 670 detects a current signal that is over a user-set limit, it will monitor the portion of the wafer that has gone over-limit. If it receives additional signal that is over the user-set limit, the PMT 495 will transmit an Abort scan signal, which will end the scan currently being performed. The scan may be re-initiated at a proper detection gain setting.

The DC saturation logic 678 performs that monitoring using data from individual PMTs, and so each PMT 495 is individually tracked for saturation.

The results of the PMT 495 saturation monitoring are input to the data collation and formatting unit 688, along with the line averaged data and thresholded data. If no PMT saturation state is found, the data are collated and formatted and transmitted at a rate of 500 Kbytes/sec to the system controller and processing unit 500.

Returning to FIG. 49, there is shown a block diagram showing communication flow in the surface inspection system 10 of the presently preferred yet merely illustrative embodiment of the present invention. The system controller and processing unit 500 communicates via the Ethernet Switch 660 with the Gauge Synchronization Board 186, Motion Servo Controller 696, Master DRN 672 and Slave DRNs 674.

The system controller 500 sends DVCO set up, AOD Level, Enable scan, and Master Reset signals to the Gauge Synchronization Board 186, which sends back Acknowledgement signals and (after a full wafer scan is complete) signals identifying the number of sweeps. The system controller 500 sends the following signals to the Motion Servo Controller 696: Normal scan, Slow scan, Servo setup, Tuning commands, Start and Stop command, Stage commands, Trajectory setup and chuck commands. The motion servo controller 696 in turn sends back acknowledgment, scan position, and Motion status signals.

The system controller 500 sends the following signals to the Master DRN 672: DRN Boot, DRN setup, DAN configuration and reset, scan control (such as start, enable, abort, end), acknowledgement. The master DRN 672 in turn sends acknowledgement of "Over Threshold and Haze" (OT&H) data, and it sends sensor calibration data signals to the system controller 500. The slave DRNs 674 also send acknowledgement, OT&H data, and sensor calibration data signals to the system controller 500.

The master DRN 672 and slave DRNs 674 are also interconnected by the Ethernet switch 660. The master DRN 672 sends the following signals to the Slave DRNs 674: DRN setup, End scan, Abort scan, and Reset for new applications. The slave DRNs 674 send acknowledgement signals to the master DRN 672. The Master DRN 672 and Slave DRNs 674 are connected via a StarFabric™ bus switch 691 to the DANs. The master DRN sends a switch setup signal to the StarFabric™ bus switch 691.

The master DRN 672 also sends the following signals to the DANs 570: Switch setup, DAN configuration, Enable scan, End scan, Abort scan, Diagnostic, Operational, DAN bootstrap commands, Switch configuration, Startup to run boot loader. The DANs 570 send detector setup and calibration signals to the collector/detector assemblies 200, which send raw data to the DANs 570. The DANs 570 send filtered and decimated data to the master DRN 672 and the slave DRNs 674, and they send Status and Acknowledgement signals to the master DRN 672. The DANs 570 and gauge synchronization board 186 send low voltage data signals via a backplane 960 to each other: the DANs 570 sending DAN Acknowledgement signals and the gauge synchronization board 186 sending Reset, Clock, and Encoder signals.

The gauge synchronization board 186 and motion servo controller 696 communicate via a Differential bus 962, the gauge synchronization board 186 sending Status signals and the motion servo controller 696 sending Trigger and Encoder signals. The gauge synchronization board 186 and digital voltage controlled oscillator ("DVCO") 182 communicate via an RS-232 bus 964, the gauge synchronization board 186 sending Chirp command and Trigger signals and the DVCO 182 sending Acknowledgement and signals identifying the number of chirps (the DVCO chirps causing an AOD sweep).

Signal-to-Noise Ratio ("SNR") Improvement

Some components of haze actually collected and detected by surface inspection systems do not originate on or in wafer under inspection and therefore have nothing to do with wafer defects. The sensitivity of the surface inspection system 10 can be strongly influenced by the background noise in the system, especially when the system is used to detect extremely small surface characteristics, such as in semiconductor applications. The relative strength of the desired signal to the undesirable background noise is embodied in the signal-to-noise ratio ("SNR"). In semiconductor applications, Rayleigh scatter from the laser beam as it propagates through the air within the scanner is an important source of background light, and therefore quantum mechanical shot noise. Light reflected internally within the system from other components, for example, such as light reflected off of apertures or stop also can constitute unwanted noise. These noise sources are sometimes referred to as "instrument signature" (e.g., scattered light that comes from the instrument itself, and not from the workpiece under inspection). In addition, the electronic components of the surface inspection system could provide a certain amount of shot noise.

One approach to improving the SNR is to improve signal strength, for example, by increasing beam power, frequency, etc. Another approach to SNR improvement involves a reduction in system noise.

In accordance with still further aspects of the invention, a number of systems, apparatus and methods are provided for improving SNR. A number of presently preferred embodiments and method implementations of these will now be described. To aid in this description, and to simplify them, they will be described as implemented in system 10. It will be understood and appreciated, however, that these aspects of the invention are not necessarily limited to system and its specific components and implementations as expressly described herein, and that they may be applied to other systems and embodiments.

In accordance with the preferred embodiments and implementations of these aspects of the invention, system 10 is designed to minimize instrument signature and other sources of unwanted background noise. The presently preferred embodiments and method implementations have been designed using, and based upon, a scatter tolerance budget within the system as a whole.

Illumination Absorbing System

To illustrate these aspects and principles of the invention, a surface inspection system 10 according to a presently preferred embodiment of these aspects of the invention will now be described. The system 10 is useful for inspecting one or more surfaces of a workpiece is provided. The surface inspection system 10 comprises an illumination subsystem 13 that projects a beam to the surface of the workpiece.

In a presently preferred embodiment and method implementation, the illumination subsystem 13 also comprises a beam scanning device, in system 10 called the beam scanning subsystem 8, which preferably comprises an acousto-optic deflector such as AOD 100. More preferably, this comprises beam scanning subsystem 8 or module 92 with variable scan speed AOD 100 as described herein above.

The system according to this aspect of the invention also comprises a collection subsystem for collecting scattered portions of the beam scattered from the surface S of the workpiece W. An illustrative but not necessarily preferred collection subsystem of the present invention has been described above as the collection subsystem 380 of which the optical collection and detection subsystem 7 is comprised. The collection subsystem 380 comprises collection optics of system 10, which comprise components of the collection and detection module 200 above described, namely, a front collector module 230 with light channel assembly 253, a center collector module 220, a pair of wing collector modules 210A, 210B, and a pair of back collector modules 240A, 240B, all as described herein above with reference to system 10.

The system according to these aspects of the invention further comprise a processing subsystem 19 operatively coupled to the optical collection subsystem 380 for processing signals received from the optical collection subsystem 380 to provide information about the surface of the workpiece.

The illumination subsystem 13 comprises a plurality of lenses or optical components through which the beam or its component portions pass. Such lenses or optical components have been described herein as components of the beam source subsystem 6 and the beam scanning subsystem 8. Preferred embodiments of these lenses or optical components, such as objective lens optics 392, have been described herein above.

Individual components of the illumination system 13 through with the beam passes, and preferably all of such lenses and optical components, have a surface roughness that does not exceed a selected value. In a presently preferred yet merely illustrative embodiment, the surface roughness does not exceed about 30 Angstroms; more preferably it does not exceed about 5 Angstroms. This limit on surface roughness limits scatter of the beam and correspondingly maintains a desired amount, preferably a maximum, of the beam energy collimated within the beam.

In addition, a reduction in system noise may be accomplished by providing the AOD and the collection system with instrument signature reduction systems employing, for example, combinations of baffles and relay lenses with glass stops that serve to reduce instrument signature.

Figure 81:
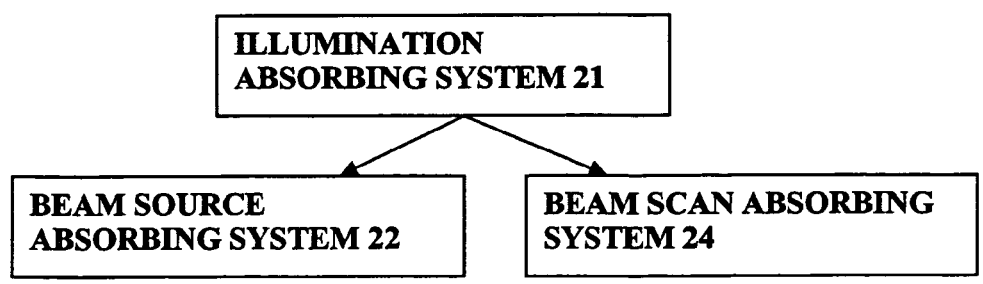
FIG. 81 is a block diagram of the illumination absorbing system 21 of the present invention.

In accordance with another aspect of the invention, the illumination subsystem 13 comprises an illumination absorbing system 21 comprised of components of the beam source subsystem 6 and the beam scanning subsystem 8 described above. As shown in FIG. 81, the illumination absorbing system 21 in this aspect of the invention comprises beam source absorbing system 22 at the beam source subsystem 6 and beam scan absorbing system 24 in the AOD 100 for absorbing scattered light. The laser beam comprises a collimated portion that lies within the main beam and a residual non-collimated portion, for example, that is scattered. The collimated beam portion is reflected off the surface of the workpiece W to provide the specular beam and the surface scatter that is collected by the front collector, wing collectors, and/or back collectors to detect and distinguish surface characteristics, such as defects. The uncollimated portion of the beam at the illumination subsystem typically comprises scattered light not useful in surface measurements. Some of the scatter comes from the Rayleigh scatter associated with laser beam itself, but most of the scatter comes from elements of the AOD 100, such as the clean-up polarizing cube 26 seen in FIG. 16 located between the cylinder lens 150a and the black glass baffles 114. By providing illumination absorbing system 21, as is done here, generally undesirable light can be absorbed and removed from the system, so that it does not inadvertently enter the collectors and become an unwanted part of the measured signal. Scattered light from the AFRU 92 generally appears as increased background signal in the DFRU 811 channels.

As implemented in the illumination subsystem 13, the beam scan absorbing system 24 comprises means for absorbing light that is not collimated in the beam, which are located both within and at the output of AOD.

Figure 12:
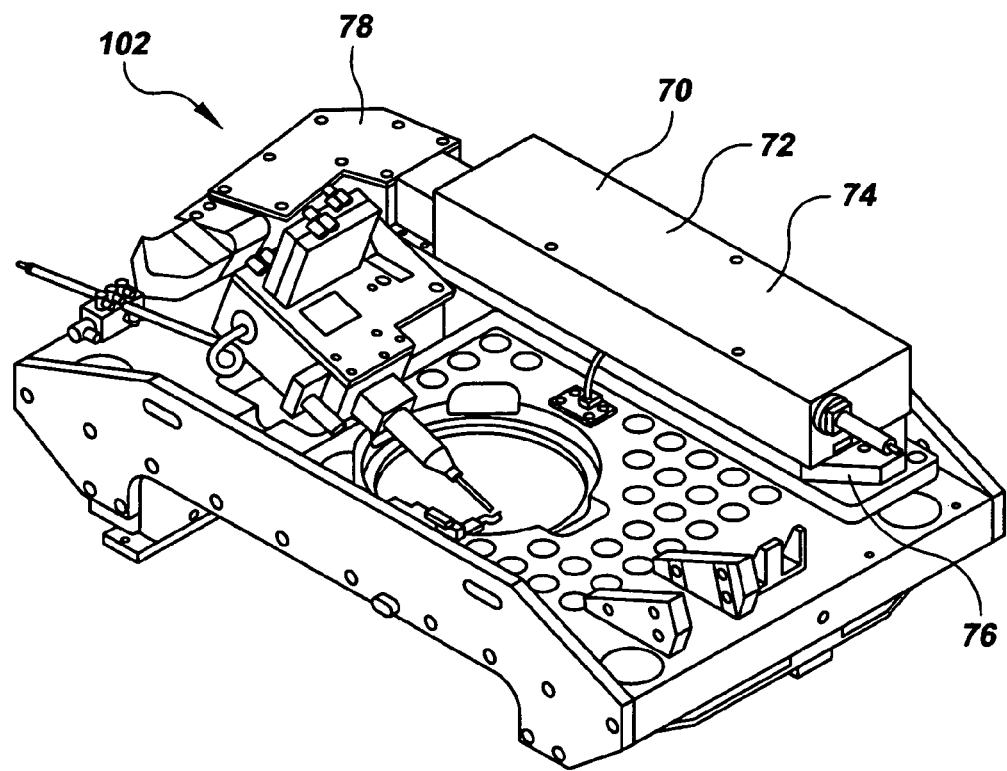
FIG. 12 is a perspective view of the base plate for the system of FIG. 1 with the beam source module and the beam scanning module mounted to the base.

Referring to FIG. 12, which is a top view of the AOD assembly 102, and FIG. 13, which is a side view of the AOD assembly 102, the means for absorbing light that is not collimated in the beam comprises a series of apertures, baffles and threads to absorb undesired scatter. The apertures are sized to allow the collimated portion of the laser beam to pass but operate as baffles for collecting scatter.

In the presently preferred yet merely illustrative embodiment and referring to FIGS. 16-17, the series of apertures, baffles and threads comprises the following:

Aperture 110 is located at the opening of the AOD assembly 102 and is sized to allow the passing of the incoming laser beam.

Aperture 111 is located at the input of the AOD 100.

Aperture 113 is located after the AOD 100.

Aperture 117 is located at the sliding plate 158 for moving the variable speed assembly cylindrical lens 150A or 150B into position.

Aperture 119 is located at the input of the AOD beam splitting cube 26 (called the polarization clean-up cube 26 above) (which, being oriented at P polarization itself, itself substantially reduces the S-polarized stray light from the AOD).

Aperture 121 is located after the beam splitting cube 26.

Baffles 114, are located after aperture 121 and are preferably comprised of one or more pieces of black glass (e.g. Schott UG1) that are disposed at the Brewster angle for the particular absorbing glass type. These absorb the zero order laser beam when the AOD 100 is not on. When the AOD is on, the laser beam is diffracted away from the baffles 114. However, the baffles 114 absorb the residual stray light scatter generated by the AOD 100, cylinder lenses 150A, 150B, and cube 26 outside the laser beam scan aperture region.

Aperture 116 is an adjustable aperture and is positioned immediately before the drive of the wave plate 118.

Aperture 123 is positioned at the interface where the beam comes into the AOD snout.

Aperture 125 is located before the telecentric lens 120.

Threads 122, which are located after the telecentric lens 120 and within the AOD snout 124, operate as a baffle structure for collecting scatter.

Aperture 126 is located at the end of the AOD snout.

Any further residual scatter then goes through the light channel specular beam aperture 251 and is absorbed either by the absorbing attenuator 242 in the light channel assembly 253 or by the Lyot stop 770, both of which are components of the collector/detector absorbing means 270 described below.

Light Channel Absorbing Means

In accordance with still another aspect of the invention, a light channel absorbing means 252 is provided at the light channel assembly 253 for attenuating the light that propagates into the light channel.

Figure 85:
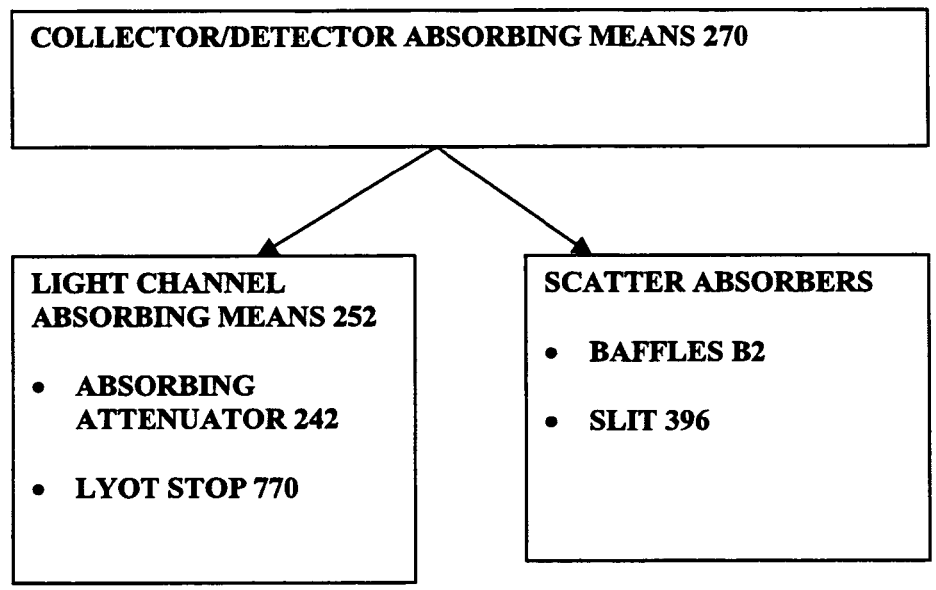
FIG. 85 is a block diagram of the collector/detector absorbing means 270 of the present invention.

As was described herein above, and as can be seen in FIG. 29, the light channel assembly 253 of system 10 uses a compact optomechanical design that splits the incident beam into two beams, directing them into the quad cell detector 258 and light position sensitive detector (LPSD) 256. As shown in FIG. 85, the collector/detector absorbing means 270 has a light channel absorbing means 252 to transmit reflected light from the wafer into the light channel assembly. In the illustrated but not necessarily preferred embodiment, the light channel absorbing means 252 comprises an absorbing attenuator (OD=2.0, typical) 242.

The attenuator 242 comprises an absorbing glass, for example, black glass, which further minimizes the amount of light that is reflected. Light that is incident on the attenuator in this embodiment and implementation is predominantly P-polarized. The attenuator 242 is oriented at the Brewster angle to maximize the amount of light that travels through the attenuator glass. The attenuator 242 does not have a coating of any type, in its preferred embodiment.

Light that is scattered from the mirror assemblies must pass back through the attenuator 242 in order to reach the wafer surface, therefore the light channel is optically isolated from the detection and collection subsystem. This can be an important noise attenuation approach given that the optical power entering the light channel can be many orders of magnitude higher than the amount of light that is collected by the collectors that are used to form the dark channel.

Lyot Stop

Figure 56:
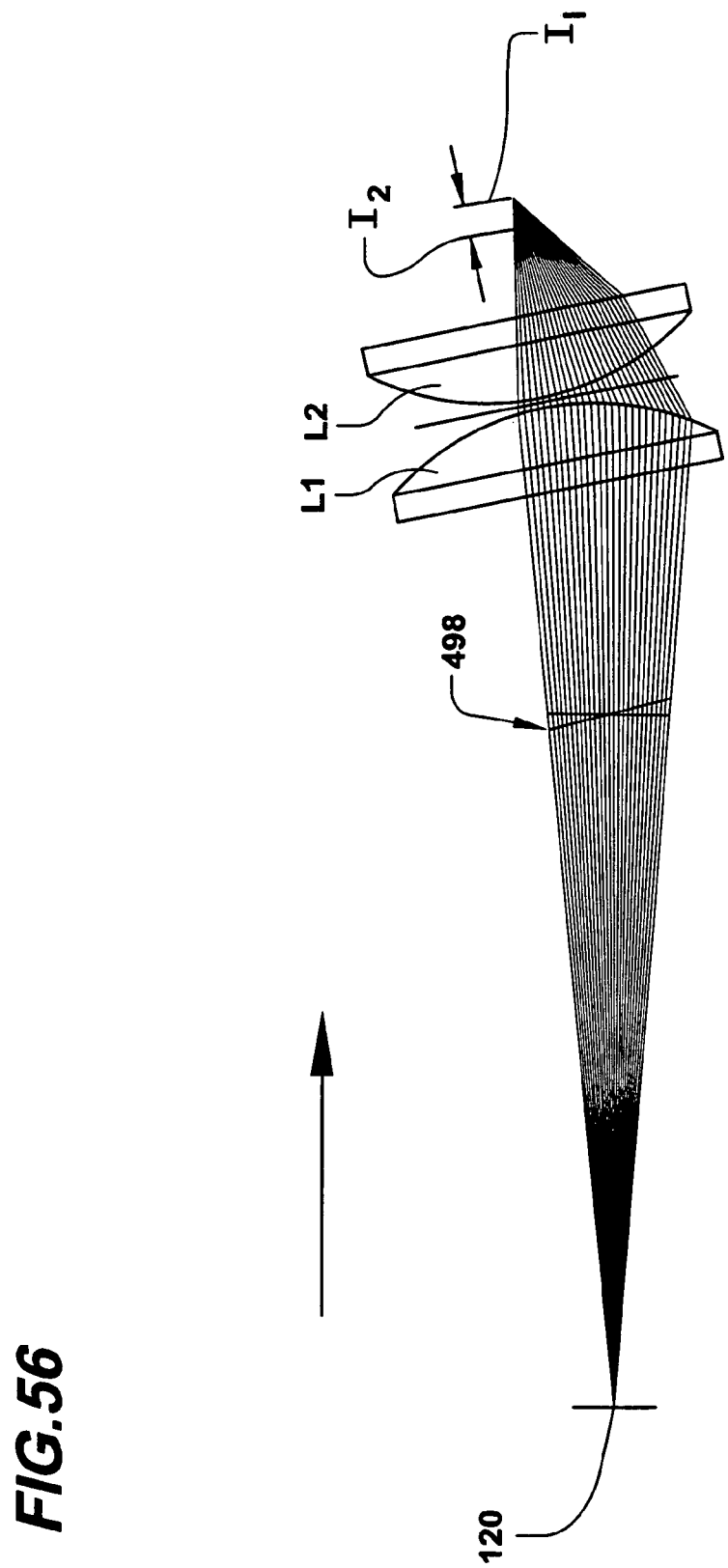
FIG. 56 is a diagram showing a beam trace of light through a lens arrangement and the placement of Lyot stop relative to the lens arrangement, according to the present invention.

In accordance with yet another aspect of the invention, a surface inspection system 10 is provided, as generally described herein above, but which further comprises a collector/detector absorbing means 270 also having a Lyot stop 770. As seen in FIG. 20, the Lyot stop 770 is located above the specular beam tube of the light channel assembly 253 and within the area containing the baffles B2 in the collector module barrel housing 394 of the front collector 330. FIG. 56 illustrates the placement of the Lyot stop 770 relative to the lenses L1, L2 and the telecentric lens 120. FIG. 56 is a beam trace of light emanating from the telecentric lens 120 to the wafer surface S at the telecentric plane 498 and scattering into the lenses L1, L2. Location I1 is the image plane for light emanating from the AOD 100. Location I2 (between the location I1 and the lens L2) is the image plane of light emanating from the telecentric lens 120. The Lyot stop 770 is positioned between locations I1, I2.

The Lyot stop 770 is cup shaped. Preferably, it is formed of anodized aluminum and sized so that, in image space, the length of the Lyot stop 770 is longitudinally the length of the AFRU 92 optical system. In the present preferred yet merely illustrative embodiment, the Lyot stop 770 is sized and shaped so that scatter from the AFRU telecentric lens 120 is focused toward the back of the Lyot stop 770, and scatter from the AOD 100 is substantially focused into the front of the Lyot stop 770.

In addition, the Lyot stop 770 is also angularly separated from the specular beam to provide improved separation of the AFRU 92 scattered light from the scattered light that propagates into the front collector 3301 and light channel assembly 253.

As shown in FIG. 25, the collector/detector absorbing means 270 also comprises a series of baffles and glare stops to absorb undesired scatter. As shown in FIG. 25, baffles B2 in the collection optics subassembly 390 are provided above the objective lens L2 to minimize stray pff-axis light. Stray light that passes by the baffles B2 will be further reduced by slit 396.

Detector Slit Tracking

As noted above, and referring to FIG. 25, the collectors have a slit 396 through which the objective lenses L1, L2 focus the incoming photons. The slit 396 operates as a field stop to absorb scatter outside the region illuminated by the laser spot. The width of the slit 396 is selected to so that the slit 396 is at least wide enough accommodate the imaged spot size on the wafer W.

In one embodiment, the width of the slit 396 is oversized to adjust for mechanical tolerances due to wafer height variations. As the wafer height changes due to wafer bow and warp, the intersection point where the laser spot and the wafer meet varies. This movement of the intersection point causes the scanned spot on the wafer to move from side to side as the wafer spins. The width of the slit 396 is selected to be oversized to allow the imaged spot to pass through the field stop as the local wafer height changes during the scan. In another embodiment, in order to minimize the Rayleigh scatter that an oversized slit 396 would allow into the collector 300, the width of the slit 396 is matched to the beam size on the wafer W, and wafer tracking means, comprising a tracker 398 formed of known hardware and software elements, is provided to move the slit 396 to accommodate changes in the wafer height. The tracking means 398 comprises any suitable mechanism to move the slit 396 in any conventional way, such as linear stages or PZT or the like. For example, the tracking means 398 could comprise a control system that uses the signal from the light channel LPSD 256 to sense the local height of the wafer, and thereby move the slits 396 in each collector 300 to compensate for the associated imaged spot movement.

Stray light that passes through the slit 396 will be further reduced by the glare stops G1, G2, G3 that are, respectively, located immediately before the collimating relay optics lens L3, after the collimating relay optics lens L3, and before the relay optics lens L4. Finally, any residual stray scatter light will be minimized by the field stop F2, immediately before the photocathode. In the two collector (dual PMT 495) embodiment of the current invention, the field stop F2 comprises a slit (such as detector slit 496 in FIG. 26). In the embodiment featuring a 90 degree collector, the field stop F2 comprises a hole.

Beam Source Pre-Alignment System

In accordance with another aspect of the invention, a method and system is provided for assembling a surface inspection system 10. This assembly may occur as part of a new system assembly, as part of a system maintenance or repair effort, or the like. A presently preferred implementation of this method and system will now be described. To simplify the description and illustration, this preferred method and system implementation will be described with respect to system 10. It will be understood and appreciated, however, that neither the method nor the system is limited to this specific system embodiment, and that either the method or the system may be implemented using other embodiments, apparatus and implementations.

Figure 73:
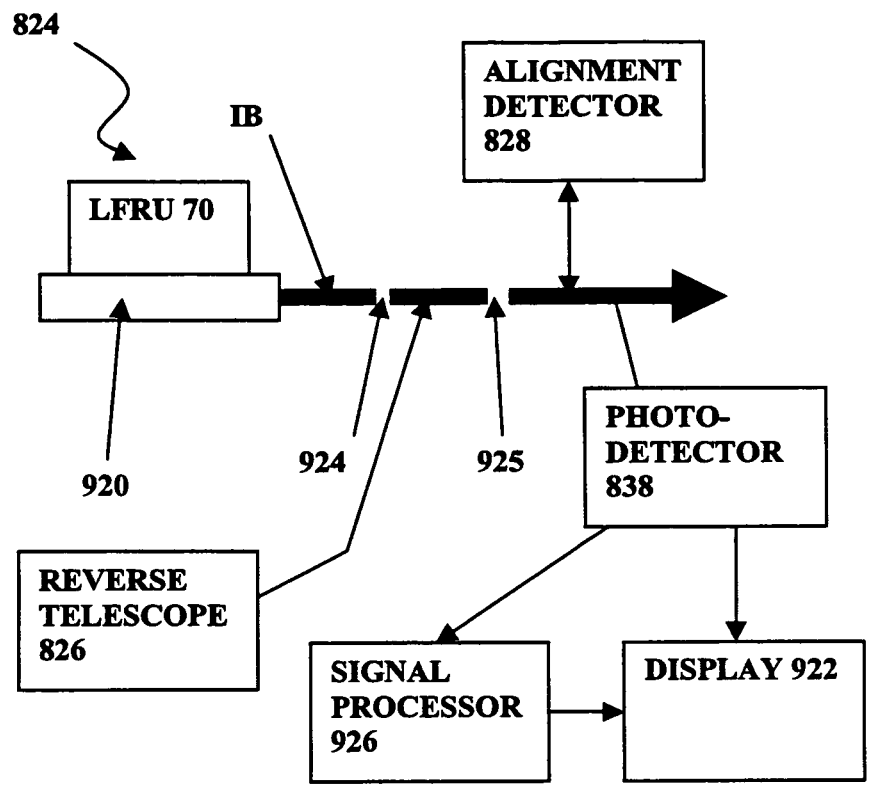
FIGS. 73 and 74 are block diagrams showing implementations of the pre-alignment method contemplated by the present invention.

In accordance with the preferred assembly method, the beam source module 70 is aligned so that the laser beam is directed to the pointing position with 50 microradian accuracy. To facilitate this task, a beam source pre-alignment system 824 is provided. FIGS. 73 and 74 are block diagrams showing implementations of the pre-alignment method contemplated by the present invention. FIG. 73 shows an implementation of the beam source pre-alignment system 824, which comprises a base, such as beam source module base plate 76, apertures, such as aperture 924, 925, a reverse telescope 826, and alignment detector 838, also known as photodetector 838 (a digital camera or other optical-to-electrical conversion means). The pre-alignment system 824 also optionally but preferably includes a display 922, and/or a signal processor 926 coupled to the photodetector 838, for processing and/or displaying the beam alignment. The beam source pre-alignment system 824 further comprises a holding device 920, also known as a beam source module mounting pad 920, such as a jig that is identical with or similar to the base 11 to which the beam source and scanning mechanism will be attached.

In the illustrative yet not necessarily preferred embodiment of the beam source pre-alignment system and method according to this aspect of the invention, and with reference to the drawing figures, particularly FIG. 13 and FIG. 73, the method of pre-alignment may be performed using the holding device 920 to hold the beam source module base plate 76 in the position at which the beam source and scanning mechanism will be attached to the optics base plate 60. As is known by persons of ordinary skill in the art, the turning mirrors 82, 84 may be used to adjust the incident beam vector IB, with the reverse telescope 826 being used to magnify any small change in the position of the incident beam vector IB at the aperture 924. The photodetector 838 is operated to detect the current pointing position of the laser after the aperture 926, and its output is sent to the signal processor 926, which identifies the current pointing position. The video display 20 to which the photodetector 838 is coupled displays the current alignment of the incident beam vector IB.

As part of the preferred assembly method for system, the beam scanning module 92 is pre-aligned to the pointing position as well. This is facilitated using a beam scanning pre-alignment system 822, a presently preferred embodiment of which is shown in the drawing figures, particularly in FIG. 11 and 74, and described above with reference to the design of the surface inspection system 10, in which the beam scanning module 92 is mounted to the beam source module 70 by operation of pins 96 mating a corresponding plurality of pinholes 94 in the beam source module base plate 76, and in which the beam scanning module 92 is mounted to the base 11 by operation of pins 128 on the bottom surface of beam scanning module base plate 90 mating a corresponding plurality of pinholes 130 in the optics base plate 60.

Inspection Method

In accordance with another aspect of the invention, methods are provided for inspecting a surface of a workpiece, as noted herein above. Presently preferred implementations of these methods will now be described. For ease and simplicity of illustration, these preferred method implementations will be described in conjunction with the system 10 according to a presently preferred embodiment of the invention as it has been described herein above. It should be understood and appreciated, however, that these preferred method implementations are not necessarily limited to the systems, subsystems, components and assemblies as described herein with respect to the preferred embodiment.

In accordance with this aspect of the invention, a method is provided for inspecting a surface of a workpiece. The workpiece and the surface to be inspected are as have been described herein above. In this preferred but illustrative implementation of the method, the workpiece W comprises an unpatterned semiconductor wafer, and the surface S comprises one of the planar surfaces of the wafer upon which dies will be formed in subsequent processing.

In accordance with this preferred method, the wafer is positioned for inspection, preferably by using a robotic wafer handling subsystem such as workpiece movement subsystem 15 to place the wafer on inspection table 9.

This preferred method comprises providing an incident beam and scanning the beam on the surface of the workpiece so that a portion of the beam is reflected along a light channel axis LC in a front quartersphere FQ. The method further preferably but optionally comprises providing a light channel collection and detection assembly 560, which is centered upon light channel axis LC. The channel developed from the output of the assembly 560, referred to herein as the light channel 650, receives the beam reflected from the workpiece surface S.

The method also comprises collecting a scattered portion of the incident beam at one or more wing collectors disposed in the front quartersphere FQ, outside the incident plane, and at a null or a local minimum, in surface roughness scatter relative to defect scatter, for example, from a defect perspective, at a maximum in the signal to noise ratio of defect scatter to surface roughness scatter when the incident beam is P polarized, or, from a surface roughness scatter perspective, when the surface roughness is at a relative minimum (BRD-$F_{MIN}$) of the BRDF when the incident beam is P polarized.

The method further comprises collecting scattered portions of the incident beam at a plurality of back collectors disposed in the back quartersphere BQ.

In addition, the method comprises detecting the collected portions of the incident beam and generating signals in response.

The method further comprises collecting scattered portions of the incident beam at a plurality of collectors 300 and identifying defects using signals from selected combinations of collectors 300.

The method further comprises collecting scattered portions of the incident beam at a plurality of collectors 300, comprising wing collectors 340 and dual back collectors 310, and classifying defects on a workpiece W based on differences in the angular distribution of the light scattered from the workpiece.

In addition, the method comprises collecting angular components of scatter light that is collected by multiple collectors 300 arranged to collect light from multiple conical regions above a surface S in the laser-based surface inspection system 10, and using the angular components to facilitate defect classification.

The method further comprises comparing the amount of light collected by one or a combination of collectors to the amount of light collected by one or more of the other collectors 300.

In addition, the method comprises comparing the amount of light collected by one or a combination of collectors 300 to the amount of light collected by one or more of the other collectors 300.

In the context of semiconductor wafer or chip inspection, and in like workpieces, a considerable fraction of the beam energy that is scattered from the workpiece surface is distributed outside the plane of incidence of the beam. The scattering of energy from a particle defect on a semiconductor wafer is known. It includes energy predominantly distributed in an annulus. For surface inspection systems wherein the detector lens assemblies are arranged solely in the plane of incidence, some of this energy may be missed. Inclusion of back collector and detector assemblies 240 therefore improve the ability of the system to take advantage of this energy to improve signal strength for defects. Moving the back collector detector assemblies 240 location to a position in the back quartersphere BQ that is 45° out of the plane of incidence improves back collector detection of polystyrene latex spheres ("PSL"s). When the back collector 240 was in the plane of incidence (as shown in U.S. Pat. No. 5,712,701), Rayleigh air scatter from the laser beam was coupled into the detector, thereby raising the background level and reducing the signal-to-noise ratio (SNR) of this collector. By moving the detector out of plane, less Rayleigh air scatter was coupled into the collector while the scattered light detected from particles on the wafer surface was nearly the same. As a result, the SNR substantially improved. A back collector orientation with an azimuthal angle of 235 degrees (0 degrees is outgoing laser beam propagation direction) and a meridional (or elevation) angle of 53 degrees is used in known prior systems.

Unfortunately, the single out-of-plane detector scheme described in U.S. Pat. No. 5,712,701 has some unfortunate drawbacks. Silicon wafers are normally polished with polishing pads to generate an extremely smooth surface. The pads also produce fine structure in the surface that behaves like a grating mirror when illuminated with a laser beam. As the wafer is scanned, the laser spot is diffracted by the grating surface in the direction perpendicular to the polisher-induced "groove" structure. The fundamental direction of the diffracted light changes as the wafer rotates, therefore the background scatter into the back collector varies with the rotation angle, producing a haze map with excessive amplitude variation, or "bow tie" effect. Users who want to sort wafers by surface roughness find it difficult to do so because of this effect. They Would prefer a surface roughness map that has minimal "bow tie" effect and is more representative of the Total Integrated Scatter (TIS) from the wafer. In addition, the scanner exhibits lower sensitivity in the regions where the background level is higher, creating a sensitivity variation around the wafer.

It must also be noted that some kinds of defects may be undetectable when detection occurs in only one plane. Scratches are an example of a defect that falls into this category. A scratch having an orientation that is perpendicular to the AOD scan direction is detectable using a front collector if no edge exclusion mask is present. However, as the wafer rotates, the orientation of the scratch changes with respect to the AOD scan direction. When the orientation of the scratch is 45 degrees with respect to the AOD scan direction, much of the scratch signal is no longer collectable by any detectors. By positioning collectors outside of the plane of incidence in order to form "wing" channels, signal from scratches oriented 45 degrees with respect to the AOD scan direction can be detected, thereby improving complete scratch detection throughout the length of the scratch at various orientations to the incident beam.

It should be noted that methods of scatter detection that use a Total Integrated Scatter (TIS) collector system will not be as sensitive to these kinds of scratches since they inherently collect scatter from all directions at once. Since the scatter from the scratches is very directional in nature, these scratch defects will be "washed out" by the background signal from regions of the collection hemisphere where there is no scratch signal, thereby reducing the effective sensitivity of the system to scratches. By using separate angle-resolved detectors, the scratch signal can be localized to a particular detector and detected independently from the other collectors, thus avoiding the effective reduction of scratch signal that results from averaging signals from multiple collectors, some of which have collected scatter representative of workpiece locations where no scratch is present.

As described in the Stover reference, incident laser light is scattered (or diffracted) from the surface in relation to the surface structure spatial frequency content of the surface roughness. The 2D grating equation relates the scattering angle (in spherical coordinates) to a specific 2D surface structure spatial frequency coordinate. The Angle Resolved Scatter (ARS) architecture described in the '701 patent, as well as U.S. Pat. No. 6,118,525 and U.S. Pat. No. 6,292,259 utilizes collection optics to collect scatter from specific angular regions of the collection sphere. These angular regions correspond to regions of the 2D surface structure spatial frequency spectrum.

Typically, surface inspection systems employ only an out-of-plane back collector to provide scatter information that is strictly in the out-of-plane or cross-plane surface structure spatial frequency region. In such systems, defects producing non-symmetrical scatter distributions can scatter light into space above the workpiece associated with surface structure spatial frequency ranges where no collection optics are located. In addition, non-symmetrical background surface structure causes the surface roughness scatter to change intensity and direction as the in-scan and cross-scan directions change with respect to the wafer surface as the wafer is rotated during the spiral scan.

Figure 52:
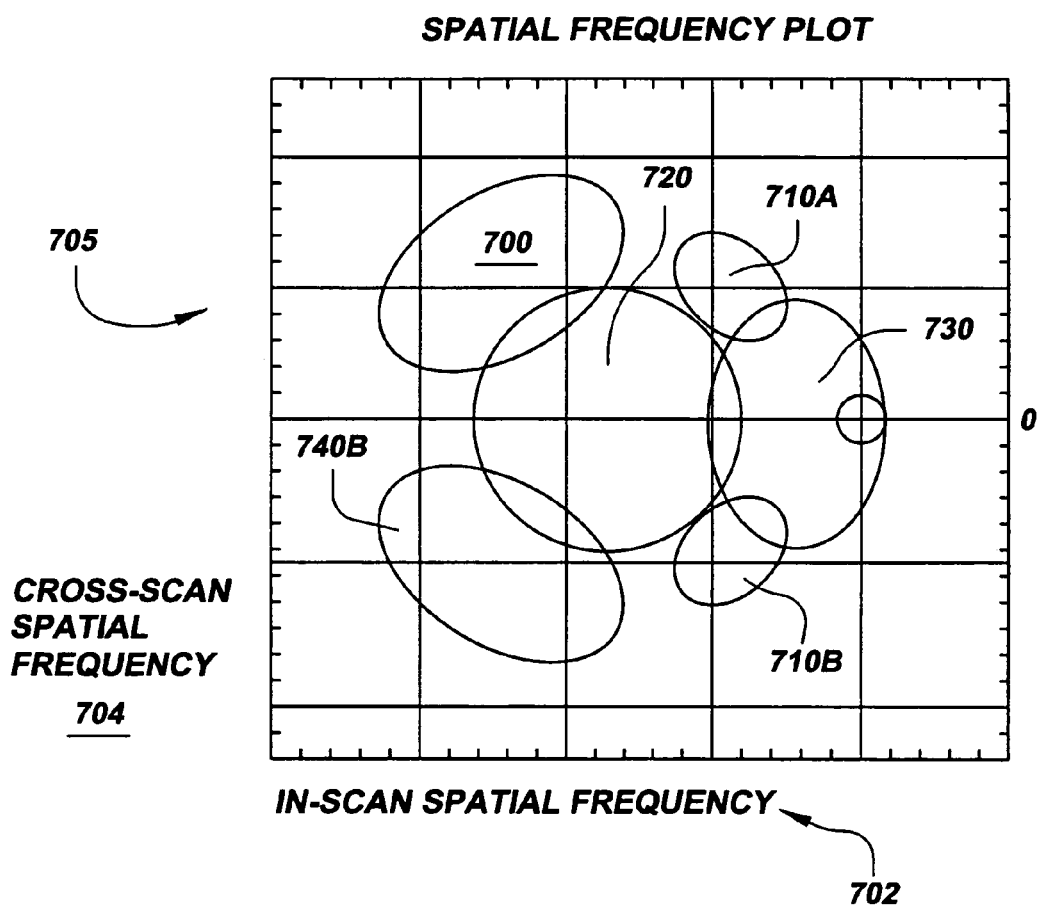
FIG. 52 is an in-scan surface structure spatial frequency plot for use in analyzing the in-scan frequency surface structure spatial response of collectors in a surface inspection system of the present invention.

The surface spatial structure frequency plot for the surface inspection system 10 of the present invention is shown in FIG. 52. As can be readily seen, the new design provides more complete collection of scattered light associated with the surface structure spatial frequency spectrum with the addition of channels. This enables simultaneous measurement of the Total Integrated Scatter (TIS) from the wafer and the Angle-Resolved distribution of the Scatter (ARS). By combining both TIS and ARS in one system, the scanner achieves both improved detection sensitivity and defect classification capability.

One may use wing collectors 310A, 310B, but no back collectors 340A, 340B, or back collectors 340A, 340B and no wing collectors 310A, 310B. Preferably both are used.

In order to determine the geometry of a defect, prior art surface inspection systems collected scattered portions of the incident beam at a plurality of detectors, applied a threshold separately to each, then evaluated the results for defect classification.

Signal Analysis

Channel Definition, Contd.

In accordance with the current invention, a system and method is provided for detecting the presence of defects by collecting scattered portions of the incident beam at a plurality of collectors 300 and identifying defects using signals from selected combinations of collectors 300.

In one embodiment of the invention, the method, hereinafter known as the combined scatter method or CFT method 812, further comprises the step 860 of combining output from selected collectors 300, the step 870 of filtering and then threshold testing. In another embodiment, the method, hereinafter known as the individual collector processing method or FTC method 814, further comprises the step 870 of filtering output from selected collectors 300 and threshold testing, and then the step 860 of combining the resultant output. Other methods of collector combining are envisioned in the scope of the present invention, and some of them will be discussed as examples in greater detail below.

Figure 39:
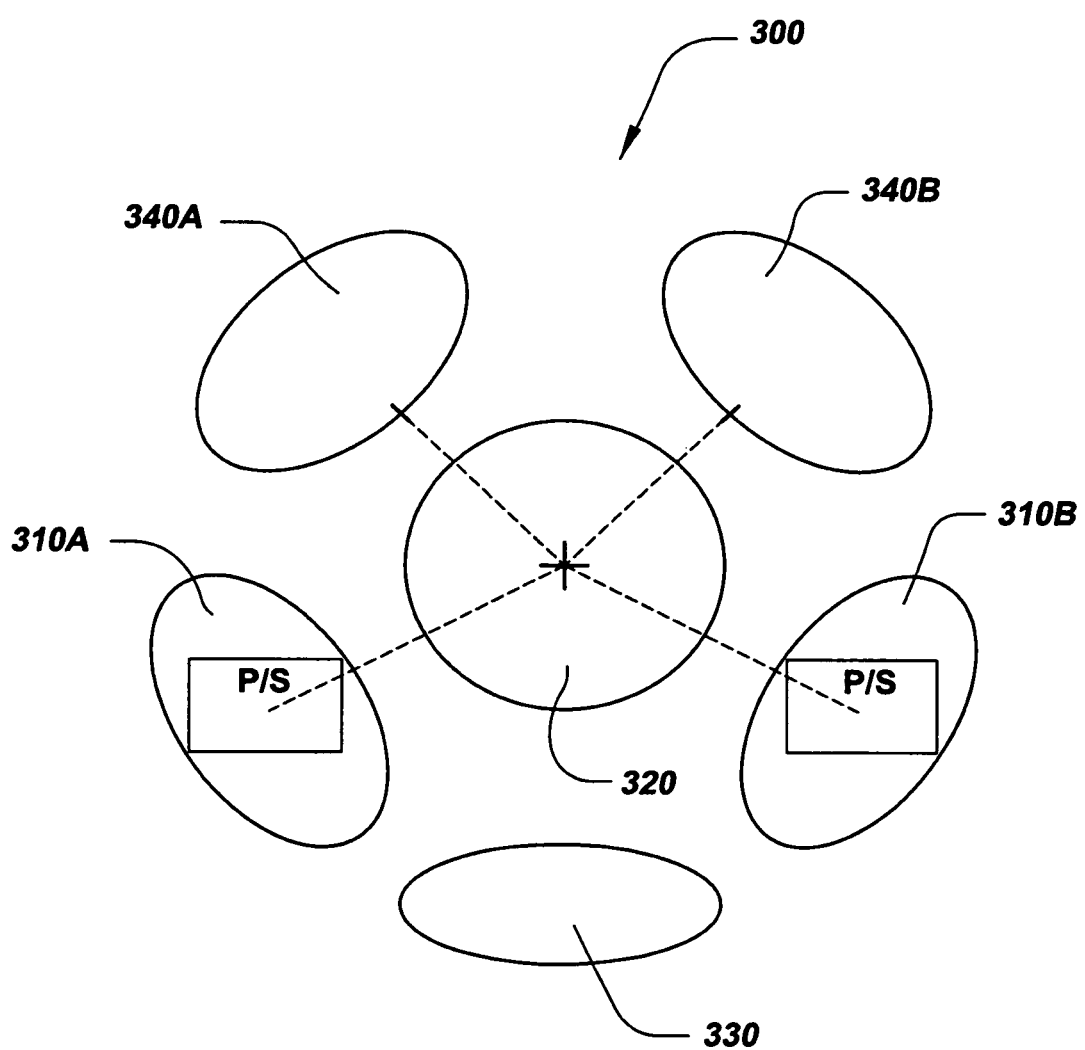
FIG. 39 is a block diagram of the collectors used in a surface inspection system according to the present invention.

The collectors 300 in the surface inspection system 10 of the present invention, shown in block diagram form in FIG. 39, comprise front collector 330, center collector 320, a pair of wing collectors 310A, 310B, each operable in P or S orientation, and a pair of back collectors 340A, 340B. The collectors 300 are positioned to collect scattered light components in a significant amount of the region in which scatter from defects are primarily distributed. Light detected by the various collectors 300 signifies a defect and surface roughness in or on the surface S of the workpiece W. Signals from the collectors 300 are selectively combinable using hardware and software elements to enable detection and classification of defects in the presence of noise.

Figure 40:
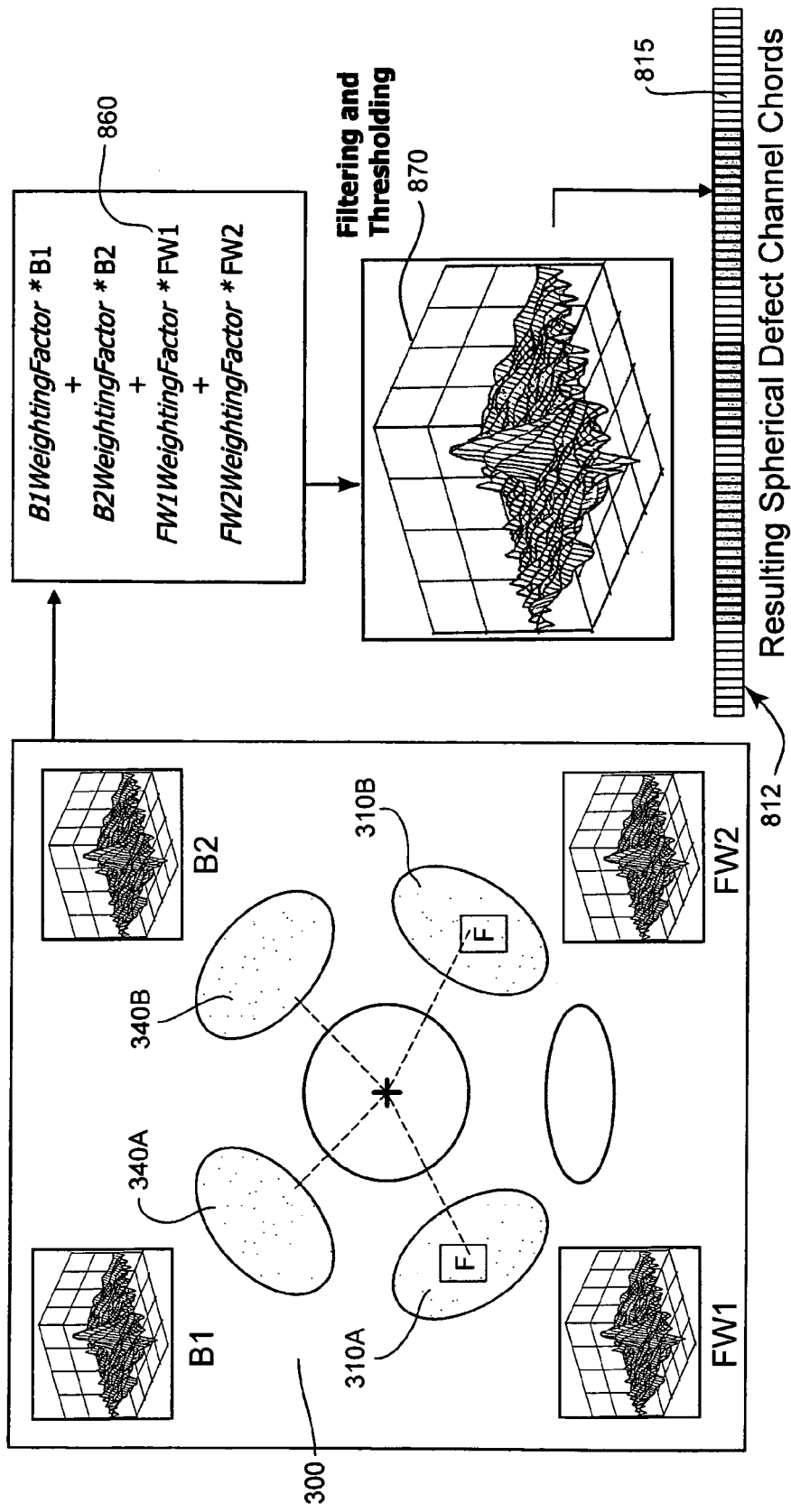
FIG. 40 is a block diagram showing one embodiment of a method for detecting the presence of defects.

FIG. 40 is a block diagram showing an embodiment of the current invention of a method for detecting the presence of defects by collecting scattered portions of the incident beam at a plurality of collector detector assemblies 200 and identifying defects using signals from selected combinations of collector detector assemblies 200. Specifically, FIG. 40 shows one method for formation of a spherical defect channel chord 815, which is particularly useful in identifying small spherical objects such as PSLs and defects with like geometries. The method illustrated comprises the combined scatter method of combining output from selected collectors (CFT method 812), having the step 860 of combining output from selected collectors, and the step 870 of filtering and then threshold testing. Chords and the various method of combining channels, such as the CFT method 812, are described in more detail below. In the channel combination example illustrated in FIG. 40, the selected combinations of collector detector assemblies 200 comprise the dual back collector detector assemblies 240A, 240B and wing collector detector assemblies 210A, 210B configured for P-polarization.

Detection of Defects in the Presence of Noise

Using Thresholding Based on Modeling Detector Module

As discussed below, summation of appropriately weighted output from collector detector assemblies 200 enables optimized detection of small defects, while other weighting schemes can optimize for detection of other defects, such as scratches. The output of the multiple and various collector detector assemblies 200, for example, as are presented in system 10, may be used to determine whether or not scatter from a Light Point Defect ("LPD") is as opposed to noise. The following is a method that employs multiple and various collector detector assemblies 200, for example, as are presented in system 10, to detect Light Point Defects ("LPD") in the presence of noise.

Recognizing that each collector detector assembly 200 will have associated with it a constant background light level and a level of background noise, the output of any single detector module 400 in a collector detector assembly 200 in the presence of an LPD is given by:

$$output_i = signal_i + P_i + noise_i, E\text{ where}$$

$signal_i$ is the scattering power of a defect at detector i, $P_i$ is the constant background level; and $Noise_i$ is the noise associated with the collector, such as shot noise, electronic noise or pick-up noise.

The output of a detector module 400 if no LPD is present is given by:

$$output_i = P_i + noise_i, E$$

In accordance with this aspect of the invention, an "optimum" or ideal detector module 400 is constructed, in which a constant expected rate of "false alarms" is established and then the rate of detecting true LPD events is maximized. It can be demonstrated that the optimum detector module 400 is implementable by using a log-likelihood ratio threshold:

$$\vec{r} \equiv \begin{bmatrix} output_1 \\ output_2 \\ \vdots \\ output_n \end{bmatrix}, \ln\left(\frac{p(\vec{r} \mid LPD \text{ present})}{p(\vec{r} \mid LPD \text{ not present})}\right) > \gamma,$$

with the value γ determined by the accepted false alarm rate.

Whenever the log likelihood ratio exceeds γ, an LPD is declared to be present; and as long as the ratio is less than γ, no LPD event is declared. Rewriting the equation in terms of the individual detector modules 400, the log likelihood ratio is given by:

$$\ln\left(\frac{p(\vec{r} \mid LPD \text{ present})}{p(\vec{r} \mid LPD \text{ not present})}\right) =$$

$$\sum \frac{(output_i - P_i)^2}{2\sigma_i^2} - \sum \frac{(output_i - P_i - signal_i)^2}{2\sigma_i^2} =$$

$$\sum \frac{(output_i - P_i) signal_i}{\sigma_i^2} - \sum \frac{signal_i^2}{2\sigma_i^2}$$

The second expression on the right side of the equation does not depend on measured values, but is solely a function of the noise levels and expected LPD signal levels of the detector module 400. Therefore, it is constant and can be pre-computed. The log likelihood ratio test then becomes a threshold test of $$\sum \frac{(output_i - P_i \, signal_i)}{\sigma_i^2} > \gamma + \sum \frac{signal_i^2}{2\sigma_i^2}.$$

Defining $$G_i \equiv \frac{signal_i}{\sigma_i^2},$$

the log likelihood ratio test becomes a threshold test of $$\sum output_i G_i - \sum P_i G_i > \gamma + \frac{\sum signal_i G_i}{2};$$

with $G_i$ becoming a weighting value for the output of each collector. Defining $$G_i \equiv \frac{signal_i}{\sigma_i^2}$$

provides a set of gains that also comprises the optimum gain weighting for maximizing the signal-to-noise ratio.

The first summation on the left side of the equation is a weighted sum of the individual collector outputs. The second summation on the left side of the equation is simply the background level of the weighted sum of the collectors. The right hand side of the inequality is a constant that may be pre-computed, and comprises the threshold value that, when exceeded by the weighted output of the collectors, causes an LPD to be declared present.

In one embodiment, a system and method for inspecting a surface of a workpiece by collecting scattered portions of the incident beam at a plurality of collectors and identifying defects using signals from selected combinations of collectors comprises the step combining the output of detector modules 400 associated with a set of collectors, filtering the combined output, and comparing the filtered combined output to a threshold value.

Figure 69:
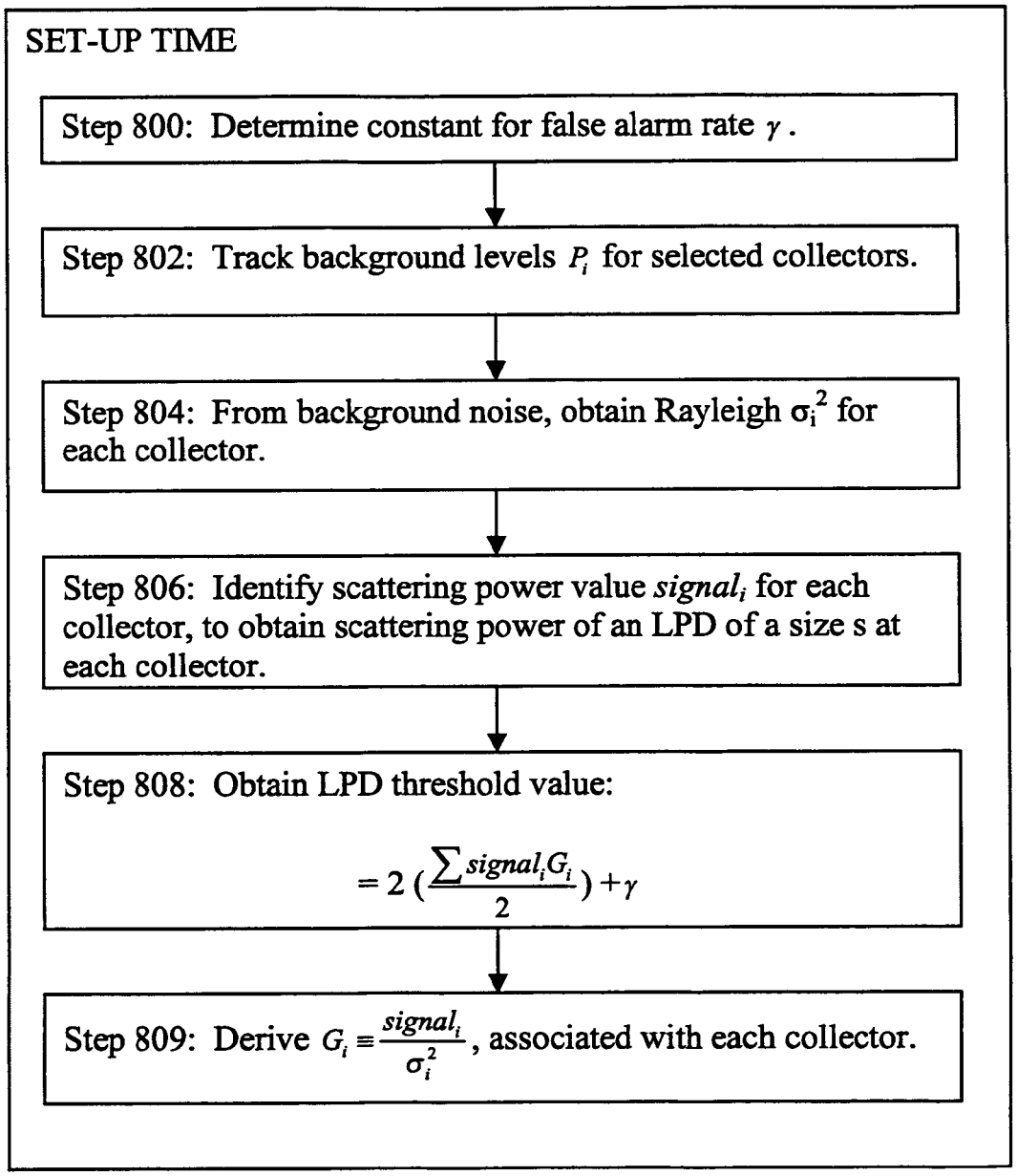
FIG. 69 is a block diagram showing a portion of a system and method for detection of a light point defect (LPD) greater than a selected size, performed at set up of a surface inspection system.
Figure 70:
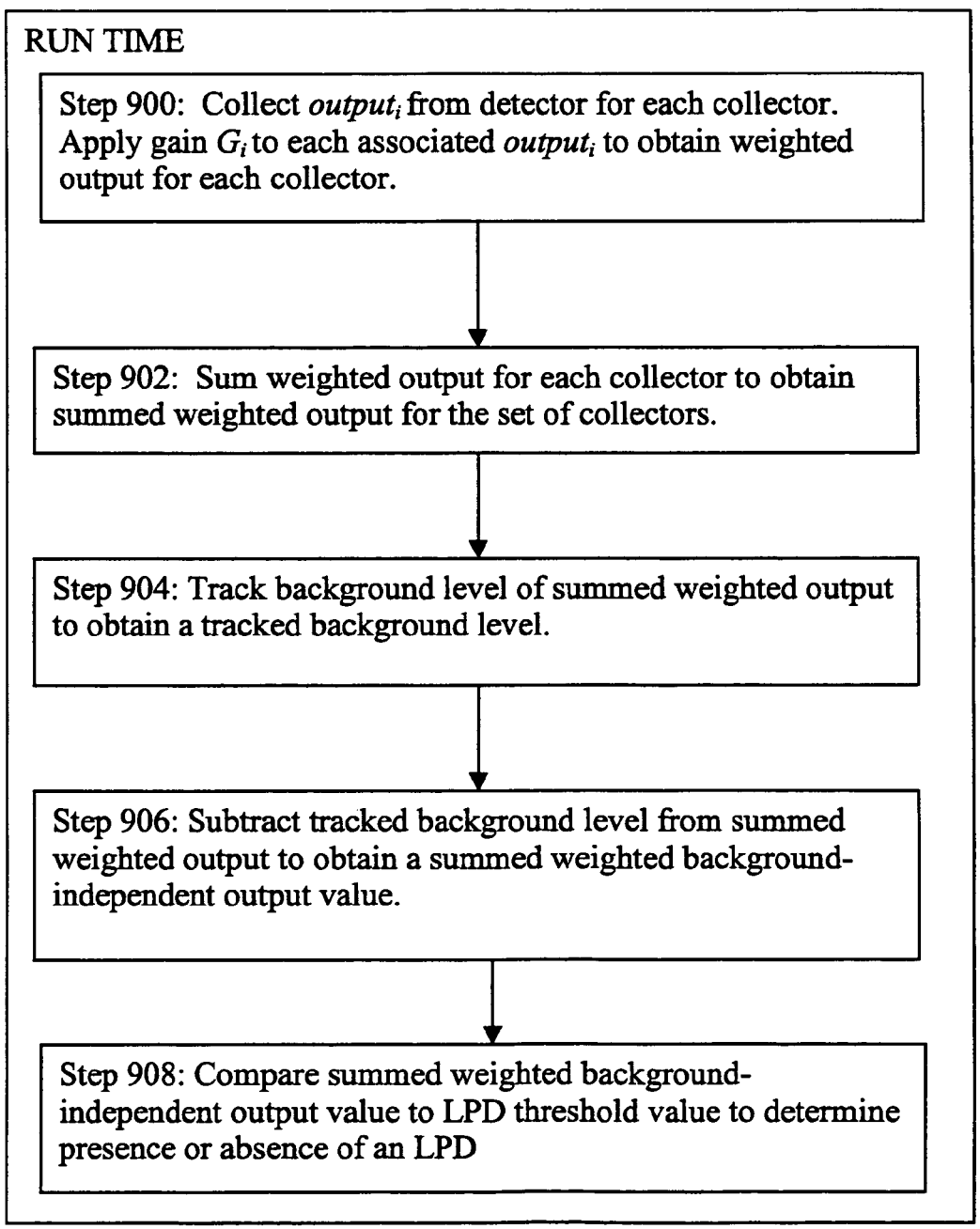
FIG. 70 is a block diagram showing another portion of a system and method for detection of a light point defect (LPD) greater than a selected size, performed at during operation of the surface inspection system.

FIGS. 69 and 70 show an illustrative but not necessarily preferred embodiment for a system and method for detecting a light point defect (LPD) greater than a selected size, comprising the following steps:

At Setup time (FIG. 69):
  Step 800: Determine the constant associated with the false alarm rate $\gamma$.
  Step 802: Track the background levels $P_i$ for a selected set of collectors.
  Step 804: From the background noise, obtain the noise variance values $\sigma_i^2$ (including values for Rayleigh noise variance, non-Gaussian noise including Poisson, speckle noise, and local haze variation) that are associated with each collector in the selected set.
  Step 806: Identify a selected scattering power value $signal_i$ associated with each collector in the selected set, to obtain the scattering power of an LPD of a selected size s at each collector in the selected set.
  Step 808: Derive collector weighting coefficients comprising a gain of $$G_i \equiv \frac{signal_i}{\sigma_i^2},$$

associated with each collector in the selected set.
  Step 809: Divide the summed weighted scattering power values by 2

$$\left(\frac{\sum signal_i G_i}{2}\right)$$

and add $\gamma$ to obtain the LPD threshold value.

The set-up method shown in FIG. 69 describes a theoretical way to find collector weighting factors. An alternative set up method comprises optimizing the collector gain coefficients (collector weighting coefficients) for optimal SNR empirically. In the empirical approach, coefficient computation comprises any conventional empirical method, such as 1) collecting raw data from a workpiece or a set of workpieces, 2) choosing a set of weighting coefficients, 3) measuring the SNR of the combined set of raw data, and 4) repeat steps 1) through 3) with different coefficients until the optimal SNR is found.

At Run time (FIG. 70):
  Step 900: Collect the output value $output_i$ from the detector module 400 associated with each collector 300 in the selected set. Apply the gain $G_i$ to each associated output value $output_i$ (either digitally or with an analog circuit) to obtain the weighted output for each collector in the selected set.
  Step 902: Sum the weighted output for each collector in the selected set (either digitally or with an analog circuit) to obtain the summed weighted output for the collectors in the selected set.
  Step 904: Track the background level of the summed weighted output to obtain a tracked background level.
  Step 906: Subtract the tracked background level from the summed weighted output to obtain a summed weighted background-independent output value.
  Step 908: Compare the summed weighted background-independent output value to the LPD threshold value to determine the presence or absence of an LPD.

A set of contiguous elements 554 that have over-threshold summed weighted background-independent output values in the output of an AOD scan are formed into a channel chord 552. The channel chords 552 so identified are analyzed by the channel analysis system 520 shown in FIG. 46, using currently known techniques to identify defects.

In the above-described combined scatter method (CFT method 812) for detection of defects, the output of detector modules 400 associated with a set of collectors 300 is combined, filtered, and compared to a threshold value. In order to obtain optimum detection of LPD events, in the presently preferred yet merely illustrative embodiment, the selected set of collectors 300 comprises the set of collectors shown in FIG. 40, namely the dual back collectors 340A, 340B and the P-polarized wing collectors 310A, 310B.

It should be noted, however, that the invention in its broader aspects is not limited to combining the collectors 300 using the CFT method as shown in FIG. 40. The present invention contemplates methods of defect detection in which collector output is combined in other configurations in order to facilitate collection of other types of defects. For instance, the back collectors 340A, 340B could comprise a set of collectors to detect certain kinds of substrate defects to which the P-polarized wing collectors are less sensitive.

The combined scatter method for detection of defects, as shown in FIG. 40, is particularly useful in improving small particle sensitivity, providing additional information for classification. In addition, if combined scatter method is utilized to combine output associated with collectors as much as possible before input to feature (defect) process methods, gauge processing requirements will be minimized.

However, the combined scatter method is not preferable for detecting asymmetric defect scatter, such as produced by scratches in the workpiece surface. As noted above, the invention in its broader aspects is not limited to the combined scatter method. Another embodiment of the present invention comprises a method of defect detection in which the output associated with a collector is compared to a threshold value associated therewith, and then combined with (similarly threshold tested) output associated with at least one collector in order to facilitate detection of other types of defects.

Confidence Level Processing

In accordance with still another aspect of the invention, another surface defect detection method for defect detection in the presence of noise comprises identifying defects using the statistical significance of collector output. This method, and more particularly preferred implementations of the method, can be used with the surface inspection system 10 described herein above, or other systems such as noise-limited defect detection systems for which the background noise statistics are well known. Preferred implementations of this method can substantially extend the effective detection sensitivity of the system, enabling users to make good use of statistically significant data that otherwise may provide little benefit or even be discarded in known systems. Preferred implementations of this method may be used to augment signal processing methods such as those described in U.S. Pat. No. 6,529,270 (the "'270 patent").

In the preferred embodiments and implementations disclosed in the '270 patent, signals from the photomultiplier tube detectors are filtered in the in-scan and cross-scan directions with a filter that is matched to the laser spot shape. A threshold is then applied to the filtered 2-dimensional data. Values above the threshold are deemed to be "real" defects while those below the threshold are discarded. Morphological processing is then performed to assess whether the defects are point, area, or line (scratch) defects. The defects are tabulated and displayed on a computer screen. Although the 2-dimensional filtered data exhibits an optimal signal-to-noise ratio ("SNR") in a least-squares sense, the method for identifying defects from this data as described in the preferred embodiment and implementation of the '270 patent in some circumstances can be improved. In the preferred embodiment and method implementation of that patent, the threshold detector is applied to the 2-dimensional filtered data to determine if any defects are present. Due to the binary characteristics of this threshold detector, points that lie above the threshold are presented to the customer as real, and are implicitly assigned a 100% confidence level. All values below the threshold are ignored by the system, and are essentially assigned a confidence level of 0%. As a consequence, the threshold value is typically set relatively high with respect to the noise background in order to minimize false positive events. Because there can be over a billion voltage samples on a 300 mm silicon wafer surface, this implies that the threshold should be set at least 6 standard deviations above the background noise level ($1 \times 10^{-9}$ probability level for a Gaussian distribution) to ensure that there are no more than a few false events. As a consequence, over 99% of the data is ignored, much of which is statistically significant and useful. This can cause essentially a mismatch between the statistical nature of the data and how it is presented to the system or method user.

One approach for a system user to accommodate this phenomenon is to lower the threshold below the $1 \times 10^{-9}$ level in order to see defects of interest. Where the false positive events due to background noise are displayed with the same statistical significance as the true defect events, however, this can result in a non-optimal display of "real" and "false" events. Although it is possible to attach a statistical significance and weighting factor to an event, typically the user assumes that a defect is either present or not present, without taking into account the statistical nature of the underlying data.

This implicates a need for a signal processing system and method that calculate the statistical significance of the data, and then faithfully represents this significance to the user. By allowing the user to weight the bins and displayed defects by the computed statistical significance, data that previously has been discarded can become useful to the user. This can extend the effective detection sensitivity range of the system and/or method by several nanometers in the context of semiconductor wafer or chip inspection, as will be described herein below.

Figure 57:
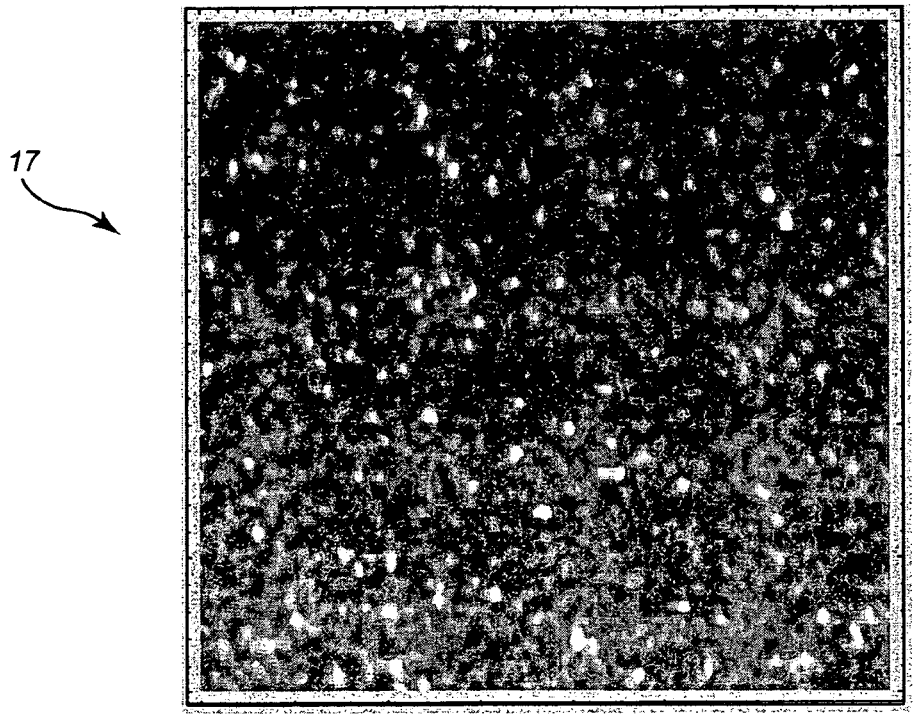
FIG. 57 is a 2-dimensional voltage map that contains both background noise and defect signals.

To illustrate this aspect of the invention, FIG. 57 is a defect map 17 depicting 2-dimensional (3.5 mm×5 mm, HxV) scanner data that has been collected using system 10 as described herein above to inspect a polished, unpatterned silicon wafer. Each pixel in the defect map 17 presents an intensity that is representative of a voltage level collected at the location on the map that is associated with the pixel. This data has been filtered in the in-scan and cross-scan directions in accordance with the preferred method described in the '270 patent. Two back collector maps and two P-polarized wing collector maps were averaged together to produce the map 17 shown in FIG. 57. A plurality of 50 nm polystyrene latex spheres ("PSLs") were deposited onto the section of the silicon wafer depicted in the map 17 prior to scanning the surface. These particles can be readily seen in the map 17 as the bright locations along with the mottled background that is caused by residual shot noise.

Figure 58:
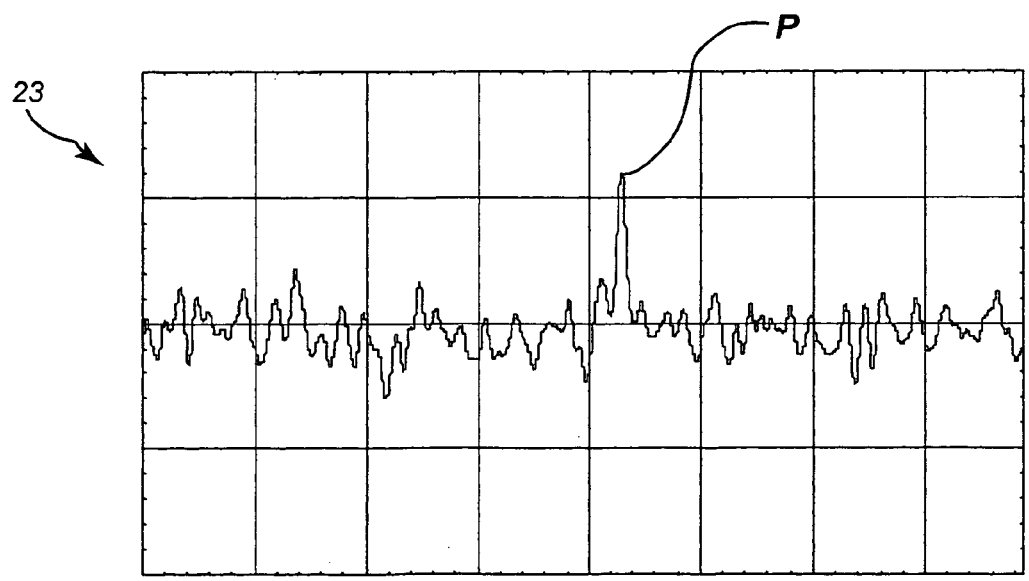
FIG. 58 is a voltage plot of signal for a selected row in FIG. 57.

FIG. 58 depicts a voltage slice plot 23 that depicts one of these 50 nm particles. Although the particle peak P in FIG. 58 appears to be substantially above the noise floor in this particular scan line, there is a small but finite probability that peaks in the noise floor can occasionally exceed this level during a complete scan of a wafer. Because there can be on the order of $10^9$ samples across the entire surface of a 300 mm wafer of this type, the probability of a noise voltage peak exceeding the height of a voltage peak representative of the PSL should be very low ($<1 \times 10^{-9}$) to ensure that the background noise pulses can be clearly distinguished from the particle pulses essentially all of the time. As a consequence, the detection threshold is usually set high enough so that the number of "false particles" on the wafer caused by noise peaks is approximately less than 5. In the case of FIG. 57, the threshold should be set at the voltage corresponding to a 50 nm PSL peak in view of the voltage distribution of the background noise to prevent an excessive number of "false particles" from appearing in the defect map 17 after the threshold level is applied.

Figure 59:
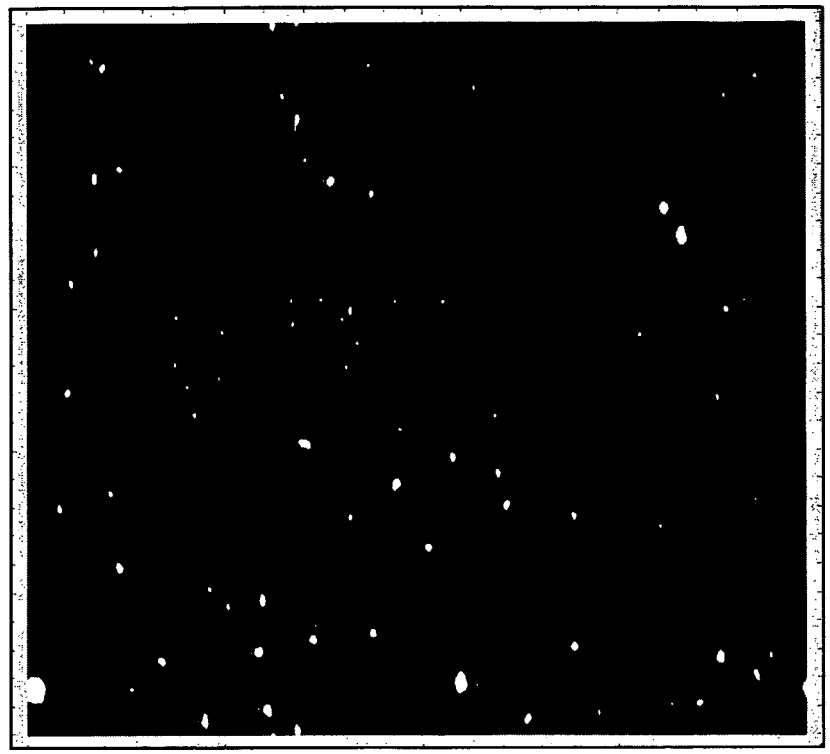
FIG. 59 is a defect map for FIG. 57, generated by inserting a constant value at each pixel position for which the threshold exceeded the voltage value corresponding to a 50 nm polystyrene latex sphere (PSL) signal peak.

FIG. 59 depicts a defect map that was generated from the defect map 17 of FIG. 57 by inserting a constant value at each pixel that represented a voltage level that exceeded the voltage threshold value corresponding to a 50 nm PSL. As can be readily seen, nearly all of the information that was present in FIG. 57 has been discarded to create the defect map 25 in FIG. 59. The voltage signal of the particle signal shown in FIG. 58 is barely above the threshold and so would cause the pixel associated therewith in the defect map of FIG. 59 to be set to its constant value, while several 50 nm particles appearing in the defect map 17 shown in FIG. 57 have associated therewith voltage signals that fall below the threshold and therefore do not appear in the defect map 25 of FIG. 59.

It could be expected that, absent the teaching of this aspect of the invention, if system users set the threshold of a prior known system based on the plot 23 in FIG. 58, they would probably set it considerably lower than the expected voltage level peak of signals associated with 50 nm particles in order to include more of the defects that appear in the defect map 17 but that do not appear in the defect map 25. However, due to the statistics of the background noise, too many noise voltage level peaks would exceed this threshold when the entire wafer is scanned. This has posed problems for users of prior known systems. Since such systems do not recognize a gradation of statistical significance, the statistical significance of the data is misrepresented. If a signal exceeds the preset threshold, the system assumes with 100% confidence that a defect is present at that location (which is not true). If the signal level falls below the preset threshold, the system assumes that there is no defect (which may or may not be true). What is needed is a method for calculating the statistical significance of an event, and properly representing that information to the system user. Because the surface defect data collected is statistical in nature, what is further needed is to provide a processing system for a surface inspection system that operates on surface defect data on a statistical basis. The statistical significance of the surface defect data can be used in the binning recipe calculation to determine whether the wafer has passed or failed inspection. A presently preferred implementation of this process, which will be referred to herein as "Confidence Level Detection Processing Method 502," will now be described.

The defect map 17 depicted in FIG. 57 is a 2-dimensional voltage map that contains representations of both background noise voltage signals and defect voltage signals from a portion of a surface S of a workpiece W. Scatter from the surface structure (measured as haze) appears as a constant background level. Scatter from defects (particles, scratches, epitaxial spikes, COPs, etc.) is added to this micro-roughness background, producing small, localized peaks in the voltage map 17. Since the detected power levels in semiconductor wafer inspection applications typically are very low (picoWatt to nanoWatt range), the map 17 is dominated by shot (quantum-mechanical) noise. Shot noise exhibits a Poisson probability distribution, but can be accurately approximated by a Gaussian distribution if the number of detected photoelectron events within the effective integration time (or bandwidth) of the detection system exceeds ~30 photoelectrons. For system 10 as described herein, this condition is normally met after 2-dimensional filtering is performed on the voltage maps 17, therefore the underlying background noise distribution of FIG. 57 can be assumed to be Gaussian.

Figure 60:
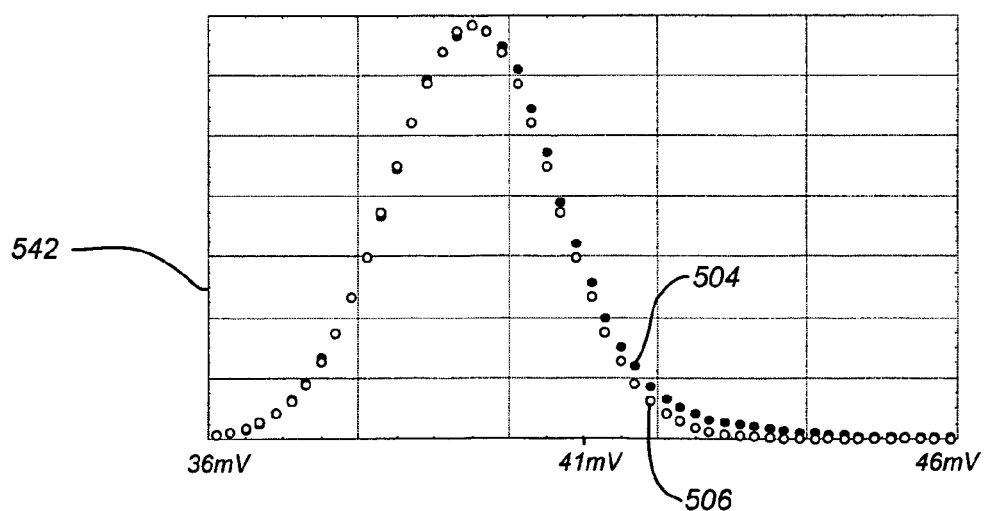
FIGS. 60 and 61 are plots showing the measured distribution (black points) and underlying Gaussian background noise distribution (X marks) of the signals in FIG. 57.
Figure 61:
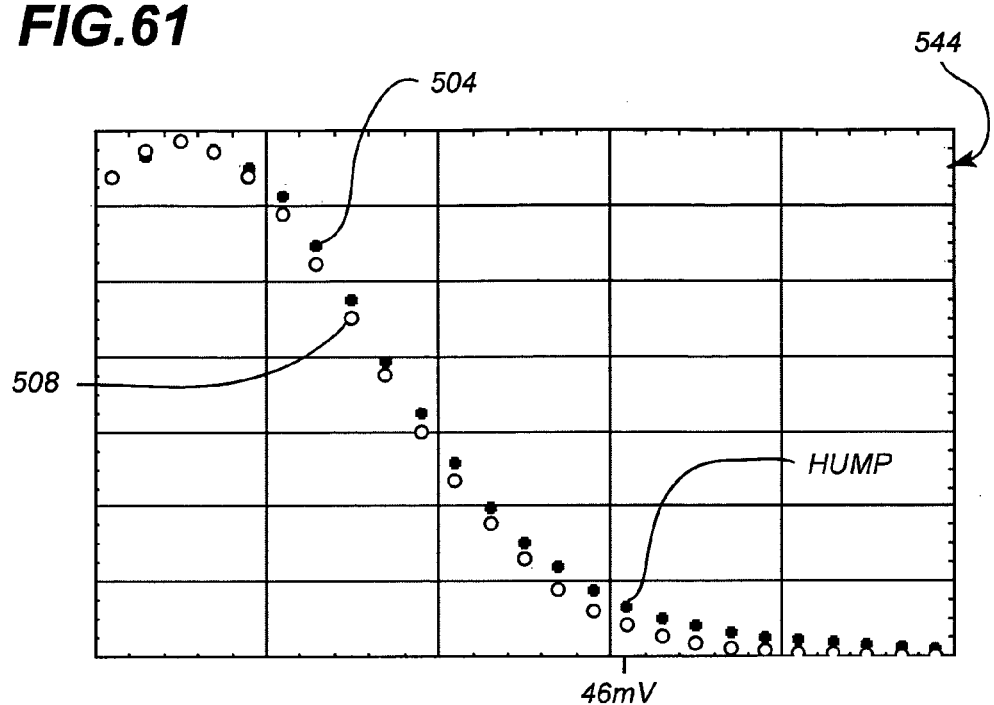
Figure 62:
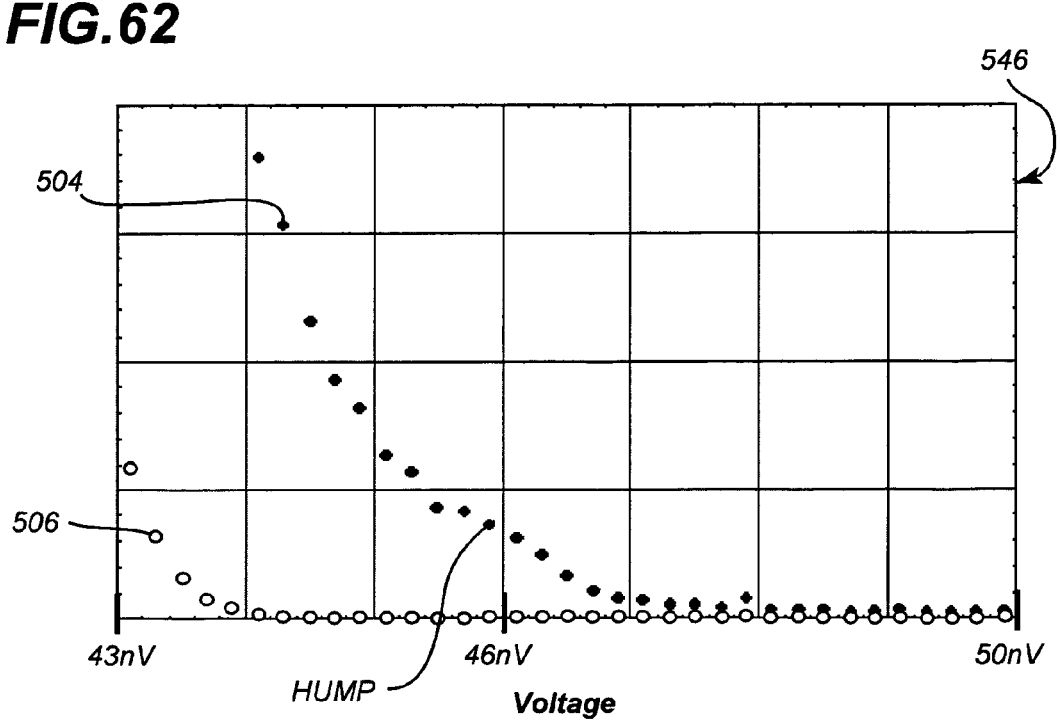
FIG. 62 is a plot showing an expanded scale view of FIG. 61.

The measured distribution (black points) and underlying Gaussian background noise distribution (X marks) of voltage values associated with the region locations represented by pixels in the defect map of FIG. 57 are shown in the plots 542, 544, 546 of, respectively, FIGS. 60, 61, 62, each of which present a distribution of voltage levels. The black points were calculated by counting the number of voltage values within a ±100 microVolt range around each selected voltage level. The resulting measured voltage count curve 504 is the measured probability distribution for the defect map of FIG. 57. The underlying Gaussian background noise probability distribution was calculated by fitting a Gaussian to the lower (left) half of the measured probability distribution where the defect signals are not present; it is represented by the noise probability curve 506. As can be seen in the plot 542 of FIG. 60, there is significant signal content above the Gaussian background noise probability distribution for voltages greater than about 41 mV. FIG. 61 is a plot 544 that gives an expanded view of a portion of the measured probability distribution and Gaussian probability distribution, as represented by curves 504, 506 of the plot 542 of FIG. 60, showing a "hump" near 45-46 mV. This hump is produced by the 50 nm PSLs on the surface S of the workpiece W represented by the defect map 17 of FIG. 57. The hump is shown even more clearly on the plot 546 of FIG. 62, which depicts an even more expanded scale view of the curves 504, 506 shown in the plot 544 of FIG. 61.

In some prior known systems and methods, the threshold level is set at the voltage corresponding to ~50 nm (6 standard deviations above the background noise mean), or 46 mV, as shown in FIG. 59. This level corresponds to the far right edge of the plot in FIG. 60. Although this threshold level ensures that there are minimal false detected events on the wafer, it is readily apparent in FIGS. 60-62 that interesting data between 42 and 46 mV would be discarded. The differences between the black points on the measured voltage count curve 504 and X marks on the noise probability curve 506 in FIGS. 60-62 indicate that there are thousands of voltage sample values above the underlying background level in this voltage range that are statistically relevant. The presently preferred method implementation provides a means to beneficially utilize this data.

As indicated above, the difference between the measured curve 504 (black points) and noise curve 506 (X marks) in FIGS. 60-62 represents meaningful signal content that is present in the map 17 of FIG. 57. To further quantify this, a Confidence Level Factor (CLF) can be defined as follows:

$$CLF[V] = \frac{H[V] - B[V]}{H[V]} \quad (1)$$

where
CLF[V]=Confidence Level Factor,
H[V]=the count of voltage values that are measured within a pre-specified voltage range centered on a selected voltage V, within a selected region of a workpiece surface,
B[V]=the count of voltage values in H[V} that are associated or expected to be associated with background noise.

When the CLF is multiplied by 100%, it is referred to as the Confidence Level (CL). If the calculated background noise distribution is very small, the CL will be approximately 100%. As the noise level increases relative to the measured signal content, the CL will decrease.

Note that the CLF is spatially dependent. For example, consider the CLF curve 508 shown in the plot 514 of FIG. 63, which was computed for the sample set of voltages that are represented in the map 17 of FIG. 57. This CLF curve 508 will not necessarily be the same as one produced for the set of voltages associated with a scan at another part of the wafer, where the background and defect-induced voltage distributions may be different from those shown in the defect map 17 of FIG. 57. In the case of FIG. 57, there are numerous 50 nm PSLs present on the region represented by the map 17, therefore the CL for the detection of these defects is >99%. The CL would be lower in a wafer region that contains very few 50 nm particles and a higher micro-roughness background. This means that the effective sensitivity (and statistical significance of defects) will vary across the wafer W as the local conditions change during the scan. Instead of using a fixed sensitivity threshold to select and bin, or categorize, defects, the statistical CL can now be used to perform this function.

Figure 63:
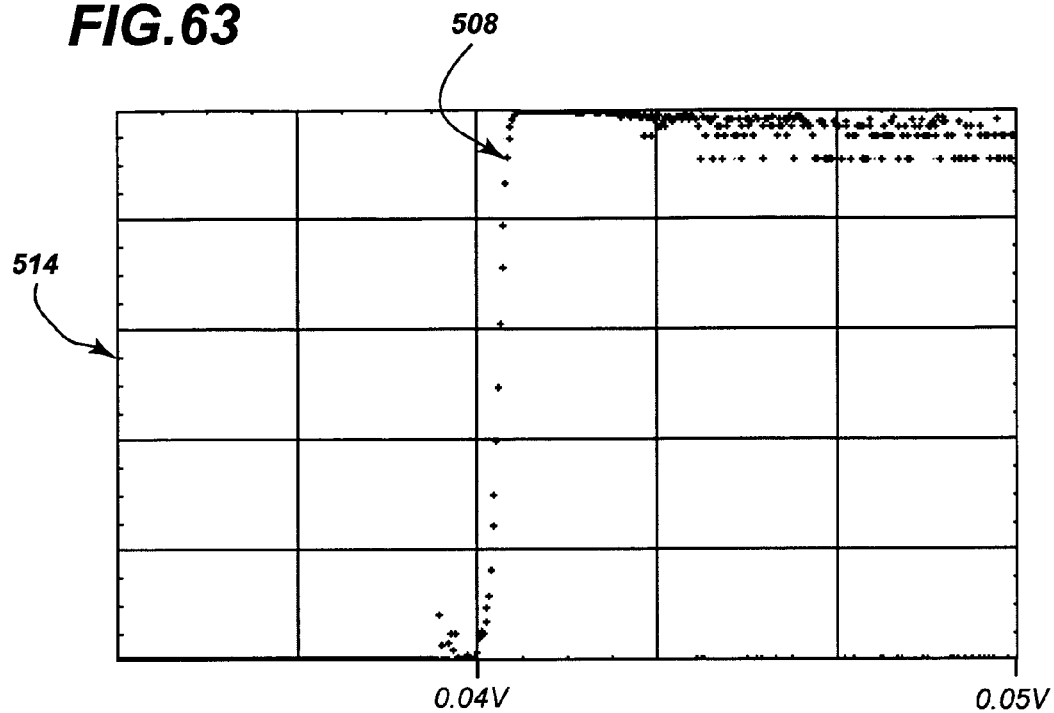
FIG. 63 is a graph showing confidence level factors as a function of voltage.

The CLF curve 508 shown in the plot 514 of FIG. 63 shows the Confidence Level Factor as a function of voltage generated by directly applying Equation 1 to the data set represented by the measured voltage count curve 504 and the noise probability curve 506 shown in FIGS. 60-62. The CLF curve 508 in FIG. 63 is accurate above 0.04V and below 0.05V. The part of the CLF curve 508 in the 0.035-0.04V range is normally ignored because non-zero CLFs in the 0.035-0.04V range in FIG. 63 represent an expected mismatch between the Gaussian background noise fit and the measured data. The CLFs in the 0.035-0.04V range are therefore artificially set to zero. Similarly, the CLFs above 0.05 V are artificially set to one. The CLF for the data represented by map 17 increases from zero at 0.04 V to 1 as the voltage increases. Above 0.05V, the CLF for the data represented by map 17 decreases in an intermittent manner due to the fact that the number of signal events decrease with increasing voltage and there is minimal signal after a certain voltage level. Therefore the CLF drops to zero at numerous voltage levels in this region. In this particular data set (map 17), there is minimal signal above 0.05V. If a deposition of larger particles were present, the values in this region would be near 1. Bearing in mind that any voltage value above 0.046V is 6 standard deviations above the background noise mean (the usual threshold used in the single-threshold technique), it is possible to set the region above 0.046V in the plot 514 of FIG. 63 to 1 without introducing any more false defects than the single-threshold technique would produce.

Figure 64:
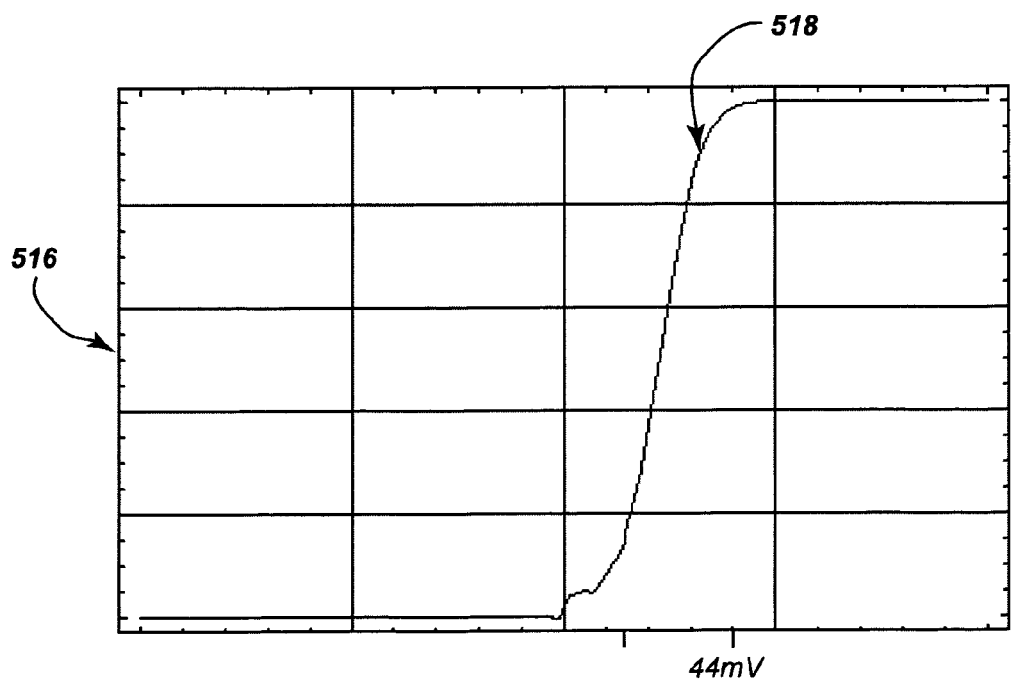
FIG. 64 is Confidence Level Factor (CLF) curve generated by applying a polynomial interpolation fit to FIG. 63, as well as setting the lower end to 0 and the upper end to 1, in which the horizontal axis is voltage, and the vertical axis is the CLF.

By setting the lower region of the plot 514 of FIG. 63 to 0, the upper region to 1, and employing a standard polynomial interpolation method to the region in between, a cleaner version of the CLF curve 508 is generated, as illustrated by the CLF curve 518 in the plot 516 of FIG. 64. As can be readily seen in the CLF curve 518, the CLF is negligible at 41.5 mV (corresponding to a ~42 nm PSL equivalent peak height) and monotonically increases to 0.99 at 44 mV (~48 nm PSL equivalent).

The confidence levels so derived may then be used to assign a confidence level to the voltage value that is measured at a location in a region of a surface under investigation, to identify an extent of confidence that the voltage level so measured represents a defect. By mapping each potential voltage level to a confidence level, a CLF curve, such as curves 508, 518 shown in FIG. 63 or 64, can then be used be utilized as a look-up table ("LUT") to assign confidence levels to voltage values.

The confidence levels could also be used to provide a visual representation of an extent of confidence that a measured voltage level represents a defect at a selected location. For example, in a defect map 17 such as the one in FIG. 57, each pixel of the map represents a location in a region of a surface under investigation. A characteristic of each pixel, such as brightness, could be defined to represent the confidence level assigned to the voltage level associated with the pixel. For example, pixels associated with voltage values having higher confidence levels would be brighter, while those associated with voltage values with lower confidence levels would be darker. The brighter the pixel on the map, the higher the statistical probability that the defect so represented is real. A defect map 522 in which the extent of confidence in an identification of defects is visually represented, known herein as a Confidence Level Map ("CLM"), is shown in FIG. 65.

Figure 65:
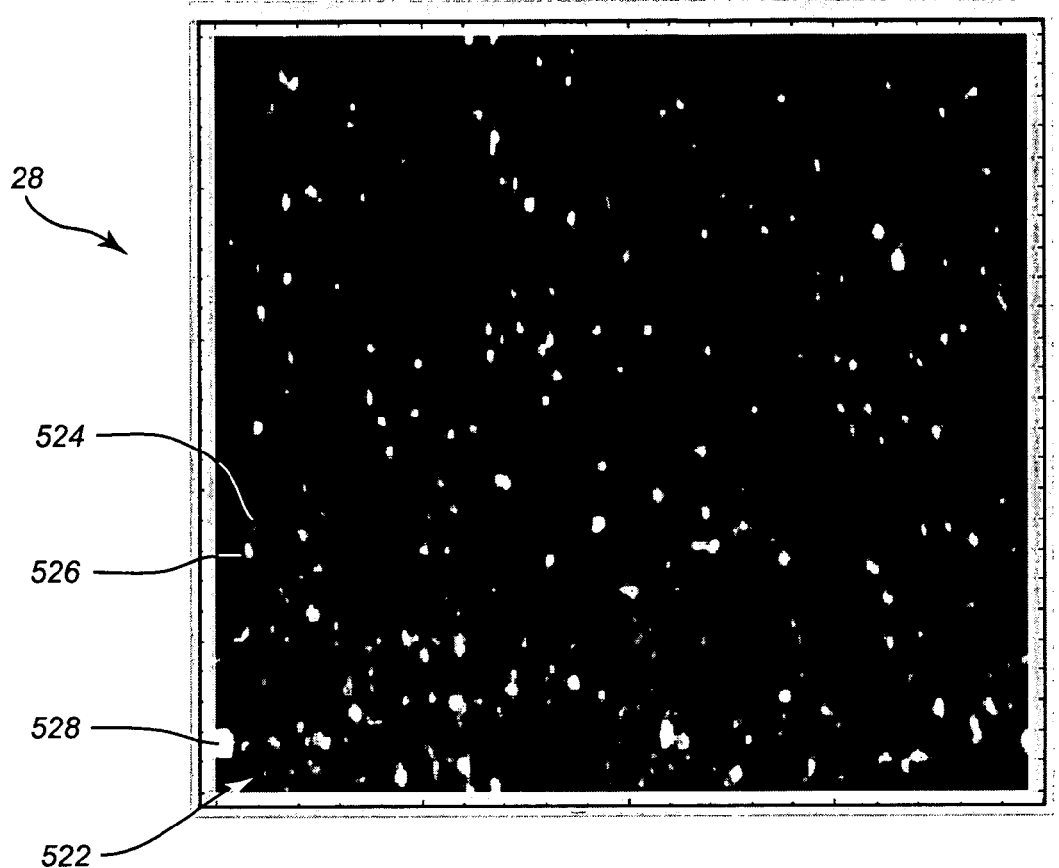
FIG. 65 is a Confidence Level Map created by mapping the voltage values in FIG. 57 using the CLF function plotted in FIG. 64.
Figure 66:
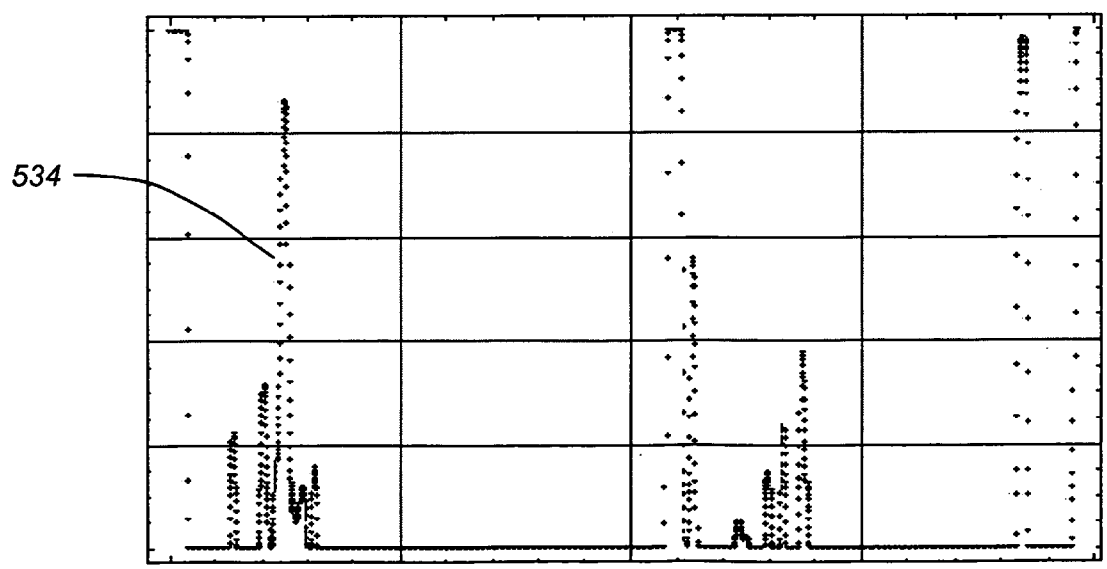
FIG. 66 is a slice plot corresponding to a selected row in FIG. 65, in which the confidence levels of various defects vary across the scan row.

The Confidence Level Map (CLM) 28 shown in FIG. 65 was achieved by associating a CLF with each pixel in the map 17 of FIG. 57, using the mapping of each potential voltage level to a confidence level expressed by the CLF curve 518 in FIG. 64. Pixels such as pixel 524 having voltage values for which the CLF is zero are black, just as they would if a simple threshold were applied. Pixels such as pixel 526 having voltage values for which there is a relatively low confidence level are dim, while those pixels such as pixel 528 that have voltage values for which there is a relatively high confidence level are bright. Therefore the defect brightness in FIG. 65 is closely related to the statistical significance of the defect signal. The variation of CLFs is further demonstrated by the slice plot 534 in FIG. 66.

Note that there are considerably more defects displayed in the CLM defect map 28 of FIG. 65 than in the conventional threshold defect map 25 of FIG. 59. The conventional threshold scheme used in FIG. 59 effectively uses a "unit step" CLF that is zero up to 46 mV, then 1.0 above 46 mV. In contrast, Confidence Level Detection Processing uses a CLF with a gradation of values, thus enabling the use of statistically significant data below 46 mV that would otherwise have been discarded by a "unit step" CLF. The smoothly-varying CLF curve more accurately represents the statistical significance of each voltage level in the map 17 of FIG. 57. For the example shown here, Confidence Level Detection Processing effectively extends the defect sensitivity range by several nanometers.

The CLM defect map 28 in FIG. 65 can be used to generate a defect map using standard and known methods of morphological processing. An aggregate defect confidence level for a defect could be assigned from the confidence levels of the set of locations on the workpiece, such as the wafer, that define the defect, in order to indicate the statistical significance of the defect defined by the set of locations. For example, the surface inspection system could consider a defect to be identified at a position on a wafer when a set of locations on the wafer have positive CLFs associated therewith, are connected together, and have an aspect ratio that is within a certain range. Once a defect is so identified at a position, the aggregate defect confidence level can be assigned to the position from the set of confidence levels associated with the set of locations that define the position. The aggregate confidence level could be assigned to be the peak confidence value, comprising the greatest value of the confidence levels of the set of locations that define the position. Alternatively, the aggregate defect confidence level could comprise the average value of the confidence levels of the set of locations, preferably weighted by the expected sample amplitudes, which would be the voltages measured at the locations. The peak confidence value can be noisy due to shot noise, therefore the preferred aggregate defect confidence level, also called a defect's CLF, is the weighted average value.

Once the aggregate defect confidence level for a defect has been assigned, the defect can be binned according to its size attributes and confidence levels of the locations that define the defect. The defect size can be computed using a peak voltage value comprising the voltage value corresponding to the peak confidence level of the locations that define the defect. Other defect sizing techniques that use other values within the defect group may be used as well.

Normally the color of each defect displayed on the display device comprises a color that is associated with a bin into which the defect is categorized. The brightness of the defect displayed on the display device is usually fixed at a specific brightness in the conventional threshold technique, whereas, in a system or method for defect identification incorporating the confidence level detection processing of the present invention, the brightness of the defect so displayed may be modulated by CLF. This enables the user to visualize the statistical significance of each defect.

The counting of defects can also be modified when using Confidence Level Detection Processing. Normally a defect is counted within a certain category (bin) if, when it is detected, it is found to possess the characteristics associated with the bin. Confidence Level Detection Processing can further refine the process of bin counting by weighting the defect count by its CLF. For example, a defect with a CLF of 0.5 will have half the weight of a defect with a CLF of ~1.0. This means that it will take twice as many defects with a CLF of 0.5 to equal the number of defects with a CLF of 1.0.

By incorporating the CLF into the binning process, the recipes for sorting wafers can utilize the statistical significance of the defect data. Unlike the conventional method of defect identification using threshold processing, defect identification incorporating confidence level processing of the present invention allows rejection of wafers if there are a large number of very small defects. An aggregate bin confidence level can be assigned for a bin from the confidence levels associated with the defects in the bin to indicate the statistical significance of each bin. One such aggregate bin confidence level comprises an average bin CL to indicate the average statistical significance of each bin.

With the present invention, confidence level detection processing as disclosed herein can be used additionally to control the binning and display of data in accordance with the CLF associated with the data. For example, data may be processed using CL cutoff limits in order to limit the identification or display of the number of defects in a region.

Figure 67:
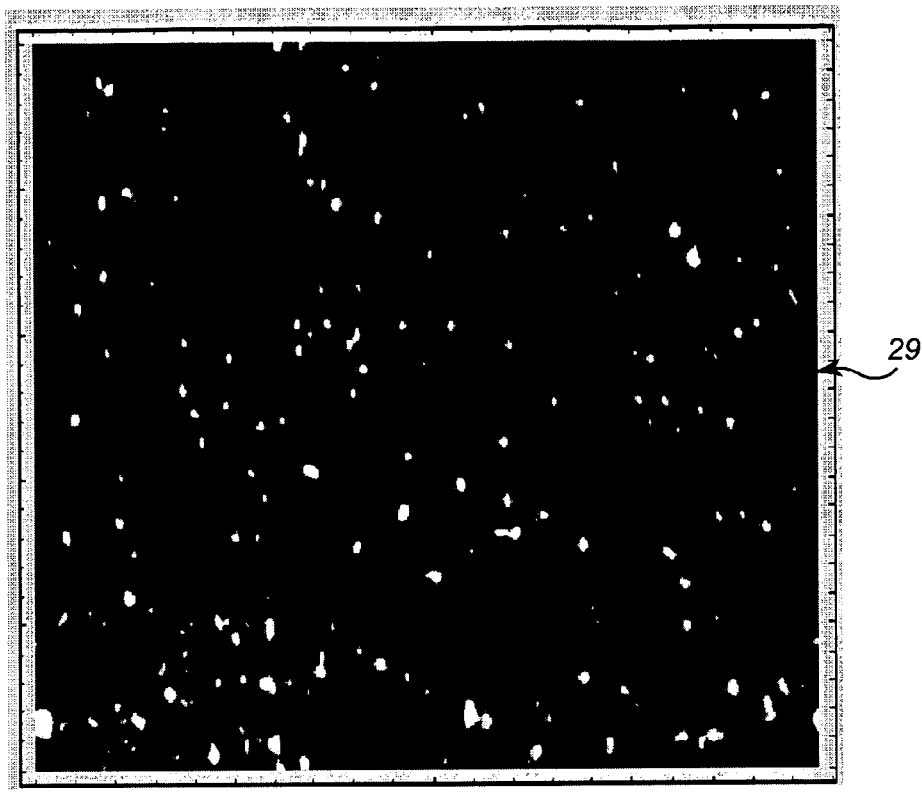
FIG. 67 is another 2-dimensional voltage map that contains both background noise and defect signals.

FIG. 67 depicts a confidence level map 29 for defect data that has been processed using a CL cutoff limit, specifically a CL cutoff limit of 50%. As in the CLM map 28 shown in FIG. 65, the thresholded CLM map 29 in FIG. 67 presents the brightness of a pixel according to the CL of the voltage level associated therewith. However, FIG. 67 differs from FIG. 65 in that the brightness of a pixel is presented in the defect map 29 of FIG. 67 only if the CL of the associated voltage level is greater than 50%.

Thus FIG. 67 depicts a confidence level map comprising a defect map of a surface of a region under inspection, in which the region comprises a plurality of locations, each of which provided with an assigned confidence level $CL_A$, in which the assigned confidence level $CL_A$ is set to zero if the voltage level measured thereat has a CL associated therewith that is lower than 50%, and with the assigned confidence level $CL_A$ comprising the CL associated therewith if the voltage level measured thereat has a CL associated therewith that is greater than or equal to 50%.

Comparing the CLM map 28 of FIG. 65 with the defect map 17 of FIG. 57, it can be seen that confidence level processing results in a significant filtering of the amount of background noise in the defect data. The defect map 17 depicts voltage values for both background noise and defect signals, without any ability to distinguish between defect and noise, while the CLM map 28 shows likely defects by their extent of their likelihood. The dimness of display of an unlikely defect indicates the likelihood that it constitutes background noise. Thus, confidence level processing creates a map that focuses on likely defects.

Comparing the thresholded CLM map 29 of FIG. 67 to the CLM map 28 of FIG. 65, it can be seen that the use of cut-limits in confidence level processing results in even greater focus on the likelihood of a position with high voltage level measurements being a defect. It can be seen that several of the small features near the bottom of the CLM map 28 of FIG. 65 have been eliminated from the thresholded CLM map 29 of FIG. 67 as a result of CL cutoff limits. For example, position 522 is displayed in map 28 (albeit dimly), but is not displayed in map 29. A position on the thresholded CLM map 29 is considered more significant because it is more likely that a defect exists at that position. Thus, thresholded confidence level processing creates a defect map that focuses on defects of greater significance.

Comparing the thresholded CLM map 29 of FIG. 67 to the thresholded defect map 25 in FIG. 59, it can be seen that map 29 depicts more positions as being potential defects, but that it also shows by the dimness of such positions the relative unlikehood of their being defects. By applying a CL cutoff limit to confidence level processing, the conventional defect size threshold process used to create the defect map 25 in FIG. 59 is replaced by a statistical CL threshold in map 29. Thus, thresholded confidence level processing exploits the statistical nature of the data to present defects by their significance.

It is also possible to re-map the CL's to another display look-up table (LUT) to accentuate the presence or absence of various defects with certain CL ranges. For example, using the example of the thresholded CLM defect map 29 of FIG. 67, in which pixels representing locations having confidence levels lower than 50% are set to zero, the brightness of the pixels representing locations having confidence levels at 50% or greater can be adjusted to accentuate the differences in their CLs. A 50% CL could be remapped to 0%; a 100% CL could remain at 100%; and the CL values in between could be assigned other intermediate values, for greater contrast between the 50% and 100% CL's. Thus, the defects so depicted in the defect map of FIG. 67 could be provided with a wider brightness range.

Confidence Level Detection Processing does not necessarily improve the underlying SNR of the system, but it can enable better utilization of the available data. If the user were interested in studying individual defects, then he or she would set the confidence level cutoff limit very high to ensure that each defect is known to be present with high statistical significance.

It is possible for a few false defects to be presented with a high CL because there is a small but non-zero probability that the noise can reach relatively high voltage levels. This effect can be mitigated by applying a "global" CLF calculation to the entire processed defect wafer map. As described in further detail below, a wafer or a region of a wafer region is often sub-divided into regions, with an image of the entire wafer sub-divided into sub-images that are associated with the sub-divided region, to enable defects to be identified on small, manageable quantities of data and to provide good estimates of local background noise. When a CLF is calculated for each sub-image, defects that are deemed significant in the region local to the sub-image may not be significant on a global basis when all of the sub-images are considered together. A global confidence level image formed by the set of sub-images can be thus be assigned from the set of confidence levels associated with the sub-images in the set to indicate the average global statistical significance of defects in the image.

In order to take the global defect map results into account, a final CL for the entire wafer may be displayed to the user, with the final CL comprising a confidence level that has been modulated by the global confidence level across the wafer, thereby reducing the CL for defect sizes that have counts that are similar to the number of false defects expected across the entire wafer. The background noise distribution for the global CLF can be calculated based on the average haze level for the entire wafer. For example, if, at the end of a wafer scan there are 5 defects in a particular bin category, and the expected number of false defects due to noise across the wafer is 4, the CL's for the defects in this bin category would be averaged with the global CL of 100%*(5−4)/5, or 20%. A final CL comprising a global confidence level and a local confidence level, ensures that the statistical significance of the data is weighted on both a local and global basis.

The example shown above demonstrates how Confidence Level Detection Processing (CLDP) can be used to detect defects in a statistically significant manner using a fixed map of voltage values. This method can be applied to virtually any map of data for which the background noise distribution is known or can be computed, and for which individual discrete events are to be detected and identified. Examples of other applications include laser defect scanners for other types of materials, digital imaging for defect inspection, and motion processing in high speed digital video applications.

CLDP is particularly effective if it is applied to a region of a surface that has a uniform background noise distribution. The entire surface can be scanned and stored as one voltage map, then processed using CLDP. This method has two main limitations, however. First, if the surface is a 300 mm silicon wafer surface, this would involve the storage and processing of over $10^9$ sample values per detector module 400, placing substantial and perhaps excessive demands on the computational hardware and software required to process this data. Second, if the background level varies substantially across the surface, the global CLFs so generated will be a poor estimate in the regions that have a significantly higher or lower background than the global average background level.

Figure 68A:
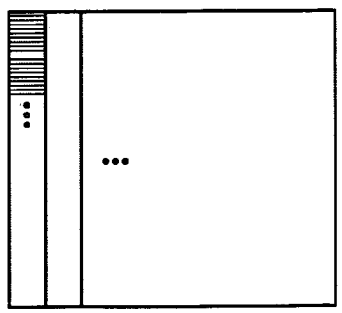
FIGS. 68a-68c are diagrams of examples of scanning geometries using sub-images that are processed using Confidence Level Detection Processing, with FIG. 68a showing Confidence Level Detection Processing performed on a series of sub-images that are sequentially positioned in the X and Y directions, FIG. 68b showing a cylinder scan geometry, and FIG. 68c showing the Archimedes spiral scan.
Figure 68B:
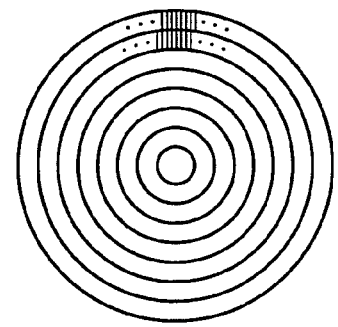

By sub-dividing the surface into sub-images, an example of which is shown in FIG. 68a, the measured distribution and underlying Gaussian background noise distributions can be computed for each sub-image, thereby ensuring that the each distribution is a good estimate of the local background and enabling CLDP to be performed on small, manageable quantities of data. FIG. 68b shows how a silicon wafer could be scanned as a series of cylinders, each of which is divided into multiple sub-images that are processed using CLDP. The sub-image technique can also be applied to a spiral scan pattern, for example, as shown in FIG. 68c.

Figure 68C:
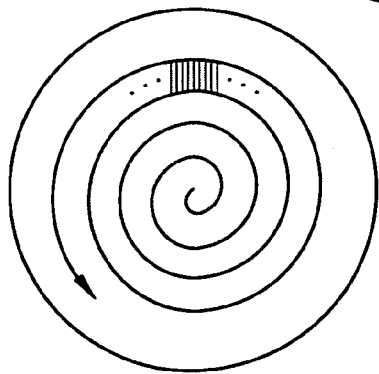

For each of the scanning geometries shown in FIGS. 68a-68c, the number of scan lines to include within a sub-image is directly limited by the slope of the mean of the background noise, or haze slope. As the maximum expected haze slope increases, the number of scan lines used in the distribution calculation should decrease in order to achieve a good distribution estimate. A distribution and confidence level map can be computed for each sub-image. The background distribution used in the confidence level map can be derived by using a known background distribution based on calibrated PMT signals, or by performing a fit on the lower half of each measured distribution. Morphological processing then may be performed on each confidence level map or sub-image. Some methods of controlling sensitivity banding may be desirable or required.

Figure 86:
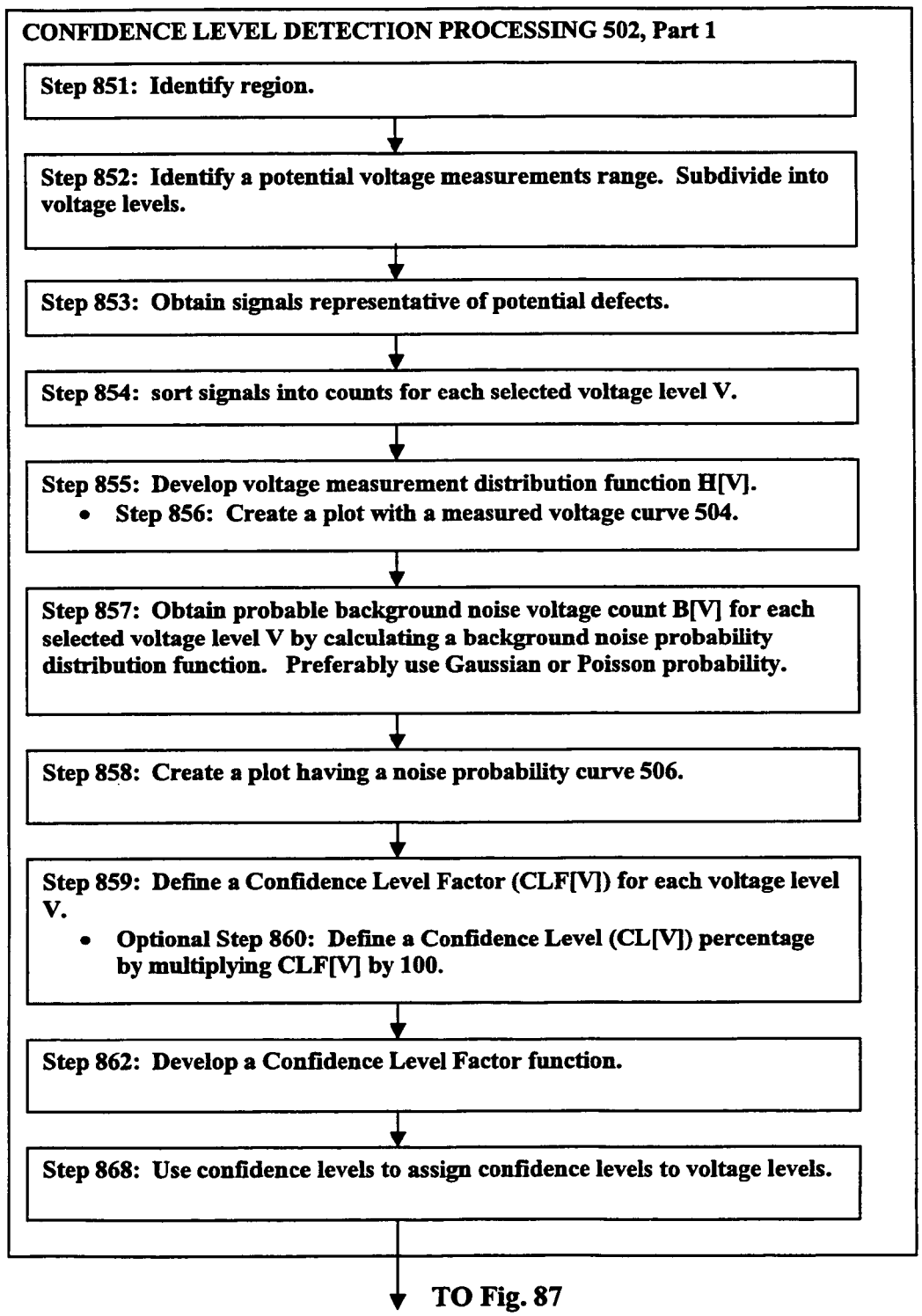
FIGS. 86 and 87 are block diagrams of the Confidence Level Detection Processing method 502 of the present invention.
Figure 87:
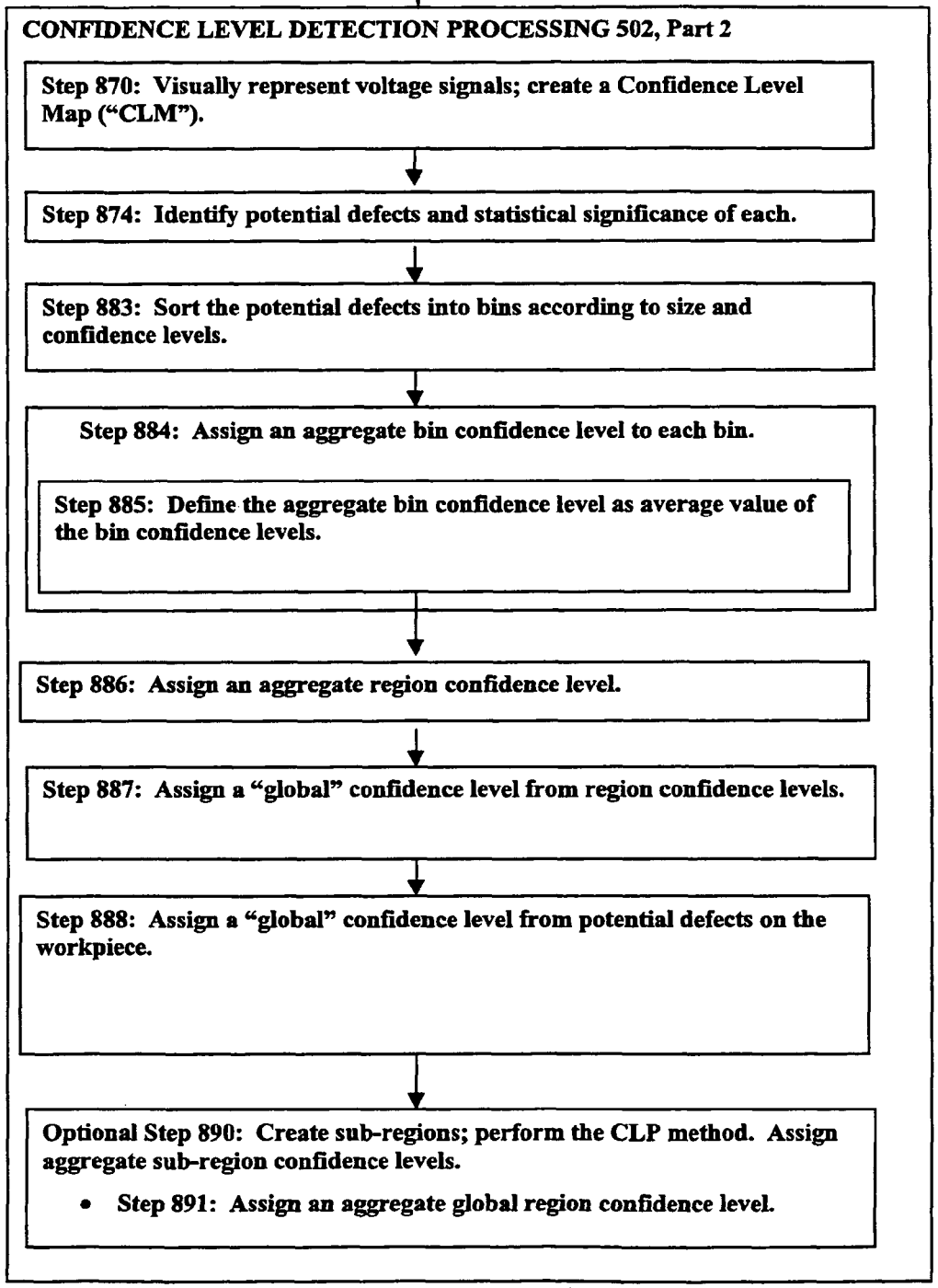

Many specific hardware and software implementations of Confidence Level Detection Processing can be used. As shown in the FIGS. 86 and 87, which is a block diagram of one Confidence Level Detection Processing method 502, the method comprises the following steps:

Step 851: A region of a workpiece to be evaluated for potential defects is identified.

Step 852: A potential signal range is identified for signal measurements to be obtained from locations in the selected region. The potential signal range is subdivided into a set of signal intervals comprising selected signal levels and a predefined range around each signal level. In an illustrative but not necessarily preferred embodiment of the current invention, employing the surface inspection system 10, the signals comprise voltage signals indicative of photon activity within a collector 200, with the photon activity resulting from light scattered from the surface of the region under inspection, and with the extent of the signal measurement being indicative of the extent of such photon activity.

In addition, in the illustrative but not necessarily preferred embodiment of the current invention, the potential signal range comprises a potential voltage range, which is subdivided into a set of voltage intervals comprising selected voltage levels V and a predefined range around each voltage level V. For purposes of describing the method 502, hereinafter the signals will be described as voltage signals. It should be understood, though, the invention should not be limited to such embodiment. In the embodiment, the voltage levels V could be spaced every 200 microVolts within the potential voltage range, and the predefined range could comprise ±100 microVolts around each voltage level.

Step 853: Voltage signal measurements are obtained for locations on the selected region in order to obtain a set of voltage measurement values for the region.

Step 854: The number of voltage measurement values within each selected voltage interval is counted to obtain a voltage measurement value count for each selected voltage level V.

Step 855: The voltage measurement value counts are sorted into a voltage measurement distribution function H[V] comprising the distribution of voltage measurement values counts in the region, by the selected voltage level V. In a step 856, a plot is created having a measured voltage curve 504 comprising the voltage measurement distribution function, with the curve 504 presenting the number of voltage signals at each voltage level.

Step 857: The portion of H[V] that likely comprises underlying background noise is identified by calculating a background noise probability distribution function B[V] comprising probable background noise voltage counts by selected voltage levels V. B[V] is derived by fitting a probability function to a portion of H[V] in which particle and haze variation effects are minimal. In such portion of H[V], voltage values are likely to represent background noise and not workpiece defects. Preferably, the portion of H[V] used to derive the B[V] comprises the lower tail of H[V]. Also, preferably, a Gaussian or Poisson probability function is used. In a step 858, a plot having a noise probability curve 506 comprising B[V] is created, with the curve 506 representing the likely number signals that comprise background noise at a voltage level.

Step 859: A Confidence Level Factor (CLF[V]) is defined for each voltage level V, in order to assign a confidence level to the voltage value that is measured at a location in a region of a surface under investigation, to identify an extent of confidence that the voltage level so measured represents an actual defect. Confidence Level Factor (CLF[V]) is calculated by:

$$CLF[V] = \frac{H[V] - B[V]}{H[V]}$$

In an optional Step 860, a Confidence Level (CL[V]) percentage is defined by multiplying CLF[V] by 100.

Figure 88:
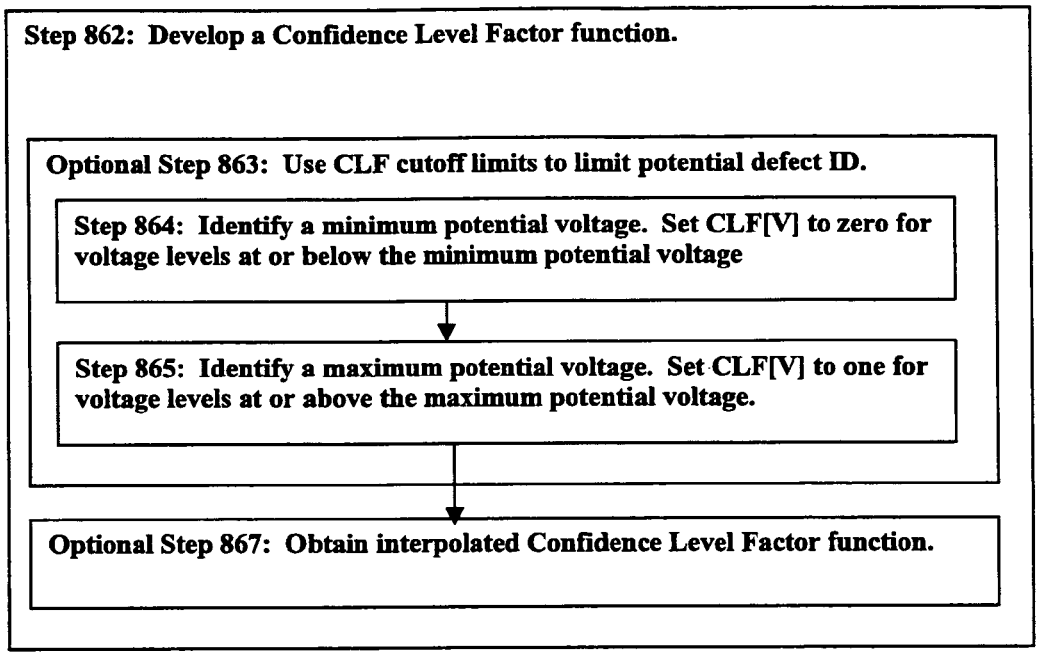
FIG. 88 is a block diagram of the Confidence Level Detection Processing method step 862 for developing a confidence level factor function.

Step 862: A Confidence Level Factor function is developed and represented by Confidence Level Factor curve 508, for values of confidence level factors (CLF[V]) and the voltage levels V with which they are associated. FIG. 88, which is a block diagram of further detail for step 862, shows an optional Step 863 of using CLF cutoff limits in order to limit the identification of voltage values as potential defects in a region. The cut-off limits may be developed in a step 864 and step 865. Step 864 involves identifying a minimum potential voltage in the potential voltage range, below which voltage values are expected to represent background noise and not actual defects. The CLF[V] is set to zero for voltage levels at or below the minimum potential voltage. A step 865 involves identifying a maximum potential voltage in the potential voltage range; above which voltage values are expected to represent actual defects and not background noise. The CLF[V] is set to one for voltage levels at or above the maximum potential voltage. Finally, the step 862 also comprises an optional Step 867, which involves employing a standard polynomial interpolation method to the Confidence Level Factor function to obtain an interpolated Confidence Level Factor function, represented by an interpolated CLF curve 518.

Step 868: A CLF curve 508, or the optional interpolated CLF curve 518, is used as a look-up table to assign confidence levels to the voltage levels with which the confidence level factor is associated.

Figure 89:
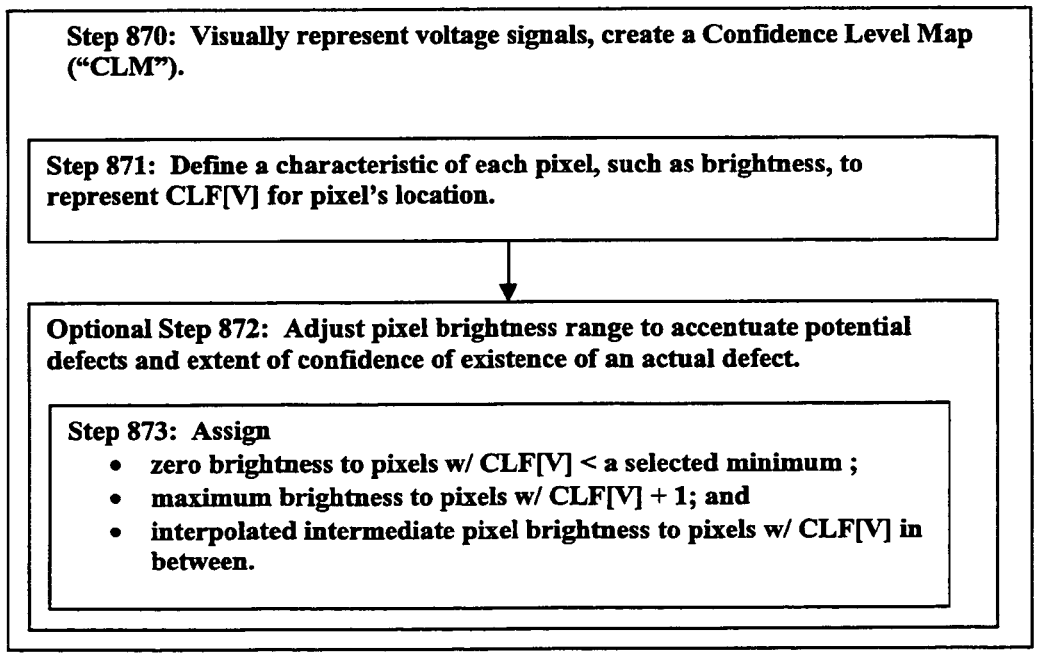
FIG. 89 is a block diagram of the Confidence Level Detection Processing method step 870 for creating a confidence level map.

Step 870: A visual display of the region under investigation is created to visually represent voltage signals measured at locations in the region and the extent of confidence that the voltage signals represent actual defects and not background noise. Preferably, a Confidence Level Map ("CLM"), such as map 522, is created in which each pixel of the map represents a location in a region of a surface under investigation and a confidence level representative of an extent of confidence that an actual defect exists at the location associated with the pixel. FIG. 89 is a block diagram of further detail for step 870. It shows a step 871, which involves defining a characteristic of each pixel, such as brightness, to represent the confidence level factor CLF[V] assigned to the voltage level V associated with the voltage measurement value obtained at the location that is represented by the pixel. Step 870 also comprise an optional Step 872, which involves adjusting the brightness range of pixels in the visual display to accentuate the presence or absence of a potential defect at the location associated with a pixel and an extent of confidence that the potential defect represents an actual defect. Finally, step 870 comprises a step 873, which involves assigning a zero brightness level to pixels associated with locations having confidence levels lower than a selected minimum confidence level, a maximum brightness level to pixels associated with locations having confidence levels CLF[V] equal to one, and adjust the brightness levels for each pixel associated with a location having a confidence level therebetween to an intermediate pixel brightness level between the zero brightness level and the maximum brightness level, with the intermediate pixel brightness level developed by interpolation from the confidence levels associated with each pixel associated with a location having a confidence level therebetween.

Figure 90:
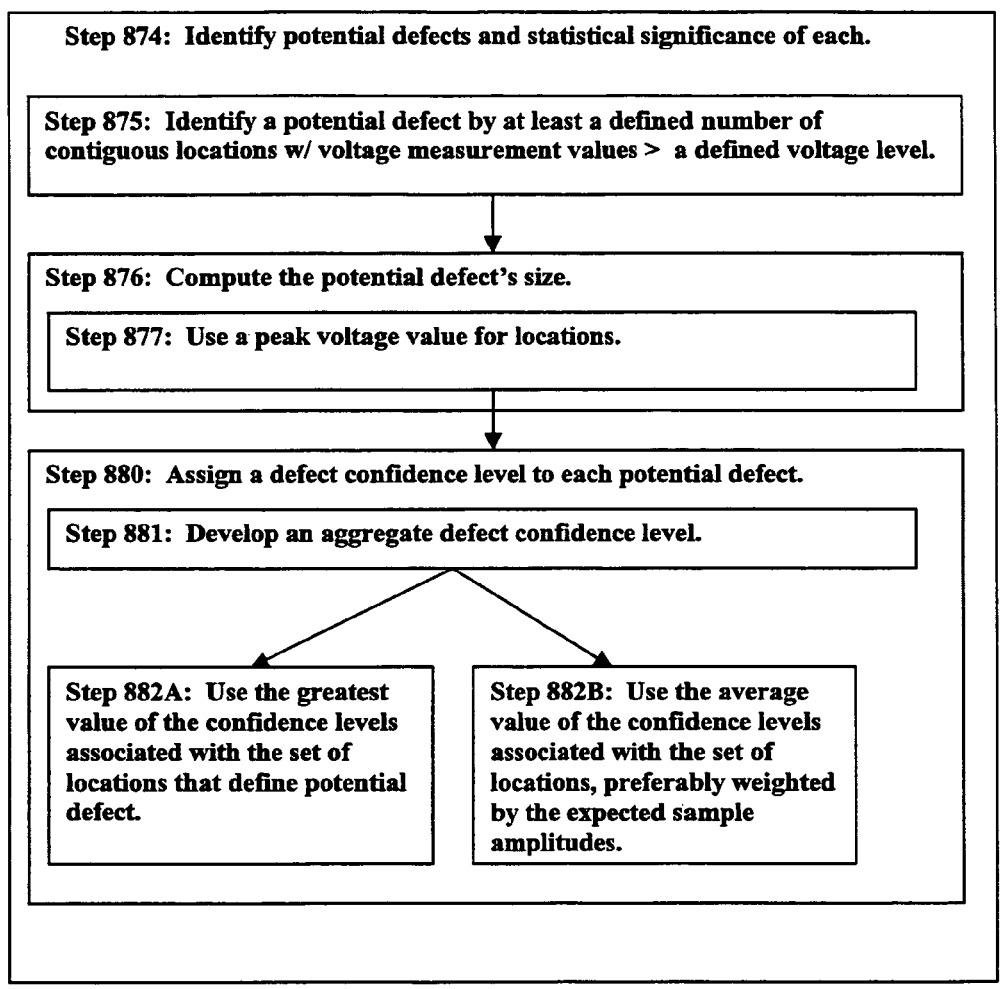
FIG. 90 is a block diagram of the Confidence Level Detection Processing method step 874 for identifying potential defects and their statistical significance.

Step 874: Potential defects are identified in the region under investigation and an extent of statistical significance is associated with each potential defect. FIG. 90 is a block diagram of further detail for step 874, and shows a step 875 involving, in one embodiment, identifying a potential defect by identifying a set of contiguous locations in the region under investigation, with the locations having voltage measurement values above a defined voltage level and with the set comprising at least a defined number of contiguous locations. Step 874 also comprises a step 876, which involves computing the potential defect's size. In one embodiment, the step 876 comprises a step 877, which involves computing the potential defect's size using a peak voltage value comprising a voltage measurement value corresponding to the peak confidence level associated with the locations that define the potential defect. The step 874 further comprises a step 880, involving assigning defect confidence level to each potential defect so identified, and a step 881, which involves developing an aggregate defect confidence level to the potential defect from the set of confidence levels associated with the set of locations that define the potential defect. The aggregate defect confidence level, and any aggregate confidence level described herein, could be created in any convention manner, for example, using step 882A or step 882B. Step 882A involves defining the aggregate defect confidence level to comprise the peak confidence value, comprising the greatest value of the confidence levels associated with the set of locations that define the potential defect. Alternative Step 882B involves defining the aggregate defect confidence level to comprise the average value of the confidence levels associated with the set of locations that define the potential defect, preferably weighted by the voltages measured at the locations.

Step 883: The potential defects are sorted into bins according to size and confidence levels.

Step 884: An extent of statistical significance of potential defects is associated with each bin by assigning an aggregate bin confidence level to each bin from the confidence levels associated with the potential defects sorted into the bin. In a step 885, an aggregate bin confidence level is assigned to comprise an average value of the confidence levels associated with the potential defects in the bin.

Step 886: An extent of statistical significance of potential defects is associated with the region under investigation by assigning an aggregate region confidence level to the region from the confidence levels associated with the bins that comprise the region.

Step 887: An extent of statistical significance of potential defects is associated with a workpiece by assigning a "global" confidence level to the workpiece from the confidence levels associated with the regions that comprise the workpiece.

Optional Step 890: A region under investigation may be sub-divided into sub-regions and the confidence level detection processing method 502 performed on the sub-regions in order to identify potential defects using a data set of reduced size and to provide more detailed estimates of local background noise. An extent of statistical significance of potential defects would be associated with a sub-region by assigning an aggregate sub-region confidence level to the sub-region from the confidence levels associated with the potential defects in the sub-region. The step 890 is particularly helpful in instances in which confidence levels, when calculated separately, would differ significantly across a test surface, such as a workpiece or a region of a workpiece. For example, a portion of a test surface could appear to raise issues that are not present in the rest of the test surface. One area of a workpiece could have scatter patterns that indicate the high likelihood of the presence of a defect, while other areas could have scatter patterns that are more equivocal about the presence of a defect. Confidence levels that are calculated separately for areas with differing scatter characteristics would thus differ significantly. The overall test surface confidence level, being lowered by the lack of confidence in the areas with equivocal scatter signal, would not reflect as strongly as it potentially could the confidence in the existence of the defect in one of its area. Thus, by allowing a test surface to be subdivided, a "global" confidence level may be modulated across the test surface. In a step 891, an extent of statistical significance of potential defects could be associated with the region subdivided in step 890 by assigning an aggregate global region confidence level to the region from the confidence levels associated with the sub-regions.

Method for Combining Collector Output

Figure 41:
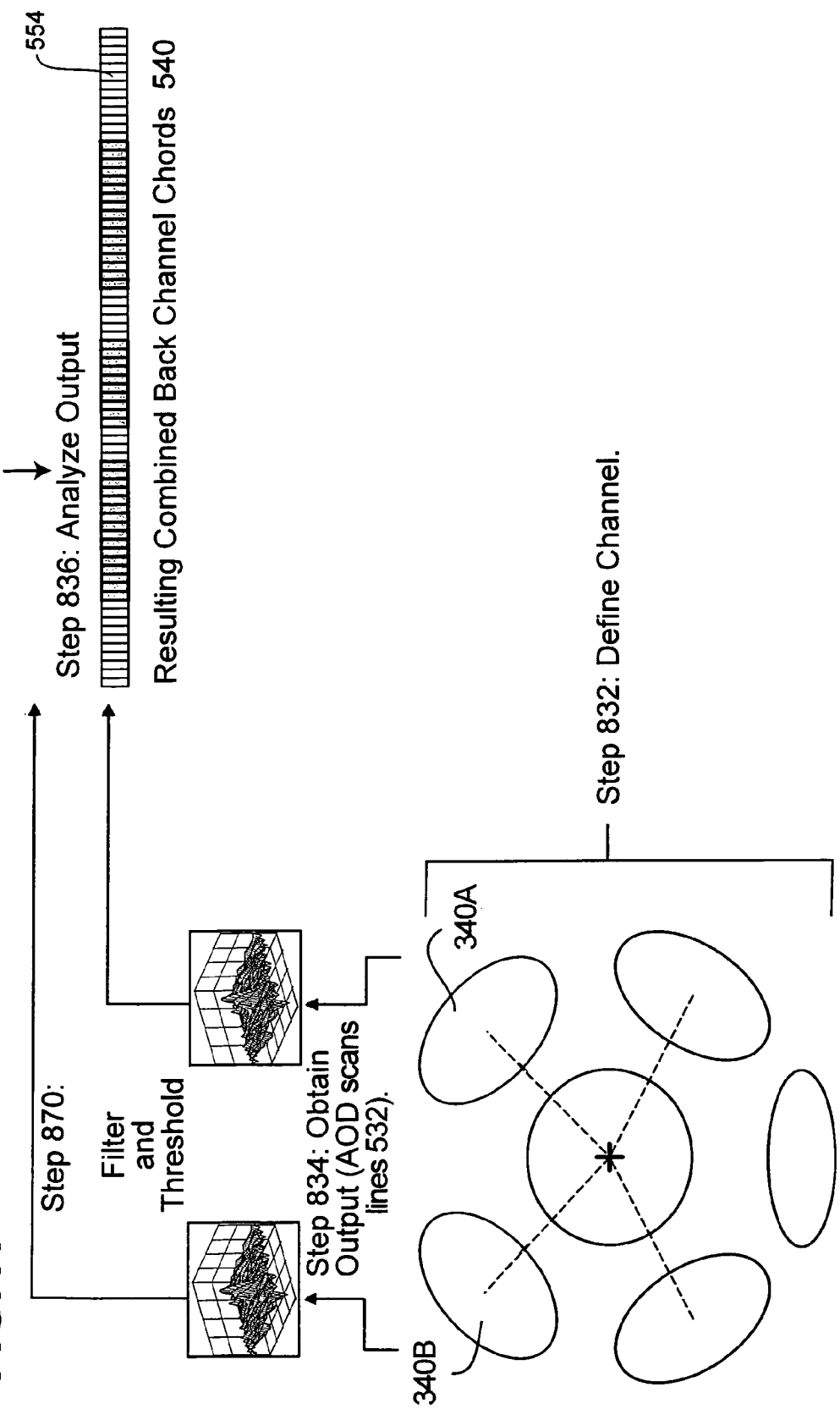
FIG. 41 is a block diagram showing another embodiment of the method for detecting the presence of defects.

FIG. 41 is a block diagram showing the embodiment of the FTC method 814 for detecting the presence of defects by collecting scattered portions of the incident beam at a plurality of collectors and identifying defects using signals from selected collectors, comprises the step 870 of filtering and threshold testing, and then the step 860 of combining output associated with selected collectors 300.

One further embodiment comprises combining thresholded output associated with the entire set of collectors in the surface inspection system. Another further embodiment comprises combining thresholded output from a selected set of collectors.

The individual collector processing method of FTC method 814 is useful in detecting and classifying asymmetric scatter, e.g. defects on rougher silicon surfaces and "flat" defects. More particularly, it is useful in detecting and classifying defects of various spatial frequencies and geometries that scatter with the symmetry of small particles.

As shown in FIG. 41, a method of using independent or individual processing of collector output to analyze defects, which employs the individual collector processing method or FTC method 814, comprises the following steps:

Step 832: Define a channel 600 by identifying a selected set of collectors 300.

Step 834: Obtain output associated with each collector 300 in the selected set of collectors.

Step 870: Filter the output associated with each collector 300 to obtain filtered output associated with each collector 300. Threshold the filtered output for each detector module 400 associated with a collector 300 in the selected set to obtain thresholded filtered output associated with each collector 300.

Step 860: Combine the thresholded filtered output associated with all of the collectors 300 in the selected set of collectors to obtain combined thresholded filtered output.

Step 836: Analyze the combined thresholded filtered output.

The step of analyzing the combined thresholded filtered output may be performed using any defect detection method, including those described herein or any known defect detection method, such as those described in U.S. Ser. No. 10/864, 962, entitled *Method and System for Classifying Defects Occurring at a Surface of a Smooth Substrate Using Graphical Representation of Multi-Collector Data*, which is assigned to ADE Corporation of Westwood, Mass. and which is herein incorporated by reference.

In the embodiment shown in FIG. 41, the method of obtaining combined thresholded filtered output comprises obtaining combined channel chords 550, which comprise the set of contiguous over-threshold filtered output values in the output of an AOD scan for the set of selected collectors 300. More specifically, in the embodiment shown in FIG. 41, the step 832 of defining a channel 600 by identifying a selected set of collectors 300 comprises identifying the dual back collectors 340A, 340B to form a combined back channel, and obtaining combined channel chords 550 comprises obtaining combined back channel chords 540.

Figure 42A:
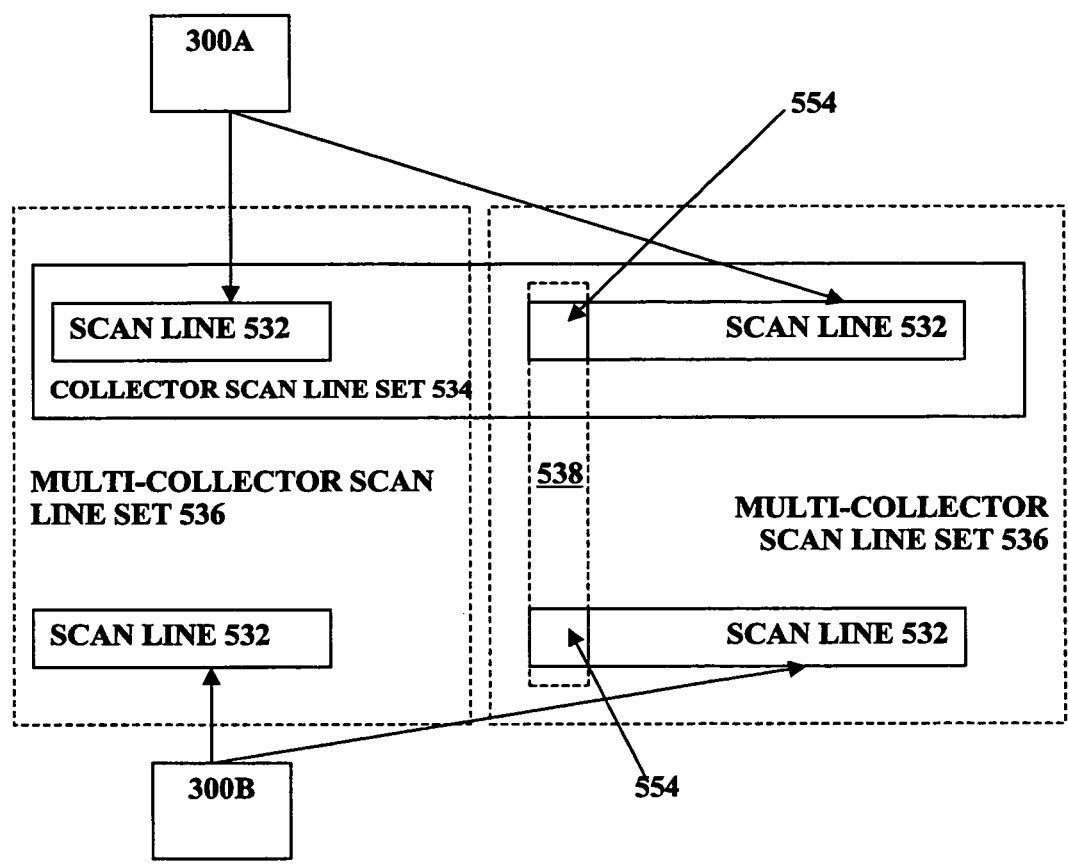
FIG. 42a is a block diagram illustrating components involved in the combining step of FIG. 41.
Figure 42B:
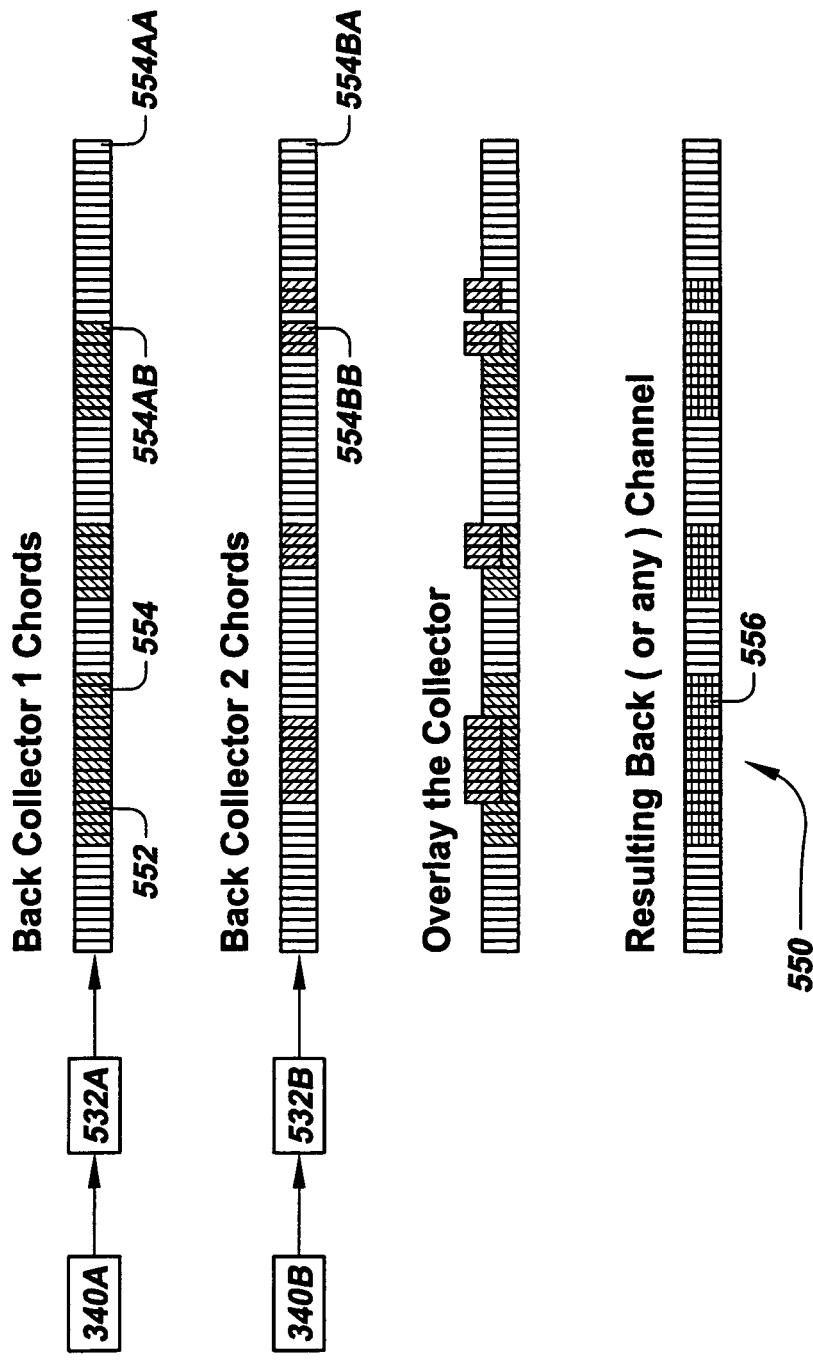
FIG. 42b is a block diagram showing the combining step of FIG. 41.
Figure 43:
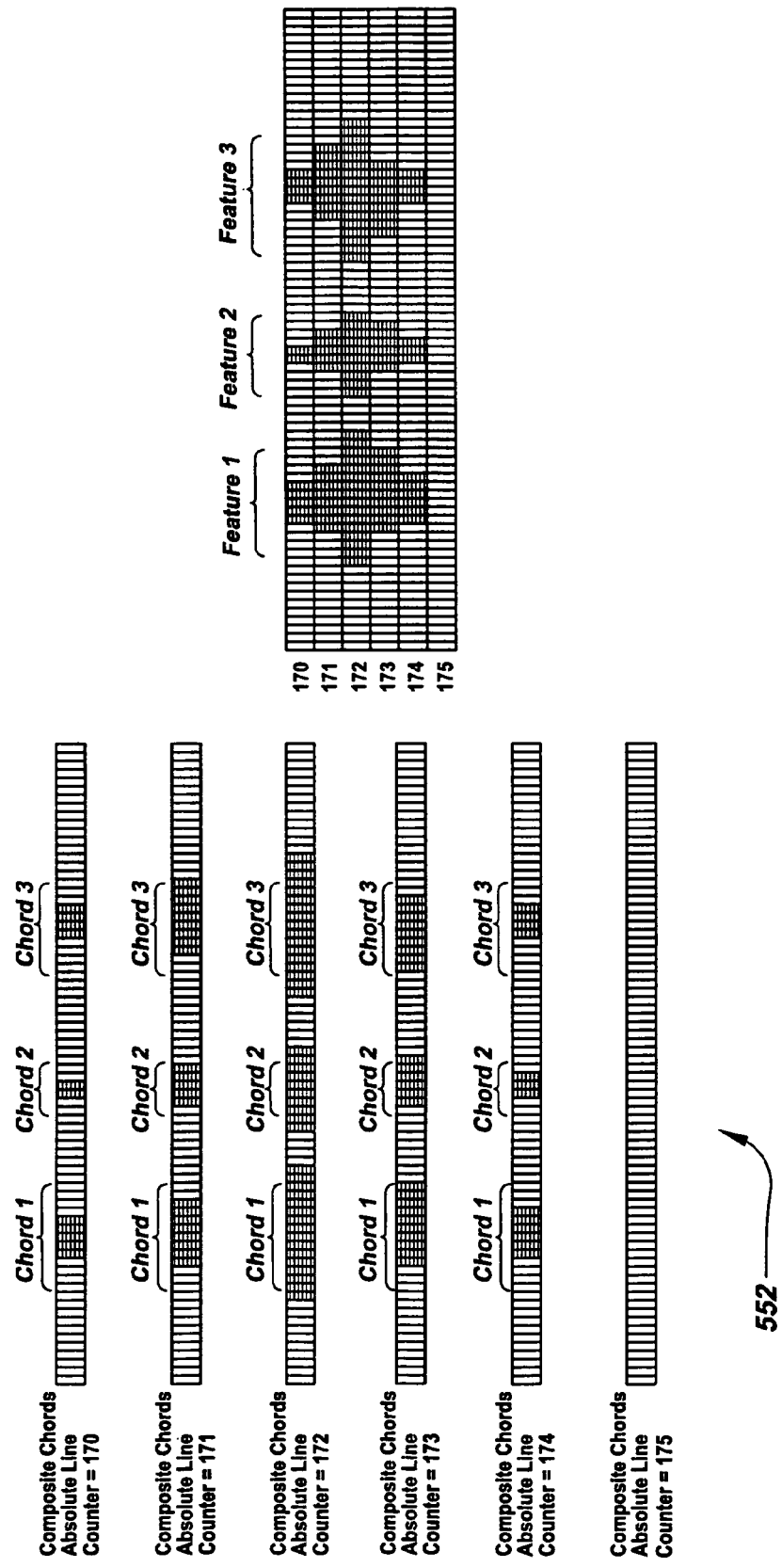
FIG. 43 is a block diagram showing the combining step of FIG. 41 shown in more detail.

The method of obtaining combined channel chords 550 when it comprises obtaining combined thresholded filtered output is shown in more detail in FIGS. 42 and 43. It comprises the following:

The step 834 of obtaining output comprises obtaining output for each AOD scan, further comprising obtaining the set of output values from the AOD scan.

The output filtering portion of step 870 further comprises obtaining filtered output for each AOD scan, further comprising obtaining the set of filtered output values for the AOD scan.

The output thresholding portion of step 870 further comprises thresholding the filtered output for each AOD scan, further comprising obtaining the set of thresholded filtered output values for the AOD scan, with thresholding comprising comparing the output values V of the AOD scan elements 554 in a collector's AOD scan line 532 against a threshold output value $V_O$ and identifying which elements 554 are over threshold.

The step 860 of combining the thresholded filtered output further comprises identifying channel chords 552 in the thresholded filtered output, and, from them, forming combined channel chords 550.

The step 836 of analyzing the combined thresholded filtered output then further comprises a step 838 of analyzing the combined channel chords 550.

As seen in FIG. 42A, in a selected set of collectors 300, each collector 300A, 300B provides as output a selected number of AOD scan lines 532, forming a collector scan 534 and comprising a selected number of scan elements 554. A channel chord 552 comprises the set of contiguous AOD scan elements 554 in a collector's AOD scan line 532 having output values V greater than a threshold output value $V_O$. Output from collectors 300A, 300B may be used to form a combined channel chord 550.

The step 838 of forming combined channel chords 550 comprises overlaying the output from an AOD scan 532 associated with the selected set of collectors 300 in the following manner: Each AOD scan line 532 in a collector's scan 534 has another AOD scan line 532 associated therewith in the scan 534 of the other collectors in the selected set, the scan lines 532 so associated forming a scan line set 536 such that all scan lines 532 in a collector's scan 534 are members of separate scan line sets 536. Further, each AOD scan element 554 in an AOD scan line 532 has another AOD scan element 554 associated therewith in each of the AOD scan lines 532 in the m scan line set 536, the scan elements 554 so associated forming a scan element set 538 such that all scan elements 554 in an AOD scan line 532 are members of separate scan element sets 538.

When output from a selected set of collectors 300 is combined, it is combined on the scan element 554 level, with all of the scan elements 554 in a scan element set 538 forming a combination element 556 that represents the associated AOD scan elements 554 in a scan element set 538.

A combined channel chord 550 comprises the set of combination elements 556 for which at least one of the associated AOD scan elements 554 that the combination element 556 represents has an output value V greater than a –threshold output value $V_O$. The magnitude of the combination element 556 in each combined channel chord 550 is the magnitude of one of the AOD scan elements 554 represented thereby, preferably the AOD scan element 554 having the greatest over-threshold output value V.

An example of the step 838 of forming combined channel chords 550 is shown in FIG. 42*b*, in which the selected set of collectors 300 comprise back collectors 340A, 340B. While it is within the spirit of this invention for each collector to have associated therewith several AOD scan lines 532, for the sake of this example, let there be only one AOD scan line per collector. For example, the collectors 340A, 340B provide, respectively, AOD scan lines 532A, 532B. AOD scan line 532A has a plurality of scan elements, e.g. scan elements 554AA, 554AB. AOD scan line 532B also has a plurality of scan elements, as an example 554BA, 554BB. Scan elements 554AA, 554 AB, would be considered to have associated with them, respectively, scan elements 554BA, 554BB. Therefore, scan elements 554AA, 554BA would form a scan element set 538, and scan elements 554AB, 554BB would form a separate scan element set 538.

In FIG. 42*b*, the scan elements 554 that have an output value V greater than a threshold-output value $V_0$ are shown as dark, forming a chord 552. The set of combination elements 556 for which at least one of the associated AOD scan elements 554 that the combination element 556 represents has an output value V greater than a –threshold output value $V_0$ are also shown as dark, forming a combination chord 556.

FIG. 43 shows channel chords 552 from a set of five collectors, and the set of combined channel chords 550 formed therefrom. The formation of combined channel chords 550 results in the recording of synchronous events therein.

By defining channels 600 out of selected combinations of collectors 300, individual collector filtered output can be consolidated into scatter "fields", which can then be used to facilitate defect detection of defects such as scratches.

The method of defect detection in which output associated with collectors is independently or individually processed is particularly helpful in identifying asymmetric defects. Further, scratch detection is facilitated by independently or individually processed collector output.

Scratches, also known as line defects, are difficult to identify because their scatter forms a very narrow geodesic on the scatter hemisphere. Since each collector is responsive to scatter in a different region of the scatter hemisphere, data related to a scratch will appear as output in different collectors. In addition, cross-scan filtering attenuates linear defect signatures. When output associated with multiple collectors is combined, the portion of the combined output related to scratches will not produce a sufficient level of output signal to exceed the thresholding value. Therefore, it is preferable to analyze the output associated with each collector for individual detection of line defects. Once the output data are filtered and tested to determine if they exceed a threshold value, the data that exceed the threshold values may be analyzed, alone or in combination with other data, using currently known techniques to identify line defects.

In addition, when output associated with the P-polarized and S-polarized wing collectors is individually processed, channels may be defined for the separation of the wing response for enhanced scratch detection sensitivity and improved detection and classification of additional defect types.

Figure 44:
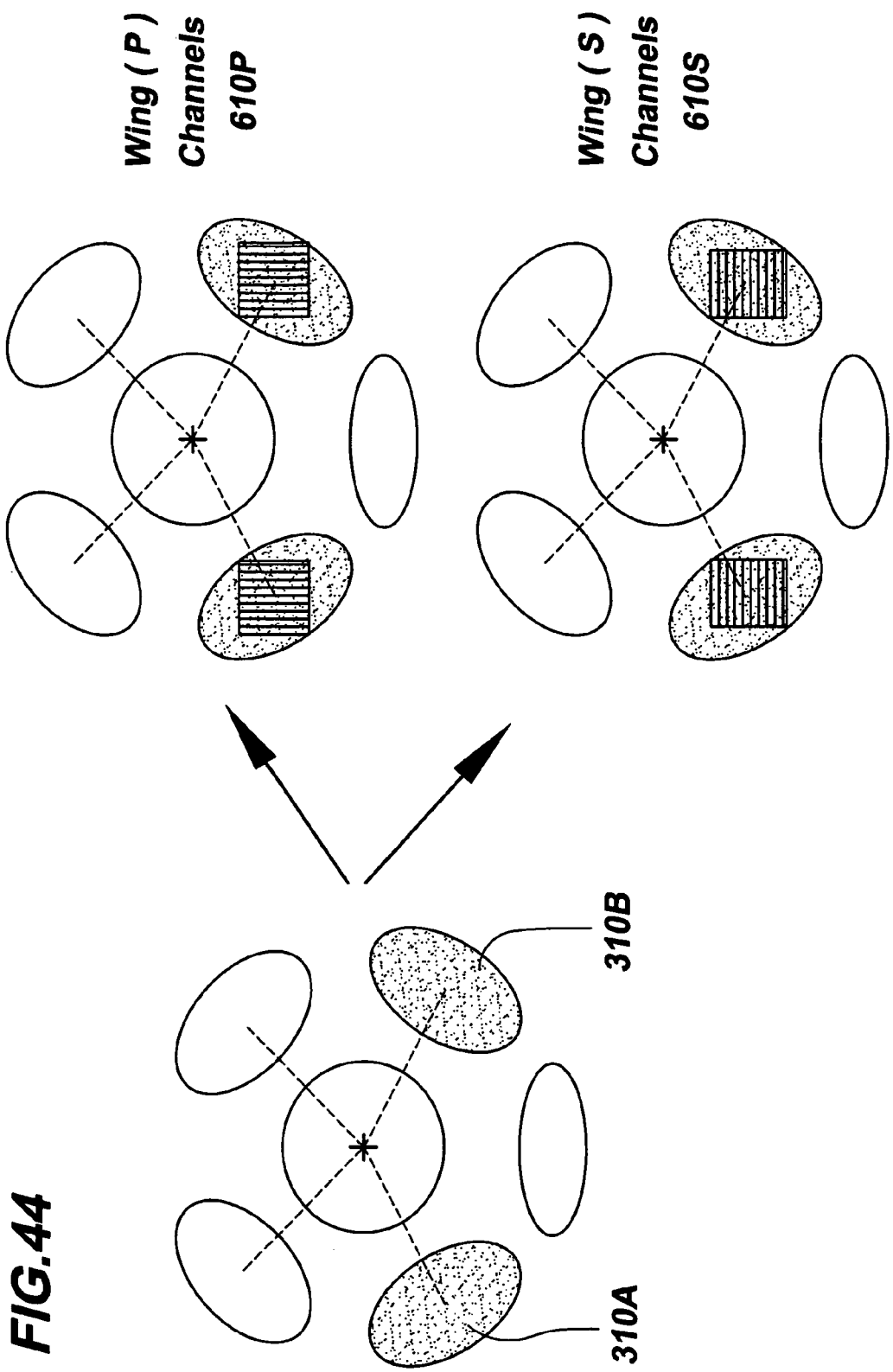
FIG. 44 is a block diagram showing a method for defining multiple channels from a collector or set of collectors.

Using the methods described herein, one may define multiple channels 600 out of a single collector 300 or a set of collectors 300. For example, in FIG. 44, wing collectors 310A, 310B are shown. The wing collectors 310A, 310B may be operated in both P and S configurations, and therefore, the output associated with them may be used to form a wing (P) channel 610P and wing (S) channel 610S

Figure 45:
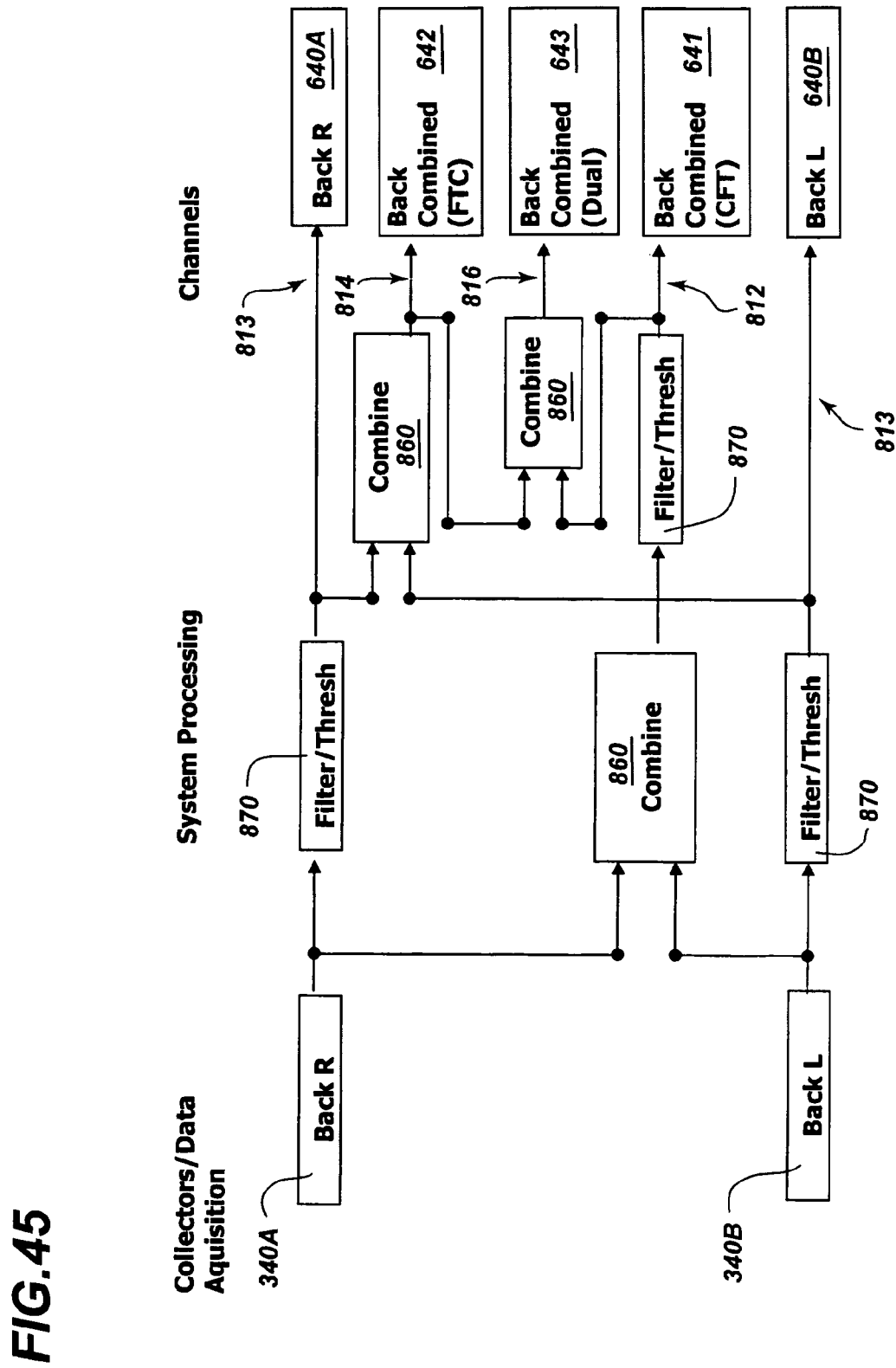
FIG. 45 is a block diagram showing the multiple channels that may be formed from the output associated with a set of collectors.

In addition, when combining collectors 300 to form channels 600, the methods described herein may be combined to generate multiple channels 600 for use in different applications. For example, as shown in FIG. 45, the output associated with the back collector 340A and the back collector 340B may be filtered and processed in the conventional manner (the FT method 813) to form, respectively, the back channel 640A and the back channel 640B. Alternatively, the output may be processed in accordance with the combined scatter method (the CFT method 812; combining collector output, then filtering and then thresholding the output) to form back combined (CFT) channel 641, or it may be processed in accordance with the individual collector processing method (the FTC method 814; filtering and thresholding the individual collector output, then combining output) to form back combined (FTC) channel 642. Finally, the output may be processed in accordance with the dual/CFTC method 816 (combining the combined scatter method and the individual collector processing method) to form a back combined (dual) channel 643.

Returning to FIG. 46, a data reduction module 670 may be provided for each of the desired combinations of collectors 300. In the presently preferred but merely illustrative embodiment described herein, the filtering and thresholding step 870 would be performed on the data in the data acquisition nodes 570 and the data reduction nodes 670 for both the combined scatter method 812 and the individual collector processing method 814. The combining step 860 for the combined scatter method (CFT method 812) would be performed on the data in the data reduction nodes 670. For the individual collector processing method (FTC method 814), the combining step 860 would be performed using software in the system controller and processing unit 500.

Method for Haze Analysis in a Multi-Collector Surface Inspection System

Figure 91A:
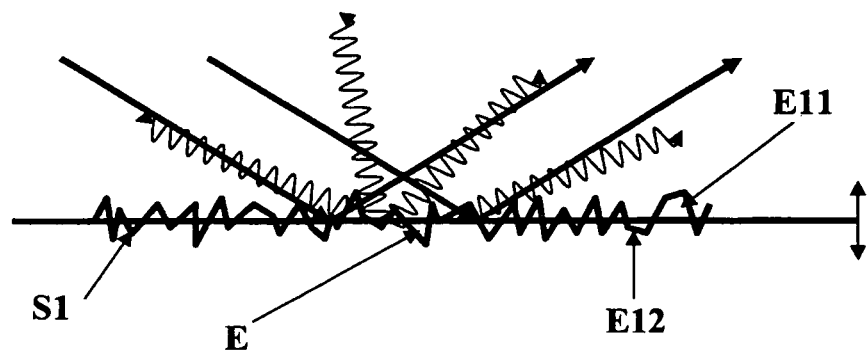
FIGS. 91a and 91b are illustrations of a workpiece surface structure.
Figure 91B:
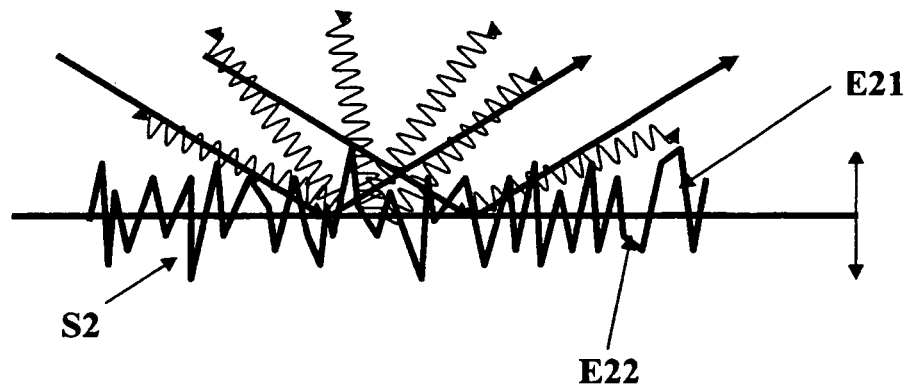

Defect detection, measurement confidence, and understanding of processes such as wafer production and manufacturing processes are improved when the contribution of surface roughness on a scattering workpiece surface is known and taken into account. A workpiece surface can be said to have an amplitude and a spatial frequency, with the spatial frequency representing the density of the elements on the surface that cause scatter (such as roughness or defects), and the amplitude comprising the height of the elements on a surface. A surface structure comprises the aggregate of the elements (such as roughness or defects) on or in the region of a surface. A surface structure's roughness may be quantified in any conventional manner, one being the average distance of the surface from the mean surface of the wafer. A surface structure's spatial frequency is determined by the density of the elements of which the structure is comprised. FIGS. 91*a* and 91*b* are illustrations of a workpiece surface structure, showing surface structures S1 and S2, each having elements E that cause scatter, structure S1 having elements E11, E12, and so on, and structure S2 having elements E21, E22, and so on. It can be seen that, while the spatial frequencies of surface structure's S1, S2 are essentially identical (the elements E of which they are comprised having essentially the same density), the elements E on structure S2 have greater amplitudes than the elements of structure S1, so structure S2 can be seen to have a higher roughness value than structure S1.

As an incident beam's photons impinge the elements of a surface, photons from the incident beam scatter off of the elements. The photons, which travel at a frequency that is determined by the incident coherent beam, scatter at a rate that is determined by the roughness of the surface structure. The rougher the surface (the higher the roughness value), the more photons are scattered. The intensity of scatter is determined, for the most part, in a defect free region, by amplitude of the surface frequency. Returning to FIGS. 91*a*, 91*b*, structure S1, which has a higher amplitude than structure S2, can be seen to scatter more photons than structure S2.

The direction of the photon scatter (the angle at which the photons scatter) is largely determined by the spatial frequency of the surface structure. As the surface structure's spatial frequency increases, the density of the elements of which the structure is comprised increases, and so the angle at which the photons scatter off of the elements becomes more acute relative to the incident beam, shifting back toward the incident beam.

A surface structure's spatial frequency may be divided into components comprising surface structure spatial frequency ranges. For example, FIG. 91a shows a graph of a surface height profile of a model surface structure comprising a region of a surface S of a workpiece W. Using commonly known mathematical techniques such as a Fourier transform, the waveform representative of the model surface structure may be expressed by waveform components. In the example, referring to FIG. 92b, the waveform representative of the model surface structure may be expressed by, specifically, a high surface structure spatial frequency waveform component 261 having a spatial frequency in a high surface structure spatial frequency range, a medium surface structure spatial frequency waveform component 262 having a spatial frequency in a medium surface structure spatial frequency range, and a low surface structure spatial frequency waveform component 263 having a spatial frequency in a low surface structure spatial frequency range. For sake of illustration, the model surface structure was selected so that the waveform defined by its surface height profile could be expressed by waveform components 261, 262, 263 with equivalent amplitudes.

Figure 92A:
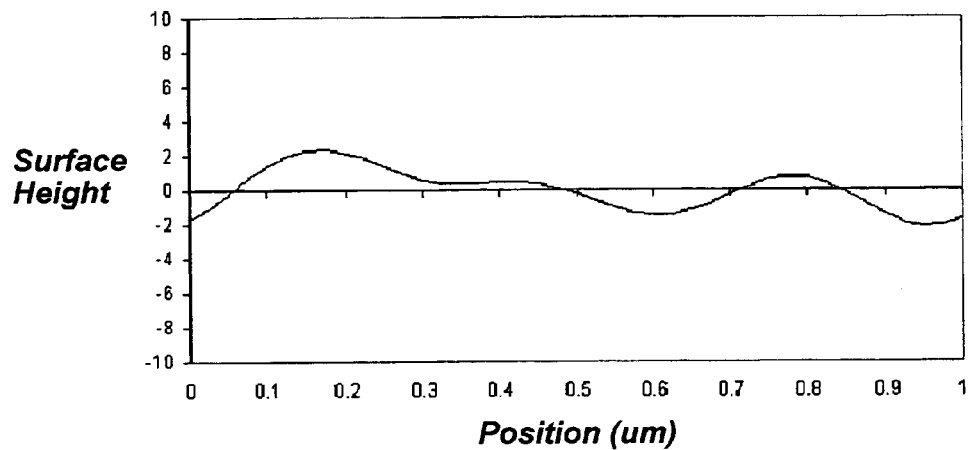
FIGS. 92a and 92b are illustrations of a the surface height profile of a model workpiece surface structure.
Figure 92B:
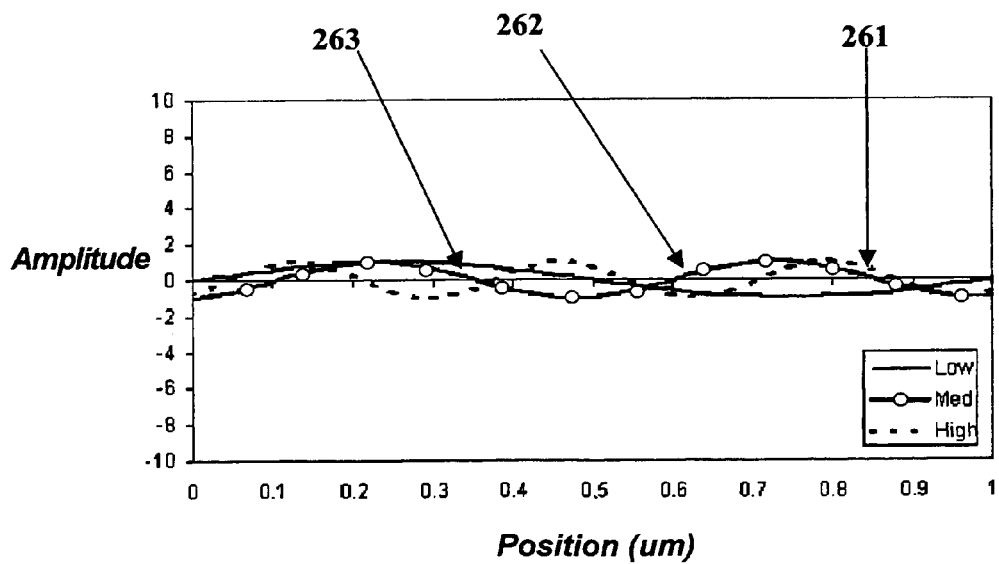
Figure 93A:
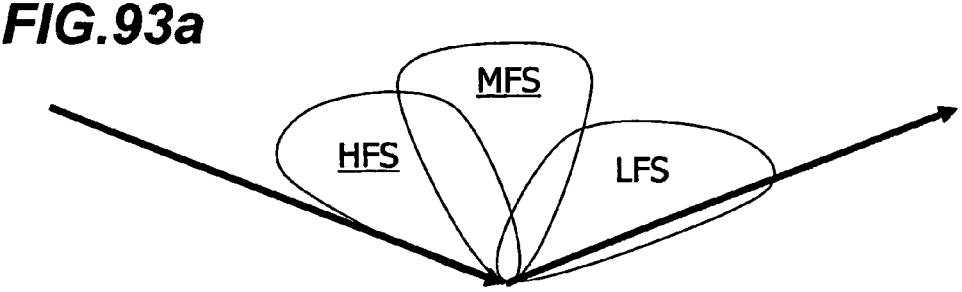
FIG. 93a-93d are diagrams that show regions representative of the amount of and direction of photons scattered from a surface structure, by waveform component.
Figure 93B:
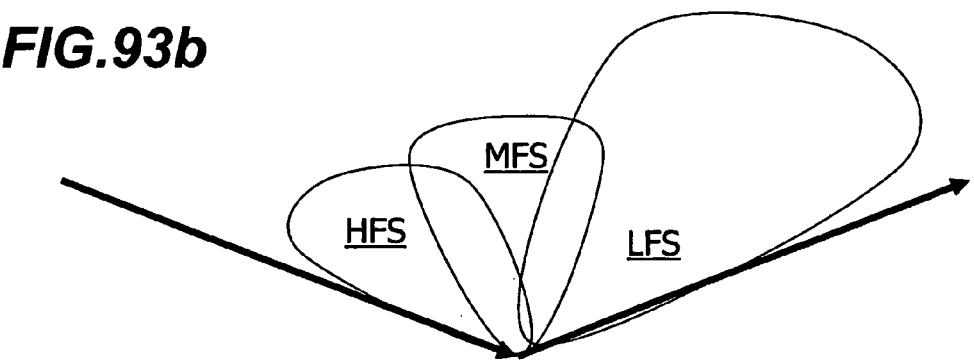
Figure 93C:
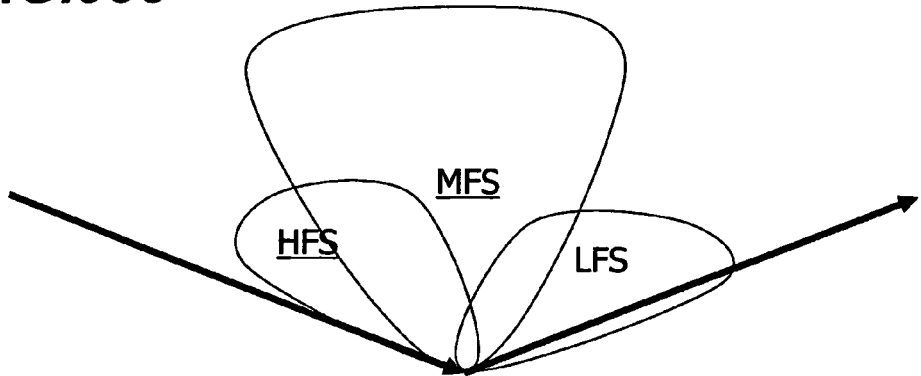
Figure 93D:
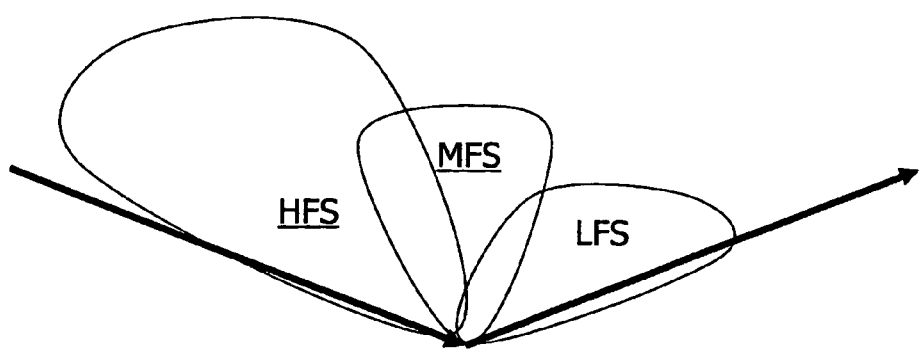

As photons scatter from a surface structure, the angles at which they scatter can be modeled using the waveform components of the waveform that is representative of the surface structure. In addition, the extent of scatter that will be present in a region above the surface can be modeled using the waveform components of the waveform that is representative of the surface structure. For example, FIG. 92a-92d are diagrams that show regions representative of the amount of and direction of photons scattered from a surface structure, by waveform component. FIG. 93a shows scatter from the model surface structure of FIG. 91b, with scatter associated with high surface structure spatial frequency waveform component 261 scattering into high surface structure spatial frequency surface scatter region HFS, scatter associated with medium surface structure spatial frequency waveform component 262 scattering into medium surface structure spatial frequency surface scatter region MFS, and scatter associated with low surface structure spatial frequency waveform component 263 scattering into low surface structure spatial frequency surface scatter region LFS.

As the amplitude of the surface structure changes, the relative contributions of the spatial frequencies to the waveform representative of the surface structure change, and the scatter pattern changes commensurate with the changes in the waveform and its components. FIG. 92b shows an increase in scatter in the low surface structure spatial frequency surface scatter region LFS which would be occur if the low surface structure spatial frequency waveform component of the waveform representative of the surface structure had an increase in amplitude relative to the other waveform components. FIG. 92c shows an increase in scatter in the medium surface structure spatial frequency surface scatter region MFS which would be due to an increase in amplitude in the medium surface structure spatial frequency waveform component relative to the other waveform components. FIG. 92d shows an increase in scatter in the high surface structure spatial frequency surface scatter region HFS due to an increase in amplitude in the high surface structure spatial frequency waveform component relative to the other waveform components.

Figure 94:
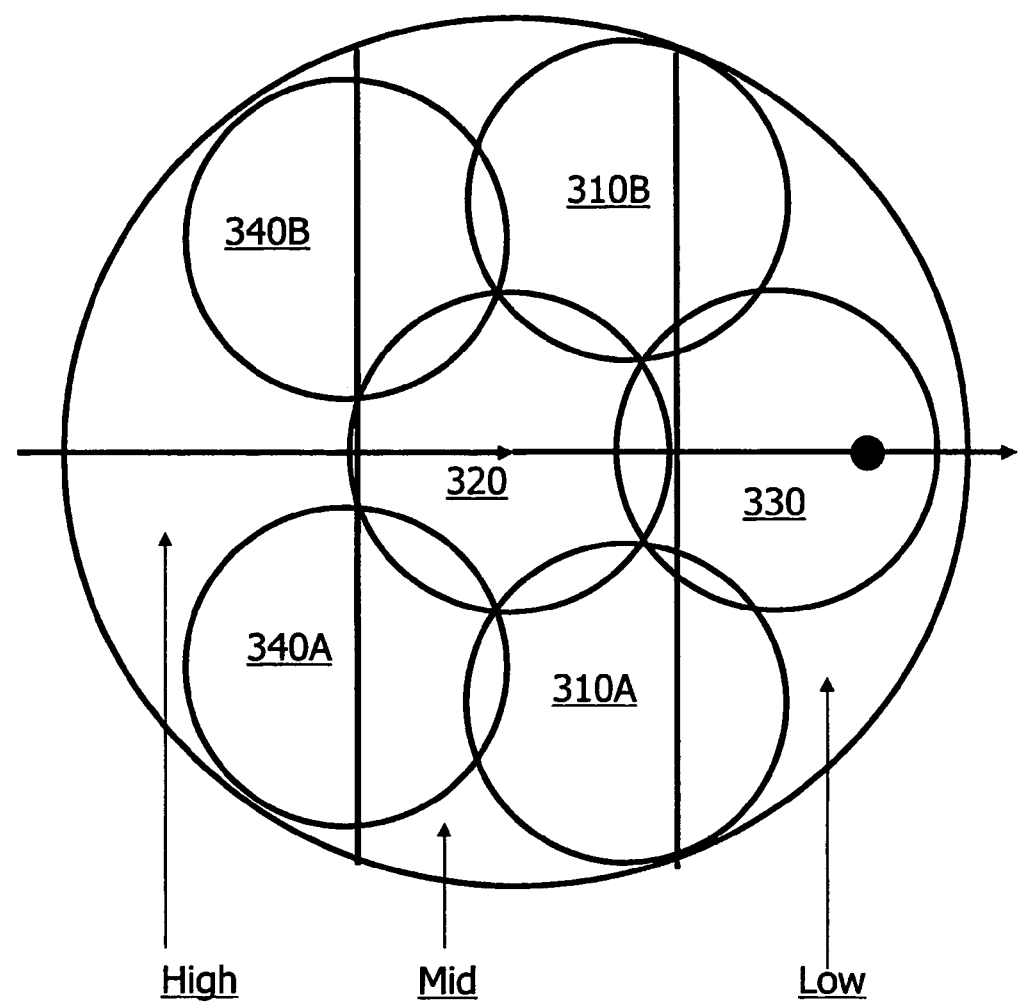
FIG. 94 is a diagram of the collection space above a workpiece surface, showing collection areas for the collectors 300 in the surface inspection system 10 and representative surface structure spatial frequency ranges associated therewith.

As noted above, in a multi-collector surface inspection system, such as system 10, collectors are positioned at selected positions in the space above a workpiece, with each collector responding to a specific range of surface structure spatial frequencies. FIG. 94 is a diagram showing the pattern of surface scatter observable by collectors in a system 10 in the space above the surface of a workpiece and representative surface structure spatial frequency ranges associated therewith. It can be seen that scatter associated with the low surface structure spatial frequency waveform component 263 is observable by the front collector 330 and wing collectors 310A, 310B, while scatter associated with the medium surface structure spatial frequency waveform component 262 is observable by the center collector 320 and wing collectors 310A, 310B, and scatter associated with the high surface structure spatial frequency waveform component 261 is observable by the back collector 340A, 340B. Therefore, it can be seen that surface structure spatial frequency data associated with scatter from a surface structure is obtainable from multi-collector surface inspection system, such as system 10.

Determining Surface Roughness of the Workpiece Surface Using the Proportionality Of Scatter Power over a range of Spatial Frequencies It is preferable to minimize or eliminate the contribution of surface roughness from discrete defects from surface contamination. Therefore, it is preferable to identify the extent of the contribution of surface roughness in order that the extent of the contribution of surface roughness may be subtracted from the output associated with the collector-detector assembly 200.

In accordance with another aspect of this invention, in a surface inspection system having a plurality of collectors, each of which is disposed at a selected collection solid angle, comprising a selected solid angle above a scattering surface, a method for determining an extent of a contribution of surface roughness on the scattering surface comprises determining an extent of a contribution of surface roughness frequencies on the scattering surface. One aspect of the invention further comprises monitoring surface structure spatial frequency contributions to collector signal. In a further aspect, the method comprises monitoring surface structure spatial frequency contributions to the workpiece surface using data from a set of collection solid angles in the space above the workpiece. In another aspect of the invention, the method comprises determining an extent of a contribution of surface roughness frequencies on the scattering surface at a set of collection solid angles that are associated with a selected set of collectors.

In another aspect of the invention, the method comprises collecting "low-surface structure spatial frequency" variations of scatter at one or more selected collection solid angles, whereby the amplitude of the scatter over the selected collection solid angle is proportional to the amplitude of surface variation causing the scatter, over a range of surface structure spatial frequencies detected at the selected collection solid angles.

In a still further aspect of this invention, the contribution/presence of surface roughness frequencies on a scattering surface is determined by displaying a histogram showing the amplitude of scattered photons (in parts per million/billion) for the selected solid angles.

Providing surface amplitude information for specific spatial frequencies so as to determine an extent of a contribution of surface roughness on the scattering surface (conducting haze analysis) allows correlations to be developed between scatter intensity values$^2$ and wafer features such as the extent of "grain" or, as referred to in the Stover reference, "surface lay" of the silicon surface or the extent or type of surface structures. Such correlations will then allow insight into the outcome of processing the wafer surface (such as to test the results of chemical mechanical planarization (CMP). In a further aspect of the invention, the step of providing surface amplitude information for specific spatial frequencies further comprises combining output associated with a set of selected collectors to form a haze field, comprising haze associated with combinations of collectors outside of the plane of incidence (e.g. backs and wings). Forming haze fields from output associated with a set of selected collectors is useful in minimizing the effects of incident beam orientation to the "grain" of the silicon surface. By collecting symmetrically above the wafer, a system 10 is able to reduce the intensity variations caused by the orientation of the incident to the surface "grain". One such set of selected collectors, the combination of output associated with which has shown to be useful in minimizing the effects of incident beam orientation to the "grain" of the silicon surface, comprises the back collectors.

The idea reflects the proportionality, not absolute determination, of s surface structure spatial frequency and direction of scatter. The method is based on the idea that each collector responds to scattered light associated with a specific range of surface structure spatial frequencies. The theory indicates the "best-case" response range for each collector. Since the response range is constant within a given measurement configuration, e.g. incident beam angle, wavelength, collector dimensions, etc., valid relationships may be drawn between surface structure and the direction of surface roughness scatter.

It should be apparent to those of skill in the art from this illustration that the present invention is not limited to the particular algorithm described herein, and that other approaches and other specific algorithms may be used to process the data obtained from the various detector modules 400 and to determine defect geometry and classify defects in accordance therewith.

In accordance with the present invention, and as shown in FIG. 75, a method 970 for determining an extent of a contribution of surface roughness frequencies on the scattering surface comprises the following steps:

Step 971: Determine the in-scan surface structure spatial frequency response 702 of a collector 300 to scatter light, comprising light that has been scattered from a surface S by an incident beam that is applied at a selected angle from normal onto the surface.

Step 972: Determine a response range comprising the range of the in-scan surface structure spatial frequency response 702.

Step 973: Determine a scatter intensity value representative of the scattered light for the response range in order to determine an extent of a contribution of surface roughness on the scattering surface.

In the presently preferred yet merely illustrative embodiment of the present invention, the incident beam angle comprises about 65 degrees from normal.

The method of the present invention further comprises

Step 974: Determine a scatter intensity value for each collector 300 in a set of selected collectors 300, and compare scatter intensity values in order to build an understanding of the haze response by the surface to impingement of an incident beam thereon.

The method of the present invention further comprises

Step 975: Determine a scatter intensity value for a collector for a plurality of surfaces, and compare scatter intensity values in order to build an understanding of the haze response by the plurality of surfaces to impingement of a coherent beam thereon.

In a further aspect of the present invention, the scatter intensity value comprises a value that is an amplitude of the scattered light. In the presently preferred yet merely illustrative embodiment of the present invention, the scatter value comprises a value representative of a maximum amplitude of the scatter light. Alternatively, the scatter value comprises a value representative of a minimum amplitude, a value representative of the difference between a minimum and maximum value, or a value derived from any desired function of the scatter light.

In the presently preferred yet merely illustrative embodiment of the present invention, the step 971 of determining the in-scan surface structure spatial frequency response of each collector further comprises creating a surface structure spatial frequency plot 705 in which the cross-scan surface structure spatial frequency 704 for each collector is mapped against in-scan surface structure spatial frequency 702, forming the spatial frequency response region 700 for each collector 300 in the multi-collector surface inspection system 10. One such surface structure spatial frequency plot is shown in FIG. 52, which presents the surface structure spatial frequency response defined by the cross-scan surface structure spatial frequency response 704 and the in-scan surface structure spatial frequency response 702 for a set of collectors 300 comprising the front collector 330, center collector 320, dual wing collectors 310A, 310B, and back collectors 340A, 340B of the presently preferred yet merely illustrative embodiment of the present invention. The mapping results in a visual representation of a spatial frequency response region 700 for each collector 300, such as front collector spatial frequency response region 730, a center collector spatial frequency response region 720, dual wing collectors spatial frequency response regions 710A, 710B, and back collector spatial frequency response regions 740A, 740B.

As seen in FIG. 52, each collector 300 responds over a specific range of wafer surface structure spatial frequencies. The response range is constant within a given measurement configuration, e.g. incident beam angle, wavelength, collector dimensions, etc. Mapping surface structure spatial frequency response in terms of cross-scan surface structure spatial frequency response 704 and the in-scan surface structure spatial frequency response 702 produces a means of monitoring the various surface structure spatial frequency contributions to surface roughness scatter.

It can also be seen that the origin in the spatial frequency plot 705 is offset to reflect the offset of the incident beam angle from surface normal of the sample. The step of determining response ranges further comprises using the surface structure spatial frequency plot to identify ideal response ranges 760 for each collector 300.

In the presently preferred yet merely illustrative embodiment of the present invention, the step 974 of comparing the scatter intensity values further comprises a step 976 of displaying the scatter intensity values for each response in a visual representation. The displaying step 976 may comprise forming a chart 706, as shown in FIG. 54, identifying the scatter intensity values. Alternatively, as shown in FIG. 53, the displaying step 976 may comprise a step 977 of mapping the ideal response ranges 760 into a histogram 780 illustrating the scatter value.

Figure 53:
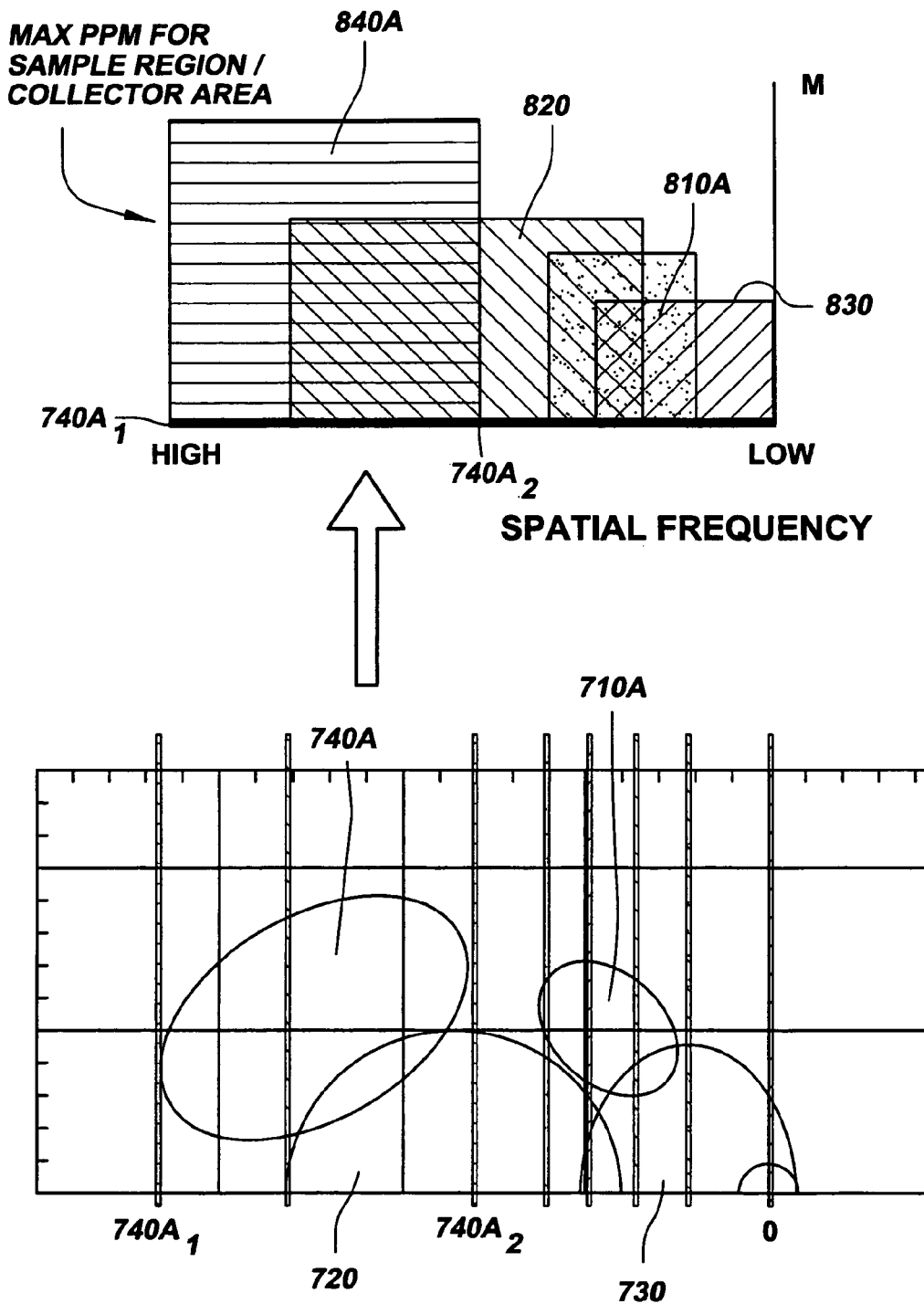
FIG. 53 is a diagram showing the mapping of the ideal response ranges shown in FIG. 52 into a histogram.
Figure 54:
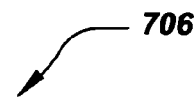
FIG. 54 is a chart for use in analyzing the in-scan surface structure spatial frequency response of collectors in a surface inspection system of the present invention.

The histogram 780 of FIG. 53 has an element 782 associated with each ideal response range 760, with the height of an element 782 comprising a power value representative of the power scattered at each collector 300 within the response range 760. In a presently preferred yet merely illustrative embodiment of the present invention, the power value comprises a value representative of an amount of scatter measured (for example, in parts per million, or nanowatt per steradian, or ppm per steradian).

In a still further embodiment, the step 977 of mapping the ideal response ranges 760 into a histogram 780 further comprises having the histogram 780 illustrate the breadth of the ideal response range 760 associated with each collector 300. As shown in FIG. 53, each element 782 on the histogram 780 is provided with a width that is representative of the ideal response range 760 associated therewith.

In a still further embodiment, as shown in FIG. 53, the histogram 780 illustrates the surface structure spatial frequency values of the in-scan spatial frequency responses 702 associated with the scattered light by placing the elements at locations on the histograms 780 that represent the range of the in-scan spatial frequency responses 702. For example, the back collector spatial frequency response regions 740A demonstrates a range of responses between in-scan spatial frequency $740A_1$ and in-scan spatial frequency $740A_2$. The difference between the frequencies $740A_1$, $740A_2$ determines the breadth of the histogram element 782A associated with the back collector spatial frequency response regions 740A. Referring to FIG. 53, it can be seen that certain of the surface structure spatial frequency responses overlap. For example, the histogram element 820 associated with the center collector surface structure spatial frequency response region 720 overlaps with the histogram element 840A (associated with the back collector surface structure spatial frequency response region 740A), the histogram element 810A (associated with the wing collector surface structure spatial frequency response region 710A), and the histogram element 830 (associated with the front collector surface structure spatial frequency response region 730. Therefore, when a histogram 780 is created for the surface structure spatial frequency responses 760, as seen in FIG. 53, the elements 782 associated with the overlapping surface structure spatial frequency response 760 also overlap on the histogram 780.

Overlapping data may be displayed in any conventional manner, such as color changes, hash marks, or using overlapping transparencies. In addition, a decision could be made to ignore data having certain characteristics or associated with certain collectors. For example, data associated with the wing collectors operating in the P configuration may be excluded from the analysis in order to reduce the extent of overlap. Such exclusion would provide minimal impact on the analysis, since most surface scatter would be filtered from the wing data due to polarization.

Figure 55:
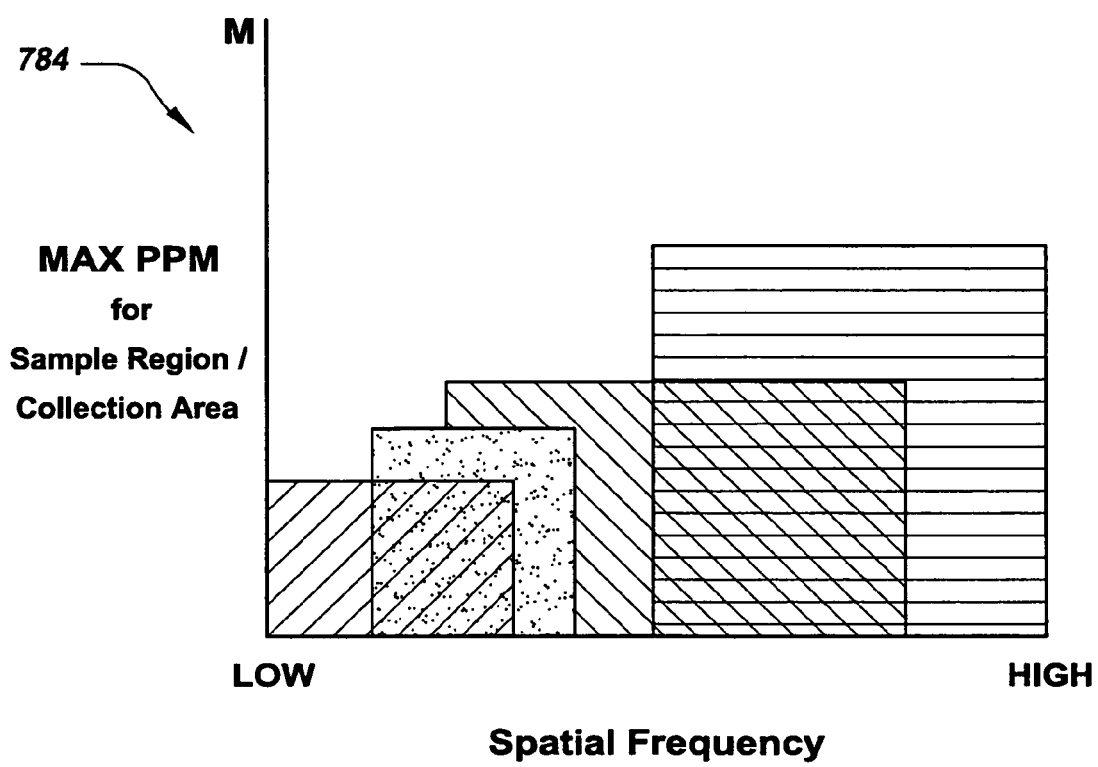
FIG. 55 is a histogram derived from the histogram shown in FIG. 53.

The histogram 780 from FIG. 53 may also be flipped horizontally to present the histogram 784 in FIG. 55, in which the x-axis is oriented in a more common manner, showing low to high frequency.

As noted above, the method of the present invention further comprises determining a scatter intensity value for a collector for a plurality of surfaces by impinging an incident beam on the plurality of surfaces, and comparing scatter intensity values in order to build an understanding of the haze response by the plurality of surfaces. Scatter intensity values and surface structure spatial frequency response ranges for a plurality of surfaces may thus be used to identify and highlight differences in surface roughness that are due to differences in processing, such as pressure polish time, slurry type, chemical concentrations. The chart of FIG. 54 identifies scatter intensity values for three different wafer processes. Levels of surface structure spatial frequencies (such as low, medium and high) may be assigned different colors so that the significant differences in the haze in wafer created using the different processes are readily shown.

The scatter intensity values associated with surface roughness[3] may be normalized for each collection area represented in a histogram such as histogram 784 in order to produce a low-resolution power spectral density (PSD)-type chart. The power spectral density (PSD) of a quasi-stationary random process is the Fourier Transform of the autocovariance function. Specifically, the spectral density $\phi(\omega)$ of a signal f(t) is the square of the magnitude of the continuous Fourier transform of the signal.

$$\Phi(\omega) = \left| \frac{1}{\sqrt{2\pi}} \int_{-\infty}^{\infty} f(t) e^{-i\omega t} dt \right|^2 = F(\omega) F^*(\omega)$$

where $\omega$ is the angular frequency ($2\pi$ times the cyclic frequency) and $F(\omega)$ is the continuous Fourier transform of f(t).

Figure 76:
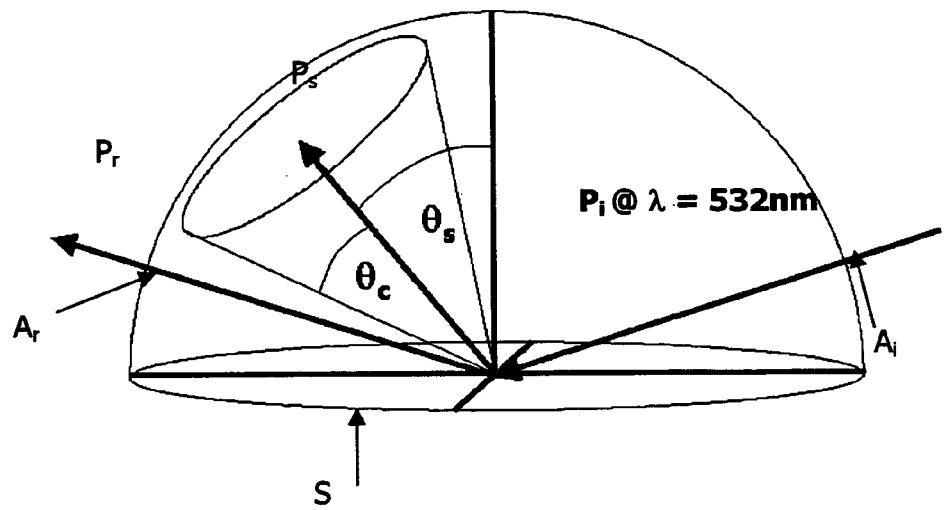
FIG. 76 is a diagram illustrating the solid angle for collection of scatter signal at a collector.

Power spectral density is usually expressed in units squared per frequency. For two-dimensional roughness, this would be $um^2/(cyles/um)^2$—equivalent to $um^4$. The contribution of surface roughness on a scattering surface to scattered light may be calculated from amount of scattered light observed in the solid angle associated with each selected collector. FIG. 76 is a diagram illustrating the solid angle of collection of scatter signal from a surface S at a collector 300. FIG. 76 shows an incident beam $A_i$ with an incident power $P_i$ and $\lambda=532$ m, impinging on a surface S, producing a reflected beam $A_r$ having a reflected power $P_rP_s$ for the solid angle defined by an angle $\theta_c$ that is disposed at a scattering angle $\theta_s \omega$ is: $2\pi$ times the cyclic frequency). Therefore, co may be determined to be:

$$\Omega = 2\pi(1 - \cos \theta_c),$$

where $\theta_s$ is the scattering angle.

The Bidirectional Reflectance Distribution Function BRDF is the differential ratio of the sample radiance normalized by its irradiance. Therefore, once the $\omega$ is determined, one can then determine $$BRDF \cong \frac{P_s/\Omega}{P_i \cos \theta_s}$$

where Pi=Incident power, and
Ps=Scattered power.

When all scattered light is being collected across the area of the hemisphere, and the total power measured at each collector is summed, the RMS roughness $\sigma_{rms}$ may then be determined by $$\sigma_{rms} \cong \frac{\lambda}{4\pi} \sqrt{\frac{P_s}{P_r}};$$

It is preferable to minimize or eliminate the contribution to scatter signal of surface roughness so that discrete defects can be distinguished from surface contamination. Therefore, it is preferable to identify the extent of the contribution of surface roughness in order that it may be subtracted from the output associated with the collector-detector assembly 200. Further, it is preferable to track haze for each of the collectors in order to understand the confidence in the measurement. The composition of all collectors is used to provide surface roughness information. RMS Roughness is derived from summing all of the scatter intensity values for each collector. Further detail on RMS roughness-based haze analysis is found below.

It is further preferable to identify the extent of the contribution of surface roughness to collector output in order to analyze collector response to light scattered from surface structural conditions.

Visualization of Spatial Frequency Distributions Occurring in a Workpiece Surface Structure Typically, surface inspection tools that measure RMS roughness have a normal incident beam. The surface inspection system 10 differs from surface inspection tools that measure RMS roughness in that it has an oblique incident beam and it collects scatter from collectors disposed at selected angles. The present invention involves an improvement in haze analysis comprising analyzing the spatial frequency distributions in surface scatter. As noted above, haze analysis, or analysis of the diminished atmospheric visibility that results, in the case of a surface inspection tool, from light scattered from a surface, is typically performed in order to analyze collector response to light scattered from surface structural conditions. Examples of systems and methods that provide haze analysis include those of the '701 patent, as well as U.S. Pat. No. 6,118,525 and U.S. Pat. No. 6,292,259, all of which are assigned to ADE Optical Systems Corporation and all of which are herein incorporated by reference.

In a multi-collector surface inspection system such as system 10 described above, the summation of haze from each of the plurality of surface collectors 300 is approximately the haze observed by a total integrated scatter tool, such as is described in the Stover reference. The placement of the plurality of collectors (front, center, backs, and wings) in the surface inspection system 10 described above, at their respective locations allows for the collection of angular information on light scattered from a surface, which, as noted above, can facilitate separation of scattered light into the spatial frequency ranges of surface structures, which then in turn can be used to provide detail about the kind of structures causing the surface roughness.

In addition, scattered light having selected light characteristics, such as a selected polarization, may be used to identify the source of the scatter on or in a workpiece surface. For example, scattered light of a selected polarization may be used to distinguish between surface roughness and a surface defect. When a P-polarized incident coherent beam hits a workpiece surface, it is rotated 90 degrees, and scatter from surface roughness becomes S-polarized at the wing locations. However, scatter caused by a P-polarized incident coherent beam hitting a particle on a workpiece surface remains P-polarized at some ratio, especially in scatter observable in the solid angles occupied by the wing collectors. Therefore, polarization may be used to distinguish between particles and surface roughness, especially in the wing collectors that were located, as described above, in a location in which P-contribution from scatter associated with surface roughness is at a minimum. In addition, power measured at each collector can be summed with all other collectors to produce total (measured) scatter power (TIS).

Therefore, it is an object of the present invention to use knowledge of the characteristics of light scattered from surface structural conditions in order to improve the analysis of collector response to light scattered from surface structural conditions.

It is a further object of the present invention to use characteristics of the light scattered from surface structural conditions, such as intensity of the scattered light and surface structure spatial frequency range associated with the scattered light, to identify characteristics of the surface structural conditions, such as average surface roughness over a selected range of wafer surface structure spatial frequencies.

It is a further object of the present invention to monitor workpiece production processes using characteristics of scattered light from workpiece surfaces, comprising intensity of the scattered light and surface structure spatial frequency range of the scattered light.

With the present invention, there is provided a method and a system for inspection of surface structural conditions of a workpiece, over a range of surface structure spatial frequencies determined by system geometry, by analyzing surface scatter, comprising light scattered from a surface and comprising surface roughness over a determinable surface structure spatial frequency range, involving analyzing relationships between portions of the scattered light associated with defined surface structure spatial frequency ranges. In one aspect of the invention, analyzing surface scatter involves treating the power measured in the collectors from the surface scatter, over a determinable range of surface structure spatial frequency responses, as a variable in the analysis.

In one embodiment of the invention, the method comprises separating surface roughness scatter into surface structure spatial frequency ranges, where direction of surface roughness scatter is predominately determined by incident beam properties and the idealized spatial frequency of the structure scattering the light, and analyzing at least a first scatter portion comprising a portion of the surface roughness scatter within a first surface structure spatial frequency range. In a further aspect, the method comprises analyzing the first scatter portion alone or in combination with a second scatter portion comprising a portion of the surface roughness scatter within a second surface structure spatial frequency range. In a still further embodiment, the method comprises analyzing a plurality of scatter portions of surface scatter, each scatter portion comprising a portion of the surface roughness scatter having surface structure spatial frequencies within a selected spatial frequency range defined by the architecture of the surface inspection system.

The method comprises observing the presence of surface roughness scatter within an area above the surface, with the area being selected for the power range of the power measured over the measurable spatial frequency within the area, in order to observe surface roughness scatter by spatial frequency over the selected frequency range, and to analyze surface roughness scatter by power measured over a known area.

In a further aspect, the method comprises collecting the surface scatter in a plurality of areas above the surface, with each area being selected for its association with a selected spatial frequency range in the frequency of surface roughness in a surface structure, order to analyze the surface roughness of the surface structure by the selected spatial frequency ranges and to analyze relationships between surface scatter associated with different ones of the spatial frequency ranges.

In one embodiment, collecting the surface roughness scatter at a plurality of areas comprises positioning a plurality of scattered light collectors at selected positions above the surface, with each position selected so that the scattered light collector, at the position, is able to observe power of a surface roughness scatter associated with a determinable surface structure spatial frequency range. The method further comprises observing surface roughness scatter at the scattered light collectors and analyzing the surface roughness scatter by scattered light collector. In a further embodiment, the step of observing surface roughness scatter comprises identifying the presence of surface scatter at the scattered light collectors and measuring an extent of the surface roughness scatter.

In another embodiment, the method further comprises using a plurality of collectors disposed at positions above the surface, identifying a surface structure spatial frequency range to be associated with scattered light observable by each of the collectors, and analyzing the surface roughness scatter by scattered light collector.

In another aspect of the invention, analyzing surface scatter involves developing visual representations of haze produced by the surface roughness scatter, with haze comprising an atmospheric condition above the surface of diminished visibility that results from conditions such as background noise or surface roughness, the visual representations showing the presence of haze arising from surface scatter, comprising scattered light from an incident beam impinging on selected locations on the surface, according to the spatial frequency range of the surface roughness scatter. In a further embodiment, developing visual representations further comprises presenting an extent of the haze.

In a still further embodiment, developing visual representations further comprises presenting haze associated with surface roughness scatter associated with a plurality of spatial frequency ranges, with the haze displayed according to the spatial frequency range with which its associated surface roughness scatter is associated. In further embodiments, presenting haze associated with surface roughness scatter associated with a plurality of spatial frequency ranges further comprises identifying an extent of haze for each spatial frequency range.

In another embodiment, developing visual representations of haze comprises developing composite haze maps, in which map positions are associated with locations on the region under investigation, and which shows multiple representations of haze associated with surface roughness scatter arising from an incident beam reflected from each of said locations, with each representation of haze associated with surface roughness scatter associated with a different spatial frequency range.

According to another aspect of the present invention, there is provided a method for inspection of surface structural conditions of a workpiece by analyzing collector response to light scattered from surface structural conditions, with the system and method involving analyzing a portion of the light associated the a selected surface structure spatial frequency range.

In a further aspect of this invention, a method and a system for inspection of surface structural conditions of a workpiece involves observing scattered light with a plurality of scattered light collectors, each collector disposed to observe scattered light over a determinable surface structure spatial frequency range, said scattered light having intensity representative of surface roughness scatter having a determinable surface structure spatial frequency range, combining output associated with at least two of the selected scattered light collectors to form combined surface roughness scatter output, and analyzing the spatial frequency contributions of the combined surface roughness scatter output.

In an even further aspect of the invention, analyzing the spatial frequency distributions further comprises forming visual displays of surface roughness scatter output. In a further embodiment, forming visual displays comprises developing displays in which spatial frequency distributions are represented by a display element, with each spatial frequency to be presented in the display being associated with a display element. Preferably, the display element comprises a display color. In a further embodiment, forming visual displays comprises developing displays showing an extent of the surface roughness scatter output of a selected spatial frequency, in order to identify the relative contribution of light associated with the selected spatial frequency in the light of the surface roughness scatter output.

In addition, forming visual displays comprises constructing composite haze maps, further comprising developing workpiece surface maps in which map regions are associated with surface structures on the workpiece, and in which a characteristic of the display, such as graphical elements or color, in a map region identifies the relative contribution of roughness having a selected spatial frequency in the surface structure associated with the map region. A further embodiment comprises defining channels in a surface inspection system, and constructing composite haze maps further comprises representing surface roughness scatter output associated with selected defined channels in a haze map.

In an even further aspect of the invention, analyzing the spatial frequency distributions further comprises forming graphical representations of the spatial frequency distributions. In a further embodiment, developing graphical displays further comprises developing bar charts of the measured power by the spatial frequency response range.

When light is scattered from surface structural conditions and observed by a collector positioned above the surface, the intensity of the portion of the light that is present in the space defined by the solid angle of the collector, coupled with the identification of the spatial frequency range of the surface structure from which the portion is scattered, allows analysis of the portion by frequency range. Determining an extent of a contribution of surface roughness on the scattering surface allows correlations to be developed between scatter intensity values and wafer features such as the extent of "grain" of the silicon surface or the extent or type of surface structures.

One aspect of the invention further comprises monitoring spatial frequency contributions to surface roughness scatter. In a further aspect, the method comprises monitoring spatial frequency contributions to surface roughness scatter at a set of collection solid angles that is associated with a selected set of collectors.

Since the response range is constant within a given measurement configuration, e.g. incident beam angle, wavelength, collector dimensions, etc., valid relationships may be drawn between surface structure and the direction of surface roughness scatter. Scatter intensity values may be compared in order to build an understanding of the surface response by haze levels.

In a surface inspection system such as system 10, in which a plurality of collectors are disposed above a surface, the identification of scattered light's intensity and frequency range allows sorting of light that is scattered from surface structural conditions by surface structure spatial frequency range and the use of surface structure spatial frequency range as a variable in the analysis of scattered light. Haze associated with a selected surface structure spatial frequency range may then be analyzed alone or in combination with haze associated with other selected surface structure spatial frequency ranges.

Collectors such as the collectors 300 in the surface inspection system 10 may be used to measure the intensity of light scattered from surface structural conditions, and positioning the collector in the space above the workpiece relative to the angle of the incident beam impinging on the surface may be used to associate the collector output with a selected surface structure spatial frequency range. It is within the scope of the present invention to place collectors at selected positions in the space above a surface under investigation, with the positions so selected to optimize the presence of haze associated with surface scatter propagating from a surface having a specific surface structure spatial frequency.

It should be noted that the output obtained by a collector such as collector 300 in a collection and detection assembly 200 does not identify the presence of scatter having a particular frequency. A collector's output indicates the presence of light in the space that is defined by the solid angle of the collector. When the light results from incidence of a coherent beam from a workpiece surface, it is the position of the collector in the space above the surface that defines to a large extent the observable scattered light for the collector. The observable scattered light will be that portion of the scattered light that is associated with the range of spatial frequency of the surface structure impinged upon by the incident beam t. Therefore, it is the knowledge of the spatial frequency range of surface structure that is associated with the scattered light that is observable by a collector (obtained from knowledge of the position of the collector relative to the surface) that allows the observation of surface scatter associated with a particular spatial frequency.

In addition, it should be noted that the output obtained by a collector such as collector 300 in a collection and detection assembly 200 indicates the amplitude of the roughness of the structures in and on the workpiece surface by identifying the intensity of light scattered from the workpiece surface when a coherent beam is incident from the surface. Output from collector 300 comprises voltage signals that are indicative of photon activity within a collector, with the photon activity resulting from light scattered from the surface of the region under inspection, and with the extent of the voltage signal being indicative of the extent of the intensity of such photon activity. In addition, the extent of the intensity of such photon activity at the collector indicates the amplitude of the roughness of the structures in and on the workpiece surface.

The intensity of the light scatter indicates the amplitude of the roughness of surface structures because, first, the scatter's intensity at the collector is proportional to the amplitude of the light waves comprising the scatter, and, second, the amplitude of the scattered light waves is proportional to the amplitude of the roughness of the structures in and on the workpiece surface. The higher the roughness of surface structures, the higher the number of photons scattered from the surface, and, in turn, the higher the number of photons collected, for example in parts per million (ppm), by the collector. The output of a collector, being a voltage value representative of the number of photons observed in the space above a workpiece surface within a solid angle about the collector, thus identifies the amplitude of structures in and on the workpiece surface.

Providing surface amplitude information for specific spatial frequencies further comprises combining output associated with a set of selected collectors to form a haze field. Forming haze fields from output associated with a set of selected collectors is useful in minimizing the effects of incident beam orientation to the "grain" of the silicon surface.

It is known that scatter patterns, also known as haze patterns, differ given the location above the workpiece surface at which the haze is observed. For example, collectors located in the front quartersphere FQ (referring to FIG. 6, FQ being the region lying above the workpiece surface, between the base plane B and the normal plane NP, through which passes the incident beam before it reaches the base plane B) receive scatter having more lower frequency components than do collectors located in the back quartersphere BQ or than do collectors in regions along or containing the normal plane NP. Therefore, front collectors will register increased levels of lower spatial frequencies.

It is also known that scatter patterns differ given characteristics of the wafer under examination. For example, wafers that have been processed with treatments (such as annealing or epitaxial processes) that result in smoother surfaces, tend to produce scatter with more lower frequency components than do wafers with polished surfaces. Given that front collectors will register scatter levels of lower spatial frequencies more than will collectors in other locations above the surface, light from the surfaces of annealed or epitaxial wafers will scatter more to front collectors than to collectors in other locations.

The following is an illustrative but not necessarily preferred method for analyzing surface scatter using a multi-collector surface inspection system such as system 10 to inspect workpieces such as wafers: The method, shown in FIG. 98, comprises a step 264 in which output representative of surface scatter is separated by surface structure spatial frequency associated with the surface scatter, and a step 268 in which the surface scatter is then analyzed by its associated surface structure spatial frequency range.

The step 264 of separating the output representative of surface scatter by the spatial frequency of the surface structures further comprises the following steps:

In a step 265, a set of expected spatial frequency ranges is selected for the surface structure to be observed. For example, the selected frequency ranges could comprise a high surface structure spatial frequency range, a medium surface structure spatial frequency range and a low surface structure spatial frequency range.

Step 266: Recognizing that collector placement above a test surface determines the surface structure spatial frequency range associated with the scattered light observable by the collector, the collectors in a multi-collector surface inspection system 10 that will provide output associated with the selected surface structure spatial frequency ranges are identified. For example, a front collector 330 would be selected as the low surface structure spatial frequency range collector for its ability to observe scatter associated with surface structure having a spatial frequency within a low surface structure spatial frequency range, a center collector 320 would be selected as the medium surface structure spatial frequency range collector for its ability to observe scatter associated with surface structure having a spatial frequency within a medium surface structure spatial frequency range, and a back collector 340A, 340B, alone or in combination as a channel 640, would be selected as the high surface structure spatial frequency range collector for its ability to observe scatter associated with surface structure having a spatial frequency within a high surface structure spatial frequency range.

Step 267: Surface scatter output is obtained for each of the selected collectors in order to obtain output to be associated with each selected surface structure spatial frequency range. If desired, output of selected collectors is combined to create output to be associated with a channel. For, example, in order to obtain scatter surface output to be associated with a high surface structure spatial frequency range, output from the back collectors 340A, 340B could be combined using the methods described above to obtain output associated with back combined (CFT) channel 641, back combined (FTC) channel 642, back combined (dual) channel 643, or another desired channel.

In one embodiment, as shown in FIG. 99, the step 268 in which the surface scatter is then analyzed by its associated surface structure spatial frequency range may comprise the step 269 of analyzing the output associated with a portion of surface scatter alone or in combination with output associated with other portions of surface scatter, with each scatter portion comprising a portion of the scatter from surface structure having a spatial frequency within a selected surface structure spatial frequency range. In one embodiment, the output analyzing step 269 comprises analyzing output associated with surface scatter by scattered light collector.

Figure 78A:
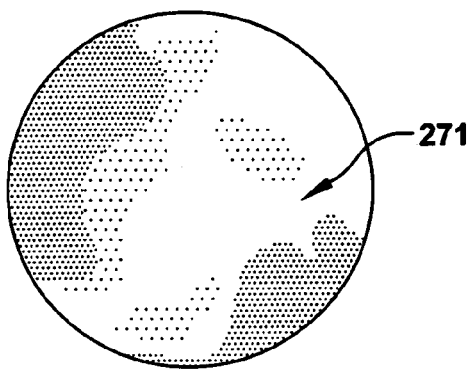
FIG. 78a, FIG. 78b, and FIG. 78c are examples of haze maps for displaying haze associated with, respectively high, medium, and low surface structure spatial frequency ranges of the present invention.
Figure 78B:
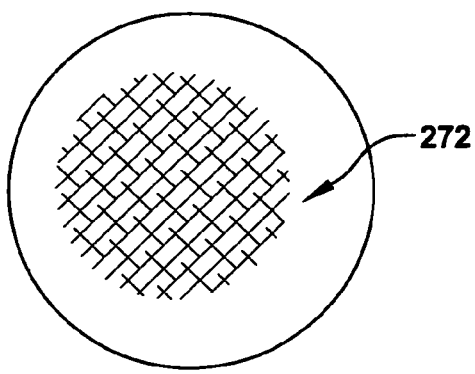
Figure 78C:
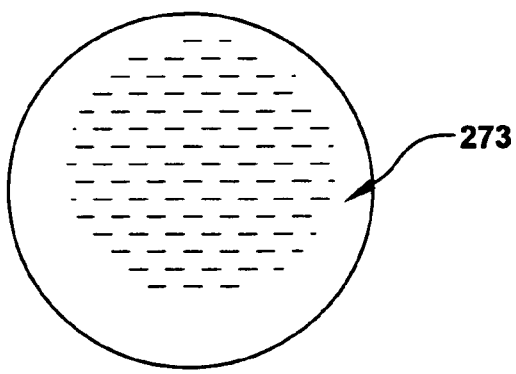

The output analyzing step 269 is facilitated by a step 274 of establishing a visual representation to be associated with the output associated with each surface structure spatial frequency range in the analysis. Establishing a visual representation further comprises the following steps:

Step 275: A characteristic of the visual representation is assigned to represent an identification of the presence of surface scatter in the output. In one embodiment, the visual representations are haze maps, with haze comprising an atmospheric condition above the surface of diminished visibility that results from conditions such as background noise or surface roughness. Haze maps comprise maps of the surface of a wafer, in which the positions on the map represent locations on a surface that caused an observation of haze by a collector during the reflection of an incident beam from the surface at the location. The haze map has a characteristic assigned thereto to represent the observation of surface scatter at a position on the haze map that represents the location on the wafer surface at which haze was observed. FIG. 78*a*, FIG. 78*b*, and FIG. 78*c* are examples of haze maps for displaying haze associated with a set of frequency ranges. FIGS. 78A, 78B, and 78C show wafer haze maps 271, 272, 273 for output associated with haze from scatter from surface structures having a surface structure spatial frequency within, respectively, the high surface structure spatial frequency range, the medium surface structure spatial frequency range, and the low surface structure spatial frequency range. In FIGS. 78A, 78B, and 78C, the characteristic of the visual representation that represents the observation of surface scatter (i.e., identifying the presence of haze) is a graphical element, with a different graphical element associated with each selected surface structure spatial frequency range. In FIG. 78A, the graphical element for identifying haze associated with high surface structure spatial frequency range comprises dots. In FIG. 78B, the graphical element for identifying haze associated with a medium surface structure spatial frequency range comprises parallel lines in a first direction. In FIG. 78C, the graphical element for identifying haze associated with a low surface structure spatial frequency range comprises parallel stripes of a second direction. In another embodiment of the present invention, the graphical representation could be color. For convenience, the haze map colors may be chosen to be consistent with the human visual spectrum, with blue representing high surface structure spatial frequency ranges, green representing medium surface structure spatial frequency ranges, and red representing low surface structure spatial frequency ranges. For purposes of illustrating this embodiment of the present invention employing color, the dots of FIG. 78*a* could represent blue, the parallel lines in a first direction of FIG. 78*b* could represent green, and the parallel lines in a second direction of FIG. 78*c* could represent red.

Step 276: An extent of surface scatter observed by each collector is represented by variation in the visual representation. In a further embodiment, the step 276 of representing extent of surface scatter further comprises presenting an extent of the haze. For example, presenting an extent of the haze could comprise modifying the characteristic to represent an extent of surface scatter. In FIGS. 78A, 78B, and 78C, variation in the amount of haze is shown by variation in the graphical element. In FIG. 78A, variation in a high structure spatial frequency range is shown by variation in dot density. In FIG. 78B, variation in the amount of haze of a medium surface structure spatial frequency range is shown by variation in density of the parallel lines in a first direction. In FIG. 78C, variation in the amount of haze in a low surface structure spatial frequency range is shown by variation in density of the parallel stripes in a second direction. In the embodiment in which color represents surface structure spatial frequency range, the variation in the visual representation could be shown by variation in the intensity of the color associated with the surface structure spatial frequency range, with no scatter represented by no color, a low amount of scatter represented by color of low intensity, and the maximum amount of scatter represented by the most intense color. For purposes of illustrating this embodiment of the present invention employing color, the density of the dots of FIG. 78A could represent the intensity of blue, the density of the parallel lines in a first direction of FIG. 78B could represent the intensity of green, and the density of the parallel lines in a second direction of FIG. 78C could represent the intensity of red. The step 276 of representing an extent of surface scatter by variation in the visual representation could comprise a step 277, in which the values representative of the extent of haze are mapped into values for the extent of variation in the visual representation. In the embodiment in which graphical elements are modified to represent scatter intensity, for each graphical element, each scatter intensity value could be mapped into a value representative of the amount of density of the graphical element. In the embodiment in which color intensity is used to represent scatter intensity, for each color, each scatter intensity value could be mapped into a pixel color value. For example, if the display system provides 256 levels of a color, each scatter intensity value could be mapped into a pixel color value ranging from 0 to 255. The manner in which the values representative of the extent of haze is assigned to values for the extent of variation in the visual representation is described in more detail below.

Step 280: For a set of surface scatter output associated with a defined surface structure spatial frequency, the visual representations are constructed, using the assigned characteristic of the visual representation to represent an identification of the presence of surface scatter in the output, the assigned variation in the visual representation to represent an extent of the surface scatter, and values for the extent of variation in the visual representation to represent the values representative of the extent of haze. In the embodiments described above, the resultant visual representations will comprise haze maps, in which each pixel in the display is associated with a location on the surface under investigation, and in which each pixel displays a variation in visual representation representative of an amount of haze observed by a collector during the incidence of a coherent beam on the surface at the location associated with the pixel. The step

Figure 79:
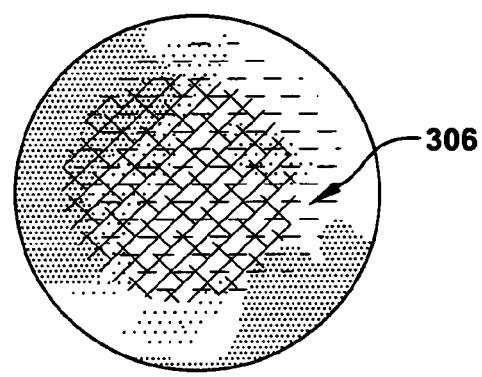
FIG. 79 is an example of a composite haze map of the present invention.

280 of constructing visual representations could comprise a step 284a of constructing one haze map for each selected surface spatial frequency range, or it could comprise a step 284b, comprising constructing a composite haze map by combining maps for at least two selected surface spatial frequency ranges into a single map. FIG. 79 shows an example of a composite haze map 306, created by superimposing the haze maps 271, 272, 273 shown in FIGS. 78A, 78B, and 78C.

Figure 95:
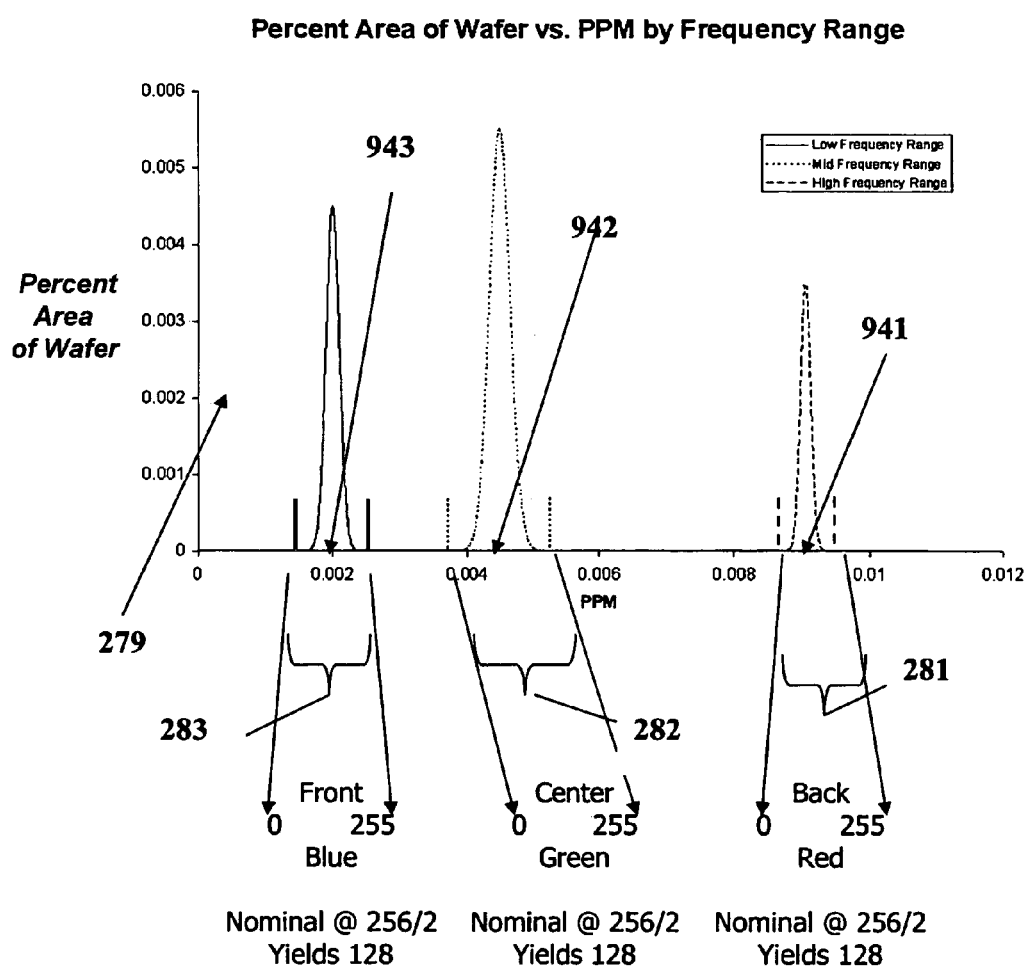
FIG. 95 is a plot showing the distribution of scatter intensity values on a wafer, by the percentage of a wafer's area at which a scatter intensity value was measured, for the output associated with three collectors.

The step 277, in which the values representative of the extent of haze are mapped into values for the extent of variation in the visual representation, could be performed using any conventional mapping process. For example, the values of surface scatter or haze could be assigned into values for extent of variation using any known technique, such as interpolation, or they could be assigned using a step 278 with reference to distributions of the scatter intensity values:

Referring to FIG. 95, there is shown a plot 279 of the distribution of scatter intensity values on a wafer, by the percentage of a wafer's area at which a scatter intensity value was measured, for the output associated with three collectors. The plot 279 can be developed for a single wafer or for a set of wafers: preferably over a set of wafers representing a process or related processes. The scatter intensity values for the output associated with three collectors are measured in photons observed in parts per million (ppm). The plot 279 specifically displays the scatter distributions associated with a a low surface structure spatial frequency range 283 (in the embedment described above, from the output associated with the front collector 330), for a medium surface structure spatial frequency range 282 (from the output associated with the center collector 320), and for a high surface structure spatial frequency range 281 (from the output associated with a back collector 340A, 340B, alone or in combination).

The plot 279 shows minimum and maximum scatter intensity values for the low surface structure spatial frequency range 283, medium surface structure spatial frequency range 282, and high surface structure spatial frequency range 281, and it identifies the scatter value associated with the greatest percentage of locations on the wafer or set of wafers, respectively, the most frequent low surface structure spatial frequency scatter intensity value 943, the most frequent medium surface structure spatial frequency scatter intensity value, and the most frequent high surface structure spatial frequency scatter intensity value 941. The most frequent surface structure spatial frequency scatter intensity values 941, 942, 943 are assigned the median value for the extent of variation in the visual representation, respectively median low surface structure spatial frequency variation value 303, median medium surface structure spatial frequency variation value 302, and median high surface structure spatial frequency variation value 301. In the embodiment in which color is used to represent surface structure spatial frequency range, the most frequent surface structure spatial frequency scatter intensity values 941, 942, 943 are assigned the median pixel color value for the display. In a display system which provides 256 levels of a color, the most frequent surface structure spatial frequency scatter intensity values 941, 942, 943 are assigned the median pixel color value 256/2, which is 128. The surface structure spatial frequency scatter intensity values above and below the most frequent surface structure spatial frequency scatter intensity values 941, 942, 943 but within the respective surface structure spatial frequency ranges 281, 282, 283 are then assigned to the values for the extent of variation in the visual representation using any known technique, such as interpolation.

Assigning of surface structure spatial frequency scatter values into values for extent of variation with reference to distributions of the surface structure spatial frequency scatter intensity values could be performed using the surface structure spatial frequency scatter intensity values distribution from the wafer under investigation, or it could be performed using surface structure spatial frequency scatter intensity values from a plurality of wafers, for example, from a production run of wafers having the same characteristics as the wafer under investigation. Using a plurality of wafers, nominal surface structure spatial frequency ranges for surface scatter may be identified and applied to the ranges of the extent of variation in the visual representation. As noted above, surface structure spatial frequency distributions may be analyzing by forming graphical displays of the surface structure spatial frequency distributions. Accordingly, the step 268, in which the surface scatter is analyzed by its associated surface structure spatial frequency range, further comprises a step 930 of forming graphical displays to present scatter intensity associated with surface structure having a spatial frequency within a selected surface structure spatial frequency range and the intensity's statistical characteristics at the displayed spatial frequency ranges, such as median or mean. In a multi-collector surface inspection system such as system 10, the graphical displays would comprise graphical displays of the outputs of selected collector. They could comprise charts or, preferably, histograms or bar charts in which the width of the bars represents the extent of the range of the surface structure spatial frequency response for the output of the collector.

The step 930 of forming graphical displays could further comprise a forming a composite graphical display in which the output of the selected collector or collector and the output's statistical characteristics is displayed at at least two surface structure spatial frequency ranges. The composite graphical display could comprise a combined view histogram or bar chart, with each bar on the histogram representative of a surface structure spatial frequency level. Histogram bars may be placed on the graph by increasing or decreasing frequency level, and overlaps in collector response ranges in surface structure spatial frequency levels could be shown by overlaps in bars.

Figure 80:
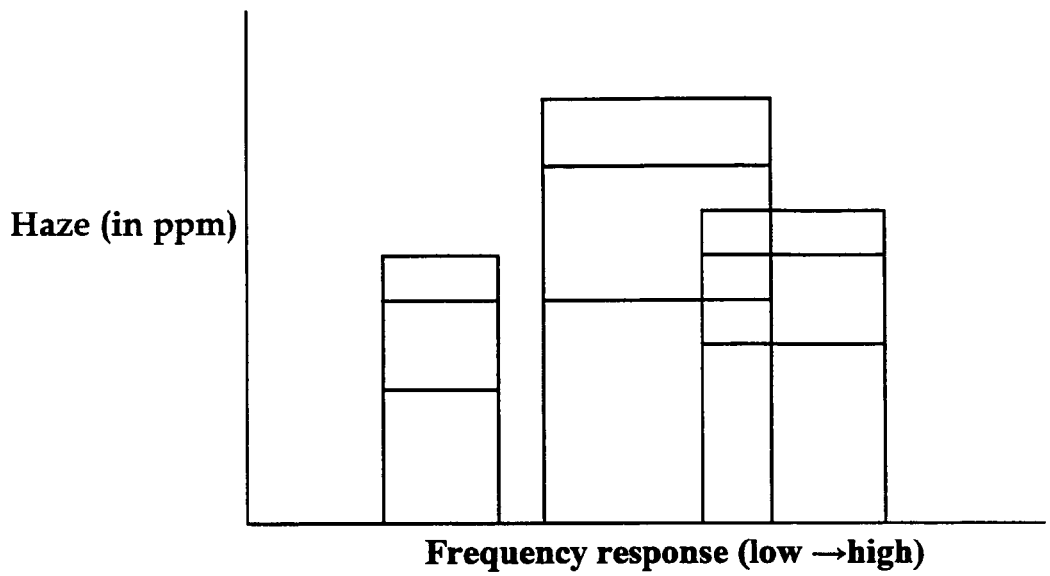
FIG. 80 is a spectral density plot of haze using methods of the present invention.

An example of a combined view histogram is shown in FIG. 80, which presents a graphical display of the output data that formed the frequency level haze maps of FIGS. 78A, 78B, and 78C. In FIG. 80, the surface structure spatial frequency ranges defining high and medium surface structure spatial frequency levels overlap. The combined view histogram of FIG. 80 comprises a form of power spectral density (PSD) plot, in which power (represented by scatter intensity measured in ppm) is plotted in terms of surface structure spatial frequency.

As noted above, collectors are placed such that they receive light scattered by surface structures having a spatial frequency within a certain surface structure spatial frequency range. In general, the relative proportionality of surface structure spatial frequencies for each collector may be derived for wafer surfaces having defined characteristics. When nominal responses by a collector or set of collectors are established for surfaces having defined characteristics, any deviation from the nominal response of a collector response for a test surface having the defined characteristic indicates a possible abnormality in the surface. For example, it could indicate a surface defect in or on a surface structure, due to a change in the production run in which the workpiece was produced.

Since changes in surface structure spatial frequency contributions from a workpiece surface may identify changes in workpiece production, deviations from nominal collector responses may be used to monitor workpiece production. Baseline or norms comprising acceptable ranges of scatter intensity measurement values for a collector in a defined position in the space above a surface could be developed for a representative set of workpieces having specified characteristics.

For example, for a collector in a multiple collector surface inspection system such as system 10 and in a defined position above the workpiece surface, nominal responses may be developed from data obtained by operating the collector to observe scatter from the surfaces of several workpieces, for example, workpieces produced using the same production process. Minimum and maximum values could be determined in the ranges of acceptable scatter intensity measurement values for each selected collector. In addition, baseline or norms comprising ranges of acceptable scatter intensity measurement values could be developed for a set of collectors in defined positions in the space above a surface for workpieces sharing specified characteristics.

Figure 100:
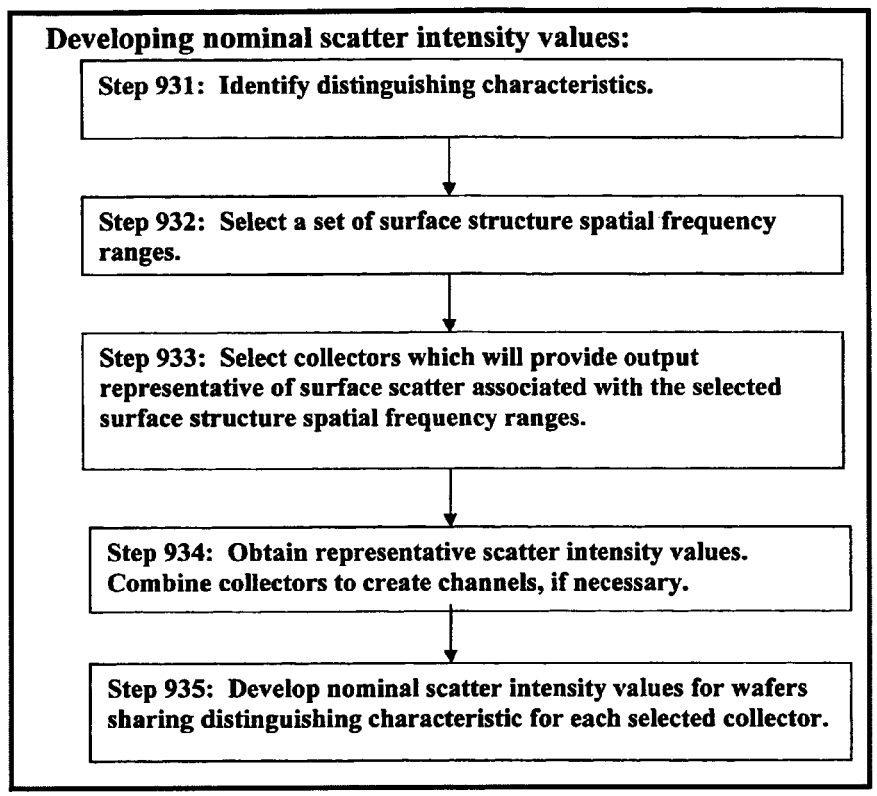
FIG. 100 is a block diagram showing one method of forming nominal surface structure spatial frequency ranges.

The baseline or norms could be associated with an acceptable level of surface roughness on a workpiece of a specified characteristic. The baseline or norms could then be used to define norm value ranges for the scatter intensity measurement values in the output of the selected collector or collectors for workpieces sharing specified characteristics, such as wafers in a production run. In a subsequent production run, deviations from the norm value ranges in the output of the selected collector or collectors could then be used to indicate problems in the production run. Nominal ranges could be developed using the following method, shown in FIG. 100:

Step 931: Distinguishing characteristics (such as wafer type, production type, polishing process, wafer annealing, epitaxial processing, grain size)) are identified for the wafers to be analyzed.

In a step 932, a set of surface structure spatial frequency ranges is selected for the surface structures to be observed.

Step 933: The collectors in a multi-collector surface inspection system such as system 10, which will provide output representative of surface scatter sort-able by surface structure spatial frequency range associated with the surface structures to be observed, are selected to provide output associated with the selected surface structure spatial frequency-ranges.

Step 934: Output comprising scatter intensity values is obtained for each of the selected collectors from a plurality of wafers, for example, from a production run of wafers having the same characteristics as the wafer under investigation. As described above, output of selected collectors may be combined to create output to be associated with a channel.

Step 935: Nominal scatter intensity values, for example in PPM units, are developed for wafers sharing the distinguishing characteristic for each selected collector (and thus each selected surface structure spatial frequency range), and are used to develop nominal scatter intensity ranges.

Figure 101:
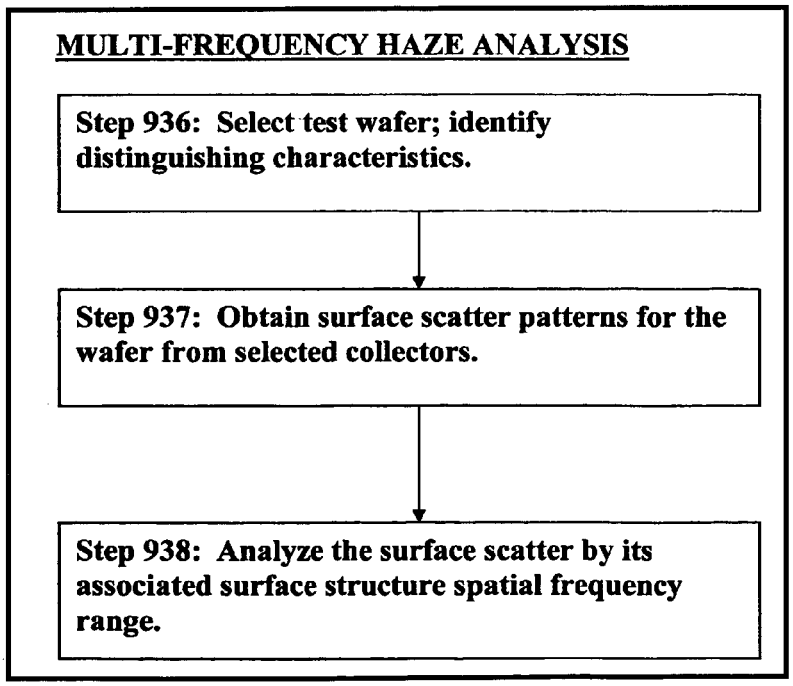
FIG. 101 is a block diagram showing one embodiment of a multiple spatial frequency haze analysis method.

Once nominal scatter intensity ranges are developed for the set of selected surface structure spatial frequency ranges for the set of distinguishing characteristics of wafers to be analyzed, multiple surface structure spatial frequency haze analysis may be performed on a workpiece. As shown in FIG. 101, one embodiment of a surface structure spatial frequency-based haze analysis method follows:

Step 936: A test wafer is selected for analysis. The wafer's distinguishing characteristics are identified, and the nominal scatter intensity ranges associated with wafer of the distinguishing characteristics are identified.

Step 937: A surface inspection system such as system 10 is used to obtain surface scatter patterns for the wafer from the selected collectors. The system 10 scans the wafer using the methods described above to identify surface scatter patterns.

Step 938: The surface scatter associated with the wafer is then analyzed by its associated surface structure spatial frequency range in the manner described above.

As noted above, the architecture of the multi-collector surface inspection system 10 supports providing a visual presentation of data in haze maps from multiple collectors based on surface structure spatial frequency content. One haze map could be used to show the entire distribution of surface structure spatial frequency content (SFC) for the system 10, with high SFC from the back collectors 340A, 340B, mid SFC from the center collector 320, low SFC from the front collector, mid to low SFC from the wing collectors 310A, 310B, and very low SFC from the light channel 650. Given a measurement system in a state of control, analysis of haze response over multiple scatter fields facilitates wafer quality control that can cater to the substrate's end use and/or required channel sensitivities.

Analysis of haze response in which the surface structure spatial frequency content associated with the haze is a variable encompasses qualitative and/or quantitative approaches. As an example of a qualitative approach, if a wafer produces a preponderance of haze associated with lower surface structure spatial frequency in one region and a preponderance of haze associated with medium surface structure spatial frequency haze in another region, the lack of uniformity of haze associated with different spatial frequency ranges might indicate that polishing uniformity is not ideal.

Lack of uniformity of haze between different surface structure spatial frequency ranges would be more easily observable in the embodiment of a composite haze map in which scatter variation is shown by color. In the example, one color would be present in one region and another color would be present in another region. If the haze readings were within nominal (standard) ranges, the surface of the wafer would be uniformly colored. For example, if the haze responses shown in a composite haze map were within nominal (standard) ranges, the uniform red/green/blue colors would blend together to present a wafer of a uniform gray color.

As another example, scratches, that could be caused by a number of problems, such as poor polishing, would be more apparent in composite haze maps in which haze is separated by surface structure spatial frequency than in haze maps showing haze associated with only one surface structure spatial frequency range (i.e., a haze map showing haze response for only one collector) or haze maps showing haze not separated by surface structure spatial frequencies. Scratches appear in haze maps as lines; the deeper the scratch, the stronger the line in the map. Certain scratches may be apparent in the haze associated with only one surface structure spatial frequency range or in only a limited number of surface structure spatial frequency ranges, and they may not be apparent at all in the haze associated with another surface structure spatial frequency range. Therefore, a scratch that is apparent in the haze associated with one surface structure spatial frequency range will not be displayable in a haze map for haze associated with other surface structure spatial frequency ranges. In addition, in output of haze not separated by surface structure spatial frequencies, signal associated with a scratch that is apparent in haze of a limited number of surface structure spatial frequency ranges is attenuated by the signals of haze associated with the other surface structure spatial frequencies in which the scratch is not apparent. The aggregation of signals in the display of haze that is not separated by surface structure spatial frequency will result in a signal in which the scratch is dim or not apparent at all. On the other hand, in a composite haze map in which haze is separated by surface structure spatial frequency, the scratch could be presented using a plurality of representations, for example in a plurality of colors, and the scratch will therefore will stand out in the physical representative of the surface structure spatial frequency ranges of haze in which the scratch is apparent (for example, a light green line will show up in a field of soft red and green haze).

In one embodiment, analysis of haze response in which the surface structure spatial frequency content of haze is a variable comprises disabling selected portions of the surface scatter intensity ranges in output associated with an individual contributing collectors. Disabling portions of a surface scatter intensity range essentially comprises subdividing data associated with a surface structure spatial frequency range with which a collector is associated into scatter intensity sub-ranges so that haze may be analyzed in even smaller sets of data. After scatter intensity range sub-division, the data associated with the scatter intensity sub ranges may be used as the data associated with the surface structure spatial frequency distributions in haze analysis.

With sub-divided scatter intensity frequency ranges, a haze map may be constructed that shows how scatter magnitudes (in ppm units) are distributed throughout the individual scatter intensity ranges in relationship to the other surface structure spatial frequency response ranges. By disabling a certain range of scattered power over a selected surface structure frequency response collector, can generate a map showing the absence of the eliminated scatter intensity ranges in a map. While scatter from surface structure is more readily differentiated when it is analyzed by selected surface structure spatial frequency ranges, signals associated with the scatter is still integrated within the selected surface structure spatial frequency range. Subdividing the selected surface structure spatial frequency range into sub-ranges associated with the scatter intensity within the range provides smaller integration and facilitates differentiation, even within a surface structure frequency range. With subdivided scatter intensity ranges, it is possible to remove a range of scatter intensities from a haze map to show only some the presence of only some intensity values within a surface structure spatial frequency range.

An example of the utility of subdividing selected surface structure spatial frequency ranges is shown in FIGS. 96 and 97. Referring to FIG. 96, a medium surface structure spatial frequency range haze map 939, comprising a haze map associated with the medium surface structure spatial frequency range, could show scatter of no discernible pattern. However, when the medium surface structure spatial frequency range is subdivided and a modified medium surface structure spatial frequency range haze map 941, such as in FIG. 97, is constructed, haze associated with all scatter intensity values in the medium surface structure spatial frequency range except the higher scatter intensity values could be displayed. It can be seen that map 941 shows a cluster of haze events in the center of the map. Such a haze pattern could indicate that locations in the center of the wafer are producing more haze than are locations elsewhere on the wafer.

Haze produced by the center of a wafer could result from increased amplitude of surface structures in the center of the wafer, which could arise from over-polishing on the outside of the wafer and incomplete polishing in the center of the wafer, which, in turn, could arise from a deformation of the wafer while it is being polished. It is known that bowing in the center of a wafer during polishing could arise from uneven pressures on the wafer platen. In response to seeing increased haze events in the center of a wafer map, a production manager could tune pressures on the platen in order to eliminate the deformation. Thus surface structure spatial frequency range-based haze analysis could be used to facilitate monitoring of wafer production.

Subdividing other surface structure spatial frequency ranges, creating modified surface structure spatial frequency range haze maps, and combining the modified surface structure spatial frequency range haze maps into modified composite haze maps could highlight with even greater specificity haze events that could be used to diagnose structural conditions and processing problems.

Surface structure spatial frequency range-based haze analysis can be particularly useful in conducting production problem troubleshooting. In the example described above, in which pressures on a platen caused wafer deformations that resulted in non-uniform polishing, confirmation of the existence of a similar but aberrant scatter pattern in another frequency range indicated the presence of a global problem with the surface structure irrespective of the surface structure spatial frequency range. On the other hand, a composite haze map or haze maps of different surface structure spatial frequency ranges that show that all but one of the response collectors is observing uniform haze could indicate a different problem, such as polishing being uniform within some surface structure spatial frequency ranges but not all surface structure spatial frequency ranges. A production manager, using the haze maps to identify de-correlated data or data with low correlation, could then concentrate on other production issues, such as deficiency in the size of a polishing slurry or a chemical reaction.

If the production manager using surface structure spatial frequency-based haze analysis identified a scatter pattern in the middle to high surface structure spatial frequency response ranges (in data from the center or back collectors) but not from the low surface structure spatial frequency range, (in data from the front collector, he or she could suspect certain issues such as problems with the slurry, which are more likely to introduce scatter associated with middle or high surface structure spatial frequencies. On the other hand, if the production manager identified a scatter pattern only in the low surface structure spatial frequency response range, he or she could eliminate slurry issues and focus on problems that are more correlated with low surface structure spatial frequency scatter, such as problems with holding the wafer (i.e. a defective gripper).

Figure 77:
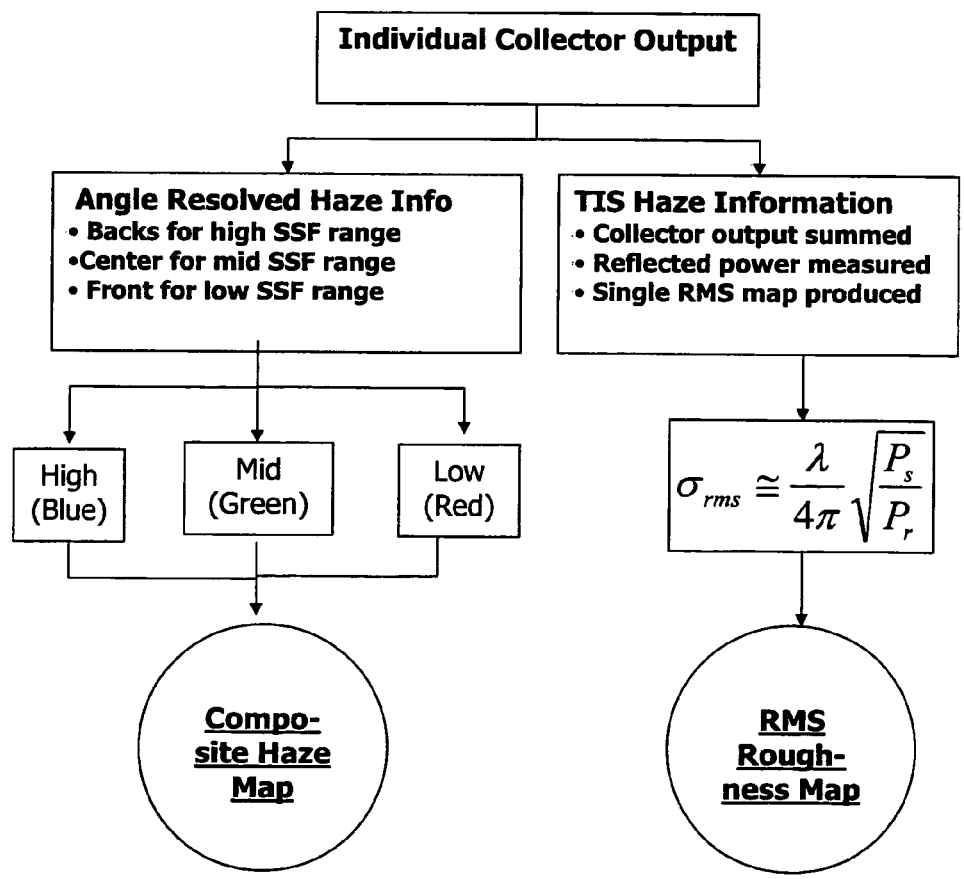
FIG. 77 is a block diagram showing methods of analyzing surface structure scatter according to the present invention.

A multi-collector surface inspection system such as system 10 is particularly advantageous in that it is capable of being used to analyze surface structure scatter. FIG. 77 is a block diagram showing methods of analyzing surface structure scatter analysis according to the present invention, in which the optical collection and detection subsystem 7 provides output associated with each collector detection module 200. The output may then be used to perform angle-resolved scatter haze analysis or total integrated scatter haze analysis.

As described above, each collector detector module 200 is positioned above a surface workpiece in order to respond to scatter associated with a particular spatial frequency range for a surface structure. Because the response range is constant within a given measurement configuration, e.g. incident beam angle, wavelength, collector dimensions, etc, the output from the module 200 may be used to perform angle-resolved scatter haze analysis, with the back collector modules 340A, 340B observing scatter associated with the high surface structure spatial frequency range 281, the center collector module 320 observing scatter associated with the medium surface structure spatial frequency range 282, and the front collector modules 330 observing scatter associated with the low surface structure spatial frequency range 283. Since the scatter is thus observable according to the surface structure spatial frequency associated with it, angle-resolved scatter haze analysis produces a means of monitoring the various spatial frequency contributions to surface roughness scatter. Collectors may be combined into haze fields to minimize the effects of incident beam orientation to the silicon surface, e.g. combined back collectors and combined wing collectors. Visual representations such as composite haze maps may be developed to assist in analysis.

The output from the module 200 may also be used to perform total integrated scatter haze analysis, with the output form all of the collectors summed, the reflected power measured and RMS roughness values produced as described above. Visual representations such as single RMS maps may then be developed to assist in haze analysis. Single RMS maps would look very similar to haze maps, with map positions being associated with locations on the region under investigation, and with each map position having a graphical element representing an extent of the single RMS roughness associated with the location on the wafer associated with the map position.

As noted above, typically, surface inspection tools that measure RMS roughness have a normal incident beam and obtain RMS roughness measurements by obtaining measurements of the Total Integrated Scatter (TIS) from the wafer. When such tools comprise multi-collector tools, they obtain RMS roughness measurements from the haze observed across all of the collection optics, by summing the scatter output associated with all of their available collectors.

The system 10 differs from other surface inspection tools that measure RMS roughness in that it has an oblique incident beam and it collects scatter from collectors disposed at selected angles. The oblique incident beam and the angular positioning of its collectors introduce a surface structure spatial frequency component to the surface scatter output that provides improved haze analysis. However, system 10 could also be operated as a total integrated scatter tool, obtaining TIS measurements by summing the scatter output associated with collectors 300.

It should be noted, though, that aspects of the architecture of the system 10 cause RMS roughness measurements developed by the system 10 to not match the RMS roughness measurements developed by typical RMS roughness surface inspection tools using normal incident beams. The surface structure spatial frequency response ranges of certain of the collectors 300 to overlap, thus causing some "double counting" of scatter when the output of the collectors is simply summed. Therefore, because of double-counting, the RMS roughness measurements developed by the system 10 will not match the RMS roughness measurements developed by typical RMS roughness tools. However, RMS roughness measurements developed by the system 10 will strongly correlate RMS roughness measurements developed by typical RMS roughness tools.

While, as noted above, it is not necessary in angle-resolved haze analysis to include data from all collectors 300, in order for system 10 to obtain strong correlation of roughness measurements with those of typical RMS roughness tools, the output associated with all collectors should be summed.

For example, as noted above, data associated with the wing collectors operating in the P configuration may be excluded from angle-resolved haze analysis in order to reduce extent of overlap. Such a practice is acceptable in angle resolved haze analysis because most surface scatter would be filtered from wing data due to polarization. However, in order to obtain strong correlation of roughness measurements with typical RMS roughness tools, it is useful to include scatter associated with wing collectors operating in P configuration.

The above invention has been described in terms of it use in the analysis of unpatterned wafers. However, it is to be understood that the invention is not limited to use in the analysis of wafers. The invention could be applied to the analysis of any suitable workpiece, such as glass and polished metallic surfaces and film wafers.

CONCLUSION

Additional advantages and modifications will readily occur to those skilled in the art. Therefore, the invention in its broader aspects is not limited to the specific details, representative devices and methods, and illustrative examples shown and described. Departures may be made from such without departing from the spirit or scope of the general inventive concept as defined by the appended claims and their equivalents.

The invention claimed is:

1. A method for inspecting a surface of a workpiece, the method comprising:
   scanning an incident beam though a back quartersphere at an oblique angle on the surface of the workpiece so that the incident beam impinges on a desired spot thereon to form a reflected beam that extends along a light channel axis in a front quartersphere and to form scattered light having a haze scatter portion, comprising a portion of the scattered light attributable to haze, and a defect scatter portion, comprising a portion of the scattered light attributable to defects on the surface, the incident beam and the light channel axis forming an incident plane;
   collecting a first portion of the scattered light with first and second wing collectors disposed in the front quartersphere, outside the incident plane, and at a minimum in the haze portion relative to the defect scatter portion when the incident beam is P polarized, with one each of the wing collectors disposed on either side of the incident plane and symmetrically with respect to the incident plane, and are equidistant from the desired spot; and
   collecting a second portion of the scattered light with first and second back collectors positioned disposed in the back quartersphere, wherein the first and second back collectors are disposed outside of the incident plane, with one each of the back collectors disposed on either side of the incident plane, and are located symmetrically with respect to the incident plane;
   collecting a third portion of the scattered light at a center position centrally disposed above the surface,
   detecting the first, second, and third portions of the scattered light and generating signals in response; and
   processing the signals to obtain information about the surface.

* * * * *